(12) United States Patent
Abellera et al.

(10) Patent No.: US 11,459,622 B2
(45) Date of Patent: Oct. 4, 2022

(54) METHODS FOR PRODUCING CORN PLANTS WITH DOWNY MILDEW RESISTANCE AND COMPOSITIONS THEREOF

(71) Applicant: MONSANTO TECHNOLOGY LLC, St. Louis, MO (US)

(72) Inventors: Jorgen Costes Abellera, General Santos (PH); Romain Fouquet, Saint-Palais (FR); Vincent Lombard, Ballwin, MO (US); Yule Pan, Chesterfield, MO (US); Jean Jose Somera, General Santos (PH); Xianghai Ye, O'Fallon, MO (US)

(73) Assignee: MONSANTO TECHNOLOGY LLC, St. Louis, MO (US)

(*) Notice: Subject to any disclaimer, the term of this patent is extended or adjusted under 35 U.S.C. 154(b) by 0 days.

(21) Appl. No.: 17/082,851

(22) Filed: Oct. 28, 2020

(65) Prior Publication Data
US 2021/0079486 A1   Mar. 18, 2021

Related U.S. Application Data

(62) Division of application No. 15/261,286, filed on Sep. 9, 2016, now Pat. No. 10,858,709.

(60) Provisional application No. 62/216,593, filed on Sep. 10, 2015.

(51) Int. Cl.
| | |
|---|---|
| *A01H 5/10* | (2018.01) |
| *A01H 6/46* | (2018.01) |
| *C12Q 1/6895* | (2018.01) |
| *A01H 1/04* | (2006.01) |

(52) U.S. Cl.
CPC .......... *C12Q 1/6895* (2013.01); *A01H 1/04* (2013.01); *A01H 5/10* (2013.01); *A01H 6/4684* (2018.05); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,217,863 | A | 6/1993 | Cotton et al. |
| 5,468,613 | A | 11/1995 | Erlich et al. |
| 5,563,055 | A | 10/1996 | Townsend et al. |
| 5,595,890 | A | 1/1997 | Newton et al. |
| 5,616,464 | A | 4/1997 | Albagli et al. |
| 5,762,876 | A | 6/1998 | Lincoln et al. |
| 5,800,944 | A | 9/1998 | Blonsky et al. |
| 5,876,930 | A | 3/1999 | Livak et al. |
| 5,945,283 | A | 8/1999 | Kwok et al. |
| 6,004,744 | A | 12/1999 | Goelet et al. |
| 6,013,431 | A | 1/2000 | Soderlund et al. |
| 6,030,787 | A | 2/2000 | Livak et al. |
| 6,090,558 | A | 7/2000 | Butler et al. |
| 6,503,710 | B2 | 1/2003 | Gut et al. |
| 6,613,509 | B1 | 9/2003 | Chen |
| 6,799,122 | B2 | 9/2004 | Benson |
| 6,913,879 | B1 | 7/2005 | Schena |
| 6,996,476 | B2 | 2/2006 | Najarian |
| 7,238,476 | B2 | 7/2007 | McKeown et al. |
| 7,250,252 | B2 | 7/2007 | Katz et al. |
| 7,270,981 | B2 | 9/2007 | Armes et al. |
| 7,282,355 | B2 | 10/2007 | Shi |
| 7,297,485 | B2 | 11/2007 | Bornarth et al. |
| 7,312,039 | B2 | 12/2007 | Barany et al. |
| 10,858,709 | B2 * | 12/2020 | Abellera ............. A01H 5/10 |
| 2009/0064360 | A1 * | 3/2009 | Kerns ................. A01H 1/04 800/265 |
| 2010/0037342 | A1 | 2/2010 | Johnson et al. |
| 2011/0008793 | A1 | 1/2011 | Butruille et al. |

FOREIGN PATENT DOCUMENTS

WO    WO 2009/029771 A2    3/2009

OTHER PUBLICATIONS

Ganal et al., 2011, A Large Maize (*Zea mays* L.) SNP Genotyping Array: Development and Germplasm Genotyping, and Genetic Mapping to Compare with the B73 Reference Genome, PLoS ONE 6(12): e28334. doi:10.1371/journal.pone.0028334, pp. 1-15.*
Agrama et al., "Mapping of QTL for downy mildew resistance in maize," *Theoretical and Applied Genetics*, 99:519-523 (1999).
Arus et al., "Marker-assisted selection," *Plant Breeding: Principles and prospects*, 314-331 (1993).
Borevitz et al., "Large-Scale Identification of Single-Feature Polymorphisms in Complex Genomes," *Genome Research*, 13:513-523 (2003).
Churchill et al., "Empirical Threshold Values for Quantitative Trait Mapping," *Genetics*, 138(3):963-971 (1994).
Cui et al., "Detecting single-feature polymorphisms using oligonucleotide array and robusti," *Bioinformatics*, 21(20):3852-3858 (2005).
Dalmacio, "Importance of and Growing Concerns for Maize Diseases in the Asian Region," *Proceedings of 7th Asian Regional Maize Workshop*, 267-276 (2000).
Flint-Garcia et al., "Structure of Linkage Disequilibrium in Plants," *Annual Review of Plant Biology*, 54:357-374 (2003).
Gaj et al., "ZFN, TALEN, and CRISPR/Cas-based methods for genome engineering," *Trends in Biotechnology*, 31(7):397-405 (2013).

(Continued)

*Primary Examiner* — Bratislav Stankovic
(74) *Attorney, Agent, or Firm* — Morrison & Foerster LLP

(57) ABSTRACT

The present disclosure is in the field of plant breeding and disease resistance. The disclosure provides methods for breeding corn plants having downy mildew (DM) resistance using marker-assisted selection. The disclosure further provides corn germplasm resistant to DM. The disclosure also provides markers associated with DM resistance loci for introgressing these loci into elite germplasm in a breeding program, thus producing novel DM resistant germplasm.

3 Claims, No Drawings

Specification includes a Sequence Listing.

(56) References Cited

OTHER PUBLICATIONS

Gruber et al., "Vectors for Plant Transformation," *Methods in Plant Molecular Biology and Biotechnology*, 89-119 (1993).
Hedrick, "Gametic Disequilibrium Measmes: Proceed With Caution," *Genetics*, 117:331-341(1987).
Horsch et al., "A Simple and General Method for Transferring Genes into Plants," *Science*, 227:1229-1231 (1985).
International Search Report and Written Opinion of the International Search Authority from International Application No. PCT/US16/50946, dated Feb. 27, 2017.
Invitation to Pay Additional Fees dated Dec. 8, 2016, in International Application No. PCT/US2016/050946.
Jampatong et al., "QTL mapping for downy mildew (*Peronosclerospora sorghi*) resistance in maize," *Proceedings of the 10 Asian Regional Maize Workshop*, 291-298 (2010).
Jampatong et al., "Mapping of QTL affecting resistance against sorghum downy mildew (*Peronosclerospora sorghi*) in maize (*Zea mays* L)," 11/laydica, 58:119-126 (2013).
Jannink et al., "Association Mapping in Plant Populations," *Quantitative Genetics, Genomics and Plant Breeding*, 59-68 (2002).
Jansen et al., "High Resolution of Quantitative Traits Into Multiple Loci via Interval Mapping," *Genetics*, 136:1447-1455 (1994).
Jansen et al., "Genotype-by-environment interaction in genetic mapping of multiple quantitative trait loci," *Theoretical and Applied Genetics*, 91:33-37 (1995).
Jansen et al., "Biometrics in Plant Breeding: Applications of Molecular Markers," *Proceedings of the Ninth Meeting of the EUCARPIA Section Biometrics in Plant Breeding* (1994).
Jeffers et al., "Status in Breeding for Resistance to Maize Diseases at CIMMYT," *Proceedings of 7th Asian Regional Maize Workshop*, 257-266 (2000).
Jeger et al., "The epidemiology, variability and control of the downy mildews of pearl millet and sorghum, with particular reference to Africa," *Plant Pathology*, 47:544-569 (1998).
Jones et al., "Mapping Quantitative Train Loci for Resistance to Downy Mildew in Pearl Millet: Field and Glasshouse Screens Detect the Same QTL," *Crop Science*, 42:1316-1323 (2002).
Kruglyak et al., "A Nonparametric Approach for Mapping Quantitative Trait Loci," *Genetics*, 139:1421-1428 (1995).
Lander et al., "Mapping Mendelian Factors Underlying Quantitative Traits Using RFLP Linkage Maps," *Genetics Society of America*, 121:185-199 (1989).
Lincoln et al., "Mapping Genes Controlling Quantitative Traits Using MAPMAKER/QTL Version 1.1: A Tutorial and Reference Manual," *Whitehead Institute for Biomedical Research*, 7-43 (1990).
Miki et al., "Procedures for Introducing Foreign DNA into Plants," *Methods in Plant Molecular Biology and Biotechnology*, 67-88 (1993).
Mueller, "Corn Disease Loss Estimates From the United States and Ontario, Canada-2012," *Purdue Extension Publication*, BP-96-12-W 1-5 (2014).
Nair et al., "Identification and validation of QTLs conferring resistance to sorghum downy mildew (*Peronosclerospora sorghi*) and Rajasthan downy mildew (*P. heteropogoni*) in maize," *Theoretical and Applied Genetics*, 110:1384-1392 (2005).
Nelson, "QGENE: software for marker-based genomic analysis and breeding," *Molecular Breeding*, 3(3):239-245 (1997).
Openshaw et al., "Marker-assisted Selection in Backcross Breeding," *Analysis of Molecular Marker Data*, 41-43 (1994).
Ragot et al., "Marker-assisted backcrossing: a practical example," *Techniques et utilisation des marqueurs moleculaires*, 72:45-56 (1995).
Reich et al., "Linkage disequilibrium in the human genome," *Nature*, 411:199-204 (2001).
Sabry et al., "A region of maize chromosome 2 affects response to downy mildew pathogens," *Theoretical and Applied Genetics*, 113:321-330 (2006).
Service, "Gene Sequencing: The Race for the $1000 Genome," *Science*, 311:1544-1546 (2006).
Singh et al., "Graphical Genotyping of Genomic Resources (QTL-NILs and RILs) and Transcriptome Profiling of Maize Genotypes in Response to Sorghum Downy Mildew (*Peronosclerospora sorghi*) in India," *Proceedings of the 10th Asian Regional Maize Workshop*, 220-223 (2010).
Telle et al., "Molecular phylogenetic analysis of Peronosclerospora (Oomycetes) reveals cryptic species and genetically distinct species parasitic to maize," *Eur. J Plant Pathol*, 130: 521-528 (2011).
Utz et al., "Comparison of different approaches to interval mapping of quantitative trait loci," *Biometrics in Plant Breeding: Applications of Molecular Markers*, 195-204 (1994).
"*Zea mays* cultivar B73 chromosome 6 clone CH201-393F21, Sequencing in Progress, 4 unordered pieces" NCBI/GenBank: AC212457, 2 pages (2013).
Zeng, "Precision Mapping of Quantitative Trait Loci," *Genetics*, 136:1457-1468 (1994).

* cited by examiner

METHODS FOR PRODUCING CORN PLANTS WITH DOWNY MILDEW RESISTANCE AND COMPOSITIONS THEREOF

CROSS-REFERENCE TO RELATED APPLICATIONS

This application is a divisional of U.S. patent application Ser. No. 15/261,286, filed Sep. 9, 2016, which claims the benefit and priority of U.S. Provisional Application No. 62/216,593, filed on Sep. 10, 2015, both of which are incorporated by reference in their entireties herein.

FIELD

The present disclosure relates to the field of agricultural biotechnology. More specifically, this disclosure relates to methods for producing corn plants or seeds with improved downy mildew resistance.

INCORPORATION OF SEQUENCE LISTING

A sequence listing contained in the file named P34336US02_SEQ.txt which is 251,097 bytes (measured in MS-Windows®) and created on Oct. 28, 2020, comprises 570 nucleotide sequences, is filed electronically herewith and incorporated by reference in its entirety.

BACKGROUND

Corn (*Zea mays* L.) is one of the most important commercial crops in the world. Like many commercial crops, corn is subjected to numerous potentially detrimental environmental conditions (e.g., moisture availability, temperature stresses, soil conditions, pests, disease) that can reduce, or entirely eliminate, crop yield. Crop disease alone accounted for the loss of more than 1.3 billion bushels of corn in the United States and Ontario, Canada in 2012. See Mueller, Corn Disease Loss Estimates from the United States and Ontario, Canada—2012. *Purdue Extension Publication* BP-96-12-W (2014).

Downy mildew (DM) is a crop disease caused by several oomycete pathogens of the genera *Peronosclerospora, Sclerophthora*, and *Sclerospora*. Some DM pathogens are known to be host-species specific. For instance, *Sclerospora graminicola* infects *Setaria* sp., but not pearl millet (*Pennisetum glaucum*). Young corn plants infected by DM often die prematurely. Plants that do not die prematurely from DM infection are often stunted in growth. Corn plants infected by DM often exhibit leaf chlorosis, and leaves that are more narrow and erect than is typical. DM infected fields routinely see yield reductions of about 40-60%, but up to 100% yield loss has been documented. Yield loss in surviving plants is primarily due to a failure to form cobs, which hold the seed, and replacement of parts of the pollen-bearing tassel with vegetative tissues (e.g., leaves). See Jeger et al, The epidemiology, variability and control of the downy mildews of pearl millet and sorghum, with particular reference to Africa. *Plant Pathology*, 47:544-569 (1998).

Currently, there are few effective control measures to combat DM infection in corn fields. The fungicide metalaxyl can be used in reducing DM infection for about 42 days, but it can be prohibitively expensive and it is most useful when applied to seed prior to planting. Additionally, at least some oomycetes that cause DM infection show signs of being resistant to fungicides, including metalaxyl. See Dalmacio, Importance of and Growing Concerns for Maize Diseases in the Asian Region. In: Vasal et al. eds. (2000) *Proceedings of 7th Asian Regional Maize Workshop. The 7th Asian Regional Maize Workshop: Strengthening hybrid maize technology and public-private partnership to accelerate maize production in the Asian region*. Los Baños, Philippines, 23-27 Feb. 1998, Laguna, Philippines: PCARRD, p 267-276.

Genetic resistance to DM presents an attractive option for combating DM infection.

Studies describing DM resistance quantitative trait loci (QTLs) have been reported, although commercialization of these genetic resistance has been lacking. See Agrama et al., Mapping of QTL for downy mildew resistance in maize. *Theoretical and Applied Genetics*, 99:519-523 (1999); Nair et al., Identification and validation of QTLs conferring resistance to sorghum downy mildew (*Peronosclerospora sorghi*) and Rajasthan downy mildew (*P. heteropogoni*) in maize. *Theoretical and Applied Genetics*, 110:1384-1392 (2005); Sabry et al. A region of maize chromosome 2 affects response to downy mildew pathogens. *Theoretical and Applied Genetics*, 113:321-330 (2006); Singh et al. Graphical Genotyping of Genomic Resources (QTL-NILs and RILs) and Transcriptome Profiling of Maize Genotypes in Response to Sorghum Downy Mildew (*Peronosclerospora sorghi*) in India. In: Zaidi et al. eds. (2010) *Maize for Asia: Emerging Trends and Technologies. Proceedings of The 10th Asian Regional Maize Workshop*. Makassar, Indonesia, 20-23 Oct. 2008, Mexico D. F.: CIMMYT, p 220-223; Jampatong et al., QTL mapping for downy mildew (*Peronosclerospora sorghi*) resistance in maize. In: Zaidi et al. eds. (2010) *Maize for Asia: Emerging Trends and Technologies. Proceedings of The 10th Asian Regional Maize Workshop*. Makassar, Indonesia, 20-23 Oct. 2008, Mexico D. F.: CIMMYT, p 291-298; Jampatong et al., Mapping of QTL affecting resistance against sorghum downy mildew (*Peronosclerospora sorghi*) in maize (*Zea mays* L). *Maydica*, 58:119-126 (2013).

There is a need in corn breeding to identify corn germplasm that provides resistance to DM infection. There is also a need to develop polymorphic markers for monitoring and introgressing DM resistance alleles, and further develop agronomically elite corn lines comprising DM resistance for enhancing plant productivity.

SUMMARY

The present disclosure identifies genetic loci conferring downy mildew (DM) resistance in corn, and provides molecular markers linked to these resistance loci. This disclosure further provides methods for introgressing resistance alleles of genetic loci conferring DM resistance into plant varieties previously lacking such alleles, thereby providing plants with DM resistance. The genetic loci, markers, and methods provided herein therefore allow for production of new varieties with enhanced DM resistance.

In an aspect, this disclosure provides a method of creating a population of corn plants or seeds, where the method comprises the steps of: (a) genotyping a first population of corn plants or seeds at one or more marker loci associated with and within about 20 cM of a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seeds comprising one or more DM resistance alleles of the marker loci; and (c)

producing from the selected one or more corn plants or seeds a second population of corn plants or seeds comprising one or more DM QTLs.

In an aspect, this disclosure provides a method of creating a population of corn plants or seeds comprising at least one allele associated with DM resistance, where the method comprises the steps of: (a) genotyping a first population of corn plants, the population comprising at least one allele associated with DM resistance, wherein the at least one DM resistance allele is associated with a marker selected from the group consisting of SEQ ID NOs: 1-114; (b) selecting from the first population one or more corn plants or seeds comprising the at least one DM resistance allele; and (c) producing from the selected corn plants or seeds a second population of corn plants or seeds comprising the at least one DM resistance allele.

In an aspect, this disclosure provides a method for introgressing a resistance allele of a locus conferring DM resistance, where the method comprises the steps of: (a) crossing a first corn plant with a second corn plant, wherein the first corn plant comprises the resistance allele wherein the at least one DM resistance allele is associated with a marker selected from the group consisting of SEQ ID NOs: 1-114; (b) genotyping a progeny corn plant or seed from the cross using a marker associated with the resistance allele; and (c) selecting a progeny plant or seed comprising the resistance allele.

In an aspect, this disclosure provides a method of introgressing a DM resistance QTL, where the method comprises the steps of: (a) crossing a first corn plant comprising a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, with a second corn plant of a different genotype to produce one or more progeny plants or seeds; (b) assaying the one or more progeny plants or seeds at a marker locus associated with the DM resistance QTL; and (c) selecting a progeny plant or seed comprising the DM resistance QTL.

In an aspect, this disclosure provides a method for creating a population of corn plants or seeds with DM resistance, where the method comprises the steps of: (a) concurrently detecting in a first population of corn plants or seeds the presence of a combination of two or more, three or more, four or more, five or more, six or more, seven or more, eight or more, nine or more, ten or more, or eleven or more introgressed DM resistance loci selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seed comprising the one or more, two or more, three or more, four or more, five or more, six or more, seven or more, eight or more, nine or more, ten or more, or eleven or more introgressed DM resistance QTLs; and (c) producing a population of offspring from the selected one or more corn plants or seeds.

In an aspect, this disclosure provides a method of producing a corn plant with enhanced DM resistance, where the method comprises the steps of: (a) crossing a first corn plant comprising a DM resistance QTL with a second corn plant of a different genotype to produce one or more progeny plants or seeds; and (b) selecting a progeny plant or seed comprising a DM resistance allele of a polymorphic locus linked to the DM resistance QTL, wherein the polymorphic locus is in a chromosomal segment flanked by: any two of marker loci SEQ ID NOs: 1 to 11; any two of marker loci SEQ ID NOs: 12 to 22; any two of marker loci SEQ ID NOs: 23 to 28; any two of marker loci SEQ ID NOs: 29 to 32; any two of marker loci SEQ ID NOs: 33 to 38; any two of marker loci SEQ ID NOs: 39 to 45; any two of marker loci SEQ ID NOs: 46 to 55, and 57; any two of marker loci SEQ ID NOs: 56, and 58 to 62; marker loci SEQ ID NOs: 63 and 64; any two of marker loci SEQ ID NOs: 65 to 90; or any two of marker loci SEQ ID NOs: 91 to 114.

In an aspect, this disclosure provides a method of obtaining a corn plant or seed with enhanced DM resistance, where the method comprises the steps of: (a) detecting in a population of corn plants or seeds a plant or seed comprising a DM resistance allele at a polymorphic locus in a chromosomal segment flanked by: any two of marker loci SEQ ID NOs: 1 to 11; any two of marker loci SEQ ID NOs: 12 to 22; any two of marker loci SEQ ID NOs: 23 to 28; any two of marker loci SEQ ID NOs: 29 to 32; any two of marker loci SEQ ID NOs: 33 to 38; any two of marker loci SEQ ID NOs: 39 to 45; any two of marker loci SEQ ID NOs: 46 to 57; any two of marker loci SEQ ID NOs: 54 to 62; marker loci SEQ ID NOs: 63 and 64; any two of marker loci SEQ ID NOs: 65 to 90; or any two of marker loci SEQ ID NOs: 91 to 114; and (b) selecting the plant or seed from the population based on the presence of the DM resistance allele.

In an aspect, this disclosure provides a method of obtaining a corn plant or seed with enhanced DM resistance, where the method comprises the steps of: (a) detecting in a population of corn plants or seeds a plant or seed comprising a DM resistance allele at a polymorphic locus in a chromosomal segment flanked by: any two of marker loci SEQ ID NOs: 1 to 11; any two of marker loci SEQ ID NOs: 12 to 22; any two of marker loci SEQ ID NOs: 23 to 28; any two of marker loci SEQ ID NOs: 29 to 32; any two of marker loci SEQ ID NOs: 33 to 38; any two of marker loci SEQ ID NOs: 39 to 45; any two of marker loci SEQ ID NOs: 46 to 55, and 57; any two of marker loci SEQ ID NOs: 56, and 58 to 62; marker loci SEQ ID NOs: 63 and 64; any two of marker loci SEQ ID NOs: 65 to 90; or any two of marker loci SEQ ID NOs: 91 to 114; and (b) selecting the plant or seed from the population based on the presence of the DM resistance allele.

In an aspect, this disclosure provides a method of producing a corn plant with enhanced DM resistance, where the method comprises the steps of: (a) crossing a first corn plant comprising a DM resistance haplotype with a second corn plant of a different genotype to produce one or more progeny plants or seeds; and (b) selecting a progeny plant or seed based on the presence of the DM resistance haplotype, wherein the haplotype comprises resistance alleles of two or more polymorphic loci in a chromosomal interval flanked by: any two marker loci selected from the group consisting of SEQ ID NOs: 1 to 11; any two marker loci selected from the group consisting of SEQ ID NOs: 12 to 22; any two marker loci selected from the group consisting of SEQ ID NOs: 23 to 28; any two marker loci selected from the group consisting of SEQ ID NOs: 29 to 32; any two marker loci selected from the group consisting of SEQ ID NOs: 33 to 38; any two marker loci selected from the group consisting of SEQ ID NOs: 39 to 45; any two marker loci selected from the group consisting of SEQ ID NOs: 46 to 57; any two marker loci selected from the group consisting of SEQ ID NOs: 54 to 62; SEQ ID NOs: 63 and 64; any two marker loci selected from the group consisting of SEQ ID NOs: 65 to 90; or any two marker loci selected from the group consisting of SEQ ID NOs: 91 to 114.

In an aspect, this disclosure provides a method of producing a corn plant with enhanced DM resistance, where the method comprises the steps of: (a) crossing a first corn plant comprising a DM resistance haplotype with a second corn plant of a different genotype to produce one or more progeny plants or seeds; and (b) selecting a progeny plant or seed based on the presence of the DM resistance haplotype, wherein the haplotype comprises resistance alleles of two or more polymorphic loci in a chromosomal interval flanked by: any two marker loci selected from the group consisting of SEQ ID NOs: 1 to 11; any two marker loci selected from the group consisting of SEQ ID NOs: 12 to 22; any two marker loci selected from the group consisting of SEQ ID NOs: 23 to 28; any two marker loci selected from the group consisting of SEQ ID NOs: 29 to 32; any two marker loci selected from the group consisting of SEQ ID NOs: 33 to 38; any two marker loci selected from the group consisting of SEQ ID NOs: 39 to 45; any two marker loci selected from the group consisting of SEQ ID NOs: 46 to 55, and 57; any two marker loci selected from the group consisting of SEQ ID NOs: 56, and 58 to 62; SEQ ID NOs: 63 and 64; any two marker loci selected from the group consisting of SEQ ID NOs: 65 to 90; or any two marker loci selected from the group consisting of SEQ ID NOs: 91 to 114.

In an aspect, this disclosure provides a method of obtaining a corn plant or seed with enhanced DM resistance, where the method comprises the steps of: (a) detecting in a population of corn plants or seeds a plant or seed comprising a DM resistance haplotype, wherein the haplotype comprises resistance alleles of two or more polymorphic loci in a chromosomal interval flanked by: any two marker loci selected from the group consisting of SEQ ID NOs: 5 to 8; SEQ ID NOs: 7 and 8; any two marker loci selected from the group consisting of SEQ ID NOs: 12 to 14; any two marker loci selected from the group consisting of SEQ ID NOs: 18 to 20; any two marker loci selected from the group consisting of SEQ ID NOs: 25 to 27; any two marker loci selected from the group consisting of SEQ ID NOs: 29 to 31; any two marker loci selected from the group consisting of SEQ ID NOs: 34 to 36; any two marker loci selected from the group consisting of SEQ ID NOs: 39 to 45; any two marker loci selected from the group consisting of SEQ ID NOs: 49 to 51; SEQ ID NOs: 58 and 59; SEQ ID NOs: 63 and 64; any two marker loci selected from the group consisting of SEQ ID NOs: 77 to 80; or any two marker loci selected from the group consisting of SEQ ID NOs: 99 to 106; and (b) selecting the plant or seed from the population based on the presence of the DM resistance haplotype.

In an aspect, this disclosure provides a method for selecting a corn plant or seed comprising the steps of: (a) genotyping a population of corn plants or seeds at a polymorphic locus associated with a marker selected from the group consisting of SEQ ID NOs: 1-114; and (b) selecting a corn plant or seed comprising a DM resistance allele at the polymorphic locus.

In an aspect, this disclosure provides a method for selecting a corn plant or seed comprising the steps of: (a) isolating nucleic acids from a corn plant or seed; (b) analyzing the nucleic acids to detect a polymorphic marker associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (c) selecting a corn plant or seed comprising the DM resistance QTL.

In an aspect, this disclosure provides a method for selecting a corn plant or seed comprising the steps of: (a) detecting in a population of corn plants or seeds a corn plant or seed comprising a DM resistance allele of a marker locus associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (b) selecting the corn plant or seed comprising the DM resistance allele.

In an aspect, this disclosure provides a method for evaluating a collection of corn germplasm comprising the steps of: (a) obtaining a collection of corn germplasm; (b) isolating nucleic acids from each germplasm; (c) assaying the nucleic acids for one or more markers linked to a DM resistance QTL selected from the group consisting of DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (d) selecting germplasm comprising a DM resistance QTL based on the marker assay.

In an aspect, this disclosure provides a method comprising providing a set of corn seeds comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, to a person desirous of planting the set of corn seeds in a field plot.

In an aspect, this disclosure provides a method of growing a population of corn plants in a field plot, wherein the method comprises planting a population of corn seeds comprising one or more, two or more, three or more, four or more, five or more, six or more, seven or more, eight or more, nine or more, ten or more, or eleven or more introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 in the field plot.

In an aspect, this disclosure provides a corn plant or seed comprising DM resistance and one or more, two or more, three or more, four or more, five or more, six or more, seven or more, eight or more, nine or more, ten or more, or eleven or more introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01.

BRIEF DESCRIPTION OF THE SEQUENCES

SEQ ID NOs: 1-114 list sequences of exemplary SNP marker loci associated with a DM resistance QTL. Example resistant and susceptible alleles of these marker loci are listed in Table 8. SEQ ID NOs: 115 to 570 list the sequences of exemplary primers and probes which can be used to detect the SNP marker loci of SEQ ID NOs: 1-114.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, a "corn plant" or "maize plant" refers to a plant of species Zea mays L and includes all plant varieties that can be bred with corn, including wild maize species.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed, or tissues from which new plants may be grown, or plant parts, such as leaves, stems, pollen, or cells that can be cultured into a whole plant.

As used herein, the phrase "associated with" or "linked to" refers to a recognizable and/or assayable relationship between two entities. For example, the phrase "associated with DM resistance" refers to a trait, locus, gene, allele, marker, phenotype, etc., or the expression thereof, the presence or absence of which can influence an extent, degree, and/or rate at which a plant or a part of interest thereof that has a DM resistance trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with a resistance allele" refers to a marker whose presence or absence can be used to predict whether and to what extent a plant will display a DM resistance phenotype.

As used herein, a centimorgan ("cM") is a unit of measure of recombination frequency and genetic distance between two loci. One cM is equal to a 1% chance that a marker at one genetic locus will be separated from a marker at, a second locus due to crossing over in a single generation.

As used herein, "closely linked" means that the marker or locus is within about 20 cM, 15 cM, 10 cM, 5 cM, 4 cM, 3 cM, 2 cM, 1 cM, 0.5 cM or less than 0.5 cM of another marker or locus. For example, 20 cM means that recombination occurs between the marker and the locus with a frequency of equal to or less than about 20%.

As used herein, "locus" is a chromosome region or chromosomal region where a polymorphic nucleic acid, trait determinant, gene, or marker is located. A locus may represent a single nucleotide, a few nucleotides or a large number of nucleotides in a genomic region. The loci of this disclosure comprise one or more polymorphisms in a population; e.g., alternative alleles are present in some individuals. A "gene locus" is a specific chromosome location in the genome of a species where a specific gene can be found.

As used herein, "allele" refers to an alternative nucleic acid sequence at a particular locus. The length of an allele can be as small as one nucleotide base. For example, a first allele can occur on one chromosome, while a second allele occurs on a second homologous chromosome, e.g., as occurs for different chromosomes of a heterozygous individual, or between different homozygous or heterozygous individuals in a population.

As used herein, "crossed" or "cross" means to produce progeny via fertilization (e.g. cells, seeds or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot et al., Marker-assisted Backcrossing: A Practical Example, in *Techniques Et Utilisations Des Marqueurs Moleculaires Les Colloques,* 72:45-56 (1995); and Openshaw et al., Marker-assisted Selection in Backcross Breeding, in Proceedings Of The Symposium "Analysis Of Molecular Marker Data," pp. 41-43 (1994). The initial cross gives rise to the $F_1$ generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "agronomically elite background" means any line that has resulted from breeding and selection for superior agronomic performance. Similarly, an "elite germplasm" or elite strain of germplasm is an agronomically superior germplasm. Numerous elite lines are available and known to those of skill in the art of corn breeding.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. The term genotype can also refer to determining the genetic constitution of an individual (or group of individuals) at one or more genetic loci.

As used herein, a "haplotype" is the genotype of an individual at a plurality of genetic loci. Typically, the genetic loci described by a haplotype are physically and genetically linked, e.g., in the same chromosome interval. A haplotype can also refer to a combination of SNP alleles located within a single gene.

As used herein, "marker assay" means a method for detecting a polymorphism at a particular locus using a particular method, e.g. measurement of at least one phenotype (such as seed color, flower color, or other visually detectable traits), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker," or "molecular marker," or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of markers and integrated genetic maps have been developed for corn, e.g., the UMC 98 map, the Nested Association Mapping (NAM) map, the Intermated B73/Mol7 (IBM2) Neighbors 2008 genetic map, and the LHRF Gnp2004 map. See maizegdb.org/data_center/map for more. All markers are used to define a specific locus in corn genomes. Large numbers of these markers have been mapped. See maizegdb.org/data_center/marker. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in corn. In an aspect, markers used herein exhibit LOD scores of 2 or greater, 3 or greater, 4 or greater, 5 or greater, 6 or greater, 7 or greater, 8 or greater, or 9 or greater with an associated trait of interest (e.g., DM resistance), measuring using a method known in the art such as Qgene Version 2.23 (1996) and default parameters.

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. Linkage disequilibrium can be measured using any one of the methods provided in Hedrick, Gametic disequilibrium measures: proceed with caution. *Genetics*, 117:331-41(1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

As used herein, a "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in MAS breeding. As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that this disclosure be limited to any particular mapping populations, use of any particular software, or any particular set of software parameters to determine linkage of a particular marker or haplotypes with a desired phenotype. It is well within the ability of one of ordinary skill in the art to extrapolate the novel features described herein to any gene pool or population of interest, and using any particular software and software parameters. Indeed, observations regarding genetic markers and haplotypes in populations in addition to those described herein are readily made using the teaching of the present disclosure.

As used herein, "selecting" or "selection" in the context of marker-assisted selection or breeding refer to the act of picking or choosing desired individuals, normally from a population, based on certain pre-determined criteria.

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

As used herein, "probe" refers to an oligonucleotide (synthetic or occurring naturally) that is complementary (though not necessarily fully complementary) to a polynucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, a "population of plants," "population of seeds", "plant population", or "seed population" means a set comprising any number, including one, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants or seeds. The population members need not be identical to the population members selected for use in subsequent cycles of analyses or those ultimately selected to obtain final progeny plants or seeds. Often, a plant or seed population is derived from a single biparental cross, but may also derive from two or more crosses between the same or different parents. Although a population of plants or seeds may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, "cultivar" and "variety" are used synonymously and mean a group of plants within a species (e.g., Z. mays L.) that share certain genetic traits that separate them from other possible varieties within that species. Corn cultivars can be inbreds or hybrids, though commercial corn cultivars are mostly hybrids to take advantage of hybrid vigor. Individuals within a corn hybrid cultivar are homogeneous, nearly genetically identical, with most loci in the heterozygous state.

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, "introgression" refers to the transmission of a desired allele of a genetic locus from one genetic background to another.

As used herein, the term "chromosome interval" or "chromosomal interval" designates a contiguous linear span of genomic DNA that resides on a single chromosome.

As used herein, "flanked by," when used to describe a chromosomal interval, refers to two loci physically surrounding the chromosomal interval, with one locus on each side of the chromosomal interval. As referenced herein, a chromosomal interval flanked by two marker loci includes the two marker loci.

As used herein, a "resistant allele" is an allele at a particular locus that confers, or contributes to, DM resistance, or alternatively, is an allele that allows the identification of plants that comprise DM resistance. A resistant allele of a marker is a marker allele that segregates with DM resistance, or alternatively, segregates with DM susceptibility, therefore providing the benefit of identifying plants having DM susceptibility. A resistant allelic form of a chromosome interval is a chromosome interval that includes a nucleotide sequence that contributes to DM resistance at one or more genetic loci physically located in the chromosome interval.

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence.

As used herein, the terms "phenotype," or "phenotypic trait," or "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "resistance" and "enhanced resistance" are used interchangeably herein and refer to any type of increase in resistance, or any type of decrease in susceptibility. A "resistant plant" or "resistant plant variety" need not possess absolute or complete resistance. Instead, a "resistant plant," "resistant plant variety," or a plant or plant variety with "enhanced resistance" will have a level of resistance which is higher than that of a comparable susceptible plant or variety. The level of downy mildew resistance can be determined based on disease ratings as determined in Example 1. Specifically, resistance to DM infection of corn plants is scored using a DM resistance scale, wherein DM resistance is measured by counting the percentage of plants infected by DM in a field plot 40 days after planting. A DM resistance scale comprises ratings of highly resistant (e.g., fewer than 5% of plants infected); moderately resistant (e.g., 5 to 15% of plants infected); intermediate (e.g., 15-35% of plants infected); moderately susceptible (e.g., 35-45% of plants infected); and highly susceptible (e.g., greater than 45% of plants infected).

As used herein, "quantitative trait locus" (QTL) or "quantitative trait loci" (QTLs) refer to a genetic domain that effects a phenotype that can be described in quantitative terms and can be assigned a "phenotypic value" which corresponds to a quantitative value for the phenotypic trait.

As used herein, "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "downy mildew" refers to a plant disease caused by oomycete species in the genera *Peronosclerospora, Sclerophthora,* and *Sclerospora.*

As used herein, a "low downy mildew stress condition" refers to a condition where very few to no DM susceptible corn plants in a field plot (e.g., fewer than 10%) exhibit signs of DM infection. Signs of DM infection can include: premature death, stunted growth, chlorotic leaves, narrow leaves, erect leaves, shredded leaves, failed cob formation, and vegetative tissue within the tassel.

As used herein, a "high downy mildew stress condition" refers to a condition where a plurality of DM susceptible corn plants in a field plot (e.g., more than 30%) exhibit signs of DM infection.

As used herein, "field plot" refers to a location that is suitable for growing corn. The location may be indoors (e.g., a greenhouse or growth chamber) or outdoors; irrigated or non-irrigated; in the ground or in a container that holds soil.

As used herein, a "planting season" is the length of time, typically about 90-120 days, in which corn may be grown from seed to maturity. One skilled in the art would recognize that a "planting season" could be significantly shorter or longer than about 90-120 days depending on the corn variety being grown and environmental conditions.

As used herein, "staggered planting" refers to planting a crop in a single field plot multiple times during the same planting season, with each planting separated by at least 1 day. For instance, planting corn seeds in a field plot on day 1 and again on day 15 would comprise a staggered planting.

As used herein, "transgenic" means a plant or seed whose genome has been altered by the stable integration of recombinant DNA. A transgenic line includes a plant regenerated from an originally-transformed plant cell and progeny transgenic plants from later generations or crosses of a transformed plant.

As used herein, "haploid" means a line that has had its normal chromosome complement reduced by half, typically by pollinating an ear with pollen from a haploid inducing line. In corn, haploid refers to an individual plant or seed that has a haploid chromosome complement where n=10, instead of the normal diploid chromosome complement where 2n=20. A "doubled haploid" refers to a haploid line (n=10) that has been induced, typically via chemical means, to double its chromosome complement and return to a diploid state (2n=20) that is homozygous at all loci within the genome.

As used herein, "yield penalty" refers to a reduction of seed yield in a line correlated with or caused by the presence of a DM resistance allele or DM resistance QTL as compared to a line that does not contain that DM resistance allele or DM resistance QTL.

As used herein, "seed yield" can refer to a measure of crop production such as test weight, seed number per plant, seed weight, seed number per unit area (i.e. seeds, or weight of seeds, per acre), bushels per acre, tons per acre, kilograms per hectare, or quintals per hectare.

Downy mildew is a plant disease caused by oomycete species of several genera, such as *Peronosclerospora, Sclerophthora,* and *Sclerospora*. Due to poor understanding of downy mildew systematics, it is not always possible to identify members of *Peronosclerospora, Sclerospora,* and *Sclerophthora* to species. However, species known to cause downy mildew include, but are not limited to: *P. eriochloae, P. graminicola, P. heteropogoni, P. maydis, P. miscanthi, P. philippinensis, P. sacchari, P. sorghi, P. spontanea, P. zeae, Sclerophthora macrospora, Scleropthora rayssiae* var. *zeae,* and *Sclerospora graminicola.* Downy mildew afflicts corn worldwide, with particularly devastating effects in Africa and Asia. About 29-31% of total areas growing tropical lowland, subtropical, mid-altitude, transition zone, and highland corn report economic losses due to downy mildew. See Jeffers et al. Status in Breeding for Resistance to Maize Diseases at CIMMYT. In: In: Vasal et al. eds. (2000) *Proceedings of 7th Asian Regional Maize Workshop. The 7th Asian Regional Maize Workshop: Strengthening hybrid maize technology and public-private partnership to accelerate maize production in the Asian region.* Los Baños, Philippines, 23-27 Feb. 1998, Laguna, Philippines: PCARRD, p 257-266.

Corn plants are at risk of contracting downy mildew infection as they emerge from the ground as seedlings; downy mildew oospores can persist in soil for at least up to 10 years. If corn plants are infected at the seedling stage they often die prematurely. Older corn plants may be infected by wind-blown downy mildew spores. Typical symptoms of corn afflicted by downy mildew include stunted growth, chlorotic leaves, narrow leaves, and erect leaves. More rarely, infected corn leaves exhibit a shredded phenotype. Corn seed yields are reduced by downy mildew due to a failure of cob formation and a replacement of tassels by vegetative structures such as leaves. See Jeger et al, The epidemiology, variability and control of the downy mildews of pearl millet and sorghum, with particular reference to Africa. *Plant Pathology,* 47:544-569 (1998). Varieties of corn that are highly susceptible to downy mildew can experience up to 50-100% yield loss, although up to 40-60% yield loss is more typical. When staggered planting is used, late-plantings suffer the greatest yield losses.

Several systemic fungicides, including metalaxyl, fosetyl-Al, furalaxyl, Patafol, and benalaxyl are used to combat downy mildew. See Dalmacio, Importance of and Growing Concerns for Maize Diseases in the Asian Region. In: Vasal et al. eds. (2000) *Proceedings of 7th Asian Regional Maize Workshop. The 7th Asian Regional Maize Workshop: Strengthening hybrid maize technology and public-private*

*partnership to accelerate maize production in the Asian region*. Los Baños, Philippines, 23-27 Feb. 1998, Laguna, Philippines: PCARRD, p 267-276. However, reliance on chemical agents to reduce DM incidence is unreliable, because DM may develop resistance to the chemical agents. Indeed, incidences of DM occurring in fields planted with metalaxyl-treated seeds and causing yield loss have been reported. Id. A corn plant or seed disclosed herein possesses one or more DM resistance QTLs and/or DM resistance alleles that confer enhanced resistance to downy mildew compared to a corn plant or seed that lacks the one or more DM resistance QTLs or DM resistance alleles. Further, a corn plant or seed disclosed herein provides increased yield in high DM pressure conditions, while suffering no yield penalties in low DM pressure conditions.

In an aspect, a corn plant or seed provided in this disclosure is *Zea mays* L. In another aspect, a corn plant or seed provided in this disclosure is *Zea mays* ssp. *mays*. In yet another aspect, a corn plant or seed provided herein is a domesticated line or variety. In an aspect, a corn plant or seed provided herein is not *Zea diploperennis*. In an aspect, a corn plant or seed provided herein is not *Zea perennis*. In an aspect, a corn plant or seed provided herein is not *Zea luxurians*. In an aspect, a corn plant or seed provided herein is not *Zea nicaraguensis*. In an aspect, a corn plant or seed provided herein is not *Zea mays* ssp. *huehuetenangensis*. In an aspect, a corn plant or seed provided herein is not *Zea mays* ssp. *mexicana*. In an aspect, a corn plant or seed provided herein is not *Zea mays* ssp. *parviglumis*.

In an aspect, this disclosure provides quantitative trait loci (QTLs) that exhibit significant co-segregation with DM resistance. The QTLs of this disclosure can be tracked during plant breeding or introgressed into a desired genetic background in order to provide plants exhibiting enhanced DM resistance and one or more other beneficial traits. In an aspect, this disclosure identifies QTL intervals that are associated with DM resistance in corn varieties CV357626 and CV368354.

In an aspect, this disclosure provides molecular markers linked to the QTLs disclosed herein and methods of using these markers for detection of and selection for DM resistance. An aspect of this disclosure includes specific markers and their resistance alleles, chromosome intervals comprising the markers, and methods of detecting markers genetically linked to DM resistance to identify plant lines with enhanced DM resistance. For example, one aspect of this disclosure provides a chromosome interval associated with DM resistance which is flanked by any two of marker loci SEQ ID NOs: 5 to 8. Another aspect of this disclosure provides a chromosome interval associated with DM resistance, where the interval is flanked by marker loci SEQ ID NOs: 7 and 8. Another aspect of this disclosure provides a chromosome interval associated with DM resistance which is flanked by any two of marker loci SEQ ID NOs: 12 to 14. Another aspect of this disclosure provides a chromosome interval associated with DM resistance which is flanked by any two of marker loci SEQ ID NOs: 18 to 20. Another aspect of this disclosure provides a chromosome interval associated with DM resistance which is flanked by any two of marker loci SEQ ID NOs: 25 to 27. Another aspect of this disclosure provides a chromosome interval associated with DM resistance which is flanked by any two of marker loci SEQ ID NOs: 29 to 31. Another aspect of this disclosure provides a chromosome interval associated with DM resistance which is flanked by any two of marker loci SEQ ID NOs: 34 to 36. Another aspect of this disclosure provides a chromosome interval associated with DM resistance which is flanked by any two of marker loci SEQ ID NOs: 39 to 45. Another aspect of this disclosure provides a chromosome interval associated with DM resistance which is flanked by any two of marker loci SEQ ID NOs: 49 to 51. Another aspect of this disclosure provides a chromosome interval associated with DM resistance, where the interval is flanked by marker loci SEQ ID NOs: 58 and 59. Another aspect of this disclosure provides a chromosome interval associated with DM resistance, where the interval is flanked by marker loci SEQ ID NOs: 63 and 64. Another aspect of this disclosure provides a chromosome interval associated with DM resistance which is flanked by any two of marker loci SEQ ID NOs: 77 to 80. Another aspect of this disclosure provides a chromosome interval associated with DM resistance which is flanked by any two of marker loci SEQ ID NOs: 99 to 106. Also provided herein are markers, e.g., SEQ ID NOs: 1-114, that are useful for tracking DM resistant alleles and can be used in marker assisted selection (MAS) breeding programs to produce plants with enhanced DM resistance.

This disclosure further provides methods of using the markers identified herein to introgress loci associated with DM resistance into DM susceptible plants. Thus, one skilled in the art can use this disclosure to create a novel corn plant or seed with DM resistance by crossing a donor line comprising a QTL disclosed herein with any desired recipient line, with or without MAS.

In another aspect, this disclosure further provides methods for introgressing multiple DM resistance QTLs identified herein to generate an enhanced DM resistant population of corn plants or seeds.

In an aspect, this disclosure provides a method of creating a population of corn plants or seeds, where the method comprises the steps of: (a) genotyping a first population of corn plants or seeds at one or more marker loci associated with one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seeds comprising one or more DM resistance alleles of the one or more marker loci; and (c) producing from the selected one or more corn plants or seeds a second population of corn plants or seeds comprising one or more DM QTLs.

In an aspect, this disclosure provides a method of creating a population of corn plants or seeds, which method comprising the steps of: (a) genotyping a first population of corn plants, the population comprising at least one allele associated with DM resistance, wherein the DM resistance allele is associated with a marker selected from the group consisting of SEQ ID NOs: 1-114; (b) selecting from the first population one or more corn plants or seeds comprising the DM resistance allele; and (c) producing from the selected corn plants or seeds a second population of corn plants or seeds comprising the at least one DM resistance allele.

In an aspect, this disclosure provides a method for introgressing a resistance allele of a locus conferring DM resistance, which method comprising the steps of: (a) crossing a first corn plant with a second corn plant, wherein the first corn plant comprises the resistance allele, wherein the DM resistance allele is associated with a marker selected from the group consisting of SEQ ID NOs: 1-114; (b) genotyping a progeny corn plant or seed from the cross using a marker associated with the resistance allele; and (c) selecting a progeny plant or seed comprising the resistance allele.

In an aspect, this disclosure provides a method for introgressing a DM resistance QTL, which method comprising the steps of: (a) crossing a first corn plant comprising a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, with a second corn plant of a different genotype to produce one or more progeny plants or seeds; (b) assaying the one or more progeny plants or seeds at a marker locus associated with the DM resistance QTL; and (c) selecting a progeny plant or seed comprising the DM resistance QTL.

In an aspect, this disclosure provides a method for creating a population of corn plants or seeds with DM resistance, which method comprising the steps of: (a) concurrently detecting in a first population of corn plants or seeds the presence of a combination of two or more, three or more, four or more, five or more, six or more, seven or more, eight or more, nine or more, ten or more, or eleven or more introgressed DM resistance loci selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seed comprising the one or more, two or more, three or more, four or more, five or more, six or more, seven or more, eight or more, nine or more, ten or more, or eleven or more introgressed DM resistance QTLs; and (c) producing a population of offspring from the selected one or more corn plants or seeds. In an aspect, a method comprises concurrent detection of one or more molecular markers located in at least one chromosome interval flanked by any two of marker loci SEQ ID NOs: 1 to 11, any two of marker loci SEQ ID NOs: 12 to 22, any two of marker loci SEQ ID NOs: 23 to 28, any two of marker loci SEQ ID NOs: 29 to 32, any two of marker loci SEQ ID NOs: 33 to 38, any two of marker loci SEQ ID NOs: 39 to 45, any two of marker loci SEQ ID NOs: 46 to 57, any two of marker loci SEQ ID NOs: 54 to 62, any two of marker loci SEQ ID NOs: 65 to 90, or any two of marker loci SEQ ID NOs: 91-114. In another aspect, a method comprises concurrent detection of one or more molecular markers located in at least one chromosome interval flanked by any two of marker loci SEQ ID NOs: 5 to 8, marker loci SEQ ID NOs: 7 and 8, any two of marker loci SEQ ID NOs: 12 to 14, any two of marker loci SEQ ID NOs: 18 to 20, any two of marker loci SEQ ID NOs: 25 to 27, any two of marker loci SEQ ID NOs: 29 to 31, any two of marker loci SEQ ID NOs: 34 to 36, any two of marker loci SEQ ID NOs: 39 to 45, any two of marker loci SEQ ID NOs: 49 to 51, marker loci SEQ ID NOs: 58 and 59, marker loci SEQ ID NOs: 63 and 64, any two of marker loci SEQ ID NOs: 77 to 80, or any two of marker loci SEQ ID NOs: 99 to 106.

In an aspect, a method comprises concurrently detecting DM resistance QTLs DM_5.01, DM_6.02, and DM_7.01. In an aspect, a method comprises concurrently detecting DM resistance QTLs DM_5.01, DM_6.02, DM_7.01, and DM_8.01. In an aspect, a method comprises concurrently detecting DM resistance QTLs DM_5.01, DM_6.02, and DM_8.01. In an aspect, a method comprises concurrently detecting DM resistance QTLs DM_6.02, DM_7.01, and DM_8.01. In an aspect, a method comprises concurrently detecting DM resistance QTLs DM_1.01, DM_2.03, and DM_6.01. In an aspect, a method comprises concurrently detecting DM resistance QTLs DM_1.01, DM_4.01, and DM_6.01.

In another aspect, a method comprises concurrently detecting DM resistance QTL 1.01 and at least one or more, two or more, three or more, five or more, six or more, seven or more, eight or more, nine or more, ten or more, eleven or more, or twelve DM resistance QTLs selected from the group consisting of DM_1.02, DM_2.01, DM_2.02, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 1.02 and at least one or more, two or more, three or more, five or more, six or more, seven or more, eight or more, nine or more, ten or more, eleven or more, or twelve DM resistance QTLs selected from the group consisting of DM_1.01, DM_2.01, DM_2.02, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 2.01 and at least one or more, two or more, three or more, five or more, six or more, seven or more, eight or more, nine or more, ten or more, eleven or more, or twelve DM resistance QTLs selected from the group consisting of DM_1.01, DM_2.02, DM_2.02, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 2.02 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 2.03 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02, DM_3.01, DM_4.01, DM_5.01, DM_6.01, DM_6.02, DM_7.01, DM_8.01, and DM_9.01.

In another aspect, a method comprises concurrently detecting DM resistance QTL 3.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_4.01, DM_5.01, DM_6.01, DM_6.02, DM_7.01, DM_8.01, and DM_9.01.

In another aspect, a method comprises concurrently detecting DM resistance QTL 4.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_5.01, DM_6.01, DM_6.02, DM_7.01, DM_8.01, and DM_9.01.

In another aspect, a method comprises concurrently detecting DM resistance QTL 5.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_6.01, DM_6.02, DM_7.01, DM_8.01, and DM_9.01.

In another aspect, a method comprises concurrently detecting DM resistance QTL 6.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.02, DM_7.01, DM_8.01, and DM_9.01.

In another aspect, a method comprises concurrently detecting DM resistance QTL DM_6.02 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_7.01, DM_8.01, and DM_9.01.

In another aspect, a method comprises concurrently detecting DM resistance QTL 7.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.01, DM_6.02, DM_8.01, and DM_9.01.

In another aspect, a method comprises concurrently detecting DM resistance QTL 8.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.01, DM_6.02, DM_7.01, and DM_9.01.

In another aspect, a method comprises concurrently detecting DM resistance QTL 9.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.01, DM_6.02, DM_7.01, and DM_8.01.

In an aspect, this disclosure provides a method of producing a corn plant with enhanced DM resistance, which method comprising the steps of: (a) crossing a first corn plant comprising a DM resistance QTL with a second corn plant of a different genotype to produce one or more progeny plants or seeds; (b) selecting a progeny plant or seed comprising a DM resistance allele of a polymorphic locus linked to a DM resistance QTL, wherein a polymorphic locus is in a chromosomal segment flanked by any two of marker loci SEQ ID NOs: 1 to 11, any two of marker loci SEQ ID NOs: 12 to 22, any two of marker loci SEQ ID NOs: 23 to 28, any two of marker loci SEQ ID NOs: 29 to 32, any two of marker loci SEQ ID NOs: 33 to 38, any two of marker loci SEQ ID NOs: 39 to 45, any two of marker loci SEQ ID NOs: 46 to 57, any two of marker loci SEQ ID NOs: 54 to 62, any two of marker loci SEQ ID NOs: 63 and 64, any two of marker loci SEQ ID NOs: 65 to 90, or any two of marker loci SEQ ID NOs: 91-114; (c) crossing the selected progeny plant with itself or the second corn plant to produce one or more further progeny plants or seeds; and (d) selecting a further progeny plant or seed comprising the DM resistance allele. In an aspect, the further progeny plant in step (d) is an $F_2$ to $F_7$ progeny plant. In another aspect, the further progeny plant in step (d) comprises 2 to 7 generations of backcrossing. In yet another aspect, a method comprises using marker-assisted selection to select a DM resistance allele in at least one polymorphic locus selected from the group consisting of SEQ ID NOs: 1-114.

In an aspect, this disclosure provides a method of obtaining a corn plant or seed with enhanced DM resistance, which method comprises the steps of: (a) detecting in a population of corn plants or seeds a plant or seed comprising a DM resistance allele at a polymorphic locus in a chromosomal segment flanked by SEQ ID NOs: 1 to 11, any two of marker loci SEQ ID NOs: 12 to 22, any two of marker loci SEQ ID NOs: 23 to 28, any two of marker loci SEQ ID NOs: 29 to 32, any two of marker loci SEQ ID NOs: 33 to 38, any two of marker loci SEQ ID NOs: 39 to 45, any two of marker loci SEQ ID NOs: 46 to 57, any two of marker loci SEQ ID NOs: 54 to 62, any two of marker loci SEQ ID NOs: 63 and 64, any two of marker loci SEQ ID NOs: 65 to 90, or any two of marker loci SEQ ID NOs: 91-114; and (b) selecting the plant or seed from the population based on the presence of the DM resistance allele.

In an aspect, this disclosure provides a method of producing a corn plant with enhanced DM resistance, which method comprising the steps of: (a) crossing a first corn plant comprising a DM resistance haplotype with a second corn plant of a different genotype to produce one or more progeny plants or seeds; (b) selecting a progeny plant or seed based on the presence of the DM resistance haplotype, wherein the haplotype comprises resistance alleles of two or more polymorphic loci in a chromosomal interval flanked by: any two marker loci selected from the group consisting of SEQ ID NOs: 1 to 11; any two marker loci selected from the group consisting of SEQ ID NOs: 12 to 22; any two marker loci selected from the group consisting of SEQ ID NOs: 23 to 28; any two marker loci selected from the group consisting of SEQ ID NOs: 29 to 32; any two marker loci selected from the group consisting of SEQ ID NOs: 33 to 38; any two marker loci selected from the group consisting of SEQ ID NOs: 39 to 45; any two marker loci selected from the group consisting of SEQ ID NOs: 46 to 57; any two marker loci selected from the group consisting of SEQ ID NOs: 54 to 62; SEQ ID NO: 63 and SEQ ID NO: 64; any two marker loci selected from the group consisting of SEQ ID NOs: 65 to 90; or any two marker loci selected from the group consisting of SEQ ID NOs: 91-114.

In an aspect, this disclosure provides a method of obtaining a corn plant or seed with enhanced DM resistance, which method comprises the steps of: (a) detecting in a population of corn plants or seeds a plant or seed comprising a DM resistance haplotype, wherein the haplotype comprises resistance alleles of two or more polymorphic loci in a chromosomal interval flanked by: any two marker loci selected from the group consisting of SEQ ID NOs: 5 to 8; SEQ ID NO: 7 and SEQ ID NO: 8; any two marker loci selected from the group consisting of SEQ ID NOs: 12 to 14; any two marker loci selected from the group consisting of SEQ ID NOs: 18 to 20; any two marker loci selected from the group consisting of SEQ ID NOs: 25 to 27; any two marker loci selected from the group consisting of SEQ ID NOs: 29 to 31; any two marker loci selected from the group consisting of SEQ ID NOs: 34 to 36; any two marker loci selected from the group consisting of SEQ ID NOs: 39 to 45; any two marker loci selected from the group consisting of SEQ ID NOs: 49 to 51; SEQ ID NO: 58 and SEQ ID NO: 59; SEQ ID NO: 63 and SEQ ID NO: 64; any two marker loci selected from the group consisting of SEQ ID NOs: 66 to 76; or any two marker loci selected from the group consisting of SEQ ID NOs: 99 to 106; and (b) selecting a plant or seed from the population based on the presence of the DM resistance haplotype. In yet another aspect, a DM resistance haplotype comprises resistance alleles of two or more polymorphic loci selected from the group consisting of SEQ ID NOs: 5-8, 12-14, 18-20, 25-27, 29-31, 34-36, 39-45, 49-51, 58, 59, 63, 64, 66-76, and 99-106.

In an aspect, this disclosure provides a method for selecting a corn plant or seed, which method comprising the steps of: (a) isolated nucleic acids from a corn plant or seed; (b) analyzing the nucleic acids to detect a polymorphic marker associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (c) selecting a corn plant or seed comprising the DM resistance QTL.

In an aspect, this disclosure provides a method for selecting a corn plant or seed, which method comprising the steps of: (a) detecting in a population of corn plants or seeds a corn plant or seed comprising a DM resistance allele of a marker locus associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (b) selecting a corn plant or seed comprising the DM resistance allele.

In an aspect, this disclosure provides a method for evaluating a collection of corn germplasm, which method comprising the steps of: (a) obtaining a collection of corn germplasm; (b) isolating nucleic acids from each germplasm; (c) assaying the nucleic acids for one or more markers linked to a DM resistance QTL selected from the group consisting of DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (d) selecting germplasm comprising a DM resistance QTL based on the marker assay.

In an aspect, a method disclosed herein comprises genotyping by a marker assay. In an aspect, a method disclosed herein comprises marker-assisted selection. In another aspect, a method disclosed herein comprises assaying a SNP marker. In yet another aspect, a method disclosed herein comprises the use of an oligonucleotide probe. In a further aspect, a method disclosed herein comprises using an oligonucleotide probe adjacent to a polymorphic nucleotide position in a marker locus being genotyped.

In an aspect, a corn plant or seed disclosed herein may be an inbred, a hybrid, a transgenic, a haploid, a doubled haploid, or in an agronomically elite background. These groups are not mutually exclusive, and a corn plant or seed could be in two or more groups (e.g., a plant could be a transgenic hybrid, another plant could be an inbred doubled haploid, etc.).

In an aspect, a method disclosed herein comprises genotyping a corn plant or seed at a polymorphic marker locus within about 20 cM, 15 cM, 10 cM, 5 cM, 4 cM, 3 cM, 2 cM, 1 cM, 0.5 cM or less than 0.5 cM of any one of marker loci SEQ ID NOs: 1-114. In an aspect, this disclosure provides a method comprising genotyping a polymorphic locus selected from the group consisting of SEQ ID NOs: 1-114.

In an aspect, a method disclosed herein comprises genotyping a corn plant or seed at a marker locus associated with DM resistance QTL DM_1.01, which DM resistance QTL DM_1.01 is located in a chromosomal interval flanked by any two of the marker loci selected from the group consisting of SEQ ID NOs: 1 to 8. In another aspect, a method disclosed herein comprises genotyping a corn plant or seed at a marker locus associated with DM resistance QTL DM_1.01, which DM resistance QTL DM_1.01 is located in a chromosomal interval flanked by any two of the marker loci selected from the group consisting of SEQ ID NOs: 5 to 8.

In an aspect, a method disclosed herein comprises genotyping a corn plant or seed at a marker locus associated with DM resistance QTL DM_1.02 which DM resistance QTL DM_1.02 is located in a chromosomal interval flanked by any two of the marker loci selected from the group consisting of SEQ ID NOs: 6 to 11. In another aspect, a method disclosed herein comprises genotyping a corn plant or seed at a marker locus associated with DM resistance QTL DM_1.02 which DM resistance QTL DM_1.02 is located in a chromosomal interval flanked by marker loci SEQ ID NO: 7 and SEQ ID NO: 8.

In an aspect, a method disclosed herein comprises genotyping a corn plant or seed at a marker locus associated with DM resistance QTL DM_2.01, which DM resistance QTL DM_2.01 is located in a chromosomal interval flanked by any two of the marker loci selected from the group consisting of SEQ ID NOs: 12 to 22. In another aspect, a method disclosed herein comprises genotyping a corn plant or seed at a marker locus associated with DM resistance QTL DM_2.01, which DM resistance QTL DM_2.01 is located in a chromosomal interval flanked by any two of the marker loci selected from the group consisting of SEQ ID NOs: 18 to 20.

In an aspect, a method disclosed herein comprises genotyping a corn plant or seed at a marker locus associated with DM resistance QTL DM_2.02, which DM resistance QTL DM_2.02 is located in a chromosomal interval flanked by any two of the marker loci selected from the group consisting of SEQ ID NOs: 23 to 28. In another aspect, a method disclosed herein comprises genotyping a corn plant or seed at a marker locus associated with DM resistance QTL DM_2.02, which DM resistance QTL DM_2.02 is located in a chromosomal interval flanked by any two of the marker loci selected from the group consisting of SEQ ID NOs: 25 to 27.

In an aspect, a method disclosed herein comprises genotyping a corn plant or seed at a marker locus associated with DM resistance QTL DM_2.03, which DM resistance QTL DM_2.03 is located in a chromosomal interval flanked by any two of the marker loci selected from the group consisting of SEQ ID NOs: 12 to 14.

In an aspect, a method disclosed herein comprises genotyping a corn plant or seed at a marker locus associated with DM resistance QTL DM_3.01, which DM resistance QTL DM_3.01 is located in a chromosomal interval flanked by any two of the marker loci selected from the group consisting of SEQ ID NOs: 29 to 32. In an aspect, a method disclosed herein comprises genotyping a corn plant or seed at a marker locus associated with DM resistance QTL DM_3.01, which DM resistance QTL DM_3.01 is located in a chromosomal interval flanked by any two of the marker loci selected from the group consisting of SEQ ID NOs: 29 to 31.

In an aspect, a method disclosed herein comprises genotyping a corn plant or seed at a marker locus associated with DM resistance QTL DM_4.01, which DM resistance QTL DM_4.01 is located in a chromosomal interval flanked by any two of the marker loci selected from the group consisting of SEQ ID NOs: 33 to 38. In another aspect, a method disclosed herein comprises genotyping a corn plant or seed at a marker locus associated with DM resistance QTL DM_4.01, which DM resistance QTL DM_4.01 is located in a chromosomal interval flanked by any two of the marker loci selected from the group consisting of SEQ ID NOs: 34 to 36.

In an aspect, a method disclosed herein comprises genotyping a corn plant or seed at a marker locus associated with DM resistance QTL DM_5.01, which DM resistance QTL DM_5.01 is located in a chromosomal interval flanked by any two of the marker loci selected from the group consisting of SEQ ID NOs: 39 to 45.

In an aspect, a method disclosed herein comprises genotyping a corn plant or seed at a marker locus associated with DM resistance QTL DM_6.01, which DM resistance QTL DM_6.01 is located in a chromosomal interval flanked by any two of the marker loci selected from the group consisting of SEQ ID NOs: 46 to 57. In another aspect, a method disclosed herein comprises genotyping a corn plant or seed at a marker locus associated with DM resistance QTL DM_6.01, which DM resistance QTL DM_6.01 is located in a chromosomal interval flanked by any two of the marker loci selected from the group consisting of SEQ ID NOs: 49 to 51.

In an aspect, a method disclosed herein comprises genotyping a corn plant or seed at a marker locus associated with DM resistance QTL DM_6.02, which DM resistance QTL DM_6.02 is located in a chromosomal interval flanked by any two of the marker loci selected from the group consisting of SEQ ID NOs: 54 to 62. In another aspect, a method disclosed herein comprises genotyping a corn plant or seed at a marker locus associated with DM resistance QTL DM_6.02, which DM resistance QTL DM_6.02 is located in a chromosomal interval flanked by marker loci SEQ ID NO: 59 and SEQ ID NO: 59.

In an aspect, a method disclosed herein comprises genotyping a corn plant or seed at a marker locus associated with DM resistance QTL DM_7.01 which DM resistance QTL DM_7.01 is located in a chromosomal interval flanked marker loci SEQ ID NO: 63 and SEQ ID NO: 64.

In an aspect, a method disclosed herein comprises genotyping a corn plant or seed at a marker locus associated with DM resistance QTL DM_8.01, which DM resistance QTL DM_8.01 is located in a chromosomal interval flanked by any two of the marker loci selected from the group consisting of SEQ ID NOs: 65 to 90. In an aspect, a method disclosed herein comprises genotyping a corn plant or seed at a marker locus associated with DM resistance QTL DM_8.01, which DM resistance QTL DM_8.01 is located in a chromosomal interval flanked by any two of the marker loci selected from the group consisting of SEQ ID NOs: 66 to 76.

In an aspect, a method disclosed herein comprises genotyping a corn plant or seed at a marker locus associated with DM resistance QTL DM_9.01, which DM resistance QTL DM_9.01 is located in a chromosomal interval flanked by any two of the marker loci selected from the group consisting of SEQ ID NOs: 91-114. In an aspect, a method disclosed herein comprises genotyping a corn plant or seed at a marker locus associated with DM resistance QTL DM_9.01, which DM resistance QTL DM_9.01 is located in a chromosomal interval flanked by any two of the marker loci selected from the group consisting of SEQ ID NOs: 99 to 106.

In a further aspect, a method disclosed herein comprises genotyping a corn plant or seed at a marker locus located in a chromosomal interval flanked by any two of marker loci SEQ ID NOs: 1 to 11. In another aspect, a method disclosed herein comprises genotyping a corn plant or seed at a marker locus located in a chromosomal interval flanked by any two of marker loci SEQ ID NOs: 5 to 8. In yet another aspect, a method disclosed herein comprises genotyping a corn plant or seed at a marker locus located in a chromosomal interval flanked by any two of marker loci SEQ ID NO: 7 and SEQ ID NO: 8.

In a further aspect, a method disclosed herein comprises genotyping a corn plant or seed at a marker locus located in a chromosomal interval flanked by any two of marker loci SEQ ID NOs: 12 to 22. In another aspect, a method disclosed herein comprises genotyping a corn plant or seed at a marker locus located in a chromosomal interval flanked by any two of marker loci SEQ ID Nos: 12 to 14. In another aspect, a method disclosed herein comprises genotyping a corn plant or seed at a marker locus located in a chromosomal interval flanked by any two of marker loci SEQ ID NOs: 18 to 20.

In a further aspect, a method disclosed herein comprises genotyping a corn plant or seed at a marker locus located in a chromosomal interval flanked by any two of marker loci SEQ ID NOs: 23 to 28. In another aspect, a method disclosed herein comprises genotyping a corn plant or seed at a marker locus located in a chromosomal interval flanked by any two of marker loci SEQ ID NOs: 25 to 27.

In a further aspect, a method disclosed herein comprises genotyping a corn plant or seed at a marker locus located in a chromosomal interval flanked by any two of marker loci SEQ ID NOs: 29 to 32. In another aspect, a method disclosed herein comprises genotyping a corn plant or seed at a marker locus located in a chromosomal interval flanked by any two of marker loci SEQ ID NOs: 29 to 31. In yet another aspect, a method disclosed herein comprises genotyping a corn plant or seed at a marker locus located in a chromosomal interval flanked by any marker loci SEQ ID NO: 30 and SEQ ID NO: 31.

In a further aspect, a method disclosed herein comprises genotyping a corn plant or seed at a marker locus located in a chromosomal interval flanked by any two of marker loci SEQ ID NOs: 33 to 38. In another aspect, a method disclosed herein comprises genotyping a corn plant or seed at a marker locus located in a chromosomal interval flanked by any two of marker loci SEQ ID NOs: 34 to 36.

In a further aspect, a method disclosed herein comprises genotyping a corn plant or seed at a marker locus located in a chromosomal interval flanked by any two of marker loci SEQ ID NOs: 39 to 45.

In a further aspect, a method disclosed herein comprises genotyping a corn plant or seed at a marker locus located in a chromosomal interval flanked by any two of marker loci SEQ ID NOs: 46 to 57. In another aspect, a method disclosed herein comprises genotyping a corn plant or seed at a marker locus located in a chromosomal interval flanked by any two of marker loci SEQ ID NOs: 49 to 51.

In a further aspect, a method disclosed herein comprises genotyping a corn plant or seed at a marker locus located in a chromosomal interval flanked by any two of marker loci SEQ ID NOs: 54 to 62. In another aspect, a method disclosed herein comprises genotyping a corn plant or seed at a marker locus located in a chromosomal interval flanked by any two of marker loci SEQ ID NO: 58 and SEQ ID NO: 59.

In a further aspect, a method disclosed herein comprises genotyping a corn plant or seed at a marker locus located in a chromosomal interval flanked by any two of marker loci SEQ ID NO: 63 and SEQ ID NO: 64.

In a further aspect, a method disclosed herein comprises genotyping a corn plant or seed at a marker locus located in a chromosomal interval flanked by any two of marker loci SEQ ID NOs: 65 to 90. In another aspect, a method disclosed herein comprises genotyping a corn plant or seed at a marker locus located in a chromosomal interval flanked by any two of marker loci SEQ ID NOs: 66 to 76.

In a further aspect, a method disclosed herein comprises genotyping a corn plant or seed at a marker locus located in a chromosomal interval flanked by any two of marker loci SEQ ID NOs: 91-114. In another aspect, a method disclosed herein comprises genotyping a corn plant or seed at a marker locus located in a chromosomal interval flanked by any two of marker loci SEQ ID NOs: 99 to 106.

In another aspect, a method disclosed herein comprises genotyping a corn plant or seed by detecting a haplotype. In an aspect, a haplotype comprises a DM resistance allele at one or more, two or more, three or more, four or more, or five or more of marker loci SEQ ID NO: 1 to 11. In an aspect, a haplotype comprises a DM resistance allele at one or more, two or more, or three or more of marker loci SEQ ID NO: 5 to 8. In an aspect, a haplotype comprises a DM resistance allele at one or more of marker loci SEQ ID NO: 7 and SEQ ID NO: 8. In an aspect, a haplotype comprises a DM resistance allele at one or more, two or more, three or more, four or more, or five or more of marker loci SEQ ID NO: 12 to 22. In an aspect, a haplotype comprises a DM resistance allele at one or more, or two or more of marker loci SEQ ID NO: 12 to 14. In an aspect, a haplotype comprises a DM resistance allele at one or more, two or more of marker loci SEQ ID NO: 18 to 20. In an aspect, a haplotype comprises a DM resistance allele at one or more, two or more, three or more, four or more, or five or more of marker loci SEQ ID NO: 23 to 28. In an aspect, a haplotype comprises a DM resistance allele at one or more, or two or more of marker loci SEQ ID NO: 25 to 27. In an aspect, a haplotype comprises a DM resistance allele at one or more, two or more, or three or more of marker loci SEQ ID NO: 29 to 32. In an aspect, a haplotype comprises a DM resistance allele at one or more, or two or more of marker loci SEQ ID NO: 29 to 31. In an aspect, a haplotype comprises a DM resistance allele at one or more, two or more, three or more, four or more, or five or more of marker loci SEQ ID NO: 33 to 38. In an aspect, a haplotype comprises a DM resistance allele at one or more, or two or more of marker loci SEQ ID NO: 34 to 36. In an aspect, a haplotype comprises a DM resistance allele at one or more, two or more, three or more, four or more, or five or more of marker loci SEQ ID NO: 39 to 45. In an aspect, a haplotype comprises a DM resistance allele at one or more, two or more, three or more, four or more, or five or more of marker loci SEQ ID NO: 46 to 57. In an aspect, a haplotype comprises a DM resistance allele at one or more, or two or more of marker loci SEQ ID NO: 49 to 51. In an aspect, a haplotype comprises a DM resistance allele at one or more of marker loci SEQ ID NO: 58 and SEQ ID NO: 59. In an aspect, a haplotype comprises a DM resistance allele at one or more, two or more, three or more, four or more, or five or more of marker loci SEQ ID NO: 54 to 62. In an aspect, a haplotype comprises a DM resistance allele at one or more of marker loci SEQ ID NO: 63 and SEQ ID NO: 64. In an aspect, a haplotype comprises a DM resistance allele at one or more, two or more, three or more, four or more, or five or more of marker loci SEQ ID NO: 65 to 90. In an aspect, a haplotype comprises a DM resistance allele at one or more, two or more, three or more, four or more, or five or more of marker loci SEQ ID NO: 66 to 76. In an aspect, a haplotype comprises a DM resistance allele at one or more, two or more, three or more, four or more, or five or more of marker loci SEQ ID NO: 91-114. In an aspect, a haplotype comprises a DM resistance allele at one or more, two or more, three or more, four or more, or five or more of marker loci SEQ ID NO: 99 to 106.

In an aspect, a corn plant or seed comprising DM resistance QTLs or DM resistant alleles disclosed herein exhibits intermediate resistance to DM infection from oomycetes from the group consisting of *Peronosclerospora, Sclerophthora*, and *Sclerospora*. In another aspect, a corn plant or seed comprising DM resistance QTLs or DM resistant alleles disclosed herein exhibits moderate resistance to DM infection from oomycetes from the group consisting of *Peronosclerospora, Sclerophthora*, and *Sclerospora*. In a further aspect, a corn plant or seed comprising DM resistance QTLs or DM resistant alleles disclosed herein exhibits high resistance to DM infection from oomycetes from the group consisting of *Peronosclerospora, Sclerophthora*, and *Sclerospora*. In an aspect, DM infection is caused by an oomycete selected from the group consisting of *Peronosclerospora* eriochloae, *Peronosclerospora graminicola, Peronosclerospora heteropogoni, Peronosclerospora maydis, Peronosclerospora miscanthi, Peronosclerospora philippinensis, Peronosclerospora sacchari, Peronosclerospora sorghi, Peronosclerospora spontanea, Peronosclerospora zeae, Sclerophthora macrospora, Scleropthora rayssiae* var. *zeae*, and *Sclerospora graminicola*. In another aspect, a corn plant or seed comprising DM resistance QTLs or DM resistant alleles disclosed herein exhibits high resistance to DM infection from *P. philippinensis*. In another aspect, a corn plant or seed comprising DM resistance QTLs or DM resistant alleles disclosed herein exhibits high resistance to DM infection from *P. maydis*. In another aspect, a corn plant or seed comprising DM resistance QTLs or DM resistant alleles disclosed herein exhibits high resistance to DM infection from *P. sorghi*.

In an aspect, a DM resistance QTL or DM resistance allele disclosed herein confers no yield penalties under a low DM stress condition. In another aspect, a combination of one or more, two or more, three or more, four or more, five or more, six or more, seven or more, eight or more, nine or more, ten or more, or eleven or more DM resistance QTLs disclosed herein confer no yield penalties under a low DM stress condition.

In another aspect, a corn plant or seed disclosed herein comprising one or more, two or more, three or more, four or more, five or more, six or more, seven or more, eight or more, nine or more, ten or more, or eleven or more DM resistance QTLs or DM resistance alleles disclosed herein exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In another aspect, a corn plant or seed disclosed herein comprising one or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the one or more QTLs under a high DM stress condition.

In another aspect, a corn plant or seed disclosed herein comprising two or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the two or more QTLs under a high DM stress condition.

In another aspect, a corn plant or seed disclosed herein comprising three or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the three or more QTLs under a high DM stress condition.

In another aspect, a corn plant or seed disclosed herein comprising four or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the four or more QTLs under a high DM stress condition.

In another aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In another aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the one or more DM resistance QTLs or DM resistance alleles under a high DM stress condition.

In another aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the two or more DM resistance QTLs or DM resistance alleles under a high DM stress condition.

In another aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the three or more DM resistance QTLs or DM resistance alleles under a high DM stress condition.

In another aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the four or more DM resistance QTLs or DM resistance alleles under a high DM stress condition.

In an aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In an aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the one or more DM resistance QTLs or DM resistance alleles under a high DM stress condition.

In an aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the two or more DM resistance QTLs or DM resistance alleles under a high DM stress condition.

In an aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the three or more DM resistance QTLs or DM resistance alleles under a high DM stress condition.

In an aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the four or more DM resistance QTLs or DM resistance alleles under a high DM stress condition.

In another aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield increase of between 1% and 100%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In another aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the one or more DM resistance QTLs or DM resistance alleles under a high DM stress condition.

In another aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the two or more DM resistance QTLs or DM resistance alleles under a high DM stress condition.

In another aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the three or more DM resistance QTLs or DM resistance alleles under a high DM stress condition.

In another aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the four or more DM resistance QTLs or DM resistance alleles under a high DM stress condition.

In an aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the one or more, two or more, three or more, four or more, five or more, six or more, seven or more, eight or more, nine or more, ten or more, eleven or more, twelve or more, or thirteen DM resistance QTLs or DM resistance alleles under a high DM stress condition.

In an aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the one or more DM resistance QTLs or DM resistance alleles under a high DM stress condition.

In an aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the two or more DM resistance QTLs or DM resistance alleles under a high DM stress condition.

In an aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the three or more DM resistance QTLs or DM resistance alleles under a high DM stress condition.

In an aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the four or more DM resistance QTLs or DM resistance alleles under a high DM stress condition.

In another aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield between 0.1 and 10 quintal/hectare, between 0.1 and 9 quintal/hectare, between 0.1 and 8 quintal/hectare, between 0.1 and 7 quintal/hectare, between 0.1 and 6 quintal/hectare, between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the one or more, two or more, three or more, four or more, five or more, six or more, seven or more, eight or more, nine or more, ten or more, eleven or more, twelve or more, or thirteen DM resistance QTLs or DM resistance alleles under a high DM stress condition.

In another aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the one or more DM resistance QTLs or DM resistance alleles under a high DM stress condition.

In another aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the two or more DM resistance QTLs or DM resistance alleles under a high DM stress condition.

In another aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the three or more DM resistance QTLs or DM resistance alleles under a high DM stress condition.

In another aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the four or more DM resistance QTLs or DM resistance alleles under a high DM stress condition.

In an aspect, this disclosure provides a DM resistant corn plant or seed comprising one or more, two or more, three or more, four or more, five or more, six or more, seven or more, eight or more, nine or more, ten or more, eleven or more, twelve or more, or thirteen introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01. In an aspect, a corn plant or seed disclosed herein comprises DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, or DM_9.01 obtainable, obtained, or introgressed from any one of corn lines CV357626 and CV368354.

In an aspect, a corn plant or seed disclosed herein comprises DM resistance QTLs DM_5.01, DM_6.02, and DM_7.01. In an aspect, a corn plant or seed disclosed herein comprises DM resistance QTLs DM_5.01, DM_6.02, DM_7.01, and DM_8.01. In an aspect, a corn plant or seed disclosed herein comprises DM resistance QTLs DM_5.01, DM_6.02, and DM_8.01. In an aspect, a corn plant or seed disclosed herein comprises DM resistance QTLs DM_6.02, DM_7.01, and DM_8.01. In an aspect, a corn plant or seed disclosed herein comprises DM resistance QTLs DM_1.01, DM_2.03, and DM_6.01. In an aspect, a corn plant or seed disclosed herein comprises DM resistance QTLs DM_1.01, DM_4.01, and DM_6.01. In an aspect, a corn plant or seed disclosed herein comprises one or more QTLs selected from the group consisting of DM resistance QTLs DM_1.01, DM_4.01, DM_6.01, DM_6.02, DM_8.01, and any combination thereof In another aspect, a corn plant or seed disclosed herein comprises DM resistance QTL DM_1.01 and at least one or more, two or more, three or more, five or more, six or more, seven or more, eight or more, nine or more, ten or more, eleven or more, or twelve DM resistance QTLs from the group consisting of DM_1.02, DM_2.01, DM_2.02, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_1.02 and at least one or more, two or more, three or more, five or more, six or more, seven or more, eight or more, nine or more, ten or more, eleven or more, or twelve DM resistance QTLs from the group consisting of DM_1.01, DM_2.01, DM_2.02, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_2.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.02, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_2.02 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_2.03 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_3.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_4.01, DM_5.01, DM_6.01, DM_6.02, DM_7.01, DM_8.01, and DM_9.01.

In another aspect, a corn plant or seed disclosed herein comprises DM resistance QTL DM_4.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_5.01, DM_6.01, DM_6.02, DM_7.01, DM_8.01, and DM_9.01.

In another aspect, a corn plant or seed disclosed herein comprises DM resistance QTL DM_5.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_6.01, DM_6.02, DM_7.01, DM_8.01, and DM_9.01.

In another aspect, a corn plant or seed disclosed herein comprises DM resistance QTL DM_6.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.02, DM_7.01, DM_8.01, and DM_9.01.

In another aspect, a corn plant or seed disclosed herein comprises DM resistance QTL DM_6.02 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_7.01, DM_8.01, and DM_9.01.

In another aspect, a corn plant or seed disclosed herein comprises DM resistance QTL DM_7.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_6.02, DM_8.01, and DM_9.01.

In another aspect, a corn plant or seed disclosed herein comprises DM resistance QTL DM_8.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_6.02, DM_7.01, and DM_9.01.

In another aspect, a corn plant or seed disclosed herein comprises DM resistance QTL DM_9.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_6.02, DM_7.01, and DM_8.01.

In an aspect, a corn plant or seed comprising one or more DM resistance QTLs disclosed herein exhibits reduced premature death compared to a corn plant or seed lacking the one or more DM resistance QTLs under a high DM stress condition. In another aspect, a corn plant or seed comprising one or more DM resistance QTLs disclosed herein exhibit reduced stunted growth, reduced leaf chlorosis, reduced number of narrow leaves, reduced number of erect leaves, reduced number of shredded leaves, reduced number of failed cobs, reduced vegetative tissue in tassels, or any combination thereof, compared to a corn plant or seed lacking the one or more DM resistance QTL under a high DM stress condition.

In an aspect, this disclosure provides a method comprising providing a set of corn seeds comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, to a person desirous of planting the set of corn seeds in a field plot. In an aspect, a method comprising a field plot that exhibits DM infection in any one of the previous one or more, two or more, three or more, four or more, five or more, six or more, seven or more, eight or more, nine or more, or ten or more planting seasons.

In an aspect, this disclosure provides a method comprising growing a population of corn plants in a field plot, which method comprising planting a population of corn seeds comprising one or more, two or more, three or more, four or more, five or more, six or more, seven or more, eight or more, nine or more, ten or more, eleven or more, twelve or more, or thirteen introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 in the field plot. In an aspect, a method disclosed herein comprises staggered planting. In another aspect, a corn plant or seed comprising a combination of one or more, two or more, three or more, four or more, five or more, six or more, seven or more, eight or more, nine or more, ten or more, eleven or more, twelve or more, or thirteen introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits increased seed yield under staggered planting conditions and a high DM stress condition compared to a corn plant or seed lacking the combination of DM resistance QTLs.

In an aspect, a method, a corn plant, or a corn seed disclosed herein is used in combination with one or more pesticides including, but not limited to, herbicides, fungicides (e.g. metalaxyl, fosetyl-Al, furalaxyl, Patafol, and benalaxyl), insecticides, microbicides, nematicides, insect repellents, bactericides, and other substances used to control pests. In another aspect, a method, a corn plant, or a corn seed disclosed herein is used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which may be applied as seed, foliar, drench, or drip treatments.

In an aspect, corn seeds disclosed herein are untreated. In another aspect, corn seeds disclosed herein can be subjected to various treatments. For example, the seeds can be treated to improve germination by priming the seeds or by disinfection to protect against seed borne pathogens. In another aspect, seeds can be coated with any available coating to improve, for example, plantability, seed emergence, and protection against seed borne pathogens. Seed coating can be any form of seed coating including, but not limited to, pelleting, film coating, and encrustments.

In a further aspect, the instant disclosure provides methods to enhance DM resistance by combining two or more DM resistance QTLs disclosed herein. In an aspect, the combined DM resistance QTLs have additive effects in providing DM resistance. In another aspect, the combined DM resistance QTLs have synergistic effects in providing DM resistance. In a further aspect, the combination of two or more, three or more, four or more, five or more, six or more, seven or more, eight or more, nine or more, ten or more, eleven or more, twelve or more, or thirteen DM resistance QTLs disclosed herein has no negative effects over corn physiology, resistance, yield, or performance in general. In a further aspect, the combination of two or more, three or more, four or more, five or more, six or more, seven or more, eight or more, nine or more, ten or more, eleven or more, twelve or more, or thirteen DM resistance QTLs disclosed herein has no statistically significant negative effects over corn physiology, resistance, yield, or performance in general.

In an aspect, this disclosure provides corn plant cells, tissues, and organs that are not reproductive material and do not mediate the natural reproduction of the plant. In another aspect, this disclosure also provides corn plant cells, tissues, and organs that are reproductive material and mediate the natural reproduction of the plant. In another aspect, this disclosure provides corn plant cells, tissues, and organs that cannot maintain themselves via photosynthesis. In another aspect, this disclosure provides somatic corn plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, bud, or vascular tissue. In another aspect, this disclosure provides a corn plant chloroplast. In a further aspect, this disclosure provides epidermal cells, stomata cell, trichomes, root hairs, a storage root, or a tuber. In another aspect, this disclosure provides a corn protoplast.

Skilled artisans understand that corn plants naturally reproduce via seeds, not via asexual reproduction or vegetative propagation. In an aspect, this disclosure provides corn endosperm. In another aspect, this disclosure provides corn endosperm cells. In a further aspect, this disclosure provides a male or female sterile corn plant, which cannot reproduce without human intervention.

In a further aspect, this disclosure provides processed products made from a disclosed corn plant or seed. Such products include, but are not limited to, meal, oil, plant extract, starch, or fermentation or digestion products. In another aspect, this disclosure also provides a corn meal, which is substantially oil free and which is produced using the oilseed of any of the plants disclosed herein. In another aspect, this disclosure also provides a method of providing a corn meal by crushing oilseed of any of the plants disclosed herein.

A corn plants or seed disclosed herein can also be genetically engineered to express various phenotypes of agronomic interest. Exemplary genes implicated in this regard include, but are not limited to, genes that confer resistance to pests or disease, genes that confer resistance or tolerance to an herbicide, genes that control male sterility, genes that affect abiotic stress resistance, and other genes and transcription factors that affect plant growth and agronomic traits such as yield, flowering, plant growth, or plant architecture.

Corn Transformation

A corn plant or seed disclosed herein can be genetically transformed. Numerous methods for plant transformation have been developed including biological and physical plant transformation protocols. See, for example, Mild, et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-Mediated Transformation—One method for introducing an expression vector into plants is based on the natural transformation system of *Agrobacterium*. See, e.g., Horsch, et al., A Simple and General Method for Transferring Genes into Plants. *Science,* 227:1229-1231 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055, incorporated herein by reference in its entirety.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of corn target tissues, expression of the above-described selectable marker genes allows for preferential selection of transformed cells, tissues, and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular corn line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

A corn plant or seed disclosed herein can also be produced by one or more genome engineering techniques or subject to further genomic editing. For example, one or more DM resistance alleles can be introduced into a DM susceptible background. Exemplary genome engineering techniques include meganucleases, zinc-finger nucleases, TALENs, and CRISPR/Cas9 systems. See, e.g., Gaj et al., ZFN, TALEN, and CRISPR/Cas-based methods for genome engineering. *Trends in Biotechnology,* 31:397-405 (2013).

Additional Breeding

A corn plant or seed disclosed herein can also be subject to additional breeding using one or more known methods in the art, e.g., pedigree breeding, recurrent selection, mass selection, and mutation breeding. Pedigree breeding starts with the crossing of two genotypes, such as a corn variety comprising a DM resistance QTL or DM resistance allele disclosed herein and another corn variety lacking such a locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-fertilization and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety may comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a corn variety may be crossed with another variety to produce a first generation progeny plant. The first generation progeny plant may then be backcrossed to one of its parent varieties to create a BC1 or BC2. Progenies are selfed and selected so that the newly developed variety has many of the attributes of the recurrent parent and yet several of the desired attributes of the non-recurrent parent. This approach leverages the value and strengths of the recurrent parent for use in new corn varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into a corn plant or seed disclosed herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, gamma rays (e.g. cobalt-60 or cesium-137), neutrons (product of nuclear fission by uranium-235 in an atomic reactor), beta radiation (emitted from radioisotopes such as phosphorus-32 or carbon-14), or ultraviolet radiation (from 2500 to 2900 nm)), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait may then be incorporated into existing germplasm by traditional breeding techniques.

In an aspect, the instant disclosure provides a doubled haploid corn plant and seed that comprise a DM resistance QTL or DM resistance marker alleles disclosed herein. The doubled haploid (DH) approach achieves isogenic plants in a shorter time frame, and is particularly useful for generating inbred lines and quantitative genetics studies. DH plants can be produced according to methods known in the art. For example, the initial step involves the haploidization of the plant which results in the production of a population comprising haploid seed. Non-homozygous lines are crossed with an inducer parent, resulting in the production of haploid seeds. Seeds that have haploid embryos, but normal triploid endosperm, advance to the second stage. After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This DH seed is cultivated and subsequently evaluated and used in hybrid testcross production.

In an aspect, this disclosure also provides methods for making a substantially homozygous corn plant by producing or obtaining a seed from a cross of a corn plant comprising a DM resistance allele and another corn plant and applying doubled haploid methods to the $F_1$ seed or $F_1$ plant or to any successive filial generation.

Hybrid Production

In an aspect, this disclosure provides a hybrid corn plant or seed, and their production. The development of a corn hybrid in a corn plant breeding program generally involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in corn, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line, is a factor in the selection of improved corn lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. A pollination control system and effective transfer of pollen from one parent to the other offers improved plant breeding and an effective method for producing hybrid corn seed and plants. For example, a male sterility system can be used to produce corn hybrids.

Male sterility genes can increase the efficiency with which hybrids are made, in that they eliminate the need to physically emasculate the plant used as a female in a given cross. Where one desires to employ male-sterility systems, it may be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

Marker Detection

In an aspect, the present disclosure provides markers that are in linkage disequilibrium with at least one DM resistance QTL or DM resistance allele and can be used to select for DM resistance. Exemplary markers comprise SEQ ID NOs: 1-114 with their DM resistance alleles shown in Table 7. Markers within approximately 20 cM, 15 cM, 10 cM, 5 cM, 4 cM, 3 cM, 2 cM, 1 cM, 0.5 cM or less than 0.5 cM of these exemplary markers can also be identified from the known art.

Genetic markers are distinguishable from each other (as well as from the plurality of alleles of any one particular marker) on the basis of polynucleotide length and/or sequence. In general, any differentially inherited polymorphic trait (including a nucleic acid polymorphism) that segregates among progeny is a potential genetic marker.

As a set, polymorphic markers serve as a useful tool for fingerprinting plants to inform the degree of identity of lines or varieties. These markers can form a basis for determining associations with phenotype and can be used to drive genetic gain. The implementation of marker-assisted selection is dependent on the ability to detect and analyze underlying genetic differences between individuals.

Herein, nucleic acid analysis methods include, but are not limited to, PCR-based detection methods, microarray methods, mass spectrometry-based methods, and/or nucleic acid sequencing methods. In an aspect, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) using primer pairs that are capable of hybridizing to the proximal sequences that define a polymorphism in its double-stranded form. Methods for typing DNA based on mass spectrometry have been disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981; and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Large-scale identification of single-feature polymorphisms in complex genomes. *Genome Research*, 13:513-523 (2003); Cui et al., Detecting single-feature polymorphisms using oligonucleotide array and robustified projection pursuit. *Bioinformatics*, 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In an aspect, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' 4 3' exonuclease activity cleaves the probe and separates the reporter dye from the quencher dye resulting in increased fluorescence of the reporter.

In another aspect, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), Pac-Bio (Menlo Park, Calif.) and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by Service, Gene sequencing: the race for the $1000 genome. *Science*, 311:1544-46 (2006).

In an alternative aspect, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST®, or even simple word processors.

Any of the aforementioned marker types can be employed in the context of this disclosure to identify chromosome intervals encompassing genetic element that contribute to superior agronomic performance (e.g., corn DM resistance).

The markers to be used in the methods of the present disclosure should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTL, particularly in the case of genotypes.

Association Mapping

In an aspect, the present disclosure also provides chromosome intervals, marker loci, germplasm for conducting genome-wide association mapping for DM resistance. Exemplary chromosome intervals and marker loci are provided in Tables 6 and 7. Genome-wide association mapping is conducted to find signals of association for various complex traits by surveying genetic variation in the whole genome.

Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding*, Kang, Ed. CAB International, pp. 59-68 (2002)).

An approach used to link phenotypic variation with genetic loci is marker-trait association (MTA) mapping, also known as linkage disequilibrium (LD) mapping. LD mapping emerged as an important gene mapping tool in the early 1990's with the advent of high-throughput genotyping technology, and has been widely used in human genetics to identify genes affecting human diseases. This approach was introduced and began to be adopted in plant gene mapping studies in early 2000's (Flint-Garcia et al., Structure of linkage disequilibrium in plants. *Annual Review of Plant Biology,* 54:357-374 (2003)).

LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al., Linkage disequilibrium in the human genome. *Nature,* 411:199-204 (2001)). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., $F_2$, BC, DH, RIL, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Identification of QTL

In an aspect, markers, alleles, and haplotypes provided herein can be used for identifying QTLs associated with DM resistance. The statistical principles of QTL identification include penalized regression analysis, ridge regression, single marker analysis, complex pedigree analysis, Bayesian MCMC, identity-by-descent analysis, interval mapping, composite interval mapping (CIM), joint linkage mapping, and Haseman-Elston regression.

A QTL can act through a single gene mechanism or by a polygenic mechanism. In an aspect, the present disclosure provides a DM resistance QTL interval, where a DM resistance QTL (or multiple DM resistance QTLs) that segregates with an DM resistance trait is contained in the chromosomal interval. As used herein, when a QTL (or multiple QTLs) segregates with the DM resistance trait, it is referred to herein as a "DM resistance locus" (or "DM resistance loci").

In an aspect of this disclosure, the boundaries of a DM resistance QTL interval are drawn to encompass markers that will be linked to or associated with one or more DM resistance QTLs. In other words, a DM resistance QTL interval is drawn such that any marker that lies within that interval (including the terminal markers that define the boundaries of the interval) is genetically linked to or associated with the DM resistance QTL. Each interval comprises at least one DM resistance QTL, and furthermore, may indeed comprise more than one DM resistance QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTLs. Regardless, knowledge of how many QTLs are in a particular interval is not necessary to make or practice the claimed subject matter.

In an aspect, the present disclosure also provides the mapping of additional SNP markers associated with or linked to one or more DM resistance QTLs disclosed herein. SNP markers are ideal for mapping because the likelihood that a particular SNP allele is derived from independent origins in the extant populations of a particular species is very low. As such, SNP markers are useful for tracking and assisting introgression of DM resistance QTLs, particularly in the case of haplotypes. In an aspect, a SNP marker is selected for mapping a DM resistance QTL based on the marker's genetic map position. In another aspect, a SNP marker is selected for mapping a DM resistance QTL based on the marker's physical map position.

The genetic linkage of additional marker molecules can be established by a gene mapping model such as, without limitation, the flanking marker model reported by Lander and Botstein, (Lander and Botstein, Mapping Mendelian Factors Underlying Quantitative Traits Using RFLP Linkage Maps. *Genetics,* 121:185-199 (1989)), and the interval mapping, based on maximum likelihood methods described by Lander and Botstein (supra), and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, (Lander and Botstein, Mapping Mendelian Factors Underlying Quantitative Traits Using RFLP Linkage Maps. *Genetics,* 121:185-199 (1989), and further described by Arús and Moreno-Gonzalez, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, A Nonparametric Approach for Mapping Quantitative Trait Loci. *Genetics,* 139:1421-1428 (1995), the entirety of which is herein incorporated by reference). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, High Resolution of Quantitative Traits Into Multiple Loci via Interval Mapping. *Genetics*, 136:1447-1455 (1994) and Zeng, Precision Mapping of Quantitative Trait Loci. *Genetics*, 136:1457-1468 (1994). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994)), thereby improving the precision and efficiency of QTL mapping (Zeng, Precision Mapping of Quantitative Trait Loci. *Genetics*, 136:1457-1468 (1994)). These models can be extended to multi-environment experiments to analyze genotype-environment interactions (Jansen et al., Genotype-by-environment interaction in genetic mapping of multiple quantitative trait loci. *Theoretical and Applied Genetics*, 91:33-37 (1995)).

In an aspect, this disclosure provides chromosomal intervals comprising QTL associated with DM resistance. In an aspect, the chromosome intervals of this disclosure are characterized by genomic regions including and flanked by any two of marker loci SEQ ID NOs: 5 to 8. In another aspect, the chromosome intervals of this disclosure are characterized by genomic regions including and flanked by marker loci SEQ ID NOs: 7 and 8. In another aspect, the chromosome intervals of this disclosure are characterized by genome regions including and flanked by any two of marker loci SEQ ID NOs: 12 to 14. In another aspect, the chromosome intervals of this disclosure are characterized by genomic regions including and flanked by any two of marker loci SEQ ID NOs: 18 to 20. In another aspect, the chromosome intervals of this disclosure are characterized by genomic regions including and flanked by any two of marker loci SEQ ID NOs: 25 to 27. In another aspect, the chromosome intervals of this disclosure are characterized by genomic regions including and flanked by any two of marker loci SEQ ID NOs: 29 to 31. In another aspect, the chromosome intervals of this disclosure are characterized by genomic regions including and flanked by any two of marker loci SEQ ID NOs: 34 to 36. In another aspect, the chromosome intervals of this disclosure are characterized by genomic regions including and flanked by any two of marker loci SEQ ID NOs: 39 to 45. In another aspect, the chromosome intervals of this disclosure are characterized by genomic regions including and flanked by any two of marker loci SEQ ID NOs: 49 to 51. In another aspect, the chromosome intervals of this disclosure are characterized by genomic regions including and flanked by marker loci SEQ ID NOs: 58 and 59. In another aspect, the chromosome intervals of this disclosure are characterized by genomic regions including and flanked by marker loci SEQ ID NOs: 63 and 64. In another aspect, the chromosome intervals of this disclosure are characterized by genomic regions including and flanked by any two of marker loci SEQ ID NOs: 77 to 80. In another aspect, the chromosome intervals of this disclosure are characterized by genomic regions including and flanked by any two of marker loci SEQ ID NOs: 99 to 106.

This disclosure also provides multiple markers linked to or associated with a DM resistance QTL, for example, the markers having the sequence selected from SEQ ID NOs: 1-114. This disclosure therefore provides plants comprising a nucleic acid molecule selected from the group consisting of SEQ ID NOs: 1-114, fragments thereof, or complements thereof. The present disclosure further provides a plant comprising alleles of the chromosome interval linked to or associated with DM resistance or fragments and complements thereof as well as any plant comprising any combination of one or more DM resistance alleles of marker loci selected from the group consisting of SEQ ID NOs: 1-114. Plants provided by this disclosure may be homozygous or heterozygous for such alleles.

The compositions and methods of the present disclosure can be utilized to guide MAS or breeding corn varieties with a desired complement (set) of allelic forms of chromosome intervals associated with superior agronomic performance (e.g. DM resistance). Any of the disclosed marker alleles can be introduced into a corn line via introgression, by traditional breeding (or introduced via transformation, or both) to yield a corn plant with superior agronomic performance. The number of alleles associated with DM resistance that can be introduced or be present in a corn plant of the present disclosure ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this disclosure.

These marker loci can be introgressed into any desired genomic background, germplasm, plant, line, variety, etc., as part of an overall MAS breeding program designed to enhance DM resistance. This disclosure also provides QTL intervals that can be used in MAS to select plants that demonstrate DM resistance. Similarly, QTL intervals can also be used to counter-select plants that are lacking DM resistance. By identifying plants lacking a desired marker locus, plants lacking DM resistance can be identified and selected or eliminated from subsequent crosses.

The present disclosure also extends to a method of making a progeny corn plant and the resulting progeny corn plants. In an aspect, the method comprises crossing a first parent corn plant with a second corn plant and growing the corn plant parent under plant growth conditions to yield corn plant progeny. Methods of crossing and growing a corn plant are well within the ability of those of ordinary skill in the art. Such corn plant progeny can be assayed for alleles associated with DM resistance as disclosed herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants may be a corn plant of the present disclosure in that it comprises at least one of the allelic forms of the markers of the present disclosure, such that the progeny are capable of inheriting the allele.

By providing the positions in the corn genome of QTL intervals and the associated markers within those intervals, this disclosure also allows one skilled in the art to identify and use other markers within the intervals disclosed herein or linked to or associated with the intervals disclosed herein. Having identified such markers, these intervals can be readily identified from public linkage maps.

Closely linked markers flanking the locus of interest that have alleles in linkage disequilibrium (LD) with a DM resistance allele at that locus may be effectively used to select for progeny plants with DM resistance. Thus, the markers described herein, such as those listed in Table 7, as well as other markers genetically linked to or associated with the same chromosome interval, may be used to select for a corn plant or seed with DM resistance. Often, a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice this disclosure is not limited and can be any marker that is genetically linked to or associated with the QTL intervals as described in Table 6, including markers within approximately 20 cM, 15 cM, 10 cM, 5 cM, 4 cM, 3 cM, 2 cM, 1 cM, 0.5 cM or less than 0.5 cM of the intervals provided herein. Examples include, but are not limited to, any marker selected from SEQ ID NOs: 1-114. Furthermore, since there are many different types of marker detection assays known in the art, it is not intended that the type of marker detection assay used to practice this disclosure be limited in any way.

Marker Assisted Selection (MAS) Breeding

Marker loci and their DM resistance alleles provided herein can be used in MAS breeding of DM resistance. The more tightly linked a marker is with a DNA locus influencing a phenotype (e.g., DM resistance), the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype. However, markers do not need to contain or correspond to causal mutations in order to be effective in MAS. In fact, most MAS breeding only uses markers linked to or associated with a causal mutation.

Developing molecular markers in crop species can increase efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that exhibit DM resistance by identifying chromosomal intervals and genetic markers associated with drought tolerance.

In general, MAS uses polymorphic markers that have been identified as having a significant likelihood of co-segregation with a desired trait. Such markers are presumed to map near a gene or genes that give the plant its desired phenotype, and are considered indicators for the desired trait.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In an aspect, it is contemplated that a plurality of markers for desired traits are sequentially or simultaneous selected and/or introgressed. The combinations of markers that are selected for in a single plant is not limited, and can include any combination of markers disclosed herein or any marker linked to the markers disclosed herein, or any markers located within the QTL intervals defined herein.

In an aspect, a first corn plant or germplasm exhibiting a desired trait (the donor, e.g., a DM resistant corn) can be crossed with a second corn plant or germplasm (the recipient, e.g., an elite or exotic corn, depending on characteristics that are desired in the progeny) to create an introgressed corn plant or germplasm as part of a breeding program. In an aspect, the recipient plant can also contain one or more loci associated with one or more desired traits, which can be qualitative or quantitative trait loci. In another aspect, the recipient plant can contain a transgene.

In an aspect, the recipient corn plant or germplasm will typically lack desired traits as compared to the first corn plant or germplasm, while the introgressed corn plant or germplasm will display improved traits as compared to the second plant or germplasm. An introgressed corn plant or germplasm produced by these methods are also a feature of this disclosure.

MAS is a powerful shortcut to select for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than cultivating and observing plants for visible traits.

Introgression of DM Resistance QTLs Using MAS

The instant disclosure provides methods and markers for introgressing a DM resistance QTL disclosed herein into a new corn variety using MAS.

Multiple methods are available to achieve the introgression. For example, introgression of a desired allele at a specified locus can be transmitted to at least one progeny via a cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The introgression of one or more desired loci from a donor line into another line is achieved via repeated backcrossing to a recurrent parent accompanied by selection to retain one or more loci from the donor parent. Markers associated with drought tolerance are assayed in progeny and those progeny with one or more desired markers are selected for advancement. In another aspect, one or more markers can be assayed in the progeny to select for plants with the genotype of the agronomically elite parent.

It is generally anticipated that trait introgression activities will require more than one generation, wherein progeny are crossed to the recurrent (agronomically elite) parent or selfed. Selections are made based on the presence of one or more markers linked to drought tolerance and can also be made based on the recurrent parent genotype, wherein screening is performed on a genetic marker and/or phenotype basis. In another aspect, markers of this disclosure can be used in conjunction with other markers, ideally at least one on each chromosome of the corn genome, to track the introgression of drought tolerance into elite germplasm. In another aspect, QTL intervals associated with drought tolerance will be useful in conjunction with SNP molecular markers of the present disclosure to combine quantitative and qualitative drought tolerance in the same plant. It is within the scope of this disclosure to utilize the methods and compositions for trait integration of drought tolerance. It is contemplated by the inventors that the present disclosure will be useful for developing commercial varieties with drought tolerance and other agronomically elite phenotypes.

EXAMPLES

Example 1. Identification of QTLs Associated with Downy Mildew Resistance in Biparental Mapping Populations Biparental mapping populations are constructed to investigate the genetic basis of downy mildew (DM) resistance in corn. Plant phenotyping is performed in field plots. Plants infected with *Peronosclerospora philippinensis*, *Peronosclerospora maydis*, or *Peronosclerospora sorghi* are planted as a point source of inoculums in the field 20 days prior to planting experimental plants. Downy mildew (DM) disease resistance is measured by counting the percentage of infected experimental plants per plot at 40 days after planting (Table 1).

TABLE 1

Description of DM rating scale.

| | |
|---|---|
| <5% | Highly Resistant |
| 5-15% | Moderately Resistant |
| 15-35% | Intermediate |
| 35-45% | Moderately Susceptible |
| >45% | Highly Susceptible |

Six mapping populations are shown in Table 2. These populations include two DM resistant parent lines, CV357626 and CV368354, which are used as male and female parents, respectively. Each mapping population is measured for DM resistance in two field replicates and the basic statistics are shown in Table 3. A standard statistical model is used to estimate the variance components and to compute the heritability ($H^2$) for DM phenotype. The heritability ($H^2$) is 0.68-0.84 for all mapping populations (Table 4) indicating that the observed DM phenotype is attributed to genetic variation.

Plants from all mapping populations are genotyped using SNP markers that collectively span each chromosome in the maize genome. Marker-trait association studies are performed to identify DM resistance QTLs and their associated markers using both single-marker analysis (SMA) and composite interval mapping (CIM).

TABLE 2

Mapping populations.

| Mapping Population | Cross | DM Resistant Parent | DM Susceptible Parent | Population Type | Population Size |
|---|---|---|---|---|---|
| A | CV374702/CV357626 | CV357626 | CV374702 | $F_3$ | 182 |
| B | CV374480/CV357626 | CV357626 | CV374480 | $F_3$ | 420 |
| C | CV371812/CV357626 | CV357626 | CV371812 | $F_3$ | 350 |
| D | CV368354/CV371792 | CV368354 | CV371792 | $F_3$ | 530 |
| E | CV368354/CV364290 | CV368354 | CV364290 | $F_3$ | 721 |
| F | CV368354/CV364209 | CV368354 | CV364209 | $F_3$ | 455 |

TABLE 3

Basic statistics for each mapping population

| Mapping Population | Replicate ID | Mean DM score (%) | Number of Lines | Standard Deviation |
|---|---|---|---|---|
| A | combined | 78.7 | 422 | 25.9 |
|   | 1 | 77.5 | 212 | 26.4 |
|   | 2 | 79.9 | 210 | 25.3 |
| B | combined | 17.1 | 868 | 14.1 |
|   | 1 | 15.3 | 434 | 13.5 |
|   | 2 | 18.9 | 434 | 14.5 |
| C | combined | 29.6 | 728 | 18.5 |
|   | 1 | 30.3 | 364 | 18.4 |
|   | 2 | 29 | 364 | 18.7 |
| D | Combined | 46.3 | 1173 | 22.7 |
|   | 1 | 46.5 | 592 | 22.7 |
|   | 2 | 46.1 | 581 | 22.7 |
| E | Combined | 33 | 1614 | 22.4 |
|   | 1 | 33.3 | 809 | 22.5 |
|   | 2 | 32.6 | 805 | 22.3 |
| F | Combined | 43.7 | 1054 | 23.3 |
|   | 1 | 44 | 536 | 22.8 |
|   | 2 | 43.3 | 518 | 23.9 |

TABLE 4

Variance component estimation and heritability analysis.

| Mapping Population | Genetic variance | Residue variance | Total phenotypic variance | $H^2$ |
|---|---|---|---|---|
| A | 269.9 | 56.3 | 326.2 | 0.83 |
| B | 87.8 | 41.6 | 129.3 | 0.68 |
| C | 205.9 | 64.3 | 270.2 | 0.76 |
| D | 311.38 | 77.44 | 388.82 | 0.8 |
| E | 272.84 | 65.23 | 338.07 | 0.81 |
| F | 339.56 | 62.96 | 402.52 | 0.84 |

Example 2. Identification of DM Resistance QTLs Via Composite Interval Mapping

A composite interval mapping (CIM) approach is taken to identify DM resistance QTL intervals based on the phenotyping and genotyping data collected in Example 1. For each marker, the thresholds of likelihood ratio between full and null models for CIM are based on 1000 random permutation tests (Churchill and Doerg, *Genetics*, 138(3):963-71 (1994)). The composite interval mapping (CIM) analysis revealed several strong QTLs associated with DM resistance. The QTLs are confirmed in multiple genetic backgrounds and summarized in Table 5.

In Table 5, genetic positions are represented in cM with position zero being the first (most distal) marker known at the beginning of the chromosome on Monsanto's internal consensus genetic map. Each row of Table 5 provides mapping population ID, number of SNP markers genotyped (#Mk), resistant parent, chromosome position, the peak of the likelihood ratio corresponding to DM resistance, left and right flanking positions, p-value, additive effect, and the phenotypic variance ($R^2$) of individual QTL or Total QTLs.

TABLE 5

CIM results from all mapping populations.
*p-value is based on 1,000 permutation tests QTL Positions (cM)

| Mapping population | #Mk | Resistant Parent | Chr | Peak | Left Flank | Right Flank | p-value | Additive | QTL $R^2$ | Total $R^2$ |
|---|---|---|---|---|---|---|---|---|---|---|
| A | 132 | CV357626 | 6 | 96.5 | 87.2 | 102.5 | 0.05 | 7.6 | 0.1 | 0.55 |
| A | 132 | CV357626 | 3 | 90.5 | 81.2 | 100.5 | 0.01 | 12.8 | 0.27 | 0.58 |
| B | 156 | CV357626 | 1 | 74 | 63 | 79.1 | 0.01 | 3.4 | 0.061 | 0.33 |
| B | 156 | CV357626 | 2 | 43.6 | 38.6 | 52.2 | 0.01 | 3 | 0.048 | 0.363 |
| C | 143 | CV357626 | 1 | 60.1 | 51.1 | 68.1 | 0.01 | 7.1 | 0.114 | 0.625 |
| C | 143 | CV357626 | 2 | 36.6 | 24.4 | 39.6 | 0.01 | 4.7 | 0.052 | 0.602 |
| C | 143 | CV357626 | 4 | 160.1 | 152.3 | 170.8 | 0.01 | 9.7 | 0.17 | 0.6 |
| C | 143 | CV357626 | 6 | 91.2 | 81.3 | 103.2 | 0.01 | 6.4 | 0.095 | 0.613 |
| D | 186 | CV368354 | 2 | 48.8 | 35.2 | 57.3 | 0.01 | 9.9 | 0.15 | 0.24 |
| D | 186 | CV368354 | 2 | 209.3 | 195.7 | 212 | 0.01 | 6.7 | 0.07 | 0.21 |
| D | 186 | CV368354 | 5 | 138.5 | 125.4 | 142.2 | 0.05 | 4.3 | 0.05 | 0.21 |
| D | 186 | CV368354 | 8 | 98.4 | 68.1 | 108.4 | 0.01 | 8.7 | 0.12 | 0.31 |
| D | 186 | CV368354 | 9 | 75.7 | 65.7 | 80.2 | 0.01 | 6.8 | 0.06 | 0.25 |
| E | 186 | CV368354 | 2 | 207.7 | 195.7 | 211.7 | 0.01 | 8.3 | 0.12 | 0.55 |
| E | 186 | CV368354 | 2 | 50.8 | 39.2 | 57.3 | 0.01 | 5.9 | 0.05 | 0.53 |
| E | 186 | CV368354 | 8 | 84.1 | 75.3 | 102.4 | 0.01 | 8.1 | 0.11 | 0.52 |
| E | 186 | CV368354 | 9 | 87.7 | 77.2 | 97.5 | 0.01 | 8.2 | 0.11 | 0.53 |
| F | 149 | CV368354 | 2 | 63.3 | 53.3 | 72.3 | 0.05 | 7.5 | 0.08 | 0.56 |
| F | 149 | CV368354 | 6 | 58.1 | 39.3 | 59.1 | 0.01 | 11.1 | 0.14 | 0.5 |
| F | 149 | CV368354 | 8 | 102.6 | 92.6 | 112.6 | 0.01 | 8.8 | 0.11 | 0.53 |
| F | 149 | CV368354 | 9 | 75.9 | 70.9 | 80.9 | 0.1 | 5 | 0.07 | 0.57 |

Example 3. Fine-Mapping Downy Mildew Resistance QTLs Via Joint Linkage Mapping

As shown in Examples 1 and 2, QTLs associated with DM resistance are identified from three bi-parental mapping populations (A, B, and C) by crossing one resistant line (CV357626) with three different susceptible lines. These three mapping populations are merged for joint linkage mapping. Additional QTLs associated with DM resistance are identified from three bi-parental mapping populations (D, E, and F) by crossing one resistant line (CV368354) with three different susceptible lines. These three mapping populations are also merged for joint linkage mapping. The most informative markers are selected with bootstrapping probabilities from 3000 bootstrapping samples. Thirteen QTLs are identified through the joint linkage fine mapping. These thirteen QTLs are designated as DM_1.01, DM_1.02, DM_2.03, DM_3.01, DM_4.01, DM_6.01, DM_2.01, DM_2.02, DM_5.01, DM_6.02, DM_7.01, DM_8.01 and DM_9.01 (Table 7).

TABLE 6

Fine-mapping of DM resistance QTL by JLM.

| Chr | JLM interval CV357626 (cM) | Left Flank Marker | Right Flank Marker | IBM2008 Map (IcM) | QTL Designation |
|---|---|---|---|---|---|
| 1 | 54-69 | SEQ ID NO: 5 | SEQ ID NO: 8 | 158.5-196 | DM_1.01 |
| 1 | 68.4-73.2 | SEQ ID NO: 7 | SEQ ID NO: 8 | 194.6-206.8 | DM_1.02 |
| 2 | 21.4-33.6 | SEQ ID NO: 12 | SEQ ID NO: 14 | 49.7-88.2 | DM_2.03 |
| 3 | 80.2-92.6 | SEQ ID NO: 29 | SEQ ID NO: 31 | 208.6-318.2 | DM_3.01 |
| 4 | 152.7-162.3 | SEQ ID NO: 34 | SEQ ID NO: 36 | 525.8-572.3 | DM_4.01 |
| 6 | 85.1-90.7 | SEQ ID NO: 58 | SEQ ID NO: 59 | 374.1-389.9 | DM_6.01 |

TABLE 6-continued

Fine-mapping of DM resistance QTL by JLM.

| Chr | JLM interval CV368354 (cM) | Left Flank Marker | Right Flank Marker | IBM2008 Map (IcM) | QTL Designation |
|---|---|---|---|---|---|
| 2 | 46.8-57 | SEQ ID NO: 18 | SEQ ID NO: 20 | 138.6-169.1 | DM_2.01 |
| 2 | 200.8-212 | SEQ ID NO: 25 | SEQ ID NO: 27 | 655.6-709.5 | DM_2.02 |
| 5 | 125.4-142.2 | SEQ ID NO: 39 | SEQ ID NO: 45 | 432.3-491.7 | DM_5.01 |
| 6 | 39.7-52.7 | SEQ ID NO: 49 | SEQ ID NO: 51 | 204.2-239.6 | DM_6.02 |
| 7 | 66.4-78.5 | SEQ ID NO: 63 | SEQ ID NO: 64 | 209.6-284.6 | DM_7.01 |
| 8 | 82.6-89.4 | SEQ ID NO: 77 | SEQ ID NO: 80 | 288.3-313.8 | DM_8.01 |
| 9 | 67.9-80.7 | SEQ ID NO: 99 | SEQ ID NO: 106 | 226.5-308.9 | DM_9.01 |

Example 4. Identification of Molecular Markers Associated with DM Resistance Via Single-Marker Analysis (SMA)

Single-marker analysis (SMA) is performed to identify markers associated with DM resistance using the genotypic data from Example 1. For each marker, the thresholds (p-value) for SMA are based on 10,000 random permutation tests (Churchill and Doerg, *Genetics*, 138(3):963-71 (1994)).

In total, 114 SNP markers are identified to be linked to DM resistance (Table 7). Table 7 also provides the effect estimates on DM rating score for each marker linked to DM resistance. Further provided are the SEQ ID NO of the marker, chromosome position, marker position on Monsanto's internal consensus genetic map, corresponding marker position on the Neighbors 2008 maize genetic map (publicly available at Maize GDB website), genetic source of favorable allele, resistant allele SNP, susceptible allele SNP, the estimated effect that the marker polymorphism had on the DM rating score, and p-value based on 10,000 random permutation tests. For example, SEQ ID NO: 1 is associated with a 4.28% reduction in DM rating score by one copy of the resistant allele. However, one of skill in the art recognizes that a "resistant" allele at one locus may be a "susceptible" allele in a different genetic background. Thus, this disclosure is not limited to the "resistant" and "susceptible" alleles exemplified herein.

The primer sequences for amplifying exemplary SNP marker loci linked to the DM and the probes used to genotype the corresponding SNP sequences are provided in Table 8. In an illustrative example, SNP marker SEQ ID NO: 1 can be amplified using the primers described in Table 5 as SEQ ID NO: 115 (forward primer) and SEQ ID NO: 229 (reverse primer), and detected with probes indicated as SEQ ID NO: 343 (Probe 1) and SEQ ID NO: 457 (Probe 2).

One of skill in the art recognizes that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, this disclosure is not limited to the primers, probes, or marker sequences specifically listed in the tables.

TABLE 7

Estimate effects of markers linked to DM resistance from all mapping populations by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability |
|---|---|---|---|---|---|---|---|---|
| 1 | 1 | 42.8 | 124.7 | CV357626 | A | G | 4.28 | 0.001 |
| 2 | 1 | 46.7 | 137 | CV357626 | G | A | 3.04 | 0.001 |
| 3 | 1 | 47.5 | 139.8 | CV357626 | C | T | 4.95 | 0.001 |
| 4 | 1 | 50.1 | 146.9 | CV357626 | C | G | 5.58 | 0.001 |
| 5 | 1 | 54 | 158.5 | CV357626 | G | A | 3.29 | 0.001 |
| 6 | 1 | 64.1 | 184.3 | CV357626 | G | A | 3.74 | 0.001 |
| 7 | 1 | 68.4 | 194.6 | CV357626 | A | G | 7.63 | 0.001 |
| 8 | 1 | 69 | 196 | CV357626 | T | C | 3.41 | 0.001 |
| 9 | 1 | 79.3 | 223.2 | CV357626 | T | C | 2.76 | 0.001 |
| 10 | 1 | 82.7 | 242.2 | CV357626 | A | G | 7.98 | 0.001 |
| 11 | 1 | 88.2 | 270.6 | CV357626 | C | T | 2.80 | 0.001 |
| 12 | 2 | 21.4 | 49.7 | CV357626 | T | A | 3.38 | 0.001 |
| 13 | 2 | 32.2 | 82.8 | CV368354 | G | A | 5.70 | 0.001 |
| 14 | 2 | 33.6 | 88 | CV357626 | G | A | 4.21 | 0.001 |
| 15 | 2 | 40.6 | 111.8 | CV368354 | A | G | 5.18 | 0.001 |
| 16 | 2 | 43 | 122.1 | CV368354 | A | G | 5.95 | 0.001 |
| 17 | 2 | 44.2 | 127.2 | CV368354 | A | T | 4.21 | 0.001 |
| 18 | 2 | 46.8 | 138.6 | CV368354 | G | A | 7.15 | 0.001 |
| 19 | 2 | 52.3 | 156.9 | CV368354 | A | C | 6.26 | 0.001 |
| 20 | 2 | 57 | 169.1 | CV368354 | A | G | 6.23 | 0.001 |
| 21 | 2 | 58.3 | 172.6 | CV368354 | G | T | 6.23 | 0.001 |
| 22 | 2 | 60.6 | 179.5 | CV368354 | T | A | 8.43 | 0.001 |
| 23 | 2 | 184.4 | 598.4 | CV368354 | C | A | 5.58 | 0.001 |
| 24 | 2 | 195.7 | 639 | CV368354 | C | A | 6.24 | 0.001 |
| 25 | 2 | 200.8 | 655.6 | CV368354 | T | G | 5.11 | 0.001 |
| 26 | 2 | 202.3 | 659.5 | CV368354 | T | C | 5.11 | 0.001 |
| 27 | 2 | 212 | 709.5 | CV368354 | A | G | 5.51 | 0.001 |
| 28 | 2 | 212.1 | 709.6 | CV368354 | G | A | 6.80 | 0.001 |
| 29 | 3 | 80.2 | 208.6 | CV357626 | A | G | 13.13 | 0.001 |
| 30 | 3 | 86.5 | 276.6 | CV357626 | G | C | 12.67 | 0.001 |
| 31 | 3 | 92.6 | 318.2 | CV357626 | A | G | 12.94 | 0.001 |
| 32 | 3 | 110.9 | 382.6 | CV357626 | G | A | 12.33 | 0.001 |
| 33 | 4 | 145.3 | 467.1 | CV357626 | C | A | 6.30 | 0.001 |
| 34 | 4 | 153.2 | 527 | CV357626 | C | T | 6.61 | 0.001 |
| 35 | 4 | 157.1 | 550.2 | CV357626 | A | G | 7.86 | 0.001 |
| 36 | 4 | 162.3 | 572.3 | CV357626 | G | T | 8.19 | 0.001 |
| 37 | 4 | 165.8 | 579.6 | CV357626 | T | A | 8.50 | 0.001 |
| 38 | 4 | 176.7 | 615.8 | CV357626 | G | A | 5.05 | 0.001 |
| 39 | 5 | 125.4 | 432.3 | CV368354 | C | T | 2.10 | 0.049 |
| 40 | 5 | 126.5 | 437.9 | CV368354 | T | A | 2.17 | 0.044 |
| 41 | 5 | 131.3 | 460.4 | CV368354 | T | A | 3.36 | 0.007 |
| 42 | 5 | 131.9 | 462.5 | CV368354 | T | C | 3.62 | 0.003 |
| 43 | 5 | 132.1 | 463.2 | CV368354 | C | T | 4.11 | 0.001 |

TABLE 7-continued

Estimate effects of markers linked to DM resistance from all mapping populations by SMA.

| SEQ ID NO. | Chromo- some | MON Map (cM) | IBM2008 Map (IcM) | Genetic Source of Favorable Allele | Exemplary Resistant Allele | Exemplary Susceptible Allele | Single Allele Effect | Permutation Testing Probability |
|---|---|---|---|---|---|---|---|---|
| 44 | 5 | 132.8 | 465.5 | CV368354 | C | T | 3.97 | 0.002 |
| 45 | 5 | 133.1 | 466.6 | CV368354 | A | G | 4.05 | 0.001 |
| 46 | 6 | 25.2 | 147.9 | CV368354 | T | C | 5.71 | 0.001 |
| 47 | 6 | 34 | 187.7 | CV368354 | A | G | 8.03 | 0.001 |
| 48 | 6 | 38.6 | 201.1 | CV368354 | G | A | 8.95 | 0.001 |
| 49 | 6 | 39.7 | 204.2 | CV368354 | G | A | 10.40 | 0.001 |
| 50 | 6 | 39.8 | 204.5 | CV368354 | A | G | 10.12 | 0.001 |
| 51 | 6 | 52.7 | 239.7 | CV368354 | T | C | 9.27 | 0.001 |
| 52 | 6 | 53.9 | 242.7 | CV368354 | G | A | 9.25 | 0.001 |
| 53 | 6 | 54.1 | 243.2 | CV368354 | C | A | 9.32 | 0.001 |
| 54 | 6 | 59.4 | 267.1 | CV368354 | A | G | 10.04 | 0.001 |
| 55 | 6 | 70 | 324.7 | CV368354 | G | A | 8.82 | 0.001 |
| 56 | 6 | 74.3 | 341.9 | CV357626 | G | A | 5.02 | 0.001 |
| 57 | 6 | 74.7 | 343.2 | CV368354 | G | A | 6.83 | 0.001 |
| 58 | 6 | 85.1 | 374.2 | CV357626 | C | A | 7.45 | 0.001 |
| 59 | 6 | 87.2 | 380.8 | CV357626 | C | G | 5.21 | 0.001 |
| 60 | 6 | 97.8 | 417.4 | CV357626 | C | T | 8.06 | 0.001 |
| 61 | 6 | 103.8 | 434.3 | CV357626 | T | A | 7.03 | 0.001 |
| 62 | 6 | 108.2 | 444.8 | CV357626 | C | T | 7.73 | 0.001 |
| 63 | 7 | 67.5 | 231.7 | CV368354 | C | T | 7.14 | 0.001 |
| 64 | 7 | 75.4 | 264.8 | CV368354 | A | G | 7.14 | 0.001 |
| 65 | 8 | 64.8 | 193.7 | CV368354 | G | A | 6.37 | 0.001 |
| 66 | 8 | 67.1 | 204 | CV368354 | C | A | 7.41 | 0.001 |
| 67 | 8 | 67.7 | 205.2 | CV368354 | G | A | 6.13 | 0.001 |
| 68 | 8 | 71.7 | 216.2 | CV368354 | C | T | 6.78 | 0.001 |
| 69 | 8 | 71.7 | 216.2 | CV368354 | A | T | 7.11 | 0.001 |
| 70 | 8 | 71.9 | 216.7 | CV368354 | T | A | 7.01 | 0.001 |
| 71 | 8 | 71.9 | 216.7 | CV368354 | A | G | 7.25 | 0.001 |
| 72 | 8 | 74.2 | 231.1 | CV368354 | G | A | 7.43 | 0.001 |
| 73 | 8 | 74.8 | 236.2 | CV368354 | G | A | 7.62 | 0.001 |
| 74 | 8 | 75.3 | 240.4 | CV368354 | A | T | 7.81 | 0.001 |
| 75 | 8 | 75.3 | 240.4 | CV368354 | T | G | 7.30 | 0.001 |
| 76 | 8 | 75.9 | 251.6 | CV368354 | C | G | 7.30 | 0.001 |
| 77 | 8 | 82.6 | 288.3 | CV368354 | A | G | 8.07 | 0.001 |
| 78 | 8 | 84.1 | 291.7 | CV368354 | C | G | 8.34 | 0.001 |
| 79 | 8 | 84.5 | 293.6 | CV368354 | C | G | 7.67 | 0.001 |
| 80 | 8 | 89.4 | 313.8 | CV368354 | A | G | 8.16 | 0.001 |
| 81 | 8 | 101.1 | 354.7 | CV368354 | G | T | 9.20 | 0.001 |
| 82 | 8 | 102.6 | 362.2 | CV368354 | G | A | 10.00 | 0.001 |
| 83 | 8 | 103.1 | 363.9 | CV368354 | G | A | 8.02 | 0.001 |
| 84 | 8 | 103.1 | 363.9 | CV368354 | A | G | 8.55 | 0.001 |
| 85 | 8 | 103.1 | 363.9 | CV368354 | G | A | 8.12 | 0.001 |
| 86 | 8 | 104 | 374.5 | CV368354 | G | T | 7.65 | 0.001 |
| 87 | 8 | 104.8 | 374.5 | CV368354 | A | G | 9.80 | 0.001 |
| 88 | 8 | 106.4 | 380.7 | CV368354 | T | G | 8.54 | 0.001 |
| 89 | 8 | 112.1 | 394.3 | CV368354 | G | A | 8.07 | 0.001 |
| 90 | 8 | 113.1 | 396.8 | CV368354 | T | C | 6.84 | 0.001 |
| 91 | 9 | 56.8 | 158.5 | CV368354 | C | T | 6.11 | 0.001 |
| 92 | 9 | 61.4 | 188.5 | CV368354 | G | A | 5.06 | 0.001 |
| 93 | 9 | 61.5 | 189.3 | CV368354 | G | C | 5.13 | 0.001 |
| 94 | 9 | 66.2 | 212.3 | CV368354 | G | A | 5.78 | 0.001 |
| 95 | 9 | 67.2 | 245.5 | CV368354 | G | C | 6.73 | 0.001 |
| 96 | 9 | 67.8 | 226.4 | CV368354 | G | A | 7.15 | 0.001 |
| 97 | 9 | 67.8 | 226.4 | CV368354 | G | A | 7.00 | 0.001 |
| 98 | 9 | 67.8 | 226.4 | CV368354 | C | A | 7.00 | 0.001 |
| 99 | 9 | 67.9 | 226.5 | CV368354 | G | A | 6.98 | 0.001 |
| 100 | 9 | 67.9 | 245.5 | CV368354 | A | C | 6.58 | 0.001 |
| 101 | 9 | 67.9 | 226.5 | CV368354 | A | G | 6.87 | 0.001 |
| 102 | 9 | 68.2 | 245.5 | CV368354 | A | G | 7.16 | 0.001 |
| 103 | 9 | 68.4 | 227 | CV368354 | G | A | 7.16 | 0.001 |
| 104 | 9 | 74.7 | 263.6 | CV368354 | C | T | 7.40 | 0.001 |
| 105 | 9 | 77.2 | 283.6 | CV368354 | A | T | 7.54 | 0.001 |
| 106 | 9 | 80.7 | 304.9 | CV368354 | T | G | 6.35 | 0.001 |
| 107 | 9 | 82.6 | 314.5 | CV368354 | G | T | 8.69 | 0.001 |
| 108 | 9 | 87.4 | 321.6 | CV368354 | C | A | 7.66 | 0.001 |
| 109 | 9 | 87.7 | 321.8 | CV368354 | A | C | 9.25 | 0.001 |
| 110 | 9 | 88.5 | 338.7 | CV368354 | C | T | 8.83 | 0.001 |
| 111 | 9 | 88.6 | 339.2 | CV368354 | A | G | 8.69 | 0.001 |
| 112 | 9 | 88.6 | 339.2 | CV368354 | G | A | 8.79 | 0.001 |
| 113 | 9 | 89.3 | 349.3 | CV368354 | C | T | 8.36 | 0.001 |
| 114 | 9 | 96.5 | 392.9 | CV368354 | A | G | 6.60 | 0.001 |

TABLE 8

Exemplary primers and probes used for genotyping representative SNP markers associated with DM resistance

| SEQ ID NO. | SNP Position | Forward Primer | Reverse Primer | Probe 1 | Probe 2 |
|---|---|---|---|---|---|
| 1 | 483 | 115 | 229 | 343 | 457 |
| 2 | 146 | 116 | 230 | 344 | 458 |
| 3 | 137 | 117 | 231 | 345 | 459 |
| 4 | 73 | 118 | 232 | 346 | 460 |
| 5 | 82 | 119 | 233 | 347 | 461 |
| 6 | 174 | 120 | 234 | 348 | 462 |
| 7 | 328 | 121 | 235 | 349 | 463 |
| 8 | 29 | 122 | 236 | 350 | 464 |
| 9 | 177 | 123 | 237 | 351 | 465 |
| 10 | 39 | 124 | 238 | 352 | 466 |
| 11 | 160 | 125 | 239 | 353 | 467 |
| 12 | 34 | 126 | 240 | 354 | 468 |
| 13 | 674 | 127 | 241 | 355 | 469 |
| 14 | 44 | 128 | 242 | 356 | 470 |
| 15 | 254 | 129 | 243 | 357 | 471 |
| 16 | 267 | 130 | 244 | 358 | 472 |
| 17 | 365 | 131 | 245 | 359 | 473 |
| 18 | 195 | 132 | 246 | 360 | 474 |
| 19 | 321 | 133 | 247 | 361 | 475 |
| 20 | 227 | 134 | 248 | 362 | 476 |
| 21 | 428 | 135 | 249 | 363 | 477 |
| 22 | 197 | 136 | 250 | 364 | 478 |
| 23 | 406 | 137 | 251 | 365 | 479 |
| 24 | 404 | 138 | 252 | 366 | 480 |
| 25 | 342 | 139 | 253 | 367 | 481 |
| 26 | 630 | 140 | 254 | 368 | 482 |
| 27 | 102 | 141 | 255 | 369 | 483 |
| 28 | 92 | 142 | 256 | 370 | 484 |
| 29 | 49 | 143 | 257 | 371 | 485 |
| 30 | 118 | 144 | 258 | 372 | 486 |
| 31 | 291 | 145 | 259 | 373 | 487 |
| 32 | 46 | 146 | 260 | 374 | 488 |
| 33 | 353 | 147 | 261 | 375 | 489 |
| 34 | 379 | 148 | 262 | 376 | 490 |
| 35 | 362 | 149 | 263 | 377 | 491 |
| 36 | 999 | 150 | 264 | 378 | 492 |
| 37 | 115 | 151 | 265 | 379 | 493 |
| 38 | 207 | 152 | 266 | 380 | 494 |
| 39 | 280 | 153 | 267 | 381 | 495 |
| 40 | 281 | 154 | 268 | 382 | 496 |
| 41 | 81 | 155 | 269 | 383 | 497 |
| 42 | 241 | 156 | 270 | 384 | 498 |
| 43 | 299 | 157 | 271 | 385 | 499 |
| 44 | 336 | 158 | 272 | 386 | 500 |
| 45 | 468 | 159 | 273 | 387 | 501 |
| 46 | 284 | 160 | 274 | 388 | 502 |
| 47 | 250 | 161 | 275 | 389 | 503 |
| 48 | 262 | 162 | 276 | 390 | 504 |
| 49 | 496 | 163 | 277 | 391 | 505 |
| 50 | 44 | 164 | 278 | 392 | 506 |
| 51 | 82 | 165 | 279 | 393 | 507 |
| 52 | 52 | 166 | 280 | 394 | 508 |
| 53 | 409 | 167 | 281 | 395 | 509 |
| 54 | 115 | 168 | 282 | 396 | 510 |
| 55 | 256 | 169 | 283 | 397 | 511 |
| 56 | 91 | 170 | 284 | 398 | 512 |
| 57 | 47 | 171 | 285 | 399 | 513 |
| 58 | 525 | 172 | 286 | 400 | 514 |
| 59 | 253 | 173 | 287 | 401 | 515 |
| 60 | 174 | 174 | 288 | 402 | 516 |
| 61 | 250 | 175 | 289 | 403 | 517 |
| 62 | 148 | 176 | 290 | 404 | 518 |
| 63 | 130 | 177 | 291 | 405 | 519 |
| 64 | 258 | 178 | 292 | 406 | 520 |
| 65 | 324 | 179 | 293 | 407 | 521 |
| 66 | 66 | 180 | 294 | 408 | 522 |
| 67 | 621 | 181 | 295 | 409 | 523 |
| 68 | 39 | 182 | 296 | 410 | 524 |
| 69 | 149 | 183 | 297 | 411 | 525 |
| 70 | 158 | 184 | 298 | 412 | 526 |
| 71 | 263 | 185 | 299 | 413 | 527 |
| 72 | 538 | 186 | 300 | 414 | 528 |
| 73 | 49 | 187 | 301 | 415 | 529 |
| 74 | 499 | 188 | 302 | 416 | 530 |
| 75 | 139 | 189 | 303 | 417 | 531 |
| 76 | 159 | 190 | 304 | 418 | 532 |
| 77 | 342 | 191 | 305 | 419 | 533 |
| 78 | 422 | 192 | 306 | 420 | 534 |
| 79 | 54 | 193 | 307 | 421 | 535 |
| 80 | 832 | 194 | 308 | 422 | 536 |
| 81 | 100 | 195 | 309 | 423 | 537 |
| 82 | 232 | 196 | 310 | 424 | 538 |
| 83 | 434 | 197 | 311 | 425 | 539 |
| 84 | 473 | 198 | 312 | 426 | 540 |
| 85 | 435 | 199 | 313 | 427 | 541 |
| 86 | 140 | 200 | 314 | 428 | 542 |
| 87 | 366 | 201 | 315 | 429 | 543 |
| 88 | 249 | 202 | 316 | 430 | 544 |
| 89 | 574 | 203 | 317 | 431 | 545 |
| 90 | 218 | 204 | 318 | 432 | 546 |
| 91 | 701 | 205 | 319 | 433 | 547 |
| 92 | 182 | 206 | 320 | 434 | 548 |
| 93 | 444 | 207 | 321 | 435 | 549 |
| 94 | 288 | 208 | 322 | 436 | 550 |
| 95 | 295 | 209 | 323 | 437 | 551 |
| 96 | 327 | 210 | 324 | 438 | 552 |
| 97 | 100 | 211 | 325 | 439 | 553 |
| 98 | 1052 | 212 | 326 | 440 | 554 |
| 99 | 204 | 213 | 327 | 441 | 555 |
| 100 | 128 | 214 | 328 | 442 | 556 |
| 101 | 242 | 215 | 329 | 443 | 557 |
| 102 | 448 | 216 | 330 | 444 | 558 |
| 103 | 560 | 217 | 331 | 445 | 559 |
| 104 | 309 | 218 | 332 | 446 | 560 |
| 105 | 58 | 219 | 333 | 447 | 561 |
| 106 | 466 | 220 | 334 | 448 | 562 |
| 107 | 363 | 221 | 335 | 449 | 563 |
| 108 | 155 | 222 | 336 | 450 | 564 |
| 109 | 436 | 223 | 337 | 451 | 565 |
| 110 | 600 | 224 | 338 | 452 | 566 |
| 111 | 418 | 225 | 339 | 453 | 567 |
| 112 | 539 | 226 | 340 | 454 | 568 |
| 113 | 382 | 227 | 341 | 455 | 569 |
| 114 | 83 | 228 | 342 | 456 | 570 |

Example 5. Validation of DM QTLs

Multiple corn populations are used to validate effects of the DM QTLs identified herein. First, effects of individual DM resistance QTLs are tested using $BC_3F_3$ inbred plants derived from CV357626/CV523685 (Table 9). Plants carrying a resistant allele of DM-4.01 show a reduction of 15.9% in DM rating score (89.6%-73.7%=15.9%) when compared to plants carrying a susceptible allele. Plants carrying a resistant allele of DM-6.01 show a reduction of 26.6% in DM rating score (83.2%-56.6%=26.6%) when compared to plants carrying a susceptible allele. $BC_3F_3$ inbred plants are also derived from or CV368354/CV358560. Plants carrying a resistant allele of DM-8.01 show a reduction of 7.5% in DM rating score (85.6%-78.1%=7.5%) when compared to plants carrying a susceptible allele (Table 9).

TABLE 9

Efficacy test of individual QTLs on BC₃F₃ inbred plants.

| Cross | QTL | QTL Profile | Mean (%) | p-value |
|---|---|---|---|---|
| CV357626/CV523685 | DM_4.01 | 4− | 89.6 | <0.001 |
|  |  | 4+ | 73.7 |  |
| CV357626/CV523685 | DM_6.01 | 6− | 83.2 | <0.001 |
|  |  | 6+ | 56.6 |  |
| CV368354/CV358560 | DM_8.01 | 8− | 85.6 | <0.001 |
|  |  | 8+ | 78.1 |  |

Effects of various DM resistance QTL combinations are also tested using $F_2$ lines derived from CV375547/CV357626, CV523685/CV357626, CV356987/CV357626, CV358560/CV368354, CV368354/CV356389, CV368354/CV356054, CV353840/CV368354, and CV353184/CV368354. Inbred plants carrying multiple DM resistant QTLs from CV357626 show a reduction of 16-34% in DM rating scores when compared to plants carrying susceptible alleles. Inbred plants carrying multiple DM resistant QTLs from CV368354 show a reduction of 17.2-57.5% in DM rating scores when compared to plants carrying susceptible alleles (Table 10).

TABLE 10

Test of multiple QTL model in $F_2$ plants.

| Cross | QTL model | DM rating score (%) All negative | DM rating score (%) All positive | Efficacy (%) | p-value |
|---|---|---|---|---|---|
| CV375547/CV357626 | DM_1.01-DM_4.01-DM_6.01 | 38 | 9.8 | 28.2 | <0.001 |
| CV523685/CV357626 | DM_1.01-DM_3.01-DM_4.01 | 43.8 | 9.8 | 34 | <0.001 |
| CV356987/CV357626 | DM_1.01-DM_3.01-DM_4.01 | 23.8 | 7.8 | 16 | <0.001 |
| CV358560/CV368354 | DM_2.01-DM_4.01 | 57.47 | 34.27 | 23.2 | <0.001 |
| CV368354/CV356389 | DM_6.02-DM_8.01 | 57.04 | 17.39 | 39.65 | <0.001 |
| CV368354/CV356054 | DM_6.02-DM_8.01-DM_9.01 | 78.79 | 21.26 | 57.53 | <0.001 |
| CV353840/CV368354 | DM_8.01-DM_9.01 | 37.29 | 17.92 | 19.37 | <0.001 |
| CV353184/CV368354 | DM_2.01-DM_6.02-DM_8.01 | 26.44 | 9.23 | 17.21 | <0.001 |

Effects of DM resistance QTL combinations in hybrid plants are also tested by crossing $BC_6F_4$ inbred lines derived from CV368354/CV371792 with two highly susceptible testers to generate hybrid plants. The efficacy, equivalency, and yield protection of various combinations of DM resistance QTLs are evaluated. Several combinations of DM resistant QTLs provide a reduction of 2.1-5.8% in DM rating score across testers (shown in bold text in Table 11). DM_6.02 appear shared among these QTL combinations.

TABLE 11

Efficacy trials of multiple QTL models. DM rating score differences by least-squares means (LSM_DIFF) are provided (LSM_DIFF = % of infected plants without DM resistant QTLs - % of infected plants with DM resistant QTLs).

| QTL model | LSM_DIFF (%) | p-value |
|---|---|---|
| Under high disease pressure |  |  |
| DM_5.01-DM_6.02-DM_7.01 | 0.9 | 0.330215 |
| DM_5.01-DM_6.02-DM_7.01-DM_8.01 | 4.7 | 1.13E−06 |
| DM_5.01-DM_6.02-DM_8.01 | 2.9 | 0.002377 |
| DM_5.01-DM_7.01 | −5.4 | 2.66E−08 |
| DM_5.01-DM_7.01-DM_8.01 | −2.4 | 0.014362 |
| DM_6.02-DM_7.01-DM_8.01 | 2.1 | 0.031126 |
| Under low disease pressure |  |  |
| DM_5.01-DM_6.02-DM_7.01 | 2.9 | 0.002548 |
| DM_5.01-DM_6.02-DM_7.01-DM_8.01 | 5.8 | 1.36E−09 |
| DM_5.01-DM_6.02-DM_8.01 | 4.4 | 4.03E−06 |
| DM_5.01-DM_7.01 | −5.4 | 2.83E−08 |
| DM_5.01-DM_7.01-DM_8.01 | −2.7 | 0.00471 |
| DM_6.02-DM_7.01-DM_8.01 | 3.4 | 0.00045 |

Under high disease pressure as exemplified in Example 1 (e.g., a field with a DM infected corn plant as a source inoculum), hybrid plants carrying multiple DM resistant QTLs provide a yield advantage of 3.7-4.3 quintal per hectare when compared to hybrid plants carrying the susceptible QTLs (highlighted in bold text in Table 12). Under low disease pressure (e.g., a field without a DM infected corn plant as a source inoculum), there is no statistical difference in yield between hybrid plants with or without DM resistant QTLs (Table 12) indicating no yield penalty from these QTLs. It is noted in Table 12 that negative values correspond to yield increases, while positive values correspond to yield decreases.

TABLE 12

Yield protection and equivalency trials of multiple QTL model. Yield differences by least-squares means (LSM_DIFF) are provided (LSM_DIFF = yield from plants without DM resistant QTLs - yield from plants with DM resistant QTLs).

| QTL model | LSM_DIFF (quintal/hectare) | p-value |
|---|---|---|
| Under high disease pressure |  |  |
| DM_5.01-DM_6.02-DM_7.01 | −1.4 | 0.348081 |
| DM_5.01-DM_6.02-DM_7.01-DM_8.01 | −3.9 | 0.009734 |
| DM_5.01-DM_6.02-DM_8.01 | −4.3 | 0.004883 |
| DM_5.01-DM_7.01 | 3.1 | 0.039359 |

TABLE 12-continued

Yield protection and equivalency trials of multiple QTL model.
Yield differences by least-squares means (LSM_DIFF)
are provided (LSM_DIFF = yield from plants without DM
resistant QTLs - yield from plants with DM resistant QTLs).

| QTL model | LSM_DIFF (quintal/hectare) | p-value |
|---|---|---|
| DM_5.01-DM_7.01-DM_8.01 | 2.6 | 0.093428 |
| DM_6.02-DM_7.01-DM_8.01 | -3.7 | 0.013656 |
| Under low disease pressure | | |
| DM_5.01-DM_6.02-DM_7.01 | 0.9 | 0.495734 |
| DM_5.01-DM_6.02-DM_7.01-DM_8.01 | 1.1 | 0.382852 |
| DM_5.01-DM_6.02-DM_8.01 | 1 | 0.4349 |
| DM_5.01-DM_7.01 | 1.3 | 0.321979 |
| DM_5.01-DM_7.01-DM_8.01 | 0.9 | 0.480224 |
| DM_6.02-DM_7.01-DM_8.01 | -1.3 | 0.318478 |

Example 6. Further Validation of DM QTLs

Efficacy of individual and multiple DM resistance QTLs are further tested using $BC_3F_3$ inbred plants derived from the crosses listed in Tables 13 and 14. Non-resistant plants are used as recurrent parent plants in the backcrosses to generate these $BC_3F_3$ plants. Inbred plants carrying resistant alleles of DM_4.01 show a reduction of 37.25% in DM rating score (67.75%-30.5%=37.25%) when compared to plants carrying susceptible alleles (Table 13). Inbred plants carrying multiple DM resistant QTLs (e.g., DM_1.0FDM 4.0FDM 6.01) show a reduction in DM rating scores when compared to plants carrying susceptible alleles (Table 14).

Efficacy of individual and multiple DM resistance QTLs are also tested by crossing $BC_3F_3$ inbred plants with two highly susceptible tester lines to generate hybrid plants. Hybrid plants carrying multiple DM resistant QTLs (e.g., DM_1.01-DM_4.01-DM_6.01) show a reduction in DM rating scores when compared to plants carrying susceptible alleles (Table 14).

These hybrid plants are also evaluated using equivalency tests (Tables 15 and 16). Hybrid plants carrying the resistant allele of DM_2.03 provide a yield advantage of 26.16 (87.77-61.61=26.16) quintal per hectare when compared to hybrid plants carrying the susceptible QTL (highlighted in bold text in Table 15). No significant yield drag was detected in equivalency tests for multiple QTLs in hybrid plants.

TABLE 13

Efficacy test of individual QTLs (* the presence and absence of a selected resistance QTL is shown by plus (+) and minus (-), respectively).

| Cross | QTL | QTL Profile* | INBRED TEST Mean (%) | p-value | HYBRID TEST Mean (%) | p-value |
|---|---|---|---|---|---|---|
| CV357626/CV375547 | DM_1.01 | 1+ | 51.30 | 0.102 | 37.67 | 0.805 |
| | | 1- | 77.00 | | 44.20 | |
| | DM_4.01 | 4+ | 30.50 | 0.007 | 38.34 | 0.140 |
| | | 4- | 67.75 | | 56.86 | |
| | DM_6.01 | 6+ | NA | NA | 47.21 | 0.299 |
| | | 6- | NA | | 19.08 | |
| CV523685/CV357626 | DM_6.01 | 6+ | 87.67 | 0.637 | NA | NA |
| | | 6- | 100.00 | | NA | |
| CV343114/CV357626 | DM_1.01 | 1+ | NA | NA | 53.23 | 0.244 |
| | | 1- | NA | | 37.21 | |
| | DM_2.03 | 2+ | 89.00 | 0.723 | 50.41 | 0.711 |
| | | 2- | 82.83 | | 45.74 | |

TABLE 14

Efficacy test of multiple QTLs. Differences in disease resistance by least-squares means (LSM_DIFF) are provided (LSM_DIFF = % of infected plants without DM resistance QTLs-% of infected plants with DM resistance QTLs). "All Negative" refers to plants lacking each of the three resistance QTLs, while "All Positive" refers to plants having all three resistance QTLs.

| Cross | QTLs | INBRED TEST DM rating score (%) | | | | HYBRID TEST DM rating score (%) | | | |
|---|---|---|---|---|---|---|---|---|---|
| | | All Negative | All Positive | LSM_DIFF (%) | p-value | All Negative | All Positive | LSM_DIFF (%) | p-value |
| CV339885/ CV357626 | DM_1.01-DM_2.03_DM 6.01 | 90.20 | 85.00 | 5.20 | 0.3031 | 4.33 | 4.87 | -0.54 | 0.7066 |
| CV523685/ CV357626 | DM_1.01-DM_4.01_ | 79.42 | 62.23 | 17.19 | 0.0001 | 67.33 | 50.16 | 17.17 | 0.0060 |
| CV338784/ CV357626 | DM_6.01 | 74.08 | 61.00 | 13.08 | <0.0001 | 57.45 | 41.99 | 15.46 | 0.0062 |
| CV337135/ CV357626 | | 73.50 | 93.68 | -20.18 | 0.3996 | 43.58 | 43.53 | 0.06 | 0.9968 |
| CV335787/ CV357626 | | 86.67 | 76.00 | 10.67 | 0.2029 | 64.88 | 54.84 | 10.03 | 0.3744 |

TABLE 14-continued

Efficacy test of multiple QTLs. Differences in disease resistance by least-squares means (LSM_DIFF) are provided (LSM_DIFF = % of infected plants without DM resistance QTLs-% of infected plants with DM resistance QTLs).
"All Negative" refers to plants lacking each of the three resistance QTLs, while "All Positive" refers to plants having all three resistance QTLs.

| | | INBRED TEST DM rating score (%) | | | | HYBRID TEST DM rating score (%) | | | |
|---|---|---|---|---|---|---|---|---|---|
| Cross | QTLs | All Negative | All Positive | LSM_DIFF (%) | p-value | All Negative | All Positive | LSM_DIFF (%) | p-value |
| CV356987/ CV357626 | | 65.58 | 35.72 | 29.86 | <0.0001 | 50.54 | 28.94 | 21.59 | <0.0001 |
| CV357626/ CV375547 | | 97.71 | 60.64 | 37.08 | 0.0005 | NA | NA | NA | NA |

TABLE 15

Equivalency test of individual QTLs (* the presence and absence of a selected resistance QTL is shown by plus (+) and minus (−), respectively).

| Cross | QTL | QTL Profile* | Yield (quintal/hectare) | p-value |
|---|---|---|---|---|
| CV357626/CV375547 | DM_1.01 | 1+ | 70.30 | 0.129 |
| | | 1− | 56.30 | |
| | DM_4.01 | 4+ | 80.78 | 0.761 |
| | | 4− | 84.53 | |
| | DM_6.01 | 6+ | 62.18 | 0.557 |
| | | 6− | 59.01 | |
| CV523685/CV357626 | DM_4.01 | 4+ | 97.99 | 0.883 |
| | | 4− | 96.49 | |
| CV343114/CV357626 | DM_1.01 | 1+ | 72.89 | 0.879 |
| | | 1− | 70.81 | |
| | DM_2.03 | 2+ | 87.77 | 0.011 |
| | | 2− | 61.61 | |

TABLE 16

Equivalency test of multiple QTLs. Yield differences by least-squares means (LSM_DIFF) are provided (LSM_DIFF = yield from plants without DM resistance QTLs - yield from plants with DM resistance QTLs; measured in quintals/hectare). "All Negative" refers to plants lacking each of the three resistance QTLs, while "All Positive" refers to plants having all three resistance QTLs.

| | | HYBRID TEST | | | |
|---|---|---|---|---|---|
| Cross | QTL model | All Negative | All Positive | LSM_DIFF | p-value |
| CV339885/CV357626 | DM_1.01-DM_2.03_DM_6.01 | 68.4383769 | 60.84911512 | 7.59 | 0.1391 |
| CV523685/CV357626 | DM_1.01-DM_4.01_DM_6.01 | 67.06 | 54.49 | 12.57 | 0.0965 |
| CV338784/CV357626 | | 63.89661472 | 60.56268131 | 3.33 | <0.0001 |
| CV337135/CV357626 | | 65.38536565 | 55.94532966 | 9.44 | 0.6530 |
| CV335787/CV357626 | | 64.48961024 | 62.26780695 | 2.22 | 0.0001 |
| CV356987/CV357626 | | 71.46531304 | 73.94449948 | −2.48 | <0.0001 |

Example 7: Introgression of Downy Mildew Resistance QTLs into Additional Maize Lines A maize plant comprising one or more, two or more, three or more, four or more, five or more, six or more, seven or more, eight or more, nine or more, or ten or more DM resistance QTLs is crossed with an elite maize line comprising a desirable trait (e.g., improved yield under water, temperature, or pest stress conditions), but susceptible to DM. $F_1$ progeny plants from this cross are assayed for one or more SNP markers exemplified in Tables 7 and 8 to select for DM resistance QTLs. A selected $F_1$ progeny plant is then backcrossed with the parent elite maize line comprising the desirable trait (recurrent parent). Plants from the BC1 generation are also genotyped using SNP markers exemplified in Table 8 to select for DM resistance QTLs. After multiple rounds of backcrossing (e.g., 5-7 generations) with the recurrent parent line, a new elite maize line is obtained comprising both DM resistance and the desirable trait in the recurrent parent line. Using the above introgression and marker-assisted selection strategy, the pyramiding or stacking of multiple DM resistance QTLs can be achieved.

As various modifications could be made in the constructions and methods herein described and illustrated without departing from the scope of this disclosure, it is intended that all matter contained in the foregoing description or shown in the accompanying drawings shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method of creating a population of corn plants or corn seeds resistant to Downy Mildew (DM), said method comprising:
   a) genotyping a first population of corn plants or corn seeds for the presence of one or more marker loci linked within 10 centimorgans (cM) of a DM resistance allele within a DM resistance quantitative trait locus (QTL) DM_1.02;
   b) selecting from said first population one or more corn plants or corn seeds comprising said one or more marker loci linked to said DM resistance allele selected from the group consisting of:
   SEQ ID NO: 7, comprising an A at position 328; and
   SEQ ID NO: 8, comprising a T at position 29; and
   c) producing from said one or more corn plants or corn seeds a second population of corn plants or corn seeds comprising said DM resistance allele at said DM resistance QTL DM_1.02, wherein said second population of corn plants or corn seeds comprises at least one corn plant or corn seed having improved resistance to DM as compared to a corn plant or corn seed lacking said DM resistance allele at said DM resistance QTL DM_1.02.

2. The method of claim 1, wherein said DM resistance allele at said DM resistance QTL DM_1.02 is linked within 5 cM of any one of said marker loci selected from the group consisting of SEQ ID NOs: 7 and 8.

3. The method of claim 1, wherein said second population of corn plants or corn seeds further comprises DM resistance QTL DM_9.01.

* * * * *

SEQUENCE LISTING

<160> NUMBER OF SEQ ID NOS: 570

<210> SEQ ID NO 1
<211> LENGTH: 599
<212> TYPE: DNA
<213> ORGANISM: Zea mays
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t

<400> SEQUENCE: 1
tcgttccnna ggaggtgtac tcctgatgag tgtctgtttt tntataccct ctttnccgct      60
ttaangaaag gcngagctcc tgccattttt caanaaaaaa angtgcaaag ttccagacag     120
ttttaaggta aattccaatc atgtacaagg gcttcagact cagtcagatg ccgatgtaca     180
aacatgttac attcgtgtgc tgctgtgctt tttttttnagg aaagccatac gacgcacttt     240
attgattatc aaacatgtta catcgtttac cagtctgaag aataacacca gagggttcat     300
cgaccccaaa tacagtttcc tttcaagaga nagctactct gctagttcat gtgccacctg     360
tgcgtttgta aattggacac agcattctgg gagcagtgca cggcatcctc gtgaaaaatg     420
agaagaaaaa aaanggatat tcttcactg cctccgtctc ctttcatctc cggtatacgt     480
atngctggac aagacacaca tctatacaga tcgcatcact ggtaaacttg cacagagtaa     540
atgattacac gtccagctct ttatgcggct acagctagag gtctttggct ggtctttat      599

<210> SEQ ID NO 2
<211> LENGTH: 805
<212> TYPE: DNA
<213> ORGANISM: Zea mays

-continued

```
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(53)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (196)..(203)
<223> OTHER INFORMATION: n is a, c, g, or t
<220> FEATURE:
<221> NAME/KEY: misc_feature
<222> LOCATION: (206)..(215)
<223> OTHER INFORMATION: n is a, c, g, or t
<220> FEATURE:
<221> NAME/KEY: misc_feature
<222> LOCATION: (219)..(223)
<223> OTHER INFORMATION: n is a, c, g, or t
<220> FEATURE:
<221> NAME/KEY: misc_feature
<222> LOCATION: (226)..(232)
<223> OTHER INFORMATION: n is a, c, g, or t
<220> FEATURE:
<221> NAME/KEY: misc_feature
<222> LOCATION: (235)..(243)
<223> OTHER INFORMATION: n is a, c, g, or t
<220> FEATURE:
<221> NAME/KEY: misc_feature
<222> LOCATION: (245)..(246)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (254)..(256)
<223> OTHER INFORMATION: n is a, c, g, or t
<220> FEATURE:
<221> NAME/KEY: misc_feature
<222> LOCATION: (259)..(261)
<223> OTHER INFORMATION: n is a, c, g, or t
<220> FEATURE:
<221> NAME/KEY: misc_feature
<222> LOCATION: (263)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (326)..(339)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (360)..(365)
<223> OTHER INFORMATION: n is a, c, g, or t
<220> FEATURE:
<221> NAME/KEY: misc_feature
<222> LOCATION: (417)..(417)
```

```
<223> OTHER INFORMATION: n is a, c, g, or t
<220> FEATURE:
<221> NAME/KEY: misc_feature
<222> LOCATION: (441)..(443)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (453)..(454)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (473)..(474)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (508)..(515)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (730)..(731)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (795)..(797)
<223> OTHER INFORMATION: n is a, c, g, or t
<220> FEATURE:
<221> NAME/KEY: misc_feature
<222> LOCATION: (802)..(803)
<223> OTHER INFORMATION: n is a, c, g, or t

<400> SEQUENCE: 2
cgcctgcgcg ctgctcatgt cggacgtagc cannagnncn nnnnnnnnnn nnntcaggtc      60
gtccacctcc tggtgcaagt tcctgatgta gttgcatgtc tcctgcaaca ccctcgcaga     120
tggcacctgc atggggaaga cggcanatta aagggagaac aatttaccgg accgtcggct     180
caagctcatc tcacannnnn nnnatnnnnn nnnnnttgnn nnncannnnn nngannnnnn     240
nnnanngctn catnnnatnn ntnnnnnnnn atntagtagg ggccattcaa cttttgactg     300
gaaatttggg ccaatttgat ngttgnnnnn nnnnnnnnnc aggtcggcng taggtaccan     360
```

| | | | | |
|---|---|---|---|---|
| nnnnnccgta | tcagatcaca | tttcttaggc | ctcaatgtgt | agcgaatgcc gccacanggt 420 |
| aatgctaatt | tttcagctaa | nnncctaana | acnntantag | agattttgga tannccattc 480 |
| agctnataaa | gtggtaacgt | acgatatnnn | nnnnngaact | tcagttacat actcttgcat 540 |
| tgctctgaag | gcgagcttcg | gggaggaggt | cctgcagctt | tgatacaagg tcgctgatct 600 |
| gctcctcagt | gatcctcgac | gaaccagact | gcctggaccg | tgacctccgg ttcgacatct 660 |
| cggtnggtgt | ggctgtctgg | gccggagata | ttggtgaacg | aagncttgcn agagaccgag 720 |
| aaagaaactn | ngatggtagg | agtgagngna | agcaatgcaa | gcaagtttga ganacacaga 780 |
| tgatgatgaa | atggnnntca | annac | | 805 |

```
<210> SEQ ID NO 3
<211> LENGTH: 842
<212> TYPE: DNA
<213> ORGANISM: Zea mays
<220> FEATURE:
<221> NAME/KEY: misc_feature
<222> LOCATION: (2)..(21)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (298)..(305)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (354)..(360)
<223> OTHER INFORMATION: n is a, c, g, or t
<220> FEATURE:
<221> NAME/KEY: misc_feature
<222> LOCATION: (400)..(401)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (762)..(763)
<223> OTHER INFORMATION: n is a, c, g, or t
<220> FEATURE:
<221> NAME/KEY: misc_feature
<222> LOCATION: (766)..(766)
<223> OTHER INFORMATION: n is a, c, g, or t
<220> FEATURE:
<221> NAME/KEY: misc_feature
<222> LOCATION: (831)..(837)
<223> OTHER INFORMATION: n is a, c, g, or t
```

<400> SEQUENCE: 3

```
tnnnnnnnnn nnnnnnnnnn naaatgcctg gcaatctcaa ggtaaaagta ctgtctgtct      60
gggtgcagtc ataacacgca ccatttcatt tatgttttg gatcctgcag gttgcgtatt      120
ttgtgaattc tgggacngaa gcgaatgagt tggcaatgtt gatggcccgg ctgtatagtg     180
ggaatctcag tatggttgcg ctcngaaatg catatcatgg cggaagtgcc ggtacgattg     240
gattgactgg tntgcagacg tggaaatacc caattcctca ggtatgtgta cagtgtannn     300
nnnnnttgcn ctttcatnaa attatttgac tggttatgtt ttcanagtca catnnnnnnn    360
gtttgctgca gtagattctt agttatcaat aattatctcn ncgttctacc cagcaaaaat    420
gtatccattt ctttattaca tctatcatag cctcataaga attttttgcag ggtgaaatac   480
atcatgtcat gaaccctgat ccttatcggg ggactttcgg gtctgatgct gcagcttatg    540
ctaaggaagt cgaagaacac ataacttatg gaagttcagg aagggttgca ggcttcattg    600
cagaaacatt ccangtataa actttgaaca gaccatttat aaaatgctag aactaattga    660
aataatatgt atcttttgtt tataaaccca attcaaaata acttatcctt gtcgcaatct    720
tgttgataca ccatctctgc tgtagggtgt gggaggtgct gnnaantagc tcctggatac    780
ctaaagttag cttatgacat tgtgcgcaag gctggtggcg tttgtattgc nnnnnnngtc    840
ca                                                                   842
```

<210> SEQ ID NO 4
<211> LENGTH: 428
<212> TYPE: DNA
<213> ORGANISM: Zea mays
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t

<400> SEQUENCE: 4

```
ctccttgaaa ccgtcctccc gggcccattc cgtcttctca ctgccctggg caccttcggg      60
attcttagct gtntcgcgtg tgccagcttt gttctggtga tgatgagatg cagaagcttt    120
cctcgacggt ttttccttct ccggtcgaga ttctttgcta ggctcaggag tgtaagcttt    180
ccagacagca ctttgctgaa cgataagcct gtgcagctcg aaaaacttgg tgattgcagc    240
ttgtggatct acttcagaag attcccttat ctcagaaaaa attctgtaaa agnacgtana    300
gattanattt atttgtccag ttcatgagct aaagtaaaca atgtagctcc ctagagaaaa    360
aaaaactaga cataaaagaa aaggtaaagc atgtgcgttg caataaggaa acaagatcct    420
gggatgca                                                              428
```

<210> SEQ ID NO 5
<211> LENGTH: 331
<212> TYPE: DNA
<213> ORGANISM: Zea mays
<220> FEATURE:
<221> NAME/KEY: misc_feature

```
<222> LOCATION: (1)..(1)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t

<400> SEQUENCE: 5
ngtgaccata caaaaatcat gcaatgaact ctacaagcca gtatgtcact ggcatttctt      60
ggcttcatct ggtagatagc anttcttatc ctcactgtcg ggtggtggcg gcacaccaaa     120
tacccagtcc agcacattca ggtacttgga ccggaagact tctctttcct gcgcatagca     180
gtgcataatg atagaggtag ctatgctgaa cacaaccaca tcagctcgct ttatctgaag     240
tattggaggg cagagtcctg catcggtcat ccatgtgaaa aaactctcga tagctctggc     300
aagacagtac agggatatct caatcctcct g                                    331

<210> SEQ ID NO 6
<211> LENGTH: 390
<212> TYPE: DNA
<213> ORGANISM: Zea mays
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (51)..(98)
<223> OTHER INFORMATION: n is a, c, g, or t
<220> FEATURE:
<221> NAME/KEY: misc_feature
<222> LOCATION: (159)..(160)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (253)..(254)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t

<400> SEQUENCE: 6
tcggagaagg acgcgacgtt gctgaagtca cgagccgcct cccgaangct nnnnnnnnn       60 nnnnnnnnnn nnnnnnnnnn nnnnnnnnnn nnnnnnnnca tgcaggcagg tgtggagcga     120
gcgagggagg tagcttggct tggctaggta cagaactann cntcttctcg tgtntctctg     180
cggagtagtt ttcagtaccg ccaccagtac gtaccaagaa ggaagtagcc ggggtgtctc     240
atagctggtg tgnngctagt aggnaacgag ggtgcatggg aaagcctcct cagcacccttt    300 ccttcgcgat cgatggatgg taaggactga ggagagcgag gagctgaagg aagcaatgga     360
gaggagagac cagggaatat aagcaagggc                                      390

<210> SEQ ID NO 7
<211> LENGTH: 553
<212> TYPE: DNA
<213> ORGANISM: Zea mays
<220> FEATURE:
<221> NAME/KEY: misc_feature
<222> LOCATION: (328)..(328)
```

<223> OTHER INFORMATION: n is a, c, g, or t

<400> SEQUENCE: 7

```
tataaatgct taaacttaac ctggtaaatt catctacagg ctctttcaaa tggcaaaccc    60
actgttgttg agtttatgc aaactgatgt gaagtctgca gggaactagc tccagatatc    120
tacaaagttg aacaacaata caagtaattt gtttacacac cacttttcac atttctgaac   180
tttaagcctt gattgagaat aacaattgtg attcatttaa taaaatcaat gcttgtcgat   240
gctttgttgc gttgcctatc ctattaacca cgttgattga accttgctat gggcatgaca   300
gttgggatcc aagttgctgc acgacagnca gaaccagcga acaccacgga caacgacgac   360
gacgaaccag agcaggtccg cttctcgctc ttgggtggca agaactgcag caacgttggt   420
gtcacgaccg ccattaggcc catgaacaac gccaggctga ggtccaggga tggaggcaac   480
gccacgccca cgaccatcac ccacagtgac tctgcatcgg ggagcatgag gacgatttgt   540
acgccatcac aat                                                     553
```

<210> SEQ ID NO 8
<211> LENGTH: 511
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t

<400> SEQUENCE: 8

```
tcacctggga gctctgggta tcacgggang cactcgatca gccactcgag gctctgcatg    60
aaacagattg catagaataa tggatgtaag gttagcagac ctgcaaactg tagcatgcat   120
gaatcntgat tcatggcaac cagtgtcttt cnaaaaacaa aagagaaaaa aagaaggaga   180
gaagcgtacc attaggcatt ctggtagatc atcgtcctgc gtcctcatgt gagtctgcat   240
atatgtaaag agctactcat taggcatttc cagtctaact cgaatctgag catgtaaatt   300
tggagtctga tatctgtttt gaagctaacc gacttgagct tctgctagtt acagttcata   360
ctttgattta tatatgnata ccaagttcta aacaatagca natntgacaa aatttataac   420
gagaaatgca ggacttgggg ggtgttcacc tccatcacca aatggcatga gggctccttg   480
cctgtggcaa ggcaagcaag agctaccact g                                 511
```

<210> SEQ ID NO 9
<211> LENGTH: 410
<212> TYPE: DNA
<213> ORGANISM: Zea mays

```
<220> FEATURE:
<221> NAME/KEY: misc_feature
<222> LOCATION: (177)..(177)
<223> OTHER INFORMATION: n is a, c, g, or t

<400> SEQUENCE: 9
tcgttgctcg gcggcggcga cagcatccgc tcaaccccag ccatgttgtt gcccaggagc    60
tcgttggcca gctcatcctc gagatcgttc tccaccagcc gcttgacacc gcggagcaca   120
tggagtgcca atccgtcggc gagcctgagc actatgatct tccagtacgc ggtcagncgt   180
gccctcaagt cgaatgcctg cgctgctaag tcagggtgcg tcctaagatg acccacgttc   240
acttccccga agcattccag ggtaacctta gatggctcgg acttgttctc cacagaaccc   300
atgaacttct tctggcctac cattatggct tcccaagtct tcatgtagtc agggctcgcc   360
gtgtagcctg ccaccagctc catctctatc atctccttgg acgtgctgag              410

<210> SEQ ID NO 10
<211> LENGTH: 812
<212> TYPE: DNA
<213> ORGANISM: Zea mays
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (710)..(712)
<223> OTHER INFORMATION: n is a, c, g, or t
<220> FEATURE:
<221> NAME/KEY: misc_feature
<222> LOCATION: (717)..(720)
<223> OTHER INFORMATION: n is a, c, g, or t
<220> FEATURE:
<221> NAME/KEY: misc_feature
<222> LOCATION: (750)..(757)
<223> OTHER INFORMATION: n is a, c, g, or t
<220> FEATURE:
<221> NAME/KEY: misc_feature
<222> LOCATION: (775)..(791)
<223> OTHER INFORMATION: n is a, c, g, or t

<400> SEQUENCE: 10
gtgctcagtg gtcagtgcga ggtgtccacg agtcaattna agttggtttc ttattcgtac    60
aaagcatgca actcttgaac agtttaataa ctacatattt gtcggatgat cctttcttct   120
ctcttagctt tggcttgtct tgggagtctt cctaatggcc acgagcctca gaatgtatgc   180
cacgtgccag cagcttgctc atgctgcagc tgccaacagt tttctcggcc acactgagct   240
gcgtgtgcat gtaccgccgt ccattaccct tgctacgaga ggccggttac agagccttag   300
acttcaactg gctcttcttg atcgtgaatt tgacgattta ggtgtgccaa tacattccat   360
tcgactcatt tgatggttta tagtgtttcc tgaaaactta gtgccatgga aattttttgt   420
ttcagattat gacactctga gagcattgga tgctgacaat agcccacatg ctccatctat   480
gagtgaagaa gaaataaatt ctcttcctgt cttcaaatat aaagttcagg cacaacagag   540 gcatcccccct gcccgaaaaa ggtaaagccg aattgtcctt tgggttgatt tgttcatatc   600
accatatcga gttggttcca gtatttccca tcaacacatg accacatttt aattctgaaa   660
tggagacatg aagtaatttt ttctaatgtt tgttttccaa tagtgatggn nnatctnnnn   720
tatcagtttc ttcaactggg tccggcaatn nnnnnntga taaatactga cttgnnnnnn   780
nnnnnnnnnn nttgaaaagt atcttattat ca                                 812

<210> SEQ ID NO 11
```

```
<211> LENGTH: 817
<212> TYPE: DNA
<213> ORGANISM: Zea mays
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (681)..(682)
<223> OTHER INFORMATION: n is a, c, g, or t

<400> SEQUENCE: 11
cggctaccgc gacggctccg agctgcggtt cgacgccacg gtgtcgggca cgctgggcga    60
gggccgcctc acggaggtgg aagggatcaa gaccaaggtg ctcgtctggg ccagggtcac   120
cgccgtcaag gccgacgccg ccaaggtcca cttcaccgcn gggatcaaga ggtcgcgcag   180
ccgggacgcc tacgaggtcg tcaggggcgg catcaccgtc gacgagttct agcttagttt   240
tgctttcgcg gctcacatgg atggacgggc ttcctcttgc tcgctgcacg ctgagatgga   300
caagattgtt gctttcagtt gcaagaataa attctacacc cattagctat gtgcaggggc   360
ggagccagga ttacgatata agggggggcca atcaactaat caatattata tgataaaaaa   420
tattatataa tgttataaag tttaagcact cgctatggaa taagaattct aaatctttat   480
aaattatttt ggtccatgag tccatttcct agctaattga tatattgaac taaagttatg   540
acgtaagaca ataccaaaaa ataaagacga taaaatgatg aatatccgac taatgagatt   600
caacttttat ataatggatc tagtattcat gagacaacta acaaatgtat gagagaattc   660
aaaaatccaa ctagccttaa nnatccatga aaattcgtca acctatgcag gtacatgtta   720
aaatttgttg tgtacacacc aactatcaga tgacaacttt agttgaaatt tgtagattta   780
ttatctacga gatctaatgg agtatgtata taagttg                            817

<210> SEQ ID NO 12
<211> LENGTH: 392
<212> TYPE: DNA
<213> ORGANISM: Zea mays
<220> FEATURE:
<221> NAME/KEY: misc_feature
<222> LOCATION: (34)..(34)
<223> OTHER INFORMATION: n is a, c, g, or t

<400> SEQUENCE: 12
gccacccgca agcacccaac cagtcgagtc tgcngccgct gctgtagacg ttgattcggt    60
cgagaaaggc ccaggtacga caccagagca accggcgaag cgaagggcac ccaacgttcg   120
acgaggacag agaagggtgc tgcgaagcgc aacgagagaa ggaagagcga cgtaggggggg   180 ggatattgtt gctgtatact aaatattaac ggcccaaatt aaaggggggca acacatgatc   240 cctagctagg ttaactagag ctatagcaat gactggccgt ttccacgcgt acgagatgcg   300
tagtgtgcat catcaacctg tatccatgtt gtattatcgt aggagtcgta ggccttacag   360
tgaccacgcg tactggttag agttggtcgt tc                                 392

<210> SEQ ID NO 13
<211> LENGTH: 1674
<212> TYPE: DNA
<213> ORGANISM: Zea mays
<220> FEATURE:
<221> NAME/KEY: misc_feature
<222> LOCATION: (562)..(576)
<223> OTHER INFORMATION: n is a, c, g, or t
<220> FEATURE:
<221> NAME/KEY: misc_feature
```

```
<222> LOCATION: (674)..(674)
<223> OTHER INFORMATION: n is a, c, g, or t

<400> SEQUENCE: 13
cctgccccgt cccgtccgtc tccgtcccaa tcggatccac ccgcccgtcg tcgcctataa      60
actctccctc ccatccgtct cttgaggggg gcccggcttc ctcccaactg ccaccgattt     120
gtttgttcgg cttcggcccc atctccagtc acccgttccc acttcattgg tcgctgctcc     180
ctccctccac ggccgatccc gtgccggcga gagggaccat ggcggggaaa gggaaggagg     240
tgtacgtggc cgccatcgac cagggcacca caagcacccg gttcatcgtc tacgaccgcc     300
acgccaaacc cgtcgcatcg caccagctcg agttcaagca acactacccg gaggcagggt     360
gggttgagca tgatcctatg gagattatag agactgttaa ggtgtgtatg aaagaggcag     420
ttggcaaagc caaagctggt aaacacaatg tggttgctgg tttgaaggcc attgggatca     480
caaatcagag ggaaaccact gttatgtgga gtaaatccac tggccgtcca ctgtataatg     540
ccattgtgtg gatggatgct cnnnnnnnnn nnnnnngcag gagattggaa aatgagctgt     600
caggcggtag aacccacttc gtggagacat gtgggttgcc aatcagtacc tatttcagtg     660
ctctgaaatt attntggttg atggaaaatg tggatgctgt caaggatgca gtccggactg     720
gtgacgcctt attcggcacg atcgacacct ggttgatttg gaaccttaca ggaggtgttg     780
ctggtgggca gcatgtcacg gattgctcaa atgcatctcg tacaatgctt atgaatctaa     840
agacacttga ctgggataag ccaacacttg ctgtgttagg agttcctgtt gagattttgc     900
caaagattat cagtaattca gagaaaatcg gtgtggtcgc caaagagttc ccgtttgcag     960
gagttcccat ctcggggtgt cttggagatc agcatgctgc tatgcttggg cagctgtgcc    1020
agaagggtga agcgaaaagc acctatggaa ctggtgcctt catccttctt aacacagggg    1080
aagagcctac ccaatcctcc catggccttc ttagtaccat tgcttacaag cttggtccag    1140
ctgcacccac taactatgct cttgaagggt ccattgcaat tgcaggcgca gcagttcagt    1200
ggctgaggga cagccttgga atcattcagt cagcagctga gatcgaaaag ttggctgaaa    1260
cagtgccaga ttcaggtgga gtgtactttg tgccagcatt taatgggttg tttgcaccat    1320
ggtggagaga tgatgcgagg ggaatttgca tcggaatcac aaggttcaca aataaggggc    1380
acattgctcg agcagtgctc gagagtatgt gttttcaggt gaatgatgtc ctcagctcca    1440
tgcacaagga tgctggagag gcaggagaag taaagagcgc agaaggagag ttcttattgc    1500
gtgttgatgg tggtgctact gttaataatc ttctaatgca gatccaggct gatttattag    1560
gcagccctgt tgtcagacca gctgacatag agaccacagc cctcggagct gcatatgctg    1620
ctgggttggc tgcaggagtt tggaccaagg agaaggtttt tgcaggtttg caca          1674

<210> SEQ ID NO 14
<211> LENGTH: 459
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t

<400> SEQUENCE: 14
cacagatctc caaaaacttt gtggcctcaa atcaattgga gtantgaatt cccactccct      60
tatctgttat cttctttctt gccagggttt ggtgcaggat cctcgcgttc cagggcagct     120
gttgccaggg ctgctccagc aatcaacaat tctcagactc ttgataatgc tcctccacat     180
```

| | |
|---|---:|
| cctgctgatg gagatgcccc tccacatgct gccgatggag gtgctcctcc acatgctgca | 240 |
| gatggagatg ctcctccaat gaacaatgaa gaaattgcaa accaagatga aattatgatt | 300 |
| ggtgaagtag ctgtagatga tgaagatgaa gacgcaaact ctcatccagt tccagccagg | 360 |
| gatgcgtcga tggaaagtga gcttgccaat gaactgaagg gggatgcctt ggatgactac | 420 |
| gatattgatg tcagtaacga aggacaggct atcgcagag | 459 |

```
<210> SEQ ID NO 15
<211> LENGTH: 678
<212> TYPE: DNA
<213> ORGANISM: Zea mays
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (577)..(578)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (641)..(651)
<223> OTHER INFORMATION: n is a, c, g, or t
<220> FEATURE:
<221> NAME/KEY: misc_feature
<222> LOCATION: (655)..(658)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (671)..(673)
<223> OTHER INFORMATION: n is a, c, g, or t

<400> SEQUENCE: 15
```

| | |
|---|---:|
| atttagcatt acaccaaaat gcaaagaaat gtccattgtt caaaactttt ttcctatatc | 60 |
| atcatagtaa ttgaactttt tcttggaatc aagtataaat gaacagataa tgcttgaata | 120 |
| ccttaaaata tacgcctttt ttccttccag tgccatcata gcgtattcca ataagcttct | 180 |
| gtacaacaaa ttcatccttg tcaagagtgt cagcatcctc ttgatcctct gaacctgcta | 240 |
| aattcgaatc cacntcttga tgaacatatt tttcacataa gactgcccat tccttaagga | 300 |
| gagcaagaaa ctcatcagct ttctcatttc gcacctacat tcaaaggtcc aaanaaactt | 360 |
| tttgagagca gctggacaga acagatgaaa tccaagatgc agcttaatat gcatacctca | 420 |
| gtctgtggat gattgtattt taaactttgg cacgcaaaac tgttaagatc aacagcccat | 480 |
| cgctgcaatc atagccataa cagtagaatc agtggtaagt aagaacatgt tctatccaac | 540 |
| agataactag gtagaatatt acagtttcaa gtttcanncc agaaagagca gcacccaagc | 600 |
| aangaccagt ggacatgccc ccacagcccg aatacangnc nnnnnnnnnn nctgnnnnct | 660 | ctgncatatt nnntgacg                                                        678

<210> SEQ ID NO 16
<211> LENGTH: 590
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (383)..(385)
<223> OTHER INFORMATION: n is a, c, g, or t
<220> FEATURE:
<221> NAME/KEY: misc_feature
<222> LOCATION: (401)..(402)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (489)..(497)
<223> OTHER INFORMATION: n is a, c, g, or t
<220> FEATURE:
<221> NAME/KEY: misc_feature
<222> LOCATION: (501)..(503)
<223> OTHER INFORMATION: n is a, c, g, or t
<220> FEATURE:
<221> NAME/KEY: misc_feature
<222> LOCATION: (505)..(511)
<223> OTHER INFORMATION: n is a, c, g, or t
<220> FEATURE:
<221> NAME/KEY: misc_feature
<222> LOCATION: (528)..(535)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (553)..(553)

```
<223> OTHER INFORMATION: n is a, c, g, or t
<220> FEATURE:
<221> NAME/KEY: misc_feature
<222> LOCATION: (557)..(565)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (576)..(579)
<223> OTHER INFORMATION: n is a, c, g, or t
<220> FEATURE:
<221> NAME/KEY: misc_feature
<222> LOCATION: (583)..(586)
<223> OTHER INFORMATION: n is a, c, g, or t

<400> SEQUENCE: 16
tacnttttcc cccnagnnnc agtaagttca ttgaactttt gggnagcnat gatcagtgaa      60
gagtaaagac ttccccaggt atgcaaaccc tagcccctag gcgacagtat ataacatgac    120
tagatgttta gaatctagat gtagaaatat ttaggtgcaa attagttaaa ttgattgatg    180
ggtacattgt tgatgnatta tgtacttcct tggattgtga agaaggattg agatatgaaa    240
agacagtaaa gtttccgcgg ttccacngac gtcgtgtgtc acccttccac ttcccgcttt    300
atgcagcaaa ataaggtaa aattgcttta tgcagcaaaa ataaggtaaa attgtgcaca    360
actnaggatt caaaacttgg tgnnnggctc cacattcaca nntatctaac caacaganca    420
acacatattt ttnngtttta ttaaaacaaa gtctactcat gtgatatata aaatcatag    480 caatgtacnn nnnnnnnact nnnannnnnn natttattag tactcccnnn nnnnnaaact    540
ataaactttc ntngatnnnn nnnnnttntt atgcannnnc atnnnncact                 590

<210> SEQ ID NO 17
<211> LENGTH: 721
<212> TYPE: DNA
<213> ORGANISM: Zea mays
<220> FEATURE:
<221> NAME/KEY: misc_feature
<222> LOCATION: (365)..(365)
<223> OTHER INFORMATION: n is a, c, g, or t

<400> SEQUENCE: 17
ggatgcgccc cacgacctcc cgtgactctc ccagtcccag gctcccagcc ccgccttcct      60
cccgcctccg cgagaccgcg atggcagtct tgctgtggcg gtgcatatgc gggccccaac    120
aatccttcag taagaatcga ggcgcatcca ccccttctcc tcctggtaag ccttcgaacc    180
actccctctc ctcccgtcct ccgtatgcct ccttcatttc ttcttgctgc ctctcgaatt    240
ctcagctcct atgcattttt ttctttcttt ctctaagtta tgttcagttc ttggatatcc    300
ttataactcg ctgaggattc cgatccctaa catcgacaat tcttgctctt gcttcatgca    360
cagcnggcag gagatccaaa tactcggac aatctgtggt aaggagcgca cgcattgagc     420
tttccctgct acaccgatgc atttggttca tttctcctga aaaaaagta cactggaggc    480 aaaagcttga aaaaaaaaca tgtcttgtga aaccaagagc ttgtgtgctc cggttctact    540
aataattcgt gtagcctcag ctttctgatc ctgatgtctg tatttccatg tccgcagaaa    600
gcaatgccca tgcgtttgtt aacggttgga agaagaggt ctcggggac acaactcctt      660 gttgaagaat acaaggagaa gctcggtcac tattgcgagt tcgaggacac tcttatcagg    720
c                                                                      721
```

```
<210> SEQ ID NO 18
<211> LENGTH: 1100
<212> TYPE: DNA
<213> ORGANISM: Zea mays
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (538)..(556)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t

<400> SEQUENCE: 18
cgacggcacg aagatgagcg cggcagcgac ggcgagagag acggccaccc atggcgacgg      60
gaagaantgc agcacgaacc ctccgcacca cncgctgaca agccggcccc ggtggcccgc     120
tacggcgtca agcatctcgc cgtagtcgtc aggaagccgc gccccgacgg tctcctcacc     180
tagctcccgg aacanggcca ccagctcggt gtccgtgcgc cgcgtgctgg caaggacccc     240
tcgcttgcgg agcatggccg cgtcctgtgg gcaacgaatc aggccctcca tccgcgctac     300
gtgcgccgtc acgcatgcgc cgtgcgccca gtagaagtgt ttctcgaagg ccaggaggtt     360
gtggagcaca gccgcgctgt actcgtggac gtggaagcac gggacggtca tcacggccac     420
cgggctcgcc gggtgtcgcc agaaccacat gtccaggtcg ccgcagctcg acgacgcctc     480
gcggaaccac accgctgacc tncgaagctc catggagcag gggaacagnc gctccgannn     540
nnnnnnnnnn nnnnnnagct tccgtggcgt cgagaggacg aagtacttgt ccttggncac     600
gcgggaccag tggaagaggt gcaggacgtg gtggaactcg ccggcggcag cgctgtnggc     660
gncgcgacgc gcncgcttgg ggcagatgtc gtcgaaacat ccgagcacga gctcctcgac     720
ggagttccgg agcttgagcc cagggcacga agcggcgaga agcttgatgg ctctgaacgg     780
gacctggttc tcgagcacga gcatgtcgag cttgatgtcg tcggcgtgct gcgccacggc     840
catgtgcagt atgaagtagt ccttgctgat ggacgccgcc cgcgtcacgc tgtcggcgtc     900
gtcgcctgtg ccggccttgc tgagcatcaa gctcaccacc aggatgaagc agctgtccag     960
```

```
cagcagcatc tccagcagct tcgcctcgtc gtctagaatc tccacggcgg gcccgtccga    1020
gccgtcgtcg gcgaactcac agcggaggcg gtcgcgctcc aggcagagcg cctcgacgta    1080
cccgtccacg tcgaggccgc                                                1100
```

```
<210> SEQ ID NO 19
<211> LENGTH: 660
<212> TYPE: DNA
<213> ORGANISM: Zea mays
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (570)..(571)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (608)..(612)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (637)..(645)
<223> OTHER INFORMATION: n is a, c, g, or t
<220> FEATURE:
<221> NAME/KEY: misc_feature
<222> LOCATION: (647)..(649)
<223> OTHER INFORMATION: n is a, c, g, or t
```

<220> FEATURE:
<221> NAME/KEY: misc_feature
<222> LOCATION: (651)..(653)
<223> OTHER INFORMATION: n is a, c, g, or t

<400> SEQUENCE: 19

```
ttttgcaagg accttttctg gtttacatgc tagaggaatc gagcctggtg ttctttatcc      60
agctgtctct gttgagcagt ttcacgaacc ccatgcttat aagtaacttc atgcttgcat     120
atctccttac atttaggtct nacttattca gtttatagan taaacanatn tttttaccat     180
tatcatatta anatttagct aaagtagaca acnatctttt gtacaggttg aatttcctat     240
caatcaaccg gtttgagagg aaaaagaatc ttgatcttgc catttcagca tttgctttgc     300
tccgttctgc tgcttggact ntacctggtg atgctctaca agaagcaaca ttaacagtgg     360
caggtgttta tattttattt ttccttctag ttgcatgttc aatgttacaa caccnccggt     420
tttaaaccat atgaaatatt gactgctgat ttcctacnat gccnattatt taggtggcta     480
tgataagcgt ctcaaggaaa atgttgaata ccttgaggaa ctcaaaagac tcgcattgac     540
ggaagggtt tctggacagg ttaantttgn nacatcttgc tcaacatctg aaaganacga     600
gcttctcnnn nnctgcctct gcgnnttata cactccnnnn nnnnntnnnt nnngcttaca     660
```

<210> SEQ ID NO 20
<211> LENGTH: 358
<212> TYPE: DNA
<213> ORGANISM: Zea mays
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t

<400> SEQUENCE: 20

```
ccaataaaca tgccactaga ttatccaata tcaatggacc aaactaaact cttgcaaaag      60
nnggnnaaca tgcactggtt aacaccaatt caccccatag ccagcaacag agctagttta     120
cagtaaagag aaattgacat tattcttcta taaatgaacc ttatttatat tcatgtgtgc     180
ttgatttgtt tttaacatac actatggaat atgcacgtcc ttaaaancat gcatgtgtgc     240
ctataaccca ataacatga cagcattaaa gaaattattc atatccgaat tacattgaat     300
cctaactgtg aaaatctgga aatggagatg tgaaggaaag agcaaaaggc acacctca      358
```

<210> SEQ ID NO 21
<211> LENGTH: 773
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:

```
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (650)..(651)
<223> OTHER INFORMATION: n is a, c, g, or t
<220> FEATURE:
<221> NAME/KEY: misc_feature
<222> LOCATION: (666)..(668)
<223> OTHER INFORMATION: n is a, c, g, or t
<220> FEATURE:
<221> NAME/KEY: misc_feature
<222> LOCATION: (672)..(680)
<223> OTHER INFORMATION: n is a, c, g, or t
<220> FEATURE:
<221> NAME/KEY: misc_feature
<222> LOCATION: (691)..(692)
<223> OTHER INFORMATION: n is a, c, g, or t
<220> FEATURE:
<221> NAME/KEY: misc_feature
<222> LOCATION: (695)..(696)
<223> OTHER INFORMATION: n is a, c, g, or t
<220> FEATURE:
<221> NAME/KEY: misc_feature
<222> LOCATION: (698)..(700)
<223> OTHER INFORMATION: n is a, c, g, or t
<220> FEATURE:
<221> NAME/KEY: misc_feature
<222> LOCATION: (703)..(707)
<223> OTHER INFORMATION: n is a, c, g, or t
<220> FEATURE:
<221> NAME/KEY: misc_feature
<222> LOCATION: (721)..(725)
<223> OTHER INFORMATION: n is a, c, g, or t
<220> FEATURE:
<221> NAME/KEY: misc_feature
<222> LOCATION: (731)..(761)
<223> OTHER INFORMATION: n is a, c, g, or t
<220> FEATURE:
<221> NAME/KEY: misc_feature
<222> LOCATION: (763)..(772)
<223> OTHER INFORMATION: n is a, c, g, or t
```

<400> SEQUENCE: 21

```
catncctgca gtgtaagctt gaatctgtct ttacaatcgt gaaccataag ctgagtcctg    60
ttacagggca actctccttt ggcagagggt tgaagagagc agagagctat ggcatctcat   120
gnttccctgc caagaaagag aagccctgaa actggacagc ttaggcattc catttcctga   180
tcatgtaaac aatgagttct ttcctctctt atcttgacct cacngttttc tgctcactgt   240
gggnctgcgg cactgcaata tttatatagt gaacatatcc ttgataagan gtgtacttct   300 tgatttttn cgaagggttt taaaccatgg atatcctctt ggcatccaac atctcccttt   360
cccttttgcc ctcatggttt tgtctctctg aagttctcac cccactatcg gattcccttt   420
ctcgttcnag atcgagaccc ttctttggca attggcacta ccacagaac ngtagctgct    480 ggtgattttc actttactaa gacaaaccga tngttcagta ntttgactac acagtaaagt   540
tagtgatgct gccacactta ctgctggcga tttccatttt cttaagagaa aacaattgtc   600
nagtacagca tttgtctatt tgaccacaca gtaaaattag ntgntgctgn ntcactaatg   660
tttctnnnct gnnnnnnnnn acatgatctg nngcnnannn gcnnnnntca ctcataatag   720
nnnnnatagt nnnnnnnnnn nnnnnnnnnn nnnnnnnnnn ngnnnnnnnn nnc           773
```

<210> SEQ ID NO 22
<211> LENGTH: 372
<212> TYPE: DNA
<213> ORGANISM: Zea mays
<220> FEATURE:
<221> NAME/KEY: misc_feature
<222> LOCATION: (29)..(32)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 22

```
ggttgtttgg ttcttgctac ttctgtaann nncatagtgc ttaatcctct tccagccntt    60
atcctcttcg atcttagcca taatananat ttgccaatca atatnttggc caataatggg   120
gagcaacgta cacaaacaag tagctagcag aacatggaga atattttccn ctttctcaca   180
tttgtgcgcg catgaanttg acaaacaatt ggcagtccgt acgtgcgagt agtattattt   240
tgtgtgctga gattagttca tggaataatc atccacgtgt cgccgtggtc atcattatcg   300
tcattcaaca aattggagtg gacgggcata cgatataatt ttctaactat accaagataa   360
ttatcagcgg ca                                                        372
```

<210> SEQ ID NO 23
<211> LENGTH: 736
<212> TYPE: DNA
<213> ORGANISM: Zea mays
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (694)..(698)
<223> OTHER INFORMATION: n is a, c, g, or t
<220> FEATURE:
<221> NAME/KEY: misc_feature
<222> LOCATION: (715)..(728)
<223> OTHER INFORMATION: n is a, c, g, or t

<400> SEQUENCE: 23

| | | | | | | |
|---|---|---|---|---|---|---|
| acctacctct | ttatgccact | gtcgccagaa | tgtgctaaaa | aaagaaaag | tacataccta | 60 |
| ttatgttaat | gttcccatat | ggcgattaga | atctagaagc | ttcattcccc | cttttctaat | 120 |
| gttctgtgca | ttggtgcccc | agtcctggtt | ggtttgactt | tgatcgatag | caaagaacaa | 180 |
| catgaatcca | tgcgcaatta | ttagatatat | atcgctacaa | atgcagaact | gctctctgga | 240 |
| tttatttctt | tgcatatcag | tactgcatgg | atatatacct | gtttaaaact | tggtcacatc | 300 |
| tgtcaaatgc | ttgctcatta | cacaggagct | tgaagatgga | agtgttctcc | ttcggtttgc | 360 |
| tcatctatat | gaggttttgc | actgctaccc | ttactctcac | ttgttncagg | tgaggtaaat | 420 |
| cctaattttc | ttttctatgt | cttgccctgt | gctgtcgtgc | acataggccg | gggaggacaa | 480 |
| ggatctttcg | tctttagcga | gtatcgacct | caagagagtg | ttcccggaga | agaaggttcc | 540 |
| ctccgtcact | ctgttgtttt | acttacgctt | attctagtct | tcagcattcc | taactcagat | 600 |
| tcttgatccc | tcgctctaga | ttggcaaggt | catcgagaca | agcttatcgg | caaaccaaga | 660 |
| acgcgcagcc | atggagaaga | agcgtttgaa | atgnnnnncg | caaggttctg | cggcnnnnnn | 720 |
| nnnnnnnntt | cggggt | | | | | 736 |

<210> SEQ ID NO 24
<211> LENGTH: 1210
<212> TYPE: DNA
<213> ORGANISM: Zea mays
<220> FEATURE:
<221> NAME/KEY: misc_feature
<222> LOCATION: (6)..(10)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t

<400> SEQUENCE: 24

| | | | | | | |
|---|---|---|---|---|---|---|
| tgcctnnnnn | accttactca | aacagtatgg | aaaagtatta | ggcctagatc | ctaaaaggat | 60 |
| tccacagaat | tgggcagcca | ctcaatttgc | tgaagcattg | gcagagcat | gggccgagta | 120 |
| taacaatgac | aggtcagcgc | ttttctatgc | agcatgagtt | gtattattca | gaatttctag | 180 |
| aaaatgtaag | tgtcaattaa | catgtttgt | tctcttttgt | cgctcagtgc | tgttgttttg | 240 |
| atggttgtcc | aacctgaaga | agaaatatg | tacgaccagt | actgtcttgt | caatcatctg | 300 |
| aaggaatcat | atcctttttt | atgtttgctt | tcttttcagt | tttcactcct | attgtcagat | 360 |
| tttcaatatc | tgggttgtga | aaaacttcat | ttagttattg | actnattcct | atcgtgatag | 420 |
| tgtttcctta | tctgtggttt | ggcggctcgt | ctccacaaca | aactaataag | atgttgattt | 480 |
| cttgtatgta | cactgctgta | ttattctttc | aacatattgc | ctgcctgata | taacttcaga | 540 |

```
gaaccattaa agtgtgcggc aagcatctgc ttttttttg ggtctggtat taagagcatc    600
caacagcatg aaaaatgtgg ctttccttaa ctagccatca catatggtgt ggcaactata    660
aggaaaacat tggcacaagt agaggctcaa gggcaggttc ttacagatgg aacacttgtg    720
gtgtaagtat cttatataga catggaaaaa ggcttattat tactatcaga atttagtatg    780
taaatttatg aattgcagag atggtcggac agtggctgtt gtgtatttca gagccgggta    840
tgcaccaact gattacccct cggaagcggt atgcaatcaa atatctatta attcaaaatc    900
tttatataga atagaagtaa attctgtttt ttgagtgaaa gaaactgttc ctgtaattgt    960
tttaaaaaaa tcatatgtct ggtgcaatgc cgcttagtct cattttcctg aaacagtcat   1020
cttcttttgt gcatgcattt ctgtctctgt tggaaagcaa tccttagcca aatggtttta   1080
ttgctttggt tgaggatgtg tagtaattca ttttgttatg attatgatat ggcaccactg   1140
ttccaccttg ataacgct atcatattcc aggagtggag agcgaggctt ctgatggaac    1200
aatcatctgc                                                          1210
```

<210> SEQ ID NO 25
<211> LENGTH: 379
<212> TYPE: DNA
<213> ORGANISM: Zea mays
<220> FEATURE:
<221> NAME/KEY: misc_feature
<222> LOCATION: (342)..(342)
<223> OTHER INFORMATION: n is a, c, g, or t

<400> SEQUENCE: 25

```
ctaccaccac tgggccagtt accaacacta caaaagctag ttatgggagg aatggacagc     60
actttgacag ttgatgaggg tttctgctgc gccggcccgg gagcctttcc tctattacag    120
gaacttcaac tatgccaaat ggagaacctg gaagtgtgga acacaacata ctcctgtggc    180
cagagcaatg aggatgtgca ggaattcatg ttcccaaacc ttagggaact gttaattcgt    240
gattgcccca agttgagact gaaaccatgc ccacctaaaa ctgtgggatg gaagatagag    300
aacagcgaca atgtactgtc gtcatgggat gaggagggag anatcgacct tgcagcattg    360
ttcccatcaa ggaaagagt                                                 379
```

<210> SEQ ID NO 26
<211> LENGTH: 829
<212> TYPE: DNA
<213> ORGANISM: Zea mays
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t

<400> SEQUENCE: 26

```
agtatgggaa ttttgtgtgt aagccagaca caagtcgcta tgctggtgtg ccattgttgg     60
ttcgacattt atgtgtattt cagtggagct ttgcatctca agttcagttg gcgcataaat    120
```

```
atgaaccgtg ctatttggcg taatcaaaat agccaacttg tgtggtggca tgcatttctg    180
aaagttgaaa atttgccncc aacataggtc ttgtttggta gagctctcaa cggctcttat    240
agtagaaatt tagaaatgcc catgttcata tgttttcgtt tttaacctct tgagctcacc    300
tctgttcaga tatatgctcc ctcgttttta acctcttgaa tctcacttct gttcagatac    360
atgctcgact tcattttacc aacctatcga tgtggtaaaa tttgttgccg attgtctcca    420
gctgacaaac cctggccaac cttttttgga cagggatcgt ttaaaggtac aatttgtgga    480
taaaagttgt cacatgcaat ttaactcagt gaccaactaa tctgttccta tctacaattt    540
tttagcttaa gagagccctg cgcggagttc ttgttgagac tgaacaccag cagggaaaga    600
gaagcatcta caggataact gggattactn ctnttccatt gnctcaactg aggtacccac    660
cggttcatat ctcttccctc cttgcctgtt tggtctagta ccaagaagac gaacttattc    720
atttccattt cttgtcttca gcttttcttg taacgaaggc cctcagctga ctgttgttga    780
gtactttgca caacggtaca atgtccagct gcgctacact gcttggccc                829

<210> SEQ ID NO 27
<211> LENGTH: 379
<212> TYPE: DNA
<213> ORGANISM: Zea mays
<220> FEATURE:
<221> NAME/KEY: misc_feature
<222> LOCATION: (102)..(102)
<223> OTHER INFORMATION: n is a, c, g, or t

<400> SEQUENCE: 27
agtttcatca tctgggtaca acatcagacc gatgacactg ctacagtgga gacgaaatgc     60
aagaatgaat taacatctct ggactttggc attctatgat gnggggtcct agaagcacca    120
aactgtacag cggaaactca acaccgtacc cacccataga atcattactc actttcataa    180
tcatcttcat ctccgaacga gaacaccgag gcatctgcgg caatcgcctt gaattcgctc    240
atgctggaag agtcagcagc tggaggaggt ggtgctgtgg tggagctggc cttgctgctg    300
acttcagttt tgagagatgt accatcaggt gcctttgtgg ttccctgttc gctgcttata    360
gccactttgt ccagtaaaa                                                 379

<210> SEQ ID NO 28
<211> LENGTH: 532
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (232)..(237)
<223> OTHER INFORMATION: n is a, c, g, or t
```

<400> SEQUENCE: 28

```
atttataacn aggaatctnt tcttctgttt gctctatagc caatgcttgt gttactgctc     60
taaatggttt gctgctgtaa gattgggtac tnacaacaag atccatttt tggatgtgca    120
gagccacctt atggccgagt ctatttctga gctacagaag aaggtaacta aagctgaaaa    180
aactttcaag gcagttgcac tcaggcttnc aaaanaaaac agcacttgag tnnnnnnggc    240
catttacctg ctgatgattt gtggttcaga atgctctgca tctgaacagc catcaacagt    300
agattgatca ttgcagaaat gactgttggt actgctgtgg tgtgcaggag aggtcactgc    360
aggaggagaa caaggctctg cagaaggaag taagctgcca gagactgact gcaccctaaa    420
ccattgcatt ggcaacagaa gggtttgatg tgtgtctcct cttttgtgt agcttgcgga     480
gaggcagaag gccgtcgcga ccggcagca gcaggtgcag tgggaccagc ag             532
```

<210> SEQ ID NO 29
<211> LENGTH: 356
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t

<400> SEQUENCE: 29

```
catatataat aactactgta ggcagcggca tctcctgctg ggacgaagnt tcaagaagct     60
agctaagaga gaagggcata acgagataat aagcagcgcg cgaagatgca agactgggcg    120
ccggtgttcg tctcgctggt gctcttcatc ctgctgtcgc cgggcctgct gttccagatg    180
ccgggcaagt gccggatcat cgagttcggc aacttccaga ccagcgccat ctccatcctc    240
gtccacgcca tcctcttctt cgccctcgcc gccatcttcc tcgtcgccgt cggggtgcac    300
atgtacctcg gctcctaggc ggcggcgcgg ggcgccgtac cttctctccc tctcta        356
```

<210> SEQ ID NO 30
<211> LENGTH: 382
<212> TYPE: DNA
<213> ORGANISM: Zea mays
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (177)..(179)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t

<400> SEQUENCE: 30

```
tgtacatctg tatgtgatgt gtcatgtgca catgctttgc cattttgcat tggcaataat     60
aggttgtgca tcccttcagc gctacaagga gcaaggatgt ccgcttcaga ttaaatcnga    120
ctgtttagac tgctgcaact gtaatcatag agataaatac actatagaaa cagtagnnng    180
```

```
agccnatacg aattaaaaac aacgaacagg ctgaaagatg cagcgcttgt ctgcacaaca    240
tccccaaagt atcttcgagt cgaatacaac agggtaactg agtgtaacca cagttcgtac    300
agaatttgta gagaaaatga attgtccaaa ccaccggata aattcatctt gttacaatgt    360
ttnctggcag aatagctcgc nc                                             382
```

```
<210> SEQ ID NO 31
<211> LENGTH: 1263
<212> TYPE: DNA
<213> ORGANISM: Zea mays
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (602)..(605)
<223> OTHER INFORMATION: n is a, c, g, or t
<220> FEATURE:
<221> NAME/KEY: misc_feature
<222> LOCATION: (782)..(783)
<223> OTHER INFORMATION: n is a, c, g, or t
<220> FEATURE:
<221> NAME/KEY: misc_feature
<222> LOCATION: (808)..(809)
<223> OTHER INFORMATION: n is a, c, g, or t
<220> FEATURE:
<221> NAME/KEY: misc_feature
<222> LOCATION: (814)..(817)
<223> OTHER INFORMATION: n is a, c, g, or t
<220> FEATURE:
<221> NAME/KEY: misc_feature
<222> LOCATION: (842)..(847)
<223> OTHER INFORMATION: n is a, c, g, or t
<220> FEATURE:
<221> NAME/KEY: misc_feature
<222> LOCATION: (850)..(853)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (873)..(875)
<223> OTHER INFORMATION: n is a, c, g, or t
<220> FEATURE:
<221> NAME/KEY: misc_feature
<222> LOCATION: (901)..(903)
<223> OTHER INFORMATION: n is a, c, g, or t
<220> FEATURE:
<221> NAME/KEY: misc_feature
<222> LOCATION: (911)..(913)
<223> OTHER INFORMATION: n is a, c, g, or t
<220> FEATURE:
<221> NAME/KEY: misc_feature
<222> LOCATION: (919)..(920)
<223> OTHER INFORMATION: n is a, c, g, or t
<220> FEATURE:
<221> NAME/KEY: misc_feature
<222> LOCATION: (922)..(927)
<223> OTHER INFORMATION: n is a, c, g, or t
<220> FEATURE:
<221> NAME/KEY: misc_feature
<222> LOCATION: (929)..(932)
<223> OTHER INFORMATION: n is a, c, g, or t
<220> FEATURE:
<221> NAME/KEY: misc_feature
<222> LOCATION: (934)..(935)
<223> OTHER INFORMATION: n is a, c, g, or t
<220> FEATURE:
<221> NAME/KEY: misc_feature
<222> LOCATION: (941)..(941)
<223> OTHER INFORMATION: n is a, c, g, or t
<220> FEATURE:
<221> NAME/KEY: misc_feature
```

```
<222> LOCATION: (948)..(951)
<223> OTHER INFORMATION: n is a, c, g, or t
<220> FEATURE:
<221> NAME/KEY: misc_feature
<222> LOCATION: (955)..(956)
<223> OTHER INFORMATION: n is a, c, g, or t
<220> FEATURE:
<221> NAME/KEY: misc_feature
<222> LOCATION: (959)..(961)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (971)..(973)
<223> OTHER INFORMATION: n is a, c, g, or t
<220> FEATURE:
<221> NAME/KEY: misc_feature
<222> LOCATION: (975)..(979)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (983)..(988)
<223> OTHER INFORMATION: n is a, c, g, or t
<220> FEATURE:
<221> NAME/KEY: misc_feature
<222> LOCATION: (993)..(994)
<223> OTHER INFORMATION: n is a, c, g, or t
<220> FEATURE:
<221> NAME/KEY: misc_feature
<222> LOCATION: (998)..(1007)
<223> OTHER INFORMATION: n is a, c, g, or t
<220> FEATURE:
<221> NAME/KEY: misc_feature
<222> LOCATION: (1009)..(1009)
<223> OTHER INFORMATION: n is a, c, g, or t
<220> FEATURE:
<221> NAME/KEY: misc_feature
<222> LOCATION: (1011)..(1037)
<223> OTHER INFORMATION: n is a, c, g, or t
<220> FEATURE:
<221> NAME/KEY: misc_feature
<222> LOCATION: (1039)..(1051)
<223> OTHER INFORMATION: n is a, c, g, or t
<220> FEATURE:
<221> NAME/KEY: misc_feature
<222> LOCATION: (1053)..(1057)
<223> OTHER INFORMATION: n is a, c, g, or t
<220> FEATURE:
<221> NAME/KEY: misc_feature
<222> LOCATION: (1062)..(1065)
<223> OTHER INFORMATION: n is a, c, g, or t
<220> FEATURE:
<221> NAME/KEY: misc_feature
<222> LOCATION: (1067)..(1076)
<223> OTHER INFORMATION: n is a, c, g, or t
<220> FEATURE:
<221> NAME/KEY: misc_feature
<222> LOCATION: (1078)..(1081)
<223> OTHER INFORMATION: n is a, c, g, or t
<220> FEATURE:
<221> NAME/KEY: misc_feature
<222> LOCATION: (1083)..(1118)
<223> OTHER INFORMATION: n is a, c, g, or t
<220> FEATURE:
<221> NAME/KEY: misc_feature
<222> LOCATION: (1121)..(1125)
<223> OTHER INFORMATION: n is a, c, g, or t
<220> FEATURE:
<221> NAME/KEY: misc_feature
<222> LOCATION: (1127)..(1127)
<223> OTHER INFORMATION: n is a, c, g, or t
<220> FEATURE:
```

<220> FEATURE:
<221> NAME/KEY: misc_feature
<222> LOCATION: (1129)..(1131)
<223> OTHER INFORMATION: n is a, c, g, or t
<220> FEATURE:
<221> NAME/KEY: misc_feature
<222> LOCATION: (1133)..(1146)
<223> OTHER INFORMATION: n is a, c, g, or t
<220> FEATURE:
<221> NAME/KEY: misc_feature
<222> LOCATION: (1151)..(1170)
<223> OTHER INFORMATION: n is a, c, g, or t
<220> FEATURE:
<221> NAME/KEY: misc_feature
<222> LOCATION: (1172)..(1174)
<223> OTHER INFORMATION: n is a, c, g, or t
<220> FEATURE:
<221> NAME/KEY: misc_feature
<222> LOCATION: (1178)..(1186)
<223> OTHER INFORMATION: n is a, c, g, or t
<220> FEATURE:
<221> NAME/KEY: misc_feature
<222> LOCATION: (1188)..(1202)
<223> OTHER INFORMATION: n is a, c, g, or t
<220> FEATURE:
<221> NAME/KEY: misc_feature
<222> LOCATION: (1204)..(1217)
<223> OTHER INFORMATION: n is a, c, g, or t
<220> FEATURE:
<221> NAME/KEY: misc_feature
<222> LOCATION: (1223)..(1230)
<223> OTHER INFORMATION: n is a, c, g, or t
<220> FEATURE:
<221> NAME/KEY: misc_feature
<222> LOCATION: (1235)..(1240)
<223> OTHER INFORMATION: n is a, c, g, or t
<220> FEATURE:
<221> NAME/KEY: misc_feature
<222> LOCATION: (1247)..(1255)
<223> OTHER INFORMATION: n is a, c, g, or t
<220> FEATURE:
<221> NAME/KEY: misc_feature
<222> LOCATION: (1259)..(1259)
<223> OTHER INFORMATION: n is a, c, g, or t

<400> SEQUENCE: 31

```
catatctctt atagtagtgg cctactacaa aataggggtc cgtgatgtac atgccgaagt      60
gaataagtac tgctcattca ttgttggcat gggtataatt actgtactag ccaacttctt     120
gcagcacttc tactttggta taatgggaga gaaaatgacc gagcgtgtca gaaggatgat     180
gttttctggt atgaccgtct tttcctttat gttacttttg tagtcccata tttaatggtg     240
caacctcagc tcttataaac tatctagttt aacatccata aataaagcac ntattcatga     300
gtattgaaca caagaaacaa tgctgctgtg ctaagttcta ttgtgtatag attatagtaa     360
accattgttg aaatatcaga gttctcacat tctgtttact gtattccagc aattctgcgc     420
aatgaagttg gttggtttga cgacgaagaa aatagcgcag acatattatc aatgagactt     480
gcaaatgatg caacatttgt ccgcgctgct ttcagtaaca gactttctat attcattcag     540
gatacatcgg ccattcttgt tgcacttctt cttggtatgt tactacaatg gcgtgttgct     600
cnnnnttgtt tccgaatcca taccgaagtt tatatctatt atttgagaaa atgtaggatg     660
aatttaagat ttatctttta tgaatcttaa caagctggat gttaaaaaca agaatacaaa     720
tttatattgt atattctata tcatatttat tcgcaatcaa agaaaaaact gattaccgaa     780
tnnataccgt ttccgaccgt tttcatcnnt aatnnnngca attctgcgca atgaagttgg     840
tnnnnnngan nnngaagaaa atagcgcagn cannntatca atgagacttg caaatgatgc     900
nnnatttgtc nnngctgcnn tnnnnnnncnn nntnnctata ntcattcnnn ntacnncgnn     960
ncntcttgtt nnncnnnnnc ntnnnnnnta ctnnaatnnn nnnnnnncnc nnnnnnnnnn    1020
```

```
nnnnnnnnnn nnnnnnncnn nnnnnnnnnn ntnnnnnccc cnnnntnnnn nnnnnncnnn    1080
ncnnnnnnnn nnnnnnnnnn nnnnnnnnnn nnnnnnncc nnnnngncnn ntnnnnnnnn     1140
nnnnnnccct nnnnnnnnnn nnnnnnnnnn cnnnctcnnn nnnnnncnnn nnnnnnnnnn    1200 nncnnnnnnnn nnnnnnnctt ccnnnnnnnn cttcnnnnnn tcttctnnnn nnnnntccnc   1260
ccc                                                                  1263

<210> SEQ ID NO 32
<211> LENGTH: 254
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t

<400> SEQUENCE: 32
agggtagtat atgtgcattc atcgtttttc attagccttg attagnccaa agtgatagtt    60
tatgcttggt catcgagagt ttggtgatca gacgatgaag attgtgagtg cacaactta   120 agaggtaaac agttgtgtga ttcaacatag tagagtgaca aatgatcgac tcatagagag   180
ccctcgtatg agacgtgagc gacactcctt cataggtgtt ctaataagga ttagttagaa   240
gtgtcaactc ttga                                                     254

<210> SEQ ID NO 33
<211> LENGTH: 1049
<212> TYPE: DNA
<213> ORGANISM: Zea mays
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t
<220> FEATURE:
<221> NAME/KEY: misc_feature
<222> LOCATION: (1038)..(1044)
<223> OTHER INFORMATION: n is a, c, g, or t

<400> SEQUENCE: 33
atagtggtgt aacccatgcc gagcatccgg aggagggcaa gtgctccta gctgatgatg    60 gaaatatcca gaagtctggg gttatggtca agaaaaaga gacacatgga caaaacgctg   120
gggctagttt ggatttaact gaaagagttg agaatgttga cactggtgaa aaggcgagcg   180
gaggtaaaat cggtgatatt ggcactagtc aactgagcat gacactgtat gagaaaagtc   240
aggctgctca cagggaggag aggccacgca ggtatgaagg cgtgcatgtt gagtctcaca   300
aagctctgat cgaagagttg gagaggtctc tttcgttcag cagtgaggat gantacttct   360
cggacgaagc agaaagcagt ggcctcagtg atgctctgcg taaccaaatg ggtagccgca   420
ggtttatgct aggggggcaga gtgaatgatg cgccccgaag cgatccacat ggtcgattga   480
ttgaagaact agagatgtct ttcagcgatg cagaagagcc attggagcag catgctatgg   540
gttcagagag agtncatgga aatgtgcttg acaaggatcc acagatcctg antgataaaa   600
gtgcacatcc atgtgaagaa agcctctcat catttgagag tggacacctc aaatctgaac   660
```

| aaactcctca ccaggaaagc agggcaatag ggcaatagg caatggcaat caaggaaatg | 720 |
| agcgtattga agataacaat aatactgccg actctgttca tgggagtgag catattgtga | 780 |
| ttgacgatga caaaattgca gatatattcc acgagaaaga acatgataag gattgccagc | 840 |
| ttgcaaacat agaaagtgca tacccttctg aaggaagcac ctctgctgtc gatgattgca | 900 |
| gtattgaagt tcagcaaagt tttcaaccaa atgacctgac agcagtcgat gagtgcagta | 960 |
| ttgaagttca gcaaagtttt caaccaaatg acctgacagc agatgtcaat caagaaatgg | 1020 |
| aagatgataa gataaccnnn nnnnacata | 1049 |

```
<210> SEQ ID NO 34
<211> LENGTH: 576
<212> TYPE: DNA
<213> ORGANISM: Zea mays
<220> FEATURE:
<221> NAME/KEY: misc_feature
<222> LOCATION: (379)..(379)
<223> OTHER INFORMATION: n is a, c, g, or t

<400> SEQUENCE: 34
```

| ttggatctcg tctcggcctc cggcacagag tttgcgcaag aagacgacaa cggcgatgag | 60 |
| gacgatgacg gctccgacga tgatgaggaa agcgactttg acgaggactt caacgacgtg | 120 |
| gttaggatga accctcaatt gtctagaccc cagagaggtt gctggtttca gttgtctaga | 180 |
| ctccagagag gttgacctag atgatgtatg taaaaacatg caggagggtg tgttttcggt | 240 |
| tgatgaggac gacgaagatg acggagagga agaggaggag gaggaggacg acgacgacga | 300 |
| cgatgacgag gacctaccaa gctggtccaa ccttgagacc gtgaattcct gccatccact | 360 |
| gtactttgca aggatgatng tagaggtaca cgatcgaagt ttggcagcat gtcttgtcag | 420 |
| caactgcact cttaactaaa tccattattc ccagactgca accaagtcta gcatagactg | 480 |
| gctggaccgg ccacctgcaa gccttgtcgt cgagggccag ctgaggcctg cctttgctga | 540 |
| ggagagcacc atggttgcca agcatatatc aagtga | 576 |

```
<210> SEQ ID NO 35
<211> LENGTH: 594
<212> TYPE: DNA
<213> ORGANISM: Zea mays
<220> FEATURE:
<221> NAME/KEY: misc_feature
<222> LOCATION: (362)..(362)
<223> OTHER INFORMATION: n is a, c, g, or t

<400> SEQUENCE: 35
```

| tatatcacga tcaagtgatg gctgtgttgg aaaaatgagg tggagtatct tacctgacta | 60 |
| cactatttct gtctaacctc aaatgatttt tgagctgttt tctgtttgga cctgacattg | 120 |
| taatggcaac aggtcaaatt ttcttggcac taaattcatc gtgcatgaca ctcgagcacc | 180 |
| acacaatgct gggagccttg tctcctgtga gcgcggcagc cgcagaatct cctctaggag | 240 |
| ggtttccccc aaggtaccca ctgccagcta ccccattgcc cgggtgaact atgagctaaa | 300 |
| cctgcttggc acaagggggc ccaggcgtat gaattgcacg atgcattcca tcccagcctc | 360 |
| ancgctggac cctcaaggca tggtgcctga gcctggccaa cccaagcagc tcttcatccc | 420 |
| tggctcgtcg tccttcgaag aatcctttcg cagtgcaaac aacacccctt ccagctcaag | 480 |
| gttctcggtc gcagaccgct ccttggactg gagctcctct cgattctcag agacgagcgg | 540 |
| attggctcag caggacgaca atgacagtga ccaggctaag aagaggcctt tggt | 594 |

<210> SEQ ID NO 36
<211> LENGTH: 1474
<212> TYPE: DNA
<213> ORGANISM: Zea mays
<220> FEATURE:
<221> NAME/KEY: misc_feature
<222> LOCATION: (999)..(999)
<223> OTHER INFORMATION: n is a, c, g, or t

<400> SEQUENCE: 36

```
tgtatgacat gttcatcgag gtcgattgca taacaatcaa gatgtagctg tcaaggttca      60
atatcctgga ttggagcagc gaatgaagat agacattatg acaatgtcat tcttgtcaaa     120
aatggtctct tgggtttttc ctgattataa atttgacaga atactaattg aatttgagaa     180
atccatgaca atggagcttg attttacgcg ggaggctaag aattctgaga gaacagccag     240
ctgcttcagg aaaaatagtg ttgttaaagt gccttatgtg ttctggcaac ttacaaccag     300
ggaggttttg acgatggagt tttgttatgg acacaaggtt aacgacttgg acttcctgcg     360
gaaaacagat attagcccta caaaggtagc taaggctttg attgaactct ttggtgaaat     420
gatatttgta catggttttg ttcacggtga tccacatcct ggaaatatat tagtttctcc     480
tgaaggccat gggaaatttt cactagttct gttggatcat ggaatttata gagaattaga     540
ccaaaagttc agattggact attgtcggct atggaaagca ctgatattgt tggattcaaa     600
caaaattctg gaattaggcg aacagtttgg cgttggcaaa tatgcgaagt acttcctgt      660
aatattcaca gggagaacta tagaaagcaa gtcagctctt ggcacacaaa tgtctggtga     720
agagcagagg cgtctgaagg aggacttaaa ctctcttggg atggatgata tatcttcatt     780
tatggaatcc ttgccaccgg acttctatgt catactacga acagacggac tattgaggtc     840
cattttaggg aatcttgggg caccacgcca tgttcggctt ctcacttatg caagatgtgc     900
tatacacggt cttgagaagc agcacaaaat ggagtctgat gttcaattgt gttcaggtgc     960
aatcagacgt atgttcttga atgtcaaaac aaatgtcanc tatctccgtc tgagagtgat    1020
tattgaaata gcggtattat tagctaaagc aaatggtgcc aagcagaaag tcctgaacac    1080
actcagacag atgttactgg agatcagtca aggttttcac cgccttattt gatgcccaga    1140
agtcagcgac gtggtgaaat taaggctacg agaaaggtgg gggaagttgg aagtacgtca    1200
ggactccgga gtagaatcat aactgtgatt gttctgtttc aacttgtaaa ttggaggttg    1260
tattgtgtca aggagtccaa tcataactgt gattgctctg ttgtaacttg taaattgtac    1320
ttctacgtcg agtctgcgct cgagagtcca ggtgtttttt ttgttggacc aagtacgcat    1380
cccaaaataa gtctacatct caaaattcga ggagtcaaac aaatcttaat ttgaagtttg    1440
gctaaattta taaaattggt attaacatta aaaa                                1474
```

<210> SEQ ID NO 37
<211> LENGTH: 669
<212> TYPE: DNA
<213> ORGANISM: Zea mays
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:

```
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (643)..(644)
<223> OTHER INFORMATION: n is a, c, g, or t
<220> FEATURE:
<221> NAME/KEY: misc_feature
<222> LOCATION: (646)..(647)
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (664)..(666)
<223> OTHER INFORMATION: n is a, c, g, or t

<400> SEQUENCE: 37
acaaatcact cgctactctt gcctacaccc tcacaatcat ntacgaatac tagtgactgc    60
tttcctctcc tcagcatttt tggcaagtgt tgtgctggcg tgccgtgtgt ggagnggaac   120
gctatataaa gcaacgtcta aaaagaaaa aaaatactat atattagcat actagtatat   180
aaatataaga gtaactccaa tagttttcta aaagactctc taaattaata atttaagtaa   240
ctaaactaaa agctcctctc caacggttct ctaaatgaac ttcataaatt tagctactnc   300
tcatctaacc ttattttctc tctacattta gnaacnattt accaactncn taaacaaaaa   360
aaaattgacn gtaattttg tatttcgctg ccttttcac tttatagtaa cgatatatta   420
acatagccca tgcgtcgaac aacgacagtc agctagagat taaataattg ccaatacaat   480
agccgcacgt ncacntgtcg gaaataaata aataaacaat tgcaacngta aatnaaaaga   540
tcaacacaac tcaccaagtt gaatatgcca tcgatnatgg tcccactcag atgagtgaca   600
tgttaaattt taacatattt agaaagtaat atatatataa ctnnntnnann agatgcgttt   660
``` tttnnntat 669

<210> SEQ ID NO 38
<211> LENGTH: 1115
<212> TYPE: DNA
<213> ORGANISM: Zea mays
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1108)..(1109)
<223> OTHER INFORMATION: n is a, c, g, or t

<400> SEQUENCE: 38 ggcttcttttt gctaaagagg gcctatgatt aacagttgga aacgaccata acaaaataga      60
cacaagttct ggcctggcac acagagatac ctatgcaaat catcagcatc aacacttctc     120
tggttgaacc taaatagagg attagatcat aggagaacat tcaagaacaa acgcagaaaa     180
cagatttagt tggccaacag cgaaggncta aagaagtcag caaatttagt agtaggcctg     240
aagccagcaa ttcattagcg tagacctaaa gaagccaaca aatccatcat cagaggccaa     300
gttttgagtt acattgacta atgactatga ggtaagaaac agggcatgga tctcaagcag     360
cggcaggctt gcgcagctca ctctcaccat gggcaaagtg gcatttgccg ccataagagc     420
atgacccttt tgcgaagttc tcacacatct tggtcttgaa gttgcttcct atgccactga     480
tgctaacaat cagctcgatg accatagcac tagcgttcct gatctgatca aaggtgccct     540
caaactcaat gttttttcaag ctggtgtctg attcatggcg gtcctcctga atgaccacct     600
tggcccctgt gacggaagat atttgcttta tgttagctcc acccttccca atgatgccac     660
ctgcaaggga cgcatcgaca ctgatcttgg ccgtggcata agcgccgaag ctagctggag     720
tggccaaacc agggttggcc ataggtggag gcgccatngg tggaggcgcc atgggtggag     780
gcgccatagg tagaggtgcc ataggtggag gcgccatagg tggaggtgcc atgggtggag     840
gcgccatagg tggaggcgcc ataggtagag gtgccatagg tggaggcgcc ataggtggag     900
gtgccatggg tagaggtgcc ataggtggag gcgccatagg tagaggtgcc atagttggag     960
gtgccatggg tggaggcgcc ataggtggag gtgccatagg tggaggtgca aaataaccgg    1020
ttggtggtgg tccgatgggg ggtggcatat agttgtccat catagacttg ccaagctccc    1080
tttcaccatg tgcaaagtgg natctgtnnc cccat                              1115

<210> SEQ ID NO 39
<211> LENGTH: 583
<212> TYPE: DNA
<213> ORGANISM: Zea mays
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (27)..(37)
<223> OTHER INFORMATION: n is a, c, g, or t
<220> FEATURE:

```
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (43)..(46)
<223> OTHER INFORMATION: n is a, c, g, or t
<220> FEATURE:
<221> NAME/KEY: misc_feature
<222> LOCATION: (48)..(51)
<223> OTHER INFORMATION: n is a, c, g, or t
<220> FEATURE:
<221> NAME/KEY: misc_feature
<222> LOCATION: (53)..(55)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (492)..(494)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (530)..(535)
<223> OTHER INFORMATION: n is a, c, g, or t
<220> FEATURE:
<221> NAME/KEY: misc_feature
<222> LOCATION: (539)..(548)
<223> OTHER INFORMATION: n is a, c, g, or t
<220> FEATURE:
<221> NAME/KEY: misc_feature
<222> LOCATION: (568)..(580)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t

<400> SEQUENCE: 39
ttttcttgta ctggatgaag tnnnccnnnn nnnnnnntnt aannnncnnn nannnatgca    60
tagaattttg gagcatgttg gaaggagacc tggaggcaca tctagggata ttcttggccc   120
acttgcgaga cgatctgagc gtcagactat cctggtttct gcaacaatac cattttcagt   180
tatacgagca gcaaggagtt ggggtcatga tccagttctc attagagcta aaagtgtagt   240
tccacttgat tcaatcactg tgccaagacc tgcgttatcn caaagtgacg ctaaccccag   300
ttcgtcatcg cagtcagtga accaagctgc tgttggcagc ttgccgccat ctttggaaca   360
ctactattgt acggccaagg cgcagcacaa ggttgacaca ttacgaggt gcatccatgc    420 tctggaagca cagacagtga ttgcatttat gaacaacacc aagccactga aggatgttgt   480
gtttaagttg gnnnccentg gtatcaaagc cactgagcta catggagacn nnnnnaagnn   540 nnnnnnncg acagttttga aaagttnnn nnnnnnnnn tnc                       583

<210> SEQ ID NO 40
<211> LENGTH: 839
<212> TYPE: DNA
<213> ORGANISM: Zea mays
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (771)..(777)
<223> OTHER INFORMATION: n is a, c, g, or t
```

<220> FEATURE:
<221> NAME/KEY: misc_feature
<222> LOCATION: (787)..(795)
<223> OTHER INFORMATION: n is a, c, g, or t
<220> FEATURE:
<221> NAME/KEY: misc_feature
<222> LOCATION: (804)..(833)
<223> OTHER INFORMATION: n is a, c, g, or t

<400> SEQUENCE: 40

| | | | | | |
|---|---|---|---|---|---|
| ctcgatcgcc | atgtctttca | ccggcacgca | ggacaagtgc | aaagcctgcg | acaagacggt | 60 |
| ccacatcatc | gacctcctca | ccgccgacgg | cgtctcgtac | cacaagacat | gcttcaagtg | 120 |
| cagccactgc | aagggcgtcc | tctcggtatg | catgcgtggc | ctgagctcaa | ctccgcatgc | 180 |
| gcattcgccc | tgcttgcgat | gtgtgcggca | atgcgctaat | gctcatttgc | atcgaaagaa | 240 |
| acgaagcttt | gtttgattcg | gttcagatca | tctcgacaga | ngaacatgta | gaaatacggt | 300 |
| ctcatttttt | catttctgca | tgcgtctcct | ccagattagc | agctactctt | ccatggacgg | 360 |
| cgtcctgtac | tgcaagacgc | actttgaaca | gctcttcaag | gagacaggga | ccttctcaaa | 420 |
| gaactttcaa | ggtaatctac | agctgaatac | tgtgccccct | atgtttctga | acccgtccac | 480 |
| agcgcgtgat | gctgtaacgc | tcaactctgg | tgcctgatgc | aatgcaatgc | aattcggacc | 540 |
| ctttaatttc | gttgtgttaa | ttactcaggt | ggagcatctt | caaacaagaa | cgaccaggtg | 600 |
| cggttcctca | aatcttctac | acaaatatgg | ctcaaatgct | caataagttc | taaaacttta | 660 |
| ttggccatgc | catcatcggt | aatagctgac | tacttacgca | cgatgccaat | ctgaaaatct | 720 |
| ctgcaggcaa | aggctccaag | caagctatca | tctgcattct | ctggaactca | nnnnnnntgc | 780 |
| gcggccnnnn | nnnnacagt | gtannnnnnnn | nnnnnnnnnn | nnnnnnnnnn | nnnctctgc | 839 |

<210> SEQ ID NO 41
<211> LENGTH: 163
<212> TYPE: DNA
<213> ORGANISM: Zea mays
<220> FEATURE:
<221> NAME/KEY: misc_feature
<222> LOCATION: (81)..(81)
<223> OTHER INFORMATION: n is a, c, g, or t

<400> SEQUENCE: 41

| | | | | | |
|---|---|---|---|---|---|
| tcatgaagaa | tgagtacttt | aacactgaaa | ttgtactgga | agactagagt | tatgttatt | 60 |
| acctagaatg | gctagctacc | nctgttgagg | aataccttga | tgcaataatg | tggcatcctt | 120 |
| ttcaacgtt | ttccacatta | attgattgtt | tacttgactc | aat | | 163 |

<210> SEQ ID NO 42
<211> LENGTH: 475
<212> TYPE: DNA
<213> ORGANISM: Zea mays
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (429)..(435)
<223> OTHER INFORMATION: n is a, c, g, or t
<220> FEATURE:
<221> NAME/KEY: misc_feature
<222> LOCATION: (438)..(443)
<223> OTHER INFORMATION: n is a, c, g, or t

<400> SEQUENCE: 42

```
atcttcggag tcgcttaggc cgagcgaccg aagcaggaac tcgacagcct ttcccttgtc      60
ccagtcgatc accgggcgaa cctctaaaac ctgcagcgta gcaaaagaat ttttttttc      120
gttgagtctt ggagcaagta tcaagatcaa nggcagtcgc agtagaacag tctaggctcc     180
taccattcgc ccgttggtta ctttgagacg agggaaggcc tccaagactt gtttcacgag     240
ncctgcgacc actttccagt cctgaaaaaa acaatagcat aaagctctca gtctcaggta     300
aattcgctac tgcttccctg taataggcgc ggtctgaatc tgatgcatcc tagtaaaaat     360
aaaaggatgt ctgaagccgt aatttcatcc atttctctac cgacaaaaaa aaggaaagat     420
aaacagatnn nnnnatnnn nnntgaaagt tcaggggca cgcaatctca ccttc            475
```

<210> SEQ ID NO 43
<211> LENGTH: 365
<212> TYPE: DNA
<213> ORGANISM: Zea mays
<220> FEATURE:
<221> NAME/KEY: misc_feature
<222> LOCATION: (299)..(299)
<223> OTHER INFORMATION: n is a, c, g, or t

<400> SEQUENCE: 43

```
ctgatatttg gatggagaca ttacactgcg agtggtacca aactgtagga aatggaaagt     60
tggttagagg ggaatcgaga gtagttccac tcacatggtc gttccaggcg tgatccctgt     120
tgtagatgat ggcagcgcca aggctcctag ctgggttgat gccagtgcca gtaatgggga     180
tggtggcaag gtggaccagg aacaccgcga acccaattgg cagtggggca aggatctgtt     240
ttcaccaaat aagggtttca ttcatcgtaa gtcttaacac aatatgaaaa atatgtatng     300
aagagtatgc atacattttc aatttgttga aacacaagat taaggaatca gctaaattcc     360
agtcc                                                                365
```

<210> SEQ ID NO 44
<211> LENGTH: 666
<212> TYPE: DNA
<213> ORGANISM: Zea mays
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (485)..(486)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (501)..(505)
<223> OTHER INFORMATION: n is a, c, g, or t
<220> FEATURE:
<221> NAME/KEY: misc_feature

```
<222> LOCATION: (515)..(528)
<223> OTHER INFORMATION: n is a, c, g, or t
<220> FEATURE:
<221> NAME/KEY: misc_feature
<222> LOCATION: (543)..(554)
<223> OTHER INFORMATION: n is a, c, g, or t
<220> FEATURE:
<221> NAME/KEY: misc_feature
<222> LOCATION: (566)..(579)
<223> OTHER INFORMATION: n is a, c, g, or t
<220> FEATURE:
<221> NAME/KEY: misc_feature
<222> LOCATION: (581)..(586)
<223> OTHER INFORMATION: n is a, c, g, or t
<220> FEATURE:
<221> NAME/KEY: misc_feature
<222> LOCATION: (588)..(600)
<223> OTHER INFORMATION: n is a, c, g, or t
<220> FEATURE:
<221> NAME/KEY: misc_feature
<222> LOCATION: (603)..(634)
<223> OTHER INFORMATION: n is a, c, g, or t
<220> FEATURE:
<221> NAME/KEY: misc_feature
<222> LOCATION: (641)..(663)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t

<400> SEQUENCE: 44
ccctgcaaat gcacttnnnc atgcaattgg attgtccacc ttgccccgcc caagcaccga    60
atcctcaatt cttggctgaa tcaggaactt ctcaatcttg caggcagaat cagcatcaat   120
gccagcagca tcaagcgaat caaggaggaa catgcaagac tgaaagcagt ttaagaagta   180
ctgtgagaag ggaagatcag cgcgatcagc gccatggtct atggctatca caatcttagg   240
agctagctgt ttcaccaacc caaggatcgc tggcagtggt ggtgcacgag cagagcaacc   300
agtcgggagg acaacaacta catcttcatc atcagnggca gaaatgaatt ctgcagggtt   360
gatcatatca gcactgatag cactgaactc aaagggaatt ccaaggtcan cagcaaactg   420
tgcaatgttg tcacgcgcaa gacacagctc cagtggatgg tgggaagcng tgttacagcg   480
cttannacac tgaagnaaca nnnnntcacc ggcannnnnn nnnnnnnngt ctttatgcac   540
cannnnnnnn nnnntctgat gactcnnnnn nnnnnnnnnc nnnnncnnn nnnnnnnnnn   600
gannnnnnnn nnnnnnnnnn nnnnnnnnnn nnntgtctg nnnnnnnnnn nnnnnnnnnn   660
nnnanc                                                              666

<210> SEQ ID NO 45
<211> LENGTH: 520
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t

<400> SEQUENCE: 45
ttgaagcatg tacattgcaa agatactact attaggttta gatnacaatt aatagatttg    60
```

| | |
|---|---|
| tttgtgacaa accgtgtttt ttgcatatcc atacacatga cattccgtag taaacatctc | 120 |
| tttagttttt ccattcctac agctactaac tatactactg caatcagata gatggtccta | 180 |
| ctctagttac gcaggattaa gtgatgcata gtattaatag caaatagntg gaacttggaa | 240 |
| ggttttgaac actcagctat gggtatggag aaaacatctt ttcaaactga tgcttttgta | 300 |
| tattcttatg tgacttgctt aaaatgcatg tcttatgcct tattagtgat ctcacaagat | 360 |
| acctgatgca aaaggtttcc accacaggtc atcatagatg aagctatcac caaattggat | 420 |
| gaggatttct tctggttggg tggcggagaa gttgacctca agctcggnat gcgaacctca | 480 |
| caattcttaa gtgtctttag tccattcgtg gtgaaatgca | 520 |

<210> SEQ ID NO 46
<211> LENGTH: 866
<212> TYPE: DNA
<213> ORGANISM: Zea mays
<220> FEATURE:
<221> NAME/KEY: misc_feature
<222> LOCATION: (7)..(13)
<223> OTHER INFORMATION: n is a, c, g, or t
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t

<400> SEQUENCE: 46

| | |
|---|---|
| gcctgcnnnn nnncannnac tggtttttcc aggccaccat ctcttagttc agatgatagt | 60 |
| gcctgggctt ggcatgaggc tgatgttata cgagttgttg atgatgtagc taatggtatt | 120 |
| ccatctacat acacaaatgg tgtatcatca ccaccctcca ctccatcttg ttctcaaaat | 180 |
| gaatctttgg atccagctgc tcacttgata acagggaatg agatcaataa tgaagctctg | 240 |
| acttctccat cttcggtgca agatagtcct gaagataaaa taangcaagt tgcaaaggct | 300 |
| gtgtcttgtg gcagtgaagt agttaaggca gatacattgc catatgccat gctgcggccg | 360 |
| atagttgttc ctagtatatc acgaaggtca tcangatctg agattaaggg tgctcatgat | 420 |
| cacaggagga gcccatgtgt accatcaaca aggagggaca tacctattct aagaagacct | 480 |
| ccatcaccag tagtacttag tgttcctcgc gtacctaggc caccacctcc ttcacctgct | 540 |
| ggagagtcaa gaaaacgagg gttccctatc gttagatccg gcagctcaag tcctcgacat | 600 |
| tgggggatga gaggtttatt ttctgaagac aaaattttc atagggctca gttttgctcg | 660 |
| gatggtcctg aagttgtatg gccttcatgg ggtaacaagg gtacttctgg tacattggtg | 720 |
| caaacaattg aggatactgt tttgcaggac caccttgtta agatttcaca gctatcttgt | 780 |
| gatcaacatg taagggtgta gtttcaaatc atccctcaat agtgagaatg attgtttatt | 840 |
| caactttttct gtctttctaa aatata | 866 |

<210> SEQ ID NO 47
<211> LENGTH: 788
<212> TYPE: DNA
<213> ORGANISM: Zea mays
<220> FEATURE:
<221> NAME/KEY: misc_feature
<222> LOCATION: (69)..(69)
<223> OTHER INFORMATION: n is a, c, g, or t

```
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (778)..(779)
<223> OTHER INFORMATION: n is a, c, g, or t

<400> SEQUENCE: 47
actatcgcgg acacactccc ttttgtaatc cagcacaatg ctggccagct catgattctc      60
aaaaatagna atcggtgcac tctgaggcaa agataaaagt aaggttaatt gcatatgtgg    120
gcaaagtctt tgtatacaag gcacttatta atatgctaat ctgtctcata ttttttggat    180
tctatctgat ccagttttgg tttagaatca gttgaccaaa tagcagagct aaccccaccc    240
ccaacacacn cattaataca gggaagaaga gctgccaatt gatgaagcag gaaggaaaac    300
caaatgacaa ctgtctccaa acangtagcc aaaaataagt gaatnatgga ccagccaaca    360
tgtagccaaa aataagtgaa tgacggacca gccaacaaca cgcggcatat catcaatcaa    420
gcaaatataa gcattatctc tacccatct tatttntgtg tagtttagag caagaaaga     480 ctaagttgat ttntacacag gctgctcttg cacaaaagca acacaagtca gtgacattgt    540
taggtgccta ggtggccaac caaatatact aaaatctcag agatgtattc cttgtccaac    600
ttgtgcattt gttgtcatga ataagttaaa aaagatacct cctaaataaa taatatatat    660
catgagatga gccattgtat ttgctaatct gatgaataaa taagtgggca cctaatcatt    720
atcaatggca gaaataagca accccccccc ccaccccac ccaaccaggg acccacannc    780
caatggcc                                                            788

<210> SEQ ID NO 48
<211> LENGTH: 397
<212> TYPE: DNA
<213> ORGANISM: Zea mays
<220> FEATURE:
<221> NAME/KEY: misc_feature
<222> LOCATION: (262)..(262)
<223> OTHER INFORMATION: n is a, c, g, or t

<400> SEQUENCE: 48
ctagagattg atctctggtc gcttggatgc attttggcag aactgatgaa actggaggct     60
ttgttcccgg ggatatctga tattgatcag attagtagaa tcatcaatgt cctgggcgat   120
ataacagaag aaacctttcc aggctgttca aacttgccag attacaacaa gatttccttt   180
aacaaagttg agaaaccgac aggccttgaa gcatgtctgc ctaacagatc tcctactgag   240
gttagcatca taaagcagct antttgctat gacacagcaa agaggaccag tgctgttgat   300
ctgctgaatg atcggtactt taccgaagag ccattgccgg cacctataga aggattacat   360
```
gtcccggcat caaaggacga ggatgatgac agctcaa 397

<210> SEQ ID NO 49
<211> LENGTH: 1049
<212> TYPE: DNA
<213> ORGANISM: Zea mays
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (558)..(563)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (687)..(796)
<223> OTHER INFORMATION: n is a, c, g, or t
<220> FEATURE:
<221> NAME/KEY: misc_feature
<222> LOCATION: (809)..(851)
<223> OTHER INFORMATION: n is a, c, g, or t
<220> FEATURE:
<221> NAME/KEY: misc_feature
<222> LOCATION: (868)..(903)
<223> OTHER INFORMATION: n is a, c, g, or t
<220> FEATURE:
<221> NAME/KEY: misc_feature
<222> LOCATION: (1015)..(1020)
<223> OTHER INFORMATION: n is a, c, g, or t
<220> FEATURE:
<221> NAME/KEY: misc_feature
<222> LOCATION: (1035)..(1038)
<223> OTHER INFORMATION: n is a, c, g, or t
<220> FEATURE:
<221> NAME/KEY: misc_feature
<222> LOCATION: (1047)..(1048)
<223> OTHER INFORMATION: n is a, c, g, or t

<400> SEQUENCE: 49
ttgcagctgt gctttagcta aagcgaacgc cgtgtatgtt tttttnntct ggtcaactaa    60
acattgttgt gtatacatac ataaacagca atcgaagcag acaataggca acaaaataac   120
gaattaatgc tgttatcaaa tgagccagca acggataaac ttgagatgct gccctagtag   180
ccgttctcaa actgaagccc tcaaggcttc aaacccatca attgcttgca actccagcca   240
caatcatact aataattaca cttgagcgca gccaaaatag caataaaaaa gttgagcaaa   300
gagtgcacct gctttgctta attgctctgc acgctcacga cgtccaaccg acgctacagc   360
ctacagcggc gtgaaaaaag aagagctgtt ttttaactcc acacacggaa caggaattac   420
caaccgaccg acccagtgta cccgattcgg accagatctt cgtggaattc accagatcta   480
tctagagaag aaacanggaa acaggaaacc agtaccttcc cgccggtcga tgagctgata   540
cgtagcgcgc tcaggcgnnn nnccatggg gcggctggcc tcaggcgggg caagctaaaa   600
agagccctcc cgcccgccgc ggttcgggct ctccttcctg aacaaggtcg agntcggctc   660
cggatccggc tgggccacgg ggaagtnnnn nnnnnnnnnn nnnnnnnnnn nnnnnnnnnn   720
nnnnnnnnnn nnnnnnnnnn nnnnnnnnnn nnnnnnnnnn nnnnnnnnnn nnnnnnnnnn   780
nnnnnnnnnn nnnnnnacgg gtgaggccnn nnnnnnnnnn nnnnnnnnnn nnnnnnnnnn   840
nnnnnnnnnn ngtggagttt gacccgannn nnnnnnnnnn nnnnnnnnnn nnnnnnnnnn   900

```
nnnagtgtag ggcgcggtgg cgtcgagggg aagggtgcgg cgcggtgggt ggcggccagc    960
ctcgggatcc gggtccagca cgggcgcacg cgcacctggc gatcggatgg gcgtnnnnnn   1020
atacgaatat gcacnnnnac ctggcgnnc                                     1049
```

<210> SEQ ID NO 50
<211> LENGTH: 798
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (625)..(627)
<223> OTHER INFORMATION: n is a, c, g, or t
<220> FEATURE:
<221> NAME/KEY: misc_feature
<222> LOCATION: (677)..(678)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (685)..(687)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (708)..(795)
<223> OTHER INFORMATION: n is a, c, g, or t

<400> SEQUENCE: 50

```
agaaacagta gttcgaggta gcacaggcag ttgagatgga gtantttgga cccatgaaac     60
caatgtccat tccaagcagg gcagaaccca tgtttgtgat agcatatggg atgaagaaag    120
gagttatctt tctgtatccc ttctcaatga gattctggac accatccgaa aacaccgtga    180
ggccacccat accagtgccc acaagcacac cggcccgggt cttgtcaatc tgccagagag    240
aatattttac caattagcat caaatgtagc attaacagtg aaaaaatctt atagtactag    300
taaaaatatc aaactaccag atgaaactac tatcaataca gtacaaacca tagttttgatg    360 tgctagaaga caatttgatt taatccaaaa atgctactcc ctctgacctg tagggcgtgt    420 ttatttttgaa gaaaccaaac tcgtaaaccc aaccaacaat tagtcaaatt atgtgtgttt    480
ggagtacaaa agctatatca acagatttat actcaaacaa cttttaatgc gacattgatt    540
ttgcagagac tagcaatatt ataaaacaat aatggttaaa atatgcttct aatgacacta    600
tccgtnnaca atatgcctgg aaaannnntag tactttgcta gaaaaatcac cataatgcaa    660
gtgaatcatc aaacgannca ncagnnnttc gcagagctat gttnntannn nnnnnnnnn    720 nnnnnnnnnn nnnnnnnnnn nnnnnnnnnn nnnnnnnnnn nnnnnnnnnn nnnnnnnnnn    780
nnnnnnnnnn nnnnncga                                                   798
```

<210> SEQ ID NO 51
<211> LENGTH: 544
<212> TYPE: DNA

```
<213> ORGANISM: Zea mays
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(10)
<223> OTHER INFORMATION: n is a, c, g, or t
<220> FEATURE:
<221> NAME/KEY: misc_feature
<222> LOCATION: (14)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (264)..(271)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (451)..(452)
<223> OTHER INFORMATION: n is a, c, g, or t
<220> FEATURE:
<221> NAME/KEY: misc_feature
<222> LOCATION: (455)..(457)
<223> OTHER INFORMATION: n is a, c, g, or t
<220> FEATURE:
<221> NAME/KEY: misc_feature
<222> LOCATION: (464)..(466)
<223> OTHER INFORMATION: n is a, c, g, or t
<220> FEATURE:
<221> NAME/KEY: misc_feature
<222> LOCATION: (468)..(470)
<223> OTHER INFORMATION: n is a, c, g, or t
<220> FEATURE:
<221> NAME/KEY: misc_feature
<222> LOCATION: (472)..(474)
<223> OTHER INFORMATION: n is a, c, g, or t
<220> FEATURE:
<221> NAME/KEY: misc_feature
<222> LOCATION: (476)..(477)
<223> OTHER INFORMATION: n is a, c, g, or t
<220> FEATURE:
<221> NAME/KEY: misc_feature
```

```
<222> LOCATION: (493)..(512)
<223> OTHER INFORMATION: n is a, c, g, or t
<220> FEATURE:
<221> NAME/KEY: misc_feature
<222> LOCATION: (514)..(518)
<223> OTHER INFORMATION: n is a, c, g, or t
<220> FEATURE:
<221> NAME/KEY: misc_feature
<222> LOCATION: (526)..(528)
<223> OTHER INFORMATION: n is a, c, g, or t
<220> FEATURE:
<221> NAME/KEY: misc_feature
<222> LOCATION: (534)..(538)
<223> OTHER INFORMATION: n is a, c, g, or t
<220> FEATURE:
<221> NAME/KEY: misc_feature
<222> LOCATION: (540)..(542)
<223> OTHER INFORMATION: n is a, c, g, or t

<400> SEQUENCE: 51
nnnnannnnn tctnnnnang tcttcgcnct cgtcgttgct gttttcatgt acattgtcgt      60
tcacatcttg ctgtccttcg anaaaatggc acgggtcatg aagaggactg agaacagtg     120 ggttccatgt ctgaagaaga tgtgggcact cattgaaant gaacctccaa accatcagcc    180
atcttcagag gaaccatgag aggctgaccc ttgncngtat ncttgtattg tgattacatg    240
aattgttcaa ttgatatgta cctnnnnnnn ntagaatcaa tatttgtttt ccccacttgt    300
ttaaggttga agtgttgtaa tcttttttatg cacttanaga taagatgcat tcatccanga   360
gggttagctt caagtacttc gttcttggtt ttaactttct cagtatattg gacggccgga    420
actacttatt tgtagctacc tctagcagtc nntcnnntta ttcnnnannn annncnntct    480
aaagtgtata atnnnnnnnn nnnnnnnnnn nnannnnnat atacannntc tacnnnnnan    540 nncc                                                                 544

<210> SEQ ID NO 52
<211> LENGTH: 276
<212> TYPE: DNA
<213> ORGANISM: Zea mays
<220> FEATURE:
<221> NAME/KEY: misc_feature
<222> LOCATION: (52)..(52)
<223> OTHER INFORMATION: n is a, c, g, or t

<400> SEQUENCE: 52
gctggatgcc aaggtcctga gcaaaatccc caggggtgcg gtcaaatcca anaagcagaa     60
ctagttagga taagccgcag attgtgaatg cccgtatcat gagtatcggg cttgtggttt    120
tgcatggcat atgtcaatct gtctgttggc ttcagcttgg ttcttctgcg actactttgt    180
tgatgttatt atagtcctat gtatgtcact gtgtacatga cagagatgtt cggatgctac    240
gtctagacta ctgctgtgct gtagcttgta aattcc                              276

<210> SEQ ID NO 53
<211> LENGTH: 733
<212> TYPE: DNA
<213> ORGANISM: Zea mays
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (571)..(571)
```

-continued

```
<223> OTHER INFORMATION: n is a, c, g, or t
<220> FEATURE:
<221> NAME/KEY: misc_feature
<222> LOCATION: (582)..(584)
<223> OTHER INFORMATION: n is a, c, g, or t
<220> FEATURE:
<221> NAME/KEY: misc_feature
<222> LOCATION: (586)..(594)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (615)..(618)
<223> OTHER INFORMATION: n is a, c, g, or t
<220> FEATURE:
<221> NAME/KEY: misc_feature
<222> LOCATION: (625)..(632)
<223> OTHER INFORMATION: n is a, c, g, or t
<220> FEATURE:
<221> NAME/KEY: misc_feature
<222> LOCATION: (634)..(652)
<223> OTHER INFORMATION: n is a, c, g, or t
<220> FEATURE:
<221> NAME/KEY: misc_feature
<222> LOCATION: (656)..(659)
<223> OTHER INFORMATION: n is a, c, g, or t
<220> FEATURE:
<221> NAME/KEY: misc_feature
<222> LOCATION: (663)..(665)
<223> OTHER INFORMATION: n is a, c, g, or t
<220> FEATURE:
<221> NAME/KEY: misc_feature
<222> LOCATION: (671)..(672)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (681)..(691)
<223> OTHER INFORMATION: n is a, c, g, or t
<220> FEATURE:
<221> NAME/KEY: misc_feature
<222> LOCATION: (693)..(696)
<223> OTHER INFORMATION: n is a, c, g, or t
<220> FEATURE:
<221> NAME/KEY: misc_feature
<222> LOCATION: (698)..(708)
<223> OTHER INFORMATION: n is a, c, g, or t
<220> FEATURE:
<221> NAME/KEY: misc_feature
<222> LOCATION: (710)..(712)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (718)..(722)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
```

```
<222> LOCATION: (727)..(732)
<223> OTHER INFORMATION: n is a, c, g, or t

<400> SEQUENCE: 53
caagttctga gtttctctct tgtcagtcaa tggcttgggt aaaaattgtg aacagagaat      60
atgaaagcct gacaaactag caatgagtcc attttctgaa gataaacagc aaggaaaatt     120
ctgaatccca tgtgtagaaa catgtaggaa acacctttct tgtttatgag tgataggcaa     180
aattttggtc attgcatcct agggttaact tacagtcttc ttttgcaggt caaggacact     240
cccacgaagt gttctgatca tagggaccca agcggtgatg ataattactt acctgctctt     300
tgcattgggc cggctcgcca cactttacgt ctctgtcgcc ttactcgggn tatgttttgg     360
tatctcgctc tccgtgataa tctcaacctc ctcagagctc ttcggactna agcactttgg     420
aaagatattc aacttcatcg cattggcgaa tccggtaggc gcgttcctgt ttaacaccct     480
cgcgggatat gtctacgatc tcgaagtgga aaagcagcac gccacaacat cagggtcgga     540
cgttgcatgt catggcccta attgcttcag nctaacattc tnnntnnnnn nnnncgtngc     600
atgcntgggc acacnnnnga gcacnnnnnn ncnnnnnnn nnnnnnnnnn nntatnnnnt     660
gcnnnatgca nncggntcnt nnnnnnnnnn nannnncnnn nnnnnnnnan nnatgncnnn     720
nnagntnnnn nnt                                                         733

<210> SEQ ID NO 54
<211> LENGTH: 385
<212> TYPE: DNA
<213> ORGANISM: Zea mays
<220> FEATURE:
<221> NAME/KEY: misc_feature
<222> LOCATION: (115)..(115)
<223> OTHER INFORMATION: n is a, c, g, or t

<400> SEQUENCE: 54
agctggcgtc tgtaagggaa gtacttaaaa agtcagaagg agaactcgag atcacctcga      60
agcagttagt tttggtttca gaagcacata gtgaccttaa taaagaattg ctggntgcat     120
ataagcagtt agagtccacg caaagtgagc tagtgaaaga gcgtaaaatc aatgctactc     180
ttaacatgga gcttgaggct ttggtgaaac aatcagtgat agagtccgaa gcaagaaaaa     240
ctcttcaagt cgacttggat gaggccacta gatcactaaa tgaggtgaat aagagtacac     300
tctgtctgtc taagcagctg gaaacaacta attccaagat ttctgctatt aaagaggaga     360
aagatatgct gtcaatgttc cttga                                            385

<210> SEQ ID NO 55
<211> LENGTH: 553
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (73)..(78)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
```

```
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (345)..(347)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 55
tgaatgtgtc gagggcctgc aaaatttant tttggtaaag cttaggacag aagcaaaatg    60
catagatatc cannnnnnaa atagcaaatg tttttatacg atntaancat taagtaaatc   120
catttctctt gacacaacta caggttattg tatatgagca tagcgttgat catanattct   180
taccttgttt agatagttca tctgtgttac natgcacaag attacaacaa atgagaacac   240
ccatgtttgt gaatanacaa gctggttcat ccctgaaaat gtcaccttca aggctatccc   300
aagagctttg acactcatga cctggcaaan caaagacaat acagnnngag agtatttatg   360
tcctagcntt cttgagaata gttatgtgaa ttcacatgga aagaactgtt aatcatgaga   420
agcataccga taaagatcca acaagagaac atatgccaat atataccatg atatgtgtct   480
gcccatactg agggacaaaa tggcatatga gcacaaaagc tgctgcaaat acaacagctg   540 catagaaatag gaa                                                    553

<210> SEQ ID NO 56
<211> LENGTH: 608
<212> TYPE: DNA
<213> ORGANISM: Zea mays
<220> FEATURE:
<221> NAME/KEY: misc_feature
<222> LOCATION: (91)..(91)
<223> OTHER INFORMATION: n is a, c, g, or t

<400> SEQUENCE: 56
tgtccgtcag ctccgccgcc tcatccagcg tcaggttgtg gttgcacccg gtgaaggcca    60
gcatgtcctt ctcgtatctg acgacgatca nggcaaacca atgcaagttc atccattgat   120
tgatctgcag ataatagccg gccaccgaac gctgtgaact ctcagctacc tcaggtgaag   180
cgcgatgtaa tgctgggact cgtttctcag ccgatcaacc agcgtgttgc cgagctcttc   240
gatctccttc ctgtactgga gcgcctcgta gttcgcgcgg caccgaagct tttgcagcga   300
aggagcgagg ccgttgttca cgatccgtga atccgtgtgt gtaaacctca ccactttgaa   360
cttcctcagg attttcgcaa agtctctgta gaaggaagcc tggaaaacgg agctggcgat   420
gcatcagcct attcagtacg tattcggtta tcctctaagc tgctgcaact gcaatgcaat   480
ccagtagagc aaaacaagtt gttgactcgta ccctggacca ggaggtgggc gctctcacgt   540
acggtttcac ccttctgtaa tgtggtggga gggaatccac gatcacaatg tcttccttca   600
acgactcc                                                          608
```

<210> SEQ ID NO 57
<211> LENGTH: 602
<212> TYPE: DNA
<213> ORGANISM: Zea mays
<220> FEATURE:
<221> NAME/KEY: misc_feature
<222> LOCATION: (8)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t

<400> SEQUENCE: 57

```
aggatccnnn nnngnagcaa tttcgaccag ggaagctcat aacagnaaaa tgatgccaca      60
gccagtgaaa ttgaatgtca cagactccaa atggctgcaa taaatgatta tggatttggt    120
aaacctgaga ttccttctag ttcctcaatg ccattttttct tggctgttga tcctcaacaa   180
ctgaaattga gaaatgagac aaatgttttct tcaacatctt ccaacattcc ttcagattct   240
gcatcaccaa acttgaaaaa tggcacggat cctcttttga tgccatttaa ttcctacatg   300
gcagattgga gcagcgataa gataacttac accactctga acactccaaa ataagcaca    360 gaacttccag gtcagtatgc atcnctttct tctattatta gctaaatcaa tttagctgac   420
aacaaaaact taaccatgca gtcaagttac accatgacaa aagtagtagc tttgaagcac   480
caaacctgaa ggagcatgaa tcagtctttg caacacatga aatgacggta gaagcaacaa   540
gaaaagaaga cgaacacaca tcaaaatcta gttttacttc ctacaatgga gtaccagata   600
ca                                                                  602
```

<210> SEQ ID NO 58
<211> LENGTH: 880
<212> TYPE: DNA
<213> ORGANISM: Zea mays
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (816)..(817)
<223> OTHER INFORMATION: n is a, c, g, or t
<220> FEATURE:
<221> NAME/KEY: misc_feature
<222> LOCATION: (876)..(878)
<223> OTHER INFORMATION: n is a, c, g, or t

<400> SEQUENCE: 58

```
cctccaatcc atgaccagac acctttttcag ctatctctct tccttctgtt tcaagtacaa    60
tcctgtgtaa tcattcaaga aaattaggta taatgccaca ataattaca tactaatgtg    120
```

```
ggacgttatt catctctaag cttgagaatg atcctattgc taaacctttg aatccagtga      180
ttaaaaccat tacaaaatag acgctcggat attactctat tgccatggcc cccagttcaa      240
aaaaaaaaca tgcggcagat gacagtcaga ttatttcaga gcaaaggaag aataataaat      300
gtacacaata aagggaacaa gaaaagaagc cctaatatca tgtatntagt aagataagga      360
tttaccctcc atcaacaatt tcatcaaggc acaataggat catatccaaa ttctcgagtg      420 ctgtccttt gtcaaccatg tttctnaaac caccaagatt ggaaacacat tcatatacaa       480
tcagcattaa cacaacaaca tgtaacagaa caaaacagtg gttgnaaaga taaagtttaa      540
tagagggaaa ataacttgag aagtcgttcg acagcatcag agaatccctg aagaactgat      600
gctaaaataa gctcattctc ttcttctcct ccagtaacaa aaaagtgcag gtcttggatg      660
aacttgtata ccacaatttg accgtcaaac attacaatct caactgttaa agagaaacaa      720
agaaaaatat gaaatacttg aagagaagaa caaaaactca aacagtcata tctgcatgtt      780
taaggagaaa tcaaggtcag tcagaaggaa aactanncca ggctcattta cagatttgtg      840
gcatgagtgg gagctcgtac aaacagtgtt atgacnnggg                            880
```

<210> SEQ ID NO 59
<211> LENGTH: 461
<212> TYPE: DNA
<213> ORGANISM: Zea mays
<220> FEATURE:
<221> NAME/KEY: misc_feature
<222> LOCATION: (253)..(253)
<223> OTHER INFORMATION: n is a, c, g, or t

<400> SEQUENCE: 59

```
acgcggcttg ttcttattga atccatcaag gacgcaggaa agataggatc ttcggctccg       60
attctcggag caacagcgcg accgcagcgg gttttggtgc ttcctttctt tagggttgtg      120
tccttgcaga agttgctctg tggaatgggg acctgtcgga ggagagttct gggggtatgg      180
tttttcttct ggttcttgtt gacacttgag cagtgcacat ccctgaatcg tgaaggtatc      240
tatcgtgttg tgntttgaat cgcttgcgtg gatggttgtt gcccgacctt tgttttttgac     300 tctgtttagg gttgtttctt tgctgaactg caggtgctgc tctgctgaga tttaaggcgg      360
cgatcgaggc agacccatat ggtgctttgt tggactggaa tcaagagagt ttgagcccct      420
gtacttggtt tggtgtggaa tgctccgatg atggactagt c                          461
```

<210> SEQ ID NO 60
<211> LENGTH: 544
<212> TYPE: DNA
<213> ORGANISM: Zea mays
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (18)..(49)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t -continued

```
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (331)..(333)
<223> OTHER INFORMATION: n is a, c, g, or t
<220> FEATURE:
<221> NAME/KEY: misc_feature
<222> LOCATION: (487)..(492)
<223> OTHER INFORMATION: n is a, c, g, or t
<220> FEATURE:
<221> NAME/KEY: misc_feature
<222> LOCATION: (519)..(542)
<223> OTHER INFORMATION: n is a, c, g, or t

<400> SEQUENCE: 60
nnnnnnnnnn gctagccnnn nnnnnnnnnn nnnnnnnnnn nnnnnnnnna acagaagcta      60
ccactgccgg tgctcatcgt cctgcacctg aagcagcagc agcagctgat ctgatcgaca     120
tacagttcgt gttcggcagc tagcccctnn agccatgctc ggagaggttt aatnaattac     180
gcagcggact ccttcgatgg gggtngattt ttggtgatca ttctgggggt atgtataaac     240
ctgcaaccta cccttgcaag gattagtttt tcttcttctg nttttcttct ttcaagtttc     300
accgaggtgg agtggaggtt gaccgacatt nnnctgttct tcccgcatat tcttgtgaga     360
ttttgattcc aatcagtgtc tatcaattca atttcgatct ccctctctgt aaccacatgt     420
cgtgtggcgt gcgtgcgtgt aaaaaatcga gaaaaccgag cctgccctgt ccgggcttca     480
gcttgtnnnn nntagctagc tcgatctagc ggaaacgann nnnnnnnnnn nnnnnnnnnn     540 nntt                                                                 544

<210> SEQ ID NO 61
<211> LENGTH: 1249
<212> TYPE: DNA
<213> ORGANISM: Zea mays
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (411)..(417)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (461)..(466)
<223> OTHER INFORMATION: n is a, c, g, or t
<220> FEATURE:
<221> NAME/KEY: misc_feature
<222> LOCATION: (474)..(478)
<223> OTHER INFORMATION: n is a, c, g, or t
<220> FEATURE:
<221> NAME/KEY: misc_feature
<222> LOCATION: (500)..(504)
<223> OTHER INFORMATION: n is a, c, g, or t
<220> FEATURE:
<221> NAME/KEY: misc_feature
<222> LOCATION: (506)..(514)
```

```
<223> OTHER INFORMATION: n is a, c, g, or t
<220> FEATURE:
<221> NAME/KEY: misc_feature
<222> LOCATION: (517)..(524)
<223> OTHER INFORMATION: n is a, c, g, or t
<220> FEATURE:
<221> NAME/KEY: misc_feature
<222> LOCATION: (541)..(542)
<223> OTHER INFORMATION: n is a, c, g, or t
<220> FEATURE:
<221> NAME/KEY: misc_feature
<222> LOCATION: (548)..(644)
<223> OTHER INFORMATION: n is a, c, g, or t
<220> FEATURE:
<221> NAME/KEY: misc_feature
<222> LOCATION: (646)..(701)
<223> OTHER INFORMATION: n is a, c, g, or t
<220> FEATURE:
<221> NAME/KEY: misc_feature
<222> LOCATION: (703)..(743)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (749)..(754)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (760)..(763)
<223> OTHER INFORMATION: n is a, c, g, or t
<220> FEATURE:
<221> NAME/KEY: misc_feature
<222> LOCATION: (765)..(769)
<223> OTHER INFORMATION: n is a, c, g, or t
<220> FEATURE:
<221> NAME/KEY: misc_feature
<222> LOCATION: (772)..(774)
<223> OTHER INFORMATION: n is a, c, g, or t
<220> FEATURE:
<221> NAME/KEY: misc_feature
<222> LOCATION: (776)..(780)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (784)..(790)
<223> OTHER INFORMATION: n is a, c, g, or t
<220> FEATURE:
<221> NAME/KEY: misc_feature
<222> LOCATION: (792)..(797)
<223> OTHER INFORMATION: n is a, c, g, or t
<220> FEATURE:
<221> NAME/KEY: misc_feature
<222> LOCATION: (818)..(819)
<223> OTHER INFORMATION: n is a, c, g, or t
<220> FEATURE:
<221> NAME/KEY: misc_feature
<222> LOCATION: (821)..(822)
<223> OTHER INFORMATION: n is a, c, g, or t
<220> FEATURE:
<221> NAME/KEY: misc_feature
<222> LOCATION: (826)..(828)
<223> OTHER INFORMATION: n is a, c, g, or t
<220> FEATURE:
<221> NAME/KEY: misc_feature
<222> LOCATION: (832)..(835)
<223> OTHER INFORMATION: n is a, c, g, or t

<400> SEQUENCE: 61
```

-continued

```
ttcnnnnatc ttcctctatt gatactgtag gttcaattgc ttcagcagtt ggcattgttt      60
tagacaattt ttgtttgatt ctgcattgac aacaaaggtt tcccaaatg gtttcccact     120 taggttgaaa atgatgattt gattgcctac ggcctgatcc cagaatttat tggaaggttg    180
ccaataacag ttggcctgac caatcttagt gaagagcaat tggttcaagt agtaaatttc    240
tttgattttn taatttaaag caatatttct taaaattacc atctcaaata tttccaccac    300
ctcaaaatat tagaaattct ctttgcaggt gctcatggag cccaaaaacg caataggaaa    360
gcaatacaag aagctattca aaatgaatga tgttagtttg tgattcgttt nnnnnnncga    420
aataattgca anatttggcn gatttttttt tactttaaac nnnnnnttat aacnnnnnaa    480
gttatttatg ttcatgttn nnnnannnnn nnnngcnnnn nnnnactgat aatgctttga    540
nnatgatnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnntnnnnn nnnnnnnnnn    660
nnnnnnnnnn nnnnnnnnnn nnnnnnnnnn nnnnnnnnnn ncnnnnnnnn nnnnnnnnnn    720
nnnnnnnnnn nnnnnnnnnn nnnggntann nnnntncttn nnnannnnna gnnngnnnnn    780
cnannnnnnn cnnnnnngtg tcgagcaaaa atttttcnng nngatnnngc cnnnnaactg    840
tatgtttacc agaacaatat caaactgccc gggctgattc agagcaaccc cagacgcaga    900 cgcatttttcc ggctctgcct tctagtcgca ttatcggcaa caaagctttg gatttaccag    960
acaattcctt gttttcatc gatatatgaa tggattgcat ggatactatg caaggtctac   1020
aattttacac aataaaatat gatgaggttg attttcgtgt taaactgttc acacagcaaa   1080
agaatggctg gaccccacgt tctgctttct tcggtagctt gcaatgattt tgcaacaaca   1140
attcgtatca tttacacgct actggtagca aacagacagt tgttttgata ctgaacctga   1200
acaaatggaa aatggtttcc aatggttaca catcaaaatt atgtttgta              1249
```

<210> SEQ ID NO 62
<211> LENGTH: 372
<212> TYPE: DNA
<213> ORGANISM: Zea mays
<220> FEATURE:
<221> NAME/KEY: misc_feature
<222> LOCATION: (148)..(148)
<223> OTHER INFORMATION: n is a, c, g, or t

<400> SEQUENCE: 62

```
tgtatgatca aggaatggtc tacaccaatg tgtttgatgc caactttgat actcttgtct      60
ggtcattaag gaaagctggt gtgcccgaca tgagaatcat tgttggtgaa gttggctggc    120
catctgatgg tgataagaat gctaacanca aatatgcaca gaggttctat aatggttttc    180
tgaagaaaat gacaaaaaat gtcggcacgc ctctgagacc tggtcgtatg gaagtttacc    240
tgtttgcgct gattgatgag aaccagaaga gtgtcctgcc tggacgcttt gagcgtcact    300
ggggactatt cacatatgat ggaaaaccaa agttctctat ggatctcagt ggaaatggca    360
agggcagtgt ag                                                        372
```

<210> SEQ ID NO 63
<211> LENGTH: 442
<212> TYPE: DNA
<213> ORGANISM: Zea mays
<220> FEATURE:
<221> NAME/KEY: misc_feature
<222> LOCATION: (130)..(130)
<223> OTHER INFORMATION: n is a, c, g, or t

<400> SEQUENCE: 63

```
gtgcacactg gcgccagatg ggtatgtgtg cagcccttga tagcctgagc ttttggcaaa        60
actaatggtc tgtgacagac taaccgatct ttggtttttt gctcttggac agttcaatga       120
catgatcaan gtgccattca cgtcgaagcc gttcgtcgct gggttggtag cctatatcct       180
ggacaacacc ctccaggtaa aggagagcgc ggtgcggaag dacagggca accactggtg        240
ggagaagttc aggagcttca agaaagacgc gaggagccaa gagttctact cgctgccgtt       300
caatctgaac aagttcttcc cgtcggtctg atctcaaatg gcgccgccgc tgaatcaatt       360
ctggaagcaa cccttgttca tatgggcctt aatgaggaac ataattctgc tggtctggcc       420
agtggaagct tctgtgtctc ca                                                 442
```

<210> SEQ ID NO 64
<211> LENGTH: 523
<212> TYPE: DNA
<213> ORGANISM: Zea mays
<220> FEATURE:
<221> NAME/KEY: misc_feature
<222> LOCATION: (258)..(258)
<223> OTHER INFORMATION: n is a, c, g, or t

<400> SEQUENCE: 64

```
tcctttgaaa tgcaggaagt ctagaggaat atacaggaat ttcacaagaa tcagtctatt        60
ttcacagaaa aaatgcagga aactgaaaaa aaatccccgc attccaaagg gggcctcatc       120
taggatttct tcataccgaa ttatcgattg acttcgacca cataccgtgc ttttgttcat       180
gtctttgaac acaggcacac ccaaatttcg aggtagcaaa ttttgcccac atacactgta       240
tataaagtag ttacagtnca agaacaatgc taactgatca ggtgatgtct cgtcctcccc       300
ccggttctat tattgttact gtatagctgt aattagtcca agtgtacagc tgaatctact       360
aaggtttaca aggaaaatcg ccaggctgta aaccttcaat tcttatggct aggttttcat       420
tctgaaagtc atgtcttccg cgtcagcata atcctgtgtt cctgtataac ctctcttcgg       480
acttagtagt gctcatttga gttctaattc ggccgggcaa cta                         523
```

<210> SEQ ID NO 65
<211> LENGTH: 687
<212> TYPE: DNA
<213> ORGANISM: Zea mays
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature

```
<222> LOCATION: (443)..(445)
<223> OTHER INFORMATION: n is a, c, g, or t
<220> FEATURE:
<221> NAME/KEY: misc_feature
<222> LOCATION: (501)..(506)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (518)..(520)
<223> OTHER INFORMATION: n is a, c, g, or t
<220> FEATURE:
<221> NAME/KEY: misc_feature
<222> LOCATION: (527)..(528)
<223> OTHER INFORMATION: n is a, c, g, or t
<220> FEATURE:
<221> NAME/KEY: misc_feature
<222> LOCATION: (530)..(532)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (561)..(565)
<223> OTHER INFORMATION: n is a, c, g, or t
<220> FEATURE:
<221> NAME/KEY: misc_feature
<222> LOCATION: (570)..(575)
<223> OTHER INFORMATION: n is a, c, g, or t
<220> FEATURE:
<221> NAME/KEY: misc_feature
<222> LOCATION: (578)..(586)
<223> OTHER INFORMATION: n is a, c, g, or t
<220> FEATURE:
<221> NAME/KEY: misc_feature
<222> LOCATION: (588)..(604)
<223> OTHER INFORMATION: n is a, c, g, or t
<220> FEATURE:
<221> NAME/KEY: misc_feature
<222> LOCATION: (608)..(612)
<223> OTHER INFORMATION: n is a, c, g, or t
<220> FEATURE:
<221> NAME/KEY: misc_feature
<222> LOCATION: (614)..(654)
<223> OTHER INFORMATION: n is a, c, g, or t
<220> FEATURE:
<221> NAME/KEY: misc_feature
<222> LOCATION: (658)..(686)
<223> OTHER INFORMATION: n is a, c, g, or t

<400> SEQUENCE: 65
ggtagncagc tgcgcttacc cgactgtctg cggcgcgtac ggcntctgcg tcagcgggca      60
gtgcacgtgc ccanccgcga cgtacttcag gcaggtcgac gaccgccgga ccgacctcgg     120
ctgcgtgccc gtggccccga tctcntgtgc ctcgacgcag gaccaccggc tcctcgctct     180
gagcaacgtt tcttacttca actacgtgga taccaaggcc gcgctgcctc ggatgntcga     240
cgaagagagc tgcaagaagg catgcttgca gaactgctcc tgcaaagccg cgttcttcca     300
```

| | |
|---|---:|
| gtacggcggc aacgacacct cccngggctc ctgttacctg ccgacgcagg tcttctcgat | 360 |
| gcaggtgaac cagtggcaag aaactcacta cagctcttct gcgtacctca aggtgcaggt | 420 |
| cacaaggtct cctcctcctc ctnnngtccc tggtccctcg aattcgaatg ggacggccat | 480 |
| acccgcaggg aaaggaagga nnnnnnnctng tgaagctnnn atcgttnncn nngcacntgc | 540 |
| ggnggccant gcnttactag nnnnnatcgn nnnnccnnn nnnnncnnn nnnnnnnnnn | 600 |
| nnnncgtnnn nntnnnnnnn nnnnnnnnnn nnnnnnnnnn nnnnnnnnnn nnnngatnnn | 660 |
| nnnnnnnnnn nnnnnnnnnn nnnnnng | 687 |

```
<210> SEQ ID NO 66
<211> LENGTH: 477
<212> TYPE: DNA
<213> ORGANISM: Zea mays
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (360)..(402)
<223> OTHER INFORMATION: n is a, c, g, or t

<400> SEQUENCE: 66
```

| | |
|---|---:|
| ccttggcctt ctctattgcc tccttcgaat taggatcaac caatttcttg atttcgatgt | 60 |
| ccttgncagc aaagtcccctt acctcagtga tctgttggat catgtgaaag tacaagttaa | 120 |
| gcgttctcac attaaagctg acaaacatat tgcaaaacca gtagagtaag tttgccatct | 180 |
| atatccacaa ttatgatgcc agagagtggc aatatttctg tgctactata agcttattgg | 240 |
| cgttttgaac ttttcaacaa gttgcagtta aaatgattta ataaaatga acttagatgg | 300 |
| caatagacat gtgaaaaaga catttggtta cagataagcc gtgctgttac attttttccn | 360 |
| nnnnnnnnn nnnnnnnnnn nnnnnnnnnn nnnnnnnnn nngtttttgtg atactgacag | 420 |
| ttcagattta cctccacttt ccctcgtcca gatgccacag cagcggcatt tttggca | 477 |

```
<210> SEQ ID NO 67
<211> LENGTH: 1253
<212> TYPE: DNA
<213> ORGANISM: Zea mays
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (1241)..(1250)
<223> OTHER INFORMATION: n is a, c, g, or t

<400> SEQUENCE: 67
```

| | |
|---|---:|
| atgagatgat gactgcgtcc agaacaataa aaaataagga aagatgcaat tccaatcttc | 60 |
| ctatccttac agatgtcaat tctgggttga tagaccttaa ggtcacatga aaaatagtaa | 120 |
| atctgttaat agattgtttt agtcgtggtg agttattggt tttaatagag aagcatgata | 180 |
| gtgatgatat agtaattact gtgcagtctt acttcctcag catcaggtag caagaacaa | 240 |
| cagtcgcact tcgactttt ccctcaaagc aatgcacaag tactttgcca cgcaagtgat | 300 |
| ccacataact gatgaaatca gaaccatctt gaaagagatc accaatgtct gcattgtcat | 360 |
| catcgtttat ctacatagag aagcaattca acactgaaag atatctaaac tgagtcttct | 420 |
| gccttatgct aaaggcaaat gattttccat ccatgcaggt attatgtaga actcaccgag | 480 |
| aaattcctat actcaaaaag gtcaggcttc tgcgattctg actgtccaat ttcatttgca | 540 |

```
cacaagcaca atatatgggt gatgccaagg tgtttaagtg tgtgtgttga ccgagcagca        600
agagcaccac caatatacag ntaatctgtg atctgtgatg gacgctcagt acttgcagca        660
tcagagatca aagatatcct ctcgagaatg tgctcaagtc gaacctaaca acagaattgc        720
tcgataggtt caattaatgt gtacacgtag ttagtacaga gtgtacattt agatttacct        780
tcaactcgta agcatcaaca acagtgctat tatcagtgcc ttcaaaaaaa cctgtttgaa        840
aattgttgtc ttgacacaac tttactactt cagtcctcag catgtcattc cattgttcta        900
tctctttgct taattcactg tctatctgta aaaatgtgtt caatgactaa tagaatcaca        960
tgataaactt gccttgtttg tttaccctct agattatata atccagctta aataagttaa       1020
aagacaaaca acaacacaa attattaggt gaattatata atctagatac ttaaattatg       1080
ataatccata agcaggtcat gaggcccttc ttacgtaaaa aaaatcatga agccatttag       1140
ctatttggct tcctgcaact aaatagtggg acaatctata agagtgaaaa aaacaactag       1200
aaacctacgt cagacagttt ataatagaca atttatcaat nnnnnnnnnn aag             1253

<210> SEQ ID NO 68
<211> LENGTH: 491
<212> TYPE: DNA
<213> ORGANISM: Zea mays
<220> FEATURE:
<221> NAME/KEY: misc_feature
<222> LOCATION: (39)..(39)
<223> OTHER INFORMATION: n is a, c, g, or t

<400> SEQUENCE: 68
ttctttgtgg ggctggacat agtggactgc ctcctggtna acaagaacgg gcgcttcacc         60
ggcgaggctt tcgtggtctt cccaacagcc atgcaggcag agtttgcgct gcatcgcgac        120
aggcagaaca tggggcggag gtatgtcgag gtgttcaggt gcaagaagca cgagtactac        180
tgtgcaatag ccaatgaggt gaaccagggc ggttattttg agccggagta ccgccgctcc        240
ccgcctcctc cgaggcctag gaagccgtct gaagataagg gcagcatgga gtacacagag        300
gttctgaagc tccgcgggct tccctactct gccaccactg aggacatcat caagttcttc        360
ctggagtacg agctggcaga ggagaacgtg catatcgcct accgctccga tgggaaggcc        420
acgggtgaag ccttcgttga gtttccgaca gctgaagtcg cgaagacggc catgtgcaag        480
gataagatga c                                                            491

<210> SEQ ID NO 69
<211> LENGTH: 1013
<212> TYPE: DNA
<213> ORGANISM: Zea mays
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
```

<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (994)..(999)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t

<400> SEQUENCE: 69

```
nnnntgnnng agcctaagan nnntatantn agcatgatca gtgtgataga acaaattaag      60
caaaacagga tgaaaatgtt tactgtgcat atataaggaa caagcatgca tatatcactc     120
gtattatcta gcatctcata tggaaagcnt ggggatgttc acagatctat atgagctcta     180
tagccctctt tacttcaggt ggcaatttca aagcattgag gctggcaact agcacgtggt     240
aattatgtat gttttgggca aacaagttca ntctatttcc tgtcgggtag gttcagtact     300
gaacgctaga tctgcaccaa atccaaccac cggccgctgc aactgccaaa agtagggtag     360
ctacctaagt tgtagatcta cagtggcaan ggggcgcgac gcttacgttg ggcagtgct     420
tggcgatggc agtgcacagc gccttaacga tgccggcgtt gatgttgaag aggtcgtccc     480
tggtcatgcc gggcttcctg ggcactcctg cggggatgat gacgatgtcg gagccctcca     540
gcgcctncc gagctggtcg tccccatga acccttcac ctgcaggagc agaaaccagt        600
gagctcggat ccagtccagt tccgtccgag ccaagccaga ggagcgcgcc gagcagggag     660
gtaccagggc ggggnagttg atgtgggaga cgtcggccgc gacgccgggg gtgccggcga     720
tatcgtagag ggagagggag gaaacgagcg ggttgagctt catgaggagc gagagcggct     780
gcccgatgcc ncccgccgcg cccaggatgg ccaccttccg ctccggattg gccgaggacg     840
cgtagccgcg gctgcggcgg aggagctcgg ccgtggactt cagcagcgac ggcctcatgg     900
cggcggctgg gtcgggatc actcgctcgg gcgtgtctcg ctgtgattg gtgggggag        960
cggcagtggg cggcggcgag aagtgagggg agcnnnnnng ganaggatcn aaa            1013
```

<210> SEQ ID NO 70
<211> LENGTH: 608
<212> TYPE: DNA
<213> ORGANISM: Zea mays

-continued

```
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (494)..(497)
<223> OTHER INFORMATION: n is a, c, g, or t
<220> FEATURE:
<221> NAME/KEY: misc_feature
<222> LOCATION: (507)..(509)
<223> OTHER INFORMATION: n is a, c, g, or t
<220> FEATURE:
<221> NAME/KEY: misc_feature
<222> LOCATION: (511)..(511)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(563)
<223> OTHER INFORMATION: n is a, c, g, or t
<220> FEATURE:
<221> NAME/KEY: misc_feature
<222> LOCATION: (569)..(570)
<223> OTHER INFORMATION: n is a, c, g, or t
<220> FEATURE:
<221> NAME/KEY: misc_feature
<222> LOCATION: (572)..(577)
<223> OTHER INFORMATION: n is a, c, g, or t
<220> FEATURE:
<221> NAME/KEY: misc_feature
<222> LOCATION: (579)..(596)
<223> OTHER INFORMATION: n is a, c, g, or t
<220> FEATURE:
<221> NAME/KEY: misc_feature
<222> LOCATION: (602)..(606)
<223> OTHER INFORMATION: n is a, c, g, or t

<400> SEQUENCE: 70
```

```
ctaagtggtg tcaatggcat tctatttat gctgcgagca tcttcaaagc tgctggtaca    60
ttcttcaaaa cangatcaat ctctgatgnt agattctaat gcaattgaga tatgctttnt   120
ggcttgcgta ttcttgaact tgtccaggaa atgaaagnta ccttgttttg gttcgattca   180
tgctttgcat ggagacactg tgacaatgat tcatttacta tgtaaaaaan gggaagagtt   240
ctagaaccta ggcttcatca aagtctgata tcttcctgaa ttctcttcct caacaggtat   300
tacaaacagt aatctagcaa catttggttt aggggctgtt caggtacatt tgttttaaag   360
ttgttacatc ccttgtttct cagacaaatt ttnggcagat gtgggcttgg cactgcatac   420
ttaatgggat cttgtcgttt canntgattg ctactggagt gacaacctng ttgactgaca   480
aagctggtcg angnnnnctt ctcattnnna ntttccaact tnccatcaca attgtttatt   540
ggacatgctt ttccagtntt nnnaattgnn cnnnnnntnn nnnnnnnnn nnnnnnaatg   600 gnnnnnac                                                            608
```

```
<210> SEQ ID NO 71
<211> LENGTH: 472
<212> TYPE: DNA
<213> ORGANISM: Zea mays
<220> FEATURE:
<221> NAME/KEY: misc_feature
<222> LOCATION: (263)..(263)
<223> OTHER INFORMATION: n is a, c, g, or t

<400> SEQUENCE: 71
ggttgcatca acatcggctg cgagtagta gttggtacag cttccaaaag aatgcgctga    60
ttgcctactt gttgtataca tacagcagag tgttttgaac caacaaagag atcaaaaaat   120
cggatttctg tatatgcagc ctctggcaat tgaatctctc agttccccgt atatgttcga   180
atcctaccaa gcaaaaggga atccaggcca gagctggaaa catcctatca agcaaacact   240
ttacaagaaa ccttctacta tcnagattgc ttggtgtatg ttcatccctg cagatgcaat   300
aggctgtgct tggttacatg agttacagag agattactgc aaacactgta agtttcgggt   360
gtttacctat acaacaggaa tcttcagaag aataagtgag cagagataca ggcacactga   420
gatggcgatc ccagcaacga aatttggta cagacggcta ttatccctac tg           472
```

```
<210> SEQ ID NO 72
<211> LENGTH: 679
<212> TYPE: DNA
<213> ORGANISM: Zea mays
<220> FEATURE:
<221> NAME/KEY: misc_feature
<222> LOCATION: (538)..(538)
<223> OTHER INFORMATION: n is a, c, g, or t

<400> SEQUENCE: 72
ttttgtaccc agcagaccag aagagtccaa acgggaaact acggtataac aaaggcaaca    60 atctttttt tacttactat tattactatt cccggaactg tagtttagct tcctgtcctc   120
acattggttg gttctatgtg gaattgcagc gttctgtatg aagtcttccc gatgtcattc   180
ctgatggaac aagctggagg ccaggctttc acaggcaaac aacgggtgtg tttcagtttc   240
cctttctcag accccaatcc ccaactgaaa atcttgatg ctagagctat cacatttgcc   300
tgagatatca gggggatttt tcaacacttt tacaggttga aattattgag aaaagggcac   360
tattttaaca tgccatgttt ttttttacca gtggttggca ttgcatataa ctgaaaatgc   420
tcctgctaaa tttataatgc aggcccttga acttgctccc gctaaacttc acgacagatc   480
cccagtgttc ctcgggagct acgatgacgt tgaggagatc aaagcactgt acgcttcnat   540
```

```
gtcaaacagc ggttgacctt tctgcctgag gaaacgagcg agatcaaaag caccgtacgc    600
ttcagagtca actgcttgat ctttatagat tgtaataaaa taataaaaga gtttgtaaaa    660
aaaacaacaa cactgcttg                                                 679
```

<210> SEQ ID NO 73
<211> LENGTH: 397
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t

<400> SEQUENCE: 73

```
cctagaggtg gtccgcttac cagtttacta tccttctgag caagaaaang atgatcctaa    60
gctctatgca aacaatgtac ggaaactgat ggcagtggag gtatcttaaa cacttgaaaa   120
tgattaatta cattgaatgg tattgctgta caagtgtttg gtattattgt aaccatgtgg   180
taatcttgat ttcttttcag ggaaacttga ttctttcaga ccttgggctg gcggagaagc   240
gagtgtacca tgccgcactg aatggtaata gtctagctcg tgctttacat cagaaagatg   300
attgaaatgc catgctatcg tgcttccata atactggctt gcttgtaact gtgtgcttgc   360
ttgtgcatcg tcatggttga gaggaatgtc gtgaata                            397
```

<210> SEQ ID NO 74
<211> LENGTH: 648
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(12)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (581)..(587)
<223> OTHER INFORMATION: n is a, c, g, or t
<220> FEATURE:
<221> NAME/KEY: misc_feature
<222> LOCATION: (589)..(593)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (611)..(638)
<223> OTHER INFORMATION: n is a, c, g, or t
<220> FEATURE:
<221> NAME/KEY: misc_feature
<222> LOCATION: (640)..(646)
<223> OTHER INFORMATION: n is a, c, g, or t

<400> SEQUENCE: 74

```
ntgcctgnnn nnggacatga gtactctgaa tccttggatc caatgggtgc agtacttttg     60
gcgttcgcct caaatgcaag aaaaatggat gggataataa cagaaccaat cagtacacca    120
tatatgtgcc cagccactac agctctcggg gaggtcgaag tcatatagcc agtcttaagg    180
tcttgcatgg cttgtgaaga cacattcaga gctgcaacag acaccccaca ggctgcaagg    240
ctagcgatga ccgcaccagg cacggcaacc catgctgcta tgacgaactg tatgaacctg    300
ccataagatt gtgcaactga ccagtctgtg agtcctgttc cgtacgtgtt gcagaaggtg    360
aaaacgggaa gaatggtgaa cagaagggcc atgtggtaga gtttaatgtg ttggaagatc    420
caagggatga cgactgagca tactattgca catccgatat atccagcaac cggcacatgg    480
agcgggattc tctgaccang aaacacatca agccttctac gatcatcata gctaaggctg    540
gggcttgtca acatgtattt gatcttccct gaatcatttt nnnnnnncnn nnngnatagg    600
tcnantgagc nnnnnnnnnn nnnnnnnnnn nnnnnnncn nnnnnnca                  648
```

<210> SEQ ID NO 75
<211> LENGTH: 381
<212> TYPE: DNA
<213> ORGANISM: Zea mays
<220> FEATURE:
<221> NAME/KEY: misc_feature
<222> LOCATION: (139)..(139)
<223> OTHER INFORMATION: n is a, c, g, or t

<400> SEQUENCE: 75

```
agactctggc tgggtacctt cccaaccgcg gaggatgcag ctagggccta tgatgaggca     60
gccagagcga tgtatggaga cttggcacgg actaacttcc ccggacagga tgcaacaacc    120
tctgcccaag ctgctctanc atcgacctct gcccaggctg ctccaacagc tgttgaagct    180
cttcagactg gcacgtcatg cgagtcgaca acgacatcaa atcactcgga catcgcatcc    240
acctcacaca agcctgagcc tgaagcctct gacatctcga gctccctaaa ggaaaaatgt    300
ccagctggat catgtggtat ccaagagggt acacccagtg tagctgacaa ggaggtcttt    360
gggccgttgg agcctatcac a                                              381
```

<210> SEQ ID NO 76
<211> LENGTH: 692
<212> TYPE: DNA
<213> ORGANISM: Zea mays
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (369)..(376)
<223> OTHER INFORMATION: n is a, c, g, or t
<220> FEATURE:
<221> NAME/KEY: misc_feature
<222> LOCATION: (381)..(382)
<223> OTHER INFORMATION: n is a, c, g, or t
<220> FEATURE:
<221> NAME/KEY: misc_feature
<222> LOCATION: (398)..(399)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (455)..(457)
<223> OTHER INFORMATION: n is a, c, g, or t

```
<220> FEATURE:
<221> NAME/KEY: misc_feature
<222> LOCATION: (635)..(639)
<223> OTHER INFORMATION: n is a, c, g, or t
<220> FEATURE:
<221> NAME/KEY: misc_feature
<222> LOCATION: (662)..(689)
<223> OTHER INFORMATION: n is a, c, g, or t

<400> SEQUENCE: 76
tgtctttcgg ttgaacttgt ttgaagccct gcccaacctg gacatttttt agtttaggtc      60
taaaaagaga aaccctaggg ttgtttgaaa gggcttgttt ctaggcttgg cattttgggg    120
tcagtgaagc aattagtatg gttgtggatt tgcatttgnt actcggcatt aggtcttatt    180
tttcgcgagc gctaactcta attgtattgc tgaaacttaa gtgttgctta tatattccgt    240
tggtaacgga tactattctg cttcaattcc cttctacatt gtagattcgc tacaggcttg    300
gctcttggct agccaagcct gcagtttagg actttgccaa aactgcattt gccatttaac    360
aggcttctnn nnnnnncatt nnctctggag gtctaggnng tggnagacgt cgcagcagga    420
gcaggagccg cagtcgcagc cctagatacc gcagnnntcc gagctataat agaaggtaac    480 cattttttg acttcttaga tttcatcagt tgtaaattaa ctctcaaatt ttgtcgctca     540
acctcaaatg ctgcttatat ctttccttgg taactgatac tattctgctt taatgccctt    600
ctattgtcga ttcattatgg gctttacttt tggcnnnnna agcctgcaat ttgctacttt    660
gnnnnnnnnn nnnnnnnnnn nnnnnnnnnt tc                                  692

<210> SEQ ID NO 77
<211> LENGTH: 672
<212> TYPE: DNA
<213> ORGANISM: Zea mays
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (9)..(17)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (475)..(486)
<223> OTHER INFORMATION: n is a, c, g, or t
<220> FEATURE:
<221> NAME/KEY: misc_feature
<222> LOCATION: (511)..(513)
<223> OTHER INFORMATION: n is a, c, g, or t
<220> FEATURE:
<221> NAME/KEY: misc_feature
<222> LOCATION: (518)..(523)
```

```
<223> OTHER INFORMATION: n is a, c, g, or t
<220> FEATURE:
<221> NAME/KEY: misc_feature
<222> LOCATION: (547)..(548)
<223> OTHER INFORMATION: n is a, c, g, or t
<220> FEATURE:
<221> NAME/KEY: misc_feature
<222> LOCATION: (552)..(554)
<223> OTHER INFORMATION: n is a, c, g, or t
<220> FEATURE:
<221> NAME/KEY: misc_feature
<222> LOCATION: (558)..(560)
<223> OTHER INFORMATION: n is a, c, g, or t
<220> FEATURE:
<221> NAME/KEY: misc_feature
<222> LOCATION: (575)..(577)
<223> OTHER INFORMATION: n is a, c, g, or t
<220> FEATURE:
<221> NAME/KEY: misc_feature
<222> LOCATION: (582)..(583)
<223> OTHER INFORMATION: n is a, c, g, or t
<220> FEATURE:
<221> NAME/KEY: misc_feature
<222> LOCATION: (587)..(589)
<223> OTHER INFORMATION: n is a, c, g, or t
<220> FEATURE:
<221> NAME/KEY: misc_feature
<222> LOCATION: (591)..(599)
<223> OTHER INFORMATION: n is a, c, g, or t
<220> FEATURE:
<221> NAME/KEY: misc_feature
<222> LOCATION: (606)..(628)
<223> OTHER INFORMATION: n is a, c, g, or t
<220> FEATURE:
<221> NAME/KEY: misc_feature
<222> LOCATION: (630)..(632)
<223> OTHER INFORMATION: n is a, c, g, or t
<220> FEATURE:
<221> NAME/KEY: misc_feature
<222> LOCATION: (634)..(636)
<223> OTHER INFORMATION: n is a, c, g, or t
<220> FEATURE:
<221> NAME/KEY: misc_feature
<222> LOCATION: (639)..(657)
<223> OTHER INFORMATION: n is a, c, g, or t

<400> SEQUENCE: 77
tcnnnnagnn nnnnnnnaag ttactagaac ctngtntngt tgatcgcatt gttgtttcaa        60
ataaatcagt agcgaaggtc tacatcagga nttcacctca tccaaagagc caaggccaag       120
atagtgatat ccatattact accactgatg ctccaggcaa gcctgctccc agcagatgca       180
agtattactt caatattggt agtgttgatt tgtttgaaga gaagttagag gaagcccagg       240
aagctttggg aatagatcca catgattttg tcccagtaac ttatgttgct gaagtaaatt       300
ggttccaaga agttatgagg tttgccccaa cagcattgat tnttggtcta ttatatttca       360
cgggaaaaag gatgcagagt ggtttcaata ttggaggtgg tgctggcaaa ggaagaggag       420
gtattttcaa cattggaaaa gctacagtga tgaagatgga caagaactcc aaaannnnnn       480
nnnnnnatta cttttcttat gttactcaat nnntgacnnn nnctatatt tgatggatga       540 taaaaannat cnnncccnnn acccaaatga ttttnnncac annctannnc nnnnnnnnng       600
atgacnnnnn nnnnnnnnnn nnnnnnnngn nncnnntgnn nnnnnnnnnn nnnnnnnagc       660
atactacatg aa                                                          672

<210> SEQ ID NO 78
<211> LENGTH: 557
<212> TYPE: DNA
<213> ORGANISM: Zea mays
<220> FEATURE:
<221> NAME/KEY: misc_feature
```

<222> LOCATION: (422)..(422)
<223> OTHER INFORMATION: n is a, c, g, or t

<400> SEQUENCE: 78

| | | | | | |
|---|---|---|---|---|---|
| cgttggcaca | gtcacgtcaa | tcgatgaaca | tcattcagaa | acattaccca | gggctgatag | 60 |
| cagccgcgat | cctttcgac | cctccaaaga | tctttgaatc | cttttggaag | gtacggtgtt | 120 |
| ccatagtgca | attctgtttc | taagtttaac | agcaggttta | ctagttctgg | catcggttgt | 180 |
| caagcatcct | gaactttaag | ccatggactt | tgtctgaacc | agtacaagct | tggtcctgta | 240 |
| gaaattgtga | catgccattt | cattaactgc | agtgtcaatg | tataatgctt | aaacctcctt | 300 |
| tttttagat | gctaagttac | ttcatcgagc | cggagctgga | aaagaaggtg | aaattcgtgt | 360 |
| acactgacaa | tcctgagagc | cagaggataa | tggccgacat | gtttgacatg | gagaagctgg | 420 |
| antccgcatt | tggtggccgc | agcgcgtctg | gcatcgacgt | tgccaagtat | tccgagagaa | 480 |
| tgcgaacagg | agatcagatt | aggggtcttc | gctaacggca | aatggaatac | tgctatctca | 540 |
| cagttcgtca | agaaact | | | | | 557 |

<210> SEQ ID NO 79
<211> LENGTH: 807
<212> TYPE: DNA
<213> ORGANISM: Zea mays
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (283)..(287)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t
<220> FEATURE:

```
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (523)..(524)
<223> OTHER INFORMATION: n is a, c, g, or t
<220> FEATURE:
<221> NAME/KEY: misc_feature
<222> LOCATION: (617)..(623)
<223> OTHER INFORMATION: n is a, c, g, or t
<220> FEATURE:
<221> NAME/KEY: misc_feature
<222> LOCATION: (672)..(678)
<223> OTHER INFORMATION: n is a, c, g, or t
<220> FEATURE:
<221> NAME/KEY: misc_feature
<222> LOCATION: (694)..(700)
<223> OTHER INFORMATION: n is a, c, g, or t
<220> FEATURE:
<221> NAME/KEY: misc_feature
<222> LOCATION: (702)..(706)
<223> OTHER INFORMATION: n is a, c, g, or t
<220> FEATURE:
<221> NAME/KEY: misc_feature
<222> LOCATION: (710)..(717)
<223> OTHER INFORMATION: n is a, c, g, or t
<220> FEATURE:
<221> NAME/KEY: misc_feature
<222> LOCATION: (720)..(739)
<223> OTHER INFORMATION: n is a, c, g, or t
<220> FEATURE:
<221> NAME/KEY: misc_feature
<222> LOCATION: (743)..(745)
<223> OTHER INFORMATION: n is a, c, g, or t
<220> FEATURE:
<221> NAME/KEY: misc_feature
<222> LOCATION: (750)..(806)
<223> OTHER INFORMATION: n is a, c, g, or t

<400> SEQUENCE: 79
gcctgcagtg gtgaagtcgg agctgctttg gttntgaggg tgcaacaaag ctcnacaacg      60
atggcaaatt gttctttttc tcaagaggtc gtggcttgtt gcnagtgagt ggcagcttag     120
tatgggcttt gactgaggtt ttttgtggga agtcggagtt gcttatcact atcttgggat     180
taagctcggc aacgatgncg cacggtnggc tacattggtt gtgtgacact tttgtgtatt     240
tgtgggttgc ttagggttag ctntctgggc tgttatgttt agnnnnngta ttttttggtng    300
gtttcccttt aataaactgt gccattgtga ggttttttagg cttggtttcc ntcataanct    360
gggtnaattc tatctctcan tctctccttt aattgaaagg caaagatcct gcnattgcgt     420
taaaaagaa atatgagagt ctctaaccaa ggatagaaat aaaacatgan ggagaaatgc      480
ttattagcta tcaagtaggg tcactgaatt atgagctgga gtnnaagacg tggacgagtg     540
gctgtggcat gtatttaagt caaattgaag gggttcataa aggtgttctc tagctggctt    600
ctatctataa gaaagannnn nnngatttct agtgccgaac ttctgtatct attcccagga     660
ctcatatcat gnnnnnnnat ttcaatttca tcannnnnnn annnnntatn nnnnnntgn      720
nnnnnnnnnn nnnnnnnnna atnnntcgtn nnnnnnnnnn nnnnnnnnnn nnnnnnnnnn     780
nnnnnnnnnn nnnnnnnnnn nnnnnna                                         807

<210> SEQ ID NO 80
<211> LENGTH: 1415
<212> TYPE: DNA
<213> ORGANISM: Zea mays
```

```
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (19)..(25)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t
<220> FEATURE:
<221> NAME/KEY: misc_feature
<222> LOCATION: (539)..(539)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (937)..(938)
<223> OTHER INFORMATION: n is a, c, g, or t
<220> FEATURE:
<221> NAME/KEY: misc_feature
<222> LOCATION: (958)..(958)
<223> OTHER INFORMATION: n is a, c, g, or t
<220> FEATURE:
<221> NAME/KEY: misc_feature
<222> LOCATION: (1021)..(1026)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1094)..(1094)
<223> OTHER INFORMATION: n is a, c, g, or t
<220> FEATURE:
<221> NAME/KEY: misc_feature
<222> LOCATION: (1155)..(1156)
<223> OTHER INFORMATION: n is a, c, g, or t
<220> FEATURE:
<221> NAME/KEY: misc_feature
<222> LOCATION: (1170)..(1170)
<223> OTHER INFORMATION: n is a, c, g, or t
<220> FEATURE:
<221> NAME/KEY: misc_feature
<222> LOCATION: (1211)..(1211)
<223> OTHER INFORMATION: n is a, c, g, or t
<220> FEATURE:
<221> NAME/KEY: misc_feature
<222> LOCATION: (1401)..(1402)
<223> OTHER INFORMATION: n is a, c, g, or t

<400> SEQUENCE: 80
ggganncgcg tcgccgtgnn nnnnncagcg atggctggcc tactctctcc gcgaagctgg      60
ccttcgagaa gtcggtcttc gccaaaaccc agaaagcgaa tgctggaacg gatggtaatt    120
```

```
tacatctgat ttctcttaat acggaagaat tgttttcgac tgatggtgag cgttgttgtg    180
ctcccttgag gtagtccgga gtacttgatt aacattatca tctcataatg aactcatgag    240
tgtgatgtat tgatgtgcct gtttgcgtgt tttttctttt cttcaagtat ttcatatgtt    300
tatttgtttc tctttaacag cagagattgt aatgtttgat ggtcaaattg tggtatacaa    360
gttnatncaa gacctgcact ttttgttac tggaggagaa gaggagaatg agcttatttt     420
agcatcagtt cttcagggat tctctgatgc tgtngaacga cttctcaagt tatcttccct    480
ctattgaagt ttatcttttc aaccattgtt tgttctgtta catgttattg tgttaatgnt    540
gattgtatat gaatgtgttt ccaaccttgg tggtttcagg aacatggttg acaaaaggac    600
agcactcgag aatttggacc tgatcctatt gtgtcttgat gaaattgttg atggagggta    660
aagccttttc ttactacgta catgatatta agggcttctt ttcttgttct ctttattgtg    720
tacatttatt atcctttgat ctgaaatcac ctgactcatc tgggccatgg caatagagct    780
ctattagggc ctctatttgt aatggttgta ttcacnggat tcaaaggttt antctggtgt    840
tctgcttctg tacctcaagc ccaagcatgc ctaacctttt aatggggtta cacaatttga    900
tntgtgaaac aatggcttag tttgctaaag acatcannaa aataaacagc ccattccntt    960 tttttgaaa tggaacaaaa ctgattatcc acatgaagaa ttgtatctat ttgattttga     1020
nnnnnngttt gagatcttga angactgcag gtaccacaac tatgcactcg cctcaatgtg   1080
tctttgataa cccnattgat gtctaaactc tgaaatgtgg aagtgatagg atcaagcata   1140
gagatgaata gaatnncaca ttgtaagcan catgtaattg tttggtgcat taaacataat   1200
tttctgaatg nttacacagg attgtacttg aaacagaagg aagagagata gctgaaaagg   1260
tgtctggtca cggatcggag ggtgcttcat cggctgagca ggtaggctgc aggctgtatc   1320
tatttcaaat tttaactgaa gaaactggtt tcttttaact tactagctat cgttatttgc   1380
gtgcagactt tagtcaatgc nntaacgcaa gcaag                              1415

<210> SEQ ID NO 81
<211> LENGTH: 364
<212> TYPE: DNA
<213> ORGANISM: Zea mays
<220> FEATURE:
<221> NAME/KEY: misc_feature
<222> LOCATION: (100)..(100)
<223> OTHER INFORMATION: n is a, c, g, or t

<400> SEQUENCE: 81
tgaggaactg caggaaggcc atccctccga gggaaggagg agggaaggtg ataatcatcg     60
acatggtggt cggggctggg ccggcggacc cgaggcacan ggagatgcag gccctgttcg    120
acctctacat catggtcgtc aacggcatgg agcgggacga gcaggagtgg aagcagatct    180
tcgtcgaggc cggggttcacc gactacagag tcacgccggt cctcggcgtc cgctccatca    240
tcgaggtgta cccttgaacg aacgaacgaa cgaacgtcgt ctggtgccat gtgtgtgtgt    300
ttgtgtggag ggagggtcat cctctatttt ctttttttgtt ttgtttctgc attctgaaga   360
cacg                                                                 364

<210> SEQ ID NO 82
<211> LENGTH: 426
<212> TYPE: DNA
<213> ORGANISM: Zea mays
<220> FEATURE:
<221> NAME/KEY: misc_feature
<222> LOCATION: (232)..(232)
<223> OTHER INFORMATION: n is a, c, g, or t
```

-continued

<400> SEQUENCE: 82

```
tggagagggt gagatcacaa aagctttcaa ccgccgggac tcaaagctag aaaagccatc    60
gccgccaact ccaagaccgg cccgtccaac ttccaggcat tccccttga cgccctctgc   120
tagagtggca ccgatacctg cgaggagaaa atctgtcacg cccaagaacg ggctttcaca   180
ggtggacgat gacgcgagga gcgtgctcag tgtgcagtct gagcggccaa gnaggcacag   240
tatagccacc tcgactgtgc gggacgacga gagcctcacg agctcccgt cgctcccaag    300
ctacatggtt cccacagaat ctgcaagggc caaatctcgc ctccagggtt cagcaatggc   360
caatggcgca gagacacctg agaaaggagg ctcaactgga ccagccaaga agaggttatc   420
cttcca                                                             426
```

<210> SEQ ID NO 83
<211> LENGTH: 1289
<212> TYPE: DNA
<213> ORGANISM: Zea mays
<220> FEATURE:
<221> NAME/KEY: misc_feature
<222> LOCATION: (2)..(17)
<223> OTHER INFORMATION: n is a, c, g, or t
<220> FEATURE:
<221> NAME/KEY: misc_feature
<222> LOCATION: (79)..(86)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (99)..(105)
<223> OTHER INFORMATION: n is a, c, g, or t
<220> FEATURE:
<221> NAME/KEY: misc_feature
<222> LOCATION: (107)..(109)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(118)
<223> OTHER INFORMATION: n is a, c, g, or t
<220> FEATURE:
<221> NAME/KEY: misc_feature
<222> LOCATION: (123)..(125)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (140)..(140)

```
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (650)..(651)
<223> OTHER INFORMATION: n is a, c, g, or t
<220> FEATURE:
<221> NAME/KEY: misc_feature
<222> LOCATION: (1171)..(1173)
<223> OTHER INFORMATION: n is a, c, g, or t
<220> FEATURE:
<221> NAME/KEY: misc_feature
<222> LOCATION: (1231)..(1235)
<223> OTHER INFORMATION: n is a, c, g, or t
<220> FEATURE:
<221> NAME/KEY: misc_feature
<222> LOCATION: (1261)..(1266)
<223> OTHER INFORMATION: n is a, c, g, or t

<400> SEQUENCE: 83
gnnnnnnnnn nnnnnnntcc taaatggact gggttactgc ctaaatctgg aaagatggtt      60
agtgcttgaa ttctttatnn nnnnnntang gnctnacann nnnnnannna nacnnnnnat     120
tcnnngntat ggtnttnacn ancatnagaa ncgtgtaacc atgaaatatt attcttggtg     180
ctctaggtaa ttaatacaga gtgggggagc ttcaaatcca acaaacttcc tctttcagaa     240
tatgacaaag ccatggactt tgaaagtttg aaccctggag agcaggtatt gttgctctgg     300
cggttgactt tnccatttca ggtgactgca tgaatatatg tggataactt angngtggct     360
tctgacagat atacgananaa atgatttctg gtatgtatct cggagagatt gttcgaagaa     420
ttttactgaa gttngcacat gaagcttctc tatttgggga tgttgttcca cctaagctgg     480
agctgccatt tatattgagg tatgctttct tgtcctatgg acatccagct gttcaagctt     540
gtttgctaca ttgttggtat ggaaaagttg tttatgtctc tttaataggc taagttagat     600
gtcacatcag taagtaatcc aaagaaggcg acatgataca atatttttn nggtcaactc     660 tgtttatttc aattggttgc aataaacatg gtctctgata tgctgcaatt ttacttttga     720
ataactatct tgatggcatg agaaaatgtg tgcctagaaa cagcttgctt cagggagctt     780
tatattagat tagatttcag ggctaataaa gtatttacct ggagctaaaa caaacggtca     840
```

-continued

```
ccttgtaact ctcgttagtc tattaacagg tacatgtatt gggtttgagg catgttgatg      900
cttaacatct ttgtgtgatg cttaacattt tctttggcac cagctctttc tgtgcccttt      960
ttatgcttat tagtaagttg aaacctatgt atcaattagt acatgttcga tgaatacatt     1020
cgttgtggta tcacaggacg ccagatatgt cagccatgca tcatgactcc tcacatgacc     1080
tcaaaactct tggagctaaa ctgaaggaca tagtcggggt acggcttgcc tgtgccaaat     1140
tggcttgttg ttcataaata gtcagtcagt nnnctctcgg tcccttacgg catatacatt     1200
tgttctcatg ttcaggtcgc ggacacttcc nnnnnagtaa ggtacatcac tcgtcacatc     1260
nnnnnncttg tcgcagagcg tgcagcacg                                       1289

<210> SEQ ID NO 84
<211> LENGTH: 665
<212> TYPE: DNA
<213> ORGANISM: Zea mays
<220> FEATURE:
<221> NAME/KEY: misc_feature
<222> LOCATION: (473)..(473)
<223> OTHER INFORMATION: n is a, c, g, or t

<400> SEQUENCE: 84
tcaaaaccca gtgcatccga gttcaggtct tcaggcttgg caggtgaaga tttctcgaga       60 aaccctgga acaactggc ttccgtttcc ggaccttgat tcccacacct gccatgcccc       120
tcaaatgcct ggtggttctg ctttacgtca tcctgatgaa cttccttggt ttttcggact      180
gtaaacatgc cttcgcatcc agaaacctaa caaagataaa ttactgattg catcgtatca      240
gggacaatat tgtttctaag ttactgagtg tttcttcttg gtccaaatcg gagcttcagg      300
ttgtccaaaa cacgggtaac attgagaagt cgtggatcgt cagaaggaat ctctcgcgcc      360
tgaatttgaa aaacaaggga gcatgagcag aacacgaatc aagaacagcc agatgaacca      420
gttcgtttta attcttcaga gcttaattgc tgacaggtga cagcagacaa atnatttcag      480
tgtacaaaca gttgagaccc aaatgaatat gtacatcaag gaccaatata gtaagttagc      540
aactcattct atagttagga agtactcaat tattcataga tgttttcaag gtgaagaaag      600
tgtaccaagt cacaagttca agatactaaa gcttaccgtc agacccttgt ggtatgcctc      660
aacac                                                                 665

<210> SEQ ID NO 85
<211> LENGTH: 1302
<212> TYPE: DNA
<213> ORGANISM: Zea mays
<220> FEATURE:
<221> NAME/KEY: misc_feature
<222> LOCATION: (3)..(9)
<223> OTHER INFORMATION: n is a, c, g, or t
<220> FEATURE:
<221> NAME/KEY: misc_feature
<222> LOCATION: (14)..(18)
<223> OTHER INFORMATION: n is a, c, g, or t
<220> FEATURE:
<221> NAME/KEY: misc_feature
<222> LOCATION: (81)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
```

```
<221> NAME/KEY: misc_feature
<222> LOCATION: (100)..(102)
<223> OTHER INFORMATION: n is a, c, g, or t
<220> FEATURE:
<221> NAME/KEY: misc_feature
<222> LOCATION: (105)..(106)
<223> OTHER INFORMATION: n is a, c, g, or t
<220> FEATURE:
<221> NAME/KEY: misc_feature
<222> LOCATION: (108)..(110)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (124)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (1159)..(1161)
<223> OTHER INFORMATION: n is a, c, g, or t
<220> FEATURE:
<221> NAME/KEY: misc_feature
<222> LOCATION: (1174)..(1174)
<223> OTHER INFORMATION: n is a, c, g, or t
<220> FEATURE:
<221> NAME/KEY: misc_feature
<222> LOCATION: (1232)..(1234)
<223> OTHER INFORMATION: n is a, c, g, or t
```

```
<220> FEATURE:
<221> NAME/KEY: misc_feature
<222> LOCATION: (1262)..(1266)
<223> OTHER INFORMATION: n is a, c, g, or t
<220> FEATURE:
<221> NAME/KEY: misc_feature
<222> LOCATION: (1279)..(1282)
<223> OTHER INFORMATION: n is a, c, g, or t
<220> FEATURE:
<221> NAME/KEY: misc_feature
<222> LOCATION: (1289)..(1295)
<223> OTHER INFORMATION: n is a, c, g, or t

<400> SEQUENCE: 85
ggnnnnnnna aatnnnnntc ctaaatggac tgggttactg cctaaatctg gaaagatggt      60
tagtgcttga attctttata nnnnnnntan ggncttacan nnttnnannn anactttta     120 ttcnnngtna tggtnttnac nancatnaga ancgtgtaac catgaaatat tattcttggt     180
gctctaggta attaatacag agtggggag cttcaaatcc aacaaacttc ctctttcaga     240
atatgacaaa gccatggact ttgaaagttt gaaccctgga gagcaggtat tgttgctctg     300
gcggttgact ttnccatttc aggtgactgc atgaatatat gtggataact tangngtggc     360
ttctgacaga tatacganaa aatgatttct ggtatgtatc tcggagagat tgttcgaaga     420 atttttactga agttngcaca tgaagcttct ctatttgggg atgttgttcc acctaagctg     480
gagctgccat ttatattgag gtatgctttc ttgtcctatg gacatccagc tgttcaagct     540
tgtttgctac attgttggta tggaaaagtt gtttatgtct ctttaatagg ctaagttaga     600
tgtcacatca gtaagtaatc caagaaggc gacatgatac aatattttt ttggtcaact     660 ctgtttattt caattggttg caataaacat ggtctctgat atgctgcaat tttacttttg     720
aataactatc ttgatggcat gagaaaatgt gtgcctagaa acagcttgct tcagggagct     780
ttatattaga ttagatttca gggctaataa agtatttacc tggagctaaa acaaacggtc     840
accttgtaac tctcgttagt ctattaacag gtacatgtat tgggtttgag gcatgttgat     900
gcttaacatc tttgtgtgat gcttaacatt ttctttggca ccagctcttt ctgtgcccttt     960 tttatgctta ttagtaagtt gaaacctatg tatcaattag tacatgttcg atgaatacat    1020
tcgttgtggt atcacaggac gccagatatg tcagccatgc atcatgactc ctcacatgac    1080
ctcaaaactc ttggagctaa actgaaggac atagtcgggg tacggcttgc ctgtgccaaa    1140
ttggcttgtt gttcataann ngtcagtcag tgtnctctcg gtcccttacg gcatatacat    1200
ttgttctcat gttcaggtcg cggacacttc cnnnaagtaa ggtacatcac tcgtcacatc    1260
tnnnnncttg tcgcagagnn nncagcacnn nnnnncgccg ca                       1302

<210> SEQ ID NO 86
<211> LENGTH: 726
<212> TYPE: DNA
<213> ORGANISM: Zea mays
<220> FEATURE:
<221> NAME/KEY: misc_feature
<222> LOCATION: (140)..(140)
<223> OTHER INFORMATION: n is a, c, g, or t

<400> SEQUENCE: 86
tcatcttcta ctgaaaaaac caggagaagt ggccatcgca tggcatgaca cacaactttg      60
tccatccctt ttactctggc atccagcctc tgtgacctgg acgagctacc ggcgcgtgga     120
gcccagaaag aacggagtgn cattctctta cgccactgtg accgccctca accccccca     180 aagccaatga aaggcggttt agtcgcttcc tacctcactt ggtgatcgtt ctctctttcc     240
```

```
ggttgatggt tggcgctgtt tattttagc atcggttgga ctatcagact aggctaaggg      300
cccctttggt agggcttatt tttcagcttc ggctctggct catgcaaaag ttgtgccaaa      360
cacctctttt tcaaatggct tcaccaatga agtgcttttc caaaatgaac tagagggcat      420
gagccaaaaa aagtggctca cccggcttca gctcacgtca ttttttgcaca atagccctcc    480 caccagtcca aattaatttt tttggtcatg ccctcaatcc ctagccacgc acaatagccc      540
tcccaccagt cccaactata caagggtctt tctaaaaaac aacttataag ccgttttgcc      600
aaatgatttt tcagaatggc tttggctcat ctaaagaagt ggcttcacct cgtgagtcag      660
agccaaagcc gttttttgtag aagccagagc cctgccaaag gggccctaaa ccttgcctta    720
gtttaa                                                                726
```

<210> SEQ ID NO 87
<211> LENGTH: 710
<212> TYPE: DNA
<213> ORGANISM: Zea mays
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (627)..(628)
<223> OTHER INFORMATION: n is a, c, g, or t
<220> FEATURE:
<221> NAME/KEY: misc_feature
<222> LOCATION: (643)..(644)
<223> OTHER INFORMATION: n is a, c, g, or t
<220> FEATURE:
<221> NAME/KEY: misc_feature
<222> LOCATION: (648)..(650)
<223> OTHER INFORMATION: n is a, c, g, or t
<220> FEATURE:
<221> NAME/KEY: misc_feature
<222> LOCATION: (670)..(672)
<223> OTHER INFORMATION: n is a, c, g, or t
<220> FEATURE:
<221> NAME/KEY: misc_feature
<222> LOCATION: (689)..(698)
<223> OTHER INFORMATION: n is a, c, g, or t

<400> SEQUENCE: 87

```
gtttgggtct acaaacattg ggttgacaga tctcgatgta ctcttccact gtaaacaaca      60
cattttgaga cattttaagc tttaccatca tagagcaagg aggatcaagt atatatagat      120
gttctgagag caagagttcc tacctggtgt gaaaatgcat atgcaagcgc tctttctctt      180
cttatcgccg cctcttgcct gcttatcagg cttgcctcga tttgctcctt ggattgggtg     240
ctgtcatccc agttctcacc catctgatat atcattattc acagacagaa tatgtttagt     300
tctctcaata atatcttata actatctcaa ggctttaagc agattagagc tttgagaagg     360
tttgcntact ctgaaattct ccagttcctg tttaagtagg agctggcgtt ggagagcctg     420
gttctcctcg gacatctttg ctctcctgga agatatctgt gactgcaccc gtgatagagt     480
ttgcatgcag cgcagagtgc ttgcagattg acgctttact gaattaccct caaccaatga    540
cttcaatcga acaaggcctc gcagtgctcg tagtgcctc cttgcctacn ttatcacaat     600
gaccgaanac tctcagcata acattgnntt gtaaaagtaa gannccttnnn ttttctttc    660
```
cttttttttn nngcaaagtg taaaagtann nnnnnnnntt actatgaaac        710

<210> SEQ ID NO 88
<211> LENGTH: 614
<212> TYPE: DNA
<213> ORGANISM: Zea mays
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (412)..(416)
<223> OTHER INFORMATION: n is a, c, g, or t
<220> FEATURE:
<221> NAME/KEY: misc_feature
<222> LOCATION: (424)..(440)
<223> OTHER INFORMATION: n is a, c, g, or t
<220> FEATURE:
<221> NAME/KEY: misc_feature
<222> LOCATION: (442)..(447)
<223> OTHER INFORMATION: n is a, c, g, or t
<220> FEATURE:
<221> NAME/KEY: misc_feature
<222> LOCATION: (465)..(474)
<223> OTHER INFORMATION: n is a, c, g, or t
<220> FEATURE:
<221> NAME/KEY: misc_feature
<222> LOCATION: (481)..(485)
<223> OTHER INFORMATION: n is a, c, g, or t
<220> FEATURE:
<221> NAME/KEY: misc_feature
<222> LOCATION: (492)..(505)
<223> OTHER INFORMATION: n is a, c, g, or t
<220> FEATURE:
<221> NAME/KEY: misc_feature
<222> LOCATION: (518)..(519)
<223> OTHER INFORMATION: n is a, c, g, or t
<220> FEATURE:
<221> NAME/KEY: misc_feature
<222> LOCATION: (530)..(546)
<223> OTHER INFORMATION: n is a, c, g, or t
<220> FEATURE:
<221> NAME/KEY: misc_feature
<222> LOCATION: (549)..(558)
<223> OTHER INFORMATION: n is a, c, g, or t
<220> FEATURE:
<221> NAME/KEY: misc_feature
<222> LOCATION: (564)..(576)
<223> OTHER INFORMATION: n is a, c, g, or t
<220> FEATURE:
<221> NAME/KEY: misc_feature
<222> LOCATION: (587)..(605)
<223> OTHER INFORMATION: n is a, c, g, or t

<400> SEQUENCE: 88
gtcggagaag ttggctgtgt tgccaggatg taatagaaaa gggctcagaa tgttgctgat        60
ccttgttaac tggataatat ggcggaaaag gaacgcaagg actttgatc gtaggttttt        120 gaccagtcag cagagcataa cttcggttaa gtgtgaggcg tcagcctgga tggcggccgg        180
ggctaggcaa ttggctactc tcttaccttc gtcaacttag ttgggttact acttgtgggt        240
tgttttctna gtgggctagt ggcggaggga tgcttaataa gccccctgacg cacttctcat        300 cataattgta ttgactttct tgccttagag cattcctctc tttattaata tataagggtt        360
tcaaaaaaaa tgcatagcag ataatttctg gacagtatgt aggagatctg gnnnnntgat        420
ctcnnnnnnn nnnnnnnnnn annnnnnngct atgcattttt tttgnnnnnn nnnatatta         480 nnnnngagag gnnnnnnnnn nnnnagaaa gtcaatanna ttatgatgan nnnnnnnnnn        540
nnnnnntann nnnnnnnnct ccgnnnnnnn nnnnnnaaga aaacaannnn nnnnnnnnn        600 nnnnnctaag ttga 614

<210> SEQ ID NO 89
<211> LENGTH: 1028
<212> TYPE: DNA
<213> ORGANISM: Zea mays
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (960)..(962)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (997)..(1003)
<223> OTHER INFORMATION: n is a, c, g, or t

<400> SEQUENCE: 89
caatccaata ccaaatcaga aggaatatta gaaaaggctt cacttgttaa atatgtcaag      60
gcattcatgt actgcaagaa tagagggggc agagaatccc atcagatagg tgctgtagaa     120
tgtggataaa gcctgaacaa gatggtctac ttgcaaaact gaagcagaga aagtgtaaaa     180
tatacagttc agaccactga ggctaaaaga acaaatctac attgggtaaa tgtcaacatt     240
cagattttaa aacataccat tttaacattg ttatggcagt ccagaagtgg tctacgagca     300
accagattgt aagccaaaca tccaaagcta aacatatcac aagcagagcc aactttagaa     360
tctctacttt ggaccaattc tggtgcagta tagttcaacg atggttgaag aggtaaagct     420
gtatcctcga catcatagtc ctagaaagaa acaagcaga taaattgtta acaggtcagg     480
gcattggaag caacaaaaaa aatcacaaaa cgtatcttga agacacaaat cacagaagat     540
gtcaccaaag tacttaggaa tgggtatgat gaancgctaa atatgcttag ttgaccattg     600
ataacttaac aatgtagcgg tctaataatg actaacatag gttcgtggtg cacatcgtat     660
atgccattac aaatcccagc agtagcaatg tgctaaacac aatcgccagt tcgccacatc     720
acagtagtgg tatattctta acttttatat gaaaagatca gttcaagaca agaagaaact     780
ctgccagaaa aatatgtatc atgcaaaact gtgtgacaat ttagaaatta aatgattgca     840
aaaaaaagaa caatataagt tcagtggaat attttctgtt acagcaaact tcaaagggat     900
aatacagatt agtaatattc ccaaaatatg gtagaagaat ctgcaaatta aagccaccan     960
nntgacaaac taaatgtata tcacttacta accnaannnn nnnatagttg tgatgaagtc    1020
aaactcaa                                                            1028

<210> SEQ ID NO 90
<211> LENGTH: 663
<212> TYPE: DNA
<213> ORGANISM: Zea mays
<220> FEATURE:
<221> NAME/KEY: misc_feature
<222> LOCATION: (218)..(218)
<223> OTHER INFORMATION: n is a, c, g, or t

<400> SEQUENCE: 90
agttctgcaa gcctgtgtct gagggtacta gtatctttct tcggttgttc accttcattc      60
ttaccaaacat atacaaggac acagataaag cgaaaaatgc caggagcgaa ggtaataaaa    120
cttttatcaa caagttcttt gatcgtgaat gattactgat attgtagcac tgtgctatac    180

```
ctaggcgagg aaggccacac agcgcattgt tccccatnaa tgatttgagt gtgatatttg      240
agaacactcc tccttctggt atctgtccat ccaatctgtt aaaagaaagg ttcaagttgg      300
caaggtaagt gagattggtc aaggattttg ggatggcacc ggagagtgca ttggaggata      360
ggtccaattc ctggatatta agtatattgc tgaatgaacc tggtattgat ccttggaata      420
aatttctgga cagattgaga tatatcatca tgtggagttc accaaaggag actgggatgt      480
cacctgacag cttgtttcct gataaatcca tcatggtaat tgctgtcaat tttccaacat      540
cagcaggcag gaacccactt aaagagttct gtgacaagtc aagctcaata agtttctgaa      600
gatcccacag acttgttggt atggttgaag acaatgagtt tgggataac gtcataattt       660 gca                                                                    663
```

<210> SEQ ID NO 91
<211> LENGTH: 785
<212> TYPE: DNA
<213> ORGANISM: Zea mays
<220> FEATURE:
<221> NAME/KEY: misc_feature
<222> LOCATION: (701)..(701)
<223> OTHER INFORMATION: n is a, c, g, or t

<400> SEQUENCE: 91

```
gtgaggcttt gaatattcta cttactacgt ccccgaaaaa caaatctact tacatatccc      60
atctatggtt tatttcttct ggctctgttt tgcatcagat ggtgtcacta ttaacgttac      120
atgcatgcct atgattcact cttatctgca atataagctc ttgtttaatc aatgatgatg      180
tattcgtgaa ttcaggaaca tttcaagaaa aacaagatga ccattaatct gaagtacata      240
ggtcagtggt tttcttcggt gtcatatttc agggccagaa ctgctagtta cacacatctc      300
agatgttgtt cttctactgc agatccaacg tacatgatac gtgccatccc aagcaatgct      360
tctgataacg tctattgcac actgctggct cacagcgtgg tccatggagc catggctgga      420
tatactggtt ttaccattgg ccaagtgaat ggtcggcact gctacatccc attctatgta      480
agtcgcaccc ctgccggagc aggacacgga attcttttta ccgcattcat catctcagca      540
tctgagacct acttatcctg cttgaaccaa tgccctccgt actaattgtt ttgcattcgc      600
gtcactcact tcagaggata acagagaagc agaacagagt ttcgataacc gacaggatgt      660
gggcaaggct tctctcgtcg acgaaccagc caagcttcct ntgcaacaaa gtcgtcgagg      720
aggcaaagaa ggaacatgaa agagcaacgc gacttttaga tggctcgcct tcccatcgaa      780
aaggt                                                                  785
```

<210> SEQ ID NO 92
<211> LENGTH: 638
<212> TYPE: DNA
<213> ORGANISM: Zea mays
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (579)..(579)

```
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (589)..(590)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (607)..(637)
<223> OTHER INFORMATION: n is a, c, g, or t

<400> SEQUENCE: 92
ccttctgctg gaaatggtcg gtgctgagcc tgctatcaga aacctccagc gagcttccga      60
tcttctgttt ctgccggcgg taccaggaga acgcaaataa accgcaaaat gcagcaccga     120
tcaccgccgc gacaacagcg acgataagaa ctccttggga cgcgtttgcg gactttgagc     180
anctagcgcc tgagcagccg tctggatttg ctgattgagg cacctgcctt gtcttgacag     240
taccgtctgg tccaaaaggc tcgggcttgc tgggcttcag gccatcctct gaagaaaggc     300
aaagctctag caaactgaag ccagcgccac aaagccccttt gttattcata tactggaagc    360
caccattcag tctcctcaat cctagcatcc aacacagaat tgtagtggtt aaaataccat     420
gaagactaac aaaaaaaagt acaagtttca gaaaggctat gagattatta ccaacaggga    480
cactcccaga aagggtgttg ttgcgaacat caaagacctc aagcaatgga acctcagcaa     540
tcttggatgg gattgaacna aacagnctgt tgaagctcna atcangccnn ctcngcnntg     600
ttagctnnnn nnnnnnnnnn nnnnnnnnnn nnnnnnnc                            638

<210> SEQ ID NO 93
<211> LENGTH: 764
<212> TYPE: DNA
<213> ORGANISM: Zea mays
<220> FEATURE:
<221> NAME/KEY: misc_feature
<222> LOCATION: (108)..(129)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t

<400> SEQUENCE: 93
tgggtacctc gcctcgagcc ggaattcggc acgaggatcc aatcgaacca ccagtccacc      60
acctgattga ctagagcaaa agcacaagcc gcccacgcat ctcgattnnn nnnnnnnnn     120 nnnnnnnnng gcgcgcagag ctcgtgacga gagcaacctt ccttccgttc ctcgatcgcc     180
atggacaagg tgctggcctt ctcgatcctg agcgcgtcgc cggccgacct ctcctccacg     240
ggcgccggct tcggcgggag ctgggcgcgg ctgtcgtggc ggcggggcgc ggacgaccag     300
cgtgcgccgt ggtggtagca ctataatcag caccaggagg aggacaggga gaagcgagac     360
ttgcgctccc gcgacggcgg agcgcacgcg agcggagggg gagcggcggc ggcgccaccg     420
cggttcgcgc cggagtttga cggnatcgac tggttcggaa ccatcgtgtc gcgctgatca     480
acaatccggg ctcggccgac gcgcccccg agttaaccac gtgaccaatc ctgtctacta      540
```
tgtttttttt accttatggt ggattaattg tcccaacaca gataattggg actccgcgtg    600
ttgtacatac agggaactgc tcaattacca ggtgggatgg ggaacattta tttgttcctg    660
tcctctgcat ttttttttctg taccgaaatg gatggatggt ctccaacttg aaattgagtc   720
cctcagcccc aggtaatctg gcggtggatg aacccaagcc gaac                     764

<210> SEQ ID NO 94
<211> LENGTH: 536
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (242)..(243)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t

<400> SEQUENCE: 94
tgcagtactc accaaatctg cgttgcacta ctgtaagaac aaatttgana ttgtaactga     60
cgaattagtg aatccaaact cttctctagg tctgtaatat tatgtgtact ataatgttta   120
tctactctac aaccatcatt ggcagcttaa ttgtgatcat accacagtat ccaaacactc   180
caacgttgta caattcactc tgatttacta tgcaacacag ttgtacaatt cactctaatt   240
tnnactatgc aacacacgcg catgtgcgcg cagtcgcaga gcacactngt ttcatatata   300
ctccctccaa ccatagatgc aagaccatta gatttgacct aaacagttag gcaatcccga   360
gcagatagag aaatcatgtg tagccgtata tctacttgaa ctatctatct atgtatggat   420
ttgagcgcca aatctctcgt ttggttgtaa ccggtggact gaaaagtggg tggaaataat   480
gtgtgaaatg acaaaattcg atgtggtctc tagctggagt atttattagt ttctgt       536

<210> SEQ ID NO 95
<211> LENGTH: 640
<212> TYPE: DNA
<213> ORGANISM: Zea mays
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (479)..(480)
<223> OTHER INFORMATION: n is a, c, g, or t
<220> FEATURE:
<221> NAME/KEY: misc_feature
<222> LOCATION: (482)..(484)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t

<400> SEQUENCE: 95

```
ggcgcatcat cttccagtca gctctgcacg tgccacactg ccactgccaa atctccgtga      60
tggtggtggg ctgcatgttt gcgcaaactt tctgccgagg ccgaatacca acgagtcgag     120
tagacgaagg aatcaccggc gagttcgatc ggccccaatg caaggttctc tgtgtgtgcg     180
tgggtgtgtg gacggtggtg gagaggtaga tggcgaggcg gaggagatgg agatggggag     240
atctatttat acatgatgat gacgcgtgcg gaggctgcga tcaccagtcg gtcgncaaac     300
gagagcgttt cccacagcgt cgtttccaag cgacccttgg cacctgttca gttgcttcct     360
tcagtcggaa ggtccctctg cttccgacgt gaatcgcacg cagggtttag aggttcantc     420
tcngtacgca gcctaatctc tcacaataag gagaagacgc caatttgatc tctctcatnn     480
cnnntatacc gtttgacaaa catggtaatg ctcttgccac acccgtgaca tatctttgcc     540
tttatctttt atgttcggtc ggttacgaga ttcntcgcta ctcacattca cacgactgac     600
tacgactaca cgagaggcgg ttggccttga tcagacagac                           640
```

<210> SEQ ID NO 96
<211> LENGTH: 714
<212> TYPE: DNA
<213> ORGANISM: Zea mays
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (622)..(627)
<223> OTHER INFORMATION: n is a, c, g, or t
<220> FEATURE:
<221> NAME/KEY: misc_feature
<222> LOCATION: (633)..(640)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t

```
<220> FEATURE:
<221> NAME/KEY: misc_feature
<222> LOCATION: (670)..(673)
<223> OTHER INFORMATION: n is a, c, g, or t
<220> FEATURE:
<221> NAME/KEY: misc_feature
<222> LOCATION: (677)..(682)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (690)..(692)
<223> OTHER INFORMATION: n is a, c, g, or t
<220> FEATURE:
<221> NAME/KEY: misc_feature
<222> LOCATION: (697)..(698)
<223> OTHER INFORMATION: n is a, c, g, or t
<220> FEATURE:
<221> NAME/KEY: misc_feature
<222> LOCATION: (702)..(706)
<223> OTHER INFORMATION: n is a, c, g, or t
<220> FEATURE:
<221> NAME/KEY: misc_feature
<222> LOCATION: (708)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t

<400> SEQUENCE: 96
tactgtcaat cctgttgttt atccttgtgt atgcttgtta gtcaaaccat atttcagtaa      60
ctaattcctt gattgtgagt tactgctgat ctcatnatgg aatgggtttt catgtagttc     120
agatgtgttt tttnactcaa ctatttctct attagtttct aggttactta cgtggatgct     180
atttatctgt ctggactttg gatagtgcaa tgttggctcn aaaangaaaa aaagatagac     240
ctggtgctga aggctcnggg gtctgggaaa gggataaaca gaggcaagcc ttcttcccac     300
aattgcggag aggctgcttt caacacncga cttagtggga cagctctcac cactgcacga     360
gacgtgtccn tctaaaacta ctaactcaca aaattataaa ntttgtgatt ttgtagccat     420
tgtgatcttg tatttgtatc aacaaatggt tgatgctgca tgtttgcagg gaatatgaga     480
attcattaca acatatcatt tatttttact actgagttat agtatggatt ganttgtatc     540
ttttgtgagt tacttctctt tgtacttgtt gagcttgtgc attgtagatt tgaactgaag     600
tcatgtggca tttgatttac tnnnnnnttt tannnnnnnn ttcatgtggc gtatangtga     660
gggatgangn nnaagnnnn nnatntcatn nngcatnnac tnnnnnannc ncng            714

<210> SEQ ID NO 97
<211> LENGTH: 353
<212> TYPE: DNA
<213> ORGANISM: Zea mays
<220> FEATURE:
<221> NAME/KEY: misc_feature
<222> LOCATION: (100)..(100)
<223> OTHER INFORMATION: n is a, c, g, or t

<400> SEQUENCE: 97
tcaccagcca tgtagttgct gggttttcct gcttgcatgc tgcaacagct tcacattatt      60
gaagaaaccg atgaggcttc tgtggaatta tgagctgagn tgaacctggc aagcattgga     120
```

| | |
|---|---|
| atctggtttc agaatgctct aattttgaag attaacttgt gttccatttt aagcgtgtag | 180 |
| taagatgcaa ggaagccctt tacttctgtt cataggttgc aatcagtttt gtgtgctcca | 240 |
| aaggtaatat ttgattgcca cagttgcagg gattcaataa atccacgagt tagaaatgac | 300 |
| catttgatga tgaataagaa tgaatgtctg ccttgtgcta ttggatatgg ata | 353 |

<210> SEQ ID NO 98
<211> LENGTH: 1097
<212> TYPE: DNA
<213> ORGANISM: Zea mays
<220> FEATURE:
<221> NAME/KEY: misc_feature
<222> LOCATION: (517)..(518)
<223> OTHER INFORMATION: n is a, c, g, or t
<220> FEATURE:
<221> NAME/KEY: misc_feature
<222> LOCATION: (521)..(524)
<223> OTHER INFORMATION: n is a, c, g, or t
<220> FEATURE:
<221> NAME/KEY: misc_feature
<222> LOCATION: (530)..(532)
<223> OTHER INFORMATION: n is a, c, g, or t
<220> FEATURE:
<221> NAME/KEY: misc_feature
<222> LOCATION: (534)..(538)
<223> OTHER INFORMATION: n is a, c, g, or t
<220> FEATURE:
<221> NAME/KEY: misc_feature
<222> LOCATION: (555)..(558)
<223> OTHER INFORMATION: n is a, c, g, or t
<220> FEATURE:
<221> NAME/KEY: misc_feature
<222> LOCATION: (561)..(565)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (592)..(593)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1091)..(1095)
<223> OTHER INFORMATION: n is a, c, g, or t

<400> SEQUENCE: 98

| | |
|---|---|
| tataatatga atggtctaaa aagataatat agaagtattt cagcataata ttgaggatta | 60 |
| agataagaac atattaggtt cacaggaaaa aaaaatgagg gtgcttttga aactcaactt | 120 |
| ggtgatggac aataaaataa gattatttat agttttaga ataattgtgc caactggttg | 180 |
| caaatggatg cctcaaatgt ttacacttca atttaatcat gccacaggaa aatttgtgaa | 240 |
| agtttagttc cacactgaga aaacaatcc aactttattt attgatacct ttatttttag | 300 |
| gtgcaaacat caaataacca aaattctaac atgtcagtat ttacctgata aaaggaagct | 360 |
| aatctaacat agccagtctt gcactcatgg ccatcgtctg ttctatgaga gataattgca | 420 |
| gttgacagag gtgaaaggtt gataatttca cgagacagct ggacctttgg aaacaaaagg | 480 |
| tagtggacat aattaggaaa cactcgatca ctgtctnngt nnnnaaatgn nncnnnnntg | 540 |
| gttaatgaat ttttnnnnga nnnnntacng caatttgatg agctctgtag gnncagatca | 600 |
| tacatttcaa attacacata taaaaatctt aagattttac aattcttcgt tcagcaagtt | 660 |
| aggcattacc tccttttgtc ttaaaccccc acacctttca tcgtcagttc cctggatata | 720 |

```
aatatgcatc ggtaagaaag taaatacaaa gacgaggagc aacgtttcca tggctgagtt      780
caccaaatta cataaagggg attcaggata tgatataata taatagaagc ctagtatgcc      840
agacttcggt gaaccaaaaa aacgcgatgt ttttttagtt ctataaacca aaaccttggc      900
cacttattca atctctgaat gttttttta aacaagtgcc ttaatgttga actggcacat       960
ctcaagttga agtatacttc acaaccagca aaatagattt aactgaagct aagtatctac     1020
tatgaagctc aagtaagga aatacatcta anaacttcac tttcactgtt gttcctacac     1080
ggcctctaag nnnnnga                                                    1097
```

<210> SEQ ID NO 99
<211> LENGTH: 458
<212> TYPE: DNA
<213> ORGANISM: Zea mays
<220> FEATURE:
<221> NAME/KEY: misc_feature
<222> LOCATION: (204)..(204)
<223> OTHER INFORMATION: n is a, c, g, or t

<400> SEQUENCE: 99

```
cggcggcaat caagcagcag cgggatgatg gagggaccgt tccgattctt gccggccgaa       60
gtgaaagaga tggaggagcg cctgttcccg gtcaccaatc gcaggctgga tcacatcctc      120
atggatgagc tcgctctgaa atttagctgc ttccggcgcc gtgctggcat ggttcccgtc      180
aagccaaagc aggtatgtgc atcnacgatg ttccgttcca catatcaatt tcaaattccc      240
tctcccatga acctgcggtt tcattccgat ctggacatgc atgcatccag gtgctcaact      300
ggttttataa caaccgtaac aagacttctg ccaaggtagc agccagggaa gcacatgctc      360
catgggagtt ttgggccaac catcagcaag ctagagctag aggaggctca tccatcagca      420
agctgaagcc aaagaaggcg actacgcacg caggatct                             458
```

<210> SEQ ID NO 100
<211> LENGTH: 1025
<212> TYPE: DNA
<213> ORGANISM: Zea mays
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (89)..(92)
<223> OTHER INFORMATION: n is a, c, g, or t
<220> FEATURE:
<221> NAME/KEY: misc_feature
<222> LOCATION: (100)..(102)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (211)..(211)

```
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (682)..(687)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (883)..(883)
<223> OTHER INFORMATION: n is a, c, g, or t
<220> FEATURE:
<221> NAME/KEY: misc_feature
<222> LOCATION: (902)..(912)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (916)..(925)
<223> OTHER INFORMATION: n is a, c, g, or t
<220> FEATURE:
<221> NAME/KEY: misc_feature
<222> LOCATION: (930)..(934)
<223> OTHER INFORMATION: n is a, c, g, or t
<220> FEATURE:
<221> NAME/KEY: misc_feature
<222> LOCATION: (949)..(951)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t
<220> FEATURE:
<221> NAME/KEY: misc_feature
<222> LOCATION: (970)..(975)
<223> OTHER INFORMATION: n is a, c, g, or t
<220> FEATURE:
<221> NAME/KEY: misc_feature
```

<222> LOCATION: (977)..(988)
<223> OTHER INFORMATION: n is a, c, g, or t
<220> FEATURE:
<221> NAME/KEY: misc_feature
<222> LOCATION: (994)..(1002)
<223> OTHER INFORMATION: n is a, c, g, or t
<220> FEATURE:
<221> NAME/KEY: misc_feature
<222> LOCATION: (1005)..(1020)
<223> OTHER INFORMATION: n is a, c, g, or t

<400> SEQUENCE: 100

```
tgtcttcctt tatttgtgtc tcnnnngact gntctctgtc ctgtcatgaa atttgtactg      60
atctcatgtc catctgcagc actgggagnn nnattttctn nncagacacc gtgtgcacgt     120
tgcaggtntg ctgcattctg aatccttaac actttgtccc ncttccatct gctnaacaca     180
cggagctgaa acgcaggtca taaaccaaga ngagacncca aggctgtaca gcctggtgtt     240
tggagaagga gttgtcaacg angcaacggc ggtcgttctt ttcaatgcca tcaaggatct     300
cgatatcagt cggctcaagg gtggggttgt gctaaaagtg atatttgact tcctctatct     360
cttttgcaacc agcactgtcc tcggaatctc agtaagaact gnttttttct tccatatata     420
tgcattagng ccatntcttt gtacaccctt aactctttac cgcaaatttg tcagatcggt     480
ctagtaactg catatgttct caaagctctg tattttggta ggtgagtaat cgttgttacc     540
gatcggtttn gtttgtgttc atctgctact cttttatctt tnaaatctct tccccatatt     600
ttgttcaggc attcgaccga tagagaggtt gccttgatgg ctctcatggc ctatctatcn     660
tatatgctgg cagaggtaag annnnnntta ccaaatttna tctnctagta cttacattat     720
gcacttccac aattcatccc aagatgctgc atgttctgca gttgctagag ctgagtggaa     780
ttttgaccgt gttcttttgc ggcattgtca tgtcccatta tgcatggcac aacgtgacag     840
agagctcaag gattacaaca aagtgagctc aataatcaat gtncaaacat tcttaagaa     900
tnnnnnnnnn nntncnnnnn nnnnnttcgn nnnnattctc agcaatgtnn ntgctgttgc     960
gaagncatcn nnnncnnnnn nnnnnnnngc aggnnnnnnn nnaannnnnn nnnnnnnnnn    1020
agaca                                                                1025
```

<210> SEQ ID NO 101
<211> LENGTH: 529
<212> TYPE: DNA
<213> ORGANISM: Zea mays
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (130)..(131)
<223> OTHER INFORMATION: n is a, c, g, or t
<220> FEATURE:
<221> NAME/KEY: misc_feature
<222> LOCATION: (135)..(136)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (141)..(142)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:

```
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (151)..(153)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (159)..(160)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (510)..(511)
<223> OTHER INFORMATION: n is a, c, g, or t

<400> SEQUENCE: 101
gtaagcgaac gcgatgttgc caagagcttg aagcgcgagc cagaccttct gggctgaatc      60
aacgtcgact ccgatctcag tgccggtcag agtggtcgta ccactacggc ctgcagtgac     120
aacanncacn naatnnatnc nntnanancg nnntgtngnn angancttta tggagtaaaa     180
tttatctact ngctagttca cctgaaatgg tccgcgccaa cgagaggccg acggcgatgc     240
tngagtaaga gaacgacatg atggcggcga cgatggacag ccacgaaagg tcgctgaagt     300
tagggagctg agagaagaag atctgaacga tcccaaatac gaccatgtac atggtgtcgt     360
aggtgctgca gtcggccgcg tggcccttnt tgtggaagca gtttgccttg tgcacggccc     420
tgctcatcgc cattcagcca aaagggggtttt ctcaatcgac gatgagactg aatctgccaa     480
aacattcact actaaatgag ccntttttttn ngcaagaatt actcacgct              529

<210> SEQ ID NO 102
<211> LENGTH: 1328
<212> TYPE: DNA
<213> ORGANISM: Zea mays
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
```

```
<222> LOCATION: (21)..(22)
<223> OTHER INFORMATION: n is a, c, g, or t
<220> FEATURE:
<221> NAME/KEY: misc_feature
<222> LOCATION: (74)..(84)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1029)..(1030)
<223> OTHER INFORMATION: n is a, c, g, or t
<220> FEATURE:
<221> NAME/KEY: misc_feature
<222> LOCATION: (1037)..(1037)
<223> OTHER INFORMATION: n is a, c, g, or t
<220> FEATURE:
<221> NAME/KEY: misc_feature
<222> LOCATION: (1058)..(1058)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1093)..(1093)
<223> OTHER INFORMATION: n is a, c, g, or t
<220> FEATURE:
<221> NAME/KEY: misc_feature
<222> LOCATION: (1107)..(1108)
<223> OTHER INFORMATION: n is a, c, g, or t
<220> FEATURE:
<221> NAME/KEY: misc_feature
<222> LOCATION: (1119)..(1121)
<223> OTHER INFORMATION: n is a, c, g, or t
<220> FEATURE:
<221> NAME/KEY: misc_feature
<222> LOCATION: (1137)..(1139)
<223> OTHER INFORMATION: n is a, c, g, or t
<220> FEATURE:
```

```
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1153)..(1153)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1301)..(1305)
<223> OTHER INFORMATION: n is a, c, g, or t
<220> FEATURE:
<221> NAME/KEY: misc_feature
<222> LOCATION: (1322)..(1327)
<223> OTHER INFORMATION: n is a, c, g, or t

<400> SEQUENCE: 102
nncatgcatg cacgacagta nngtgatttt ttttgttagt tgcagtgctg atgtcatact      60
atgaatatat atannnnnnn nnnntgacga tatttacctc ttcgtactg gtaaatgacg     120
attccgctga aatttcagaa actccagang ccagcagatg gcgagcacgc tcgcgtgtgt    180
tgtacagctt gtcccttaca tggcctagta tcacccggta gggctcgttt ggaggaattt    240
gcttccagaa ttctgcgcca gcaaatacac ttcagaaaan ntgccaaaag agccctcaaa    300
ttaatttgaa acactagtg gagactttng caaaagnctg tacggcaggc aaaaattaag     360
caaacataaa tgcttctgtt tgtggttacc tatgtaatac ttggtaactt tggaaccaga    420
cgaactgtgg agctcttcgg cacgaacncg aagctcatcg ttgcagcgcc acatagagag    480
ctacagatat atcagacgat gcatgcatga gagttctggt atggaccgga gacagcaaaa    540
aacagggcaa gcaaaaaant catagagcat tcaatcaaac aaatctgcag tatggatgta    600
cagtacctca aacatcagct cttcaatctg atcgatgtac aagtttgcag ccatcattct    660
ggccagcaag catacatctc ttgtcacctc cggggtaact cttggatttc ctatatagcg    720
anagattgca aagatataca ggcttagnaa aaacatataa ttctgtatat ataattttct    780
ggcgagaaaa gaaaaacgtt agccttgaat attgacagga caagtactga tataatataa    840
gcactctttg atatataaaa taatactaca cgtataattc tgtgatataa aaaattcaac    900
aagttaggtt ccaggttgca atataaagat ttgattaaat tatgcttata tgttgtgcta    960
gcatgtatgg atgataantt tttattagtg aggtgtacta aataatttcn attttaaaat   1020
tctagctcnn gagagcncga aatgatagac tagttttnct gaacatctat tgcagtnaga   1080
gtaaagcagg aangtttctc tcaagcnnaa agacagagnn nagctcctgc cactttnnng   1140
aaaanggtag gcngaaatgt accatcgcgg tcaccaccca tccaagaaga gaaccgaatg   1200
agagaaacat tgtagggaag gcgctcattg atgccgatat tcttcagggc tgtatccaca   1260
cggcgcaaga acttaggcac ncccttccat acagtctcat nnnnnagctc atcccatagc   1320
gnnnnnng                                                             1328

<210> SEQ ID NO 103
<211> LENGTH: 619
<212> TYPE: DNA
<213> ORGANISM: Zea mays
<220> FEATURE:
<221> NAME/KEY: misc_feature
<222> LOCATION: (560)..(560)
<223> OTHER INFORMATION: n is a, c, g, or t

<400> SEQUENCE: 103
```

```
tggggtggac ctcgccactt cagctcgtct ttgcagttgc cacgctcttc tgggcactca    60 agcttgggc tcttcctggt ctagtcccgc tagtcatctt tggtttcctc aacgtgccat   120
tcgcgaaaat gctgcagggg taccaggcca agttcatggt tgcacaggac gagaggctcc   180
ggtccacgtc ggagatactc aacagcatga agatcatcaa gctgcagtcg tgggaagaca   240
agttccgcag cacgatcgag tcgctcaggg acggcgagtt caaatggctg agggagaccc   300
agatgaagaa ggcctatggt gcagtcatgt actggatgtc cccgacggtc gtctctgctg   360
tcatgtacac agcaacggcc atcatgggga gtgctcccct gaatgctagc acgctcttca   420
cggtcttggc caccctgagg gtaatgtctg agccagtgag gatgcttccg gaggtcctca   480
caatgatgat ccagtacaag gtgtcattag atcgaattga aagttccttc tcgaagacg   540 agatcagaga ggaggatgtn aaaagggtac cttcagatga ctctggtgtc agagttcgag   600
tccaagccgg aaatttcag                                                  619
```

<210> SEQ ID NO 104
<211> LENGTH: 543
<212> TYPE: DNA
<213> ORGANISM: Zea mays
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (470)..(472)
<223> OTHER INFORMATION: n is a, c, g, or t
<220> FEATURE:
<221> NAME/KEY: misc_feature
<222> LOCATION: (474)..(479)
<223> OTHER INFORMATION: n is a, c, g, or t
<220> FEATURE:
<221> NAME/KEY: misc_feature
<222> LOCATION: (487)..(493)
<223> OTHER INFORMATION: n is a, c, g, or t
<220> FEATURE:
<221> NAME/KEY: misc_feature
<222> LOCATION: (495)..(499)
<223> OTHER INFORMATION: n is a, c, g, or t
<220> FEATURE:
<221> NAME/KEY: misc_feature
<222> LOCATION: (502)..(509)
<223> OTHER INFORMATION: n is a, c, g, or t
<220> FEATURE:
<221> NAME/KEY: misc_feature
<222> LOCATION: (511)..(517)
<223> OTHER INFORMATION: n is a, c, g, or t
<220> FEATURE:
<221> NAME/KEY: misc_feature
<222> LOCATION: (522)..(531)
<223> OTHER INFORMATION: n is a, c, g, or t
<220> FEATURE:
<221> NAME/KEY: misc_feature
<222> LOCATION: (535)..(539)
<223> OTHER INFORMATION: n is a, c, g, or t

<400> SEQUENCE: 104

```
ctgcagtacc tttaccaaca tgatgctttt gtttttctat aagcatgtgt ggcacactag    60
ttatcagctc cgcaggaact acatcagcat tgtgaaattc atcggtagtg gactgcctag   120
ttgaagtcat atcgttgttt tcaaaattag cagccttgct tctggaaaca ttcgactcag   180
tgctagacaa gcttcttctc aagaagcccc ttcccttcat cttgaggaca ccaccaccct   240
tttggtccat tgatggctgg agaatcttcc atgtctcttc ccaatagttg ggtgtagaca   300
agagagaant tcctctcgat gaggatgaag gaagatttgc ttcaagggca aaagattgca   360
```

-continued

```
gtaacttggc tttctcaatt aagctctttta agtcaatatc ttctggaaaa tttaacaacc    420
tcactaggca agaagtcgca tgttcactcc ctaataagga ggatctgagn nngnnnnnna    480
ttgatannnn nnncnnnnna annnnnnnnc nnnnnnnaga annnnnnnnn ntaannnnnt    540
aat                                                                  543
```

<210> SEQ ID NO 105
<211> LENGTH: 393
<212> TYPE: DNA
<213> ORGANISM: Zea mays
<220> FEATURE:
<221> NAME/KEY: misc_feature
<222> LOCATION: (58)..(58)
<223> OTHER INFORMATION: n is a, c, g, or t

<400> SEQUENCE: 105

```
tgctgagtta agatgctctg tgggatattt gaagtccatt attgcagtga cagagggntt     60
ggtgttcagt gaagacagta aagttgctgg aaattgcagt gcctgtctct ctgtgattt    120 gggatgggag aaatttggaa gccaagaaaa ggtggcagtc agagaatcta aatggtttag    180
gctaataatg gaggaatttg ttgtggcctt gactgctcct ggtttgacgt cgaaatcttt    240
ctccagtcag cagaagtttg ctgcgaatat agctgtttcg ttgctcaggc tgagccaagt    300
gccagattgg ctgacatcgt tgtttgatgg gcatctgata tctggcatcg tggctaatct    360
ttctgctagg atcccacaga gcatcttaac tca                                393
```

<210> SEQ ID NO 106
<211> LENGTH: 572
<212> TYPE: DNA
<213> ORGANISM: Zea mays
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (517)..(518)
<223> OTHER INFORMATION: n is a, c, g, or t
<220> FEATURE:
<221> NAME/KEY: misc_feature
<222> LOCATION: (520)..(521)
<223> OTHER INFORMATION: n is a, c, g, or t
<220> FEATURE:
<221> NAME/KEY: misc_feature
<222> LOCATION: (538)..(539)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (560)..(564)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (569)..(571)
<223> OTHER INFORMATION: n is a, c, g, or t

<400> SEQUENCE: 106

```
tctaggggtt ttgggtgaat tgtaagtagg gtaacgcgaa ggaaaaccac taaatttaca     60
```

```
tttattcctt ctcattacat cacggagtct gcaaattgag atccttcact gacgatccat        120
gttttcctac atgaaaatgt gatgcgttca gttacatggc tctgatattt ggtattatcg        180
aatagtactt ttggatttta atatatattt gtttctctca aggttctgca aagagcattg        240
gattttagtc gataatttga cattccattt agtagttatt tttatattgg aaaggtgtgt        300
gtaggatgca gcattgaatg ttagtttaat ttaattgtta taaacattga acacaaccag        360
gacaacatga ggaaaccaga gtactatagt agatggtaat gtttgattaa ggttttcaac        420
cagtgatatg atacccaatt tctcttggta atctgtttcg accatncaac atatggatgg        480 ttttgatga aatctggatc tcnttttttt ttgaaanngn natctagatc taggactnna         540
ttgatttacn tcctagttcn nnnntnttnn na                                      572
```

<210> SEQ ID NO 107
<211> LENGTH: 658
<212> TYPE: DNA
<213> ORGANISM: Zea mays
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (223)..(226)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (333)..(334)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (465)..(466)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (647)..(653)

<223> OTHER INFORMATION: n is a, c, g, or t

<400> SEQUENCE: 107

```
cctaccttct gatcctccgg ctagctagct acttcaaatc cccgccgctg cgctgcgcat      60
gtgttcacgc tctaaatacg atggcatatg catgcatgca gaacggagtc cgggcgctga    120
tgctcgacac gtacgacttc aagggagacg tgtggctgtg ccattcgagc ggagggaaat    180
gcaacgactt caccgcgttc gngagtacgc tggctcgctc tgnnnnaant gaacagggcg    240
tgcgnccgta cgtctcaaag ctgagcattt gttttggggg gntcattgta ggaacctgca    300
ctggacactt tcaaggagat cgaggcgttc ctnncagcaa accgtccga aatcgtcacg     360
ctnatcctag aggactacgt ccacgcgccg aacgggctga cgaacgtgtt caacgcgtct    420
ggcctgctca agtactggtt cccgntgtcg agnatgccgc cgagnngcca ggactggcct    480
ctcgtcagcg acatggtcgc gaccaaccag cgcctcctgg tgttcacctc cgtnagctcc    540
aaacagagcg cggaaggcat cgcttaccag tggaacttca tggtcgagaa naactgtgag    600
gcatcncgat tggttcctgc tttctatcta tctttttttt ttctctnnnn nnntgcag      658
```

<210> SEQ ID NO 108
<211> LENGTH: 444
<212> TYPE: DNA
<213> ORGANISM: Zea mays
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t

<400> SEQUENCE: 108

```
acatgaagta cggtaactat aaaatgacac cagtggaaat agcatacaac gccatttcct      60
tcgtcatcgc tatcgccctc acggtcgcct tcacggtgta cgcgaagaga gctctgggtg    120
acataaaaag tccggacgat ggcatcggta agangaaga agatcacggc ccaaatggct     180
caggggggggt gcgtatgaat cgtcgtcagg agcgtgcgcg tgccgatgca cgttacatag    240
aactagatga tatgtgatgg tgtgttgacc cggatcttgc ttggaaggag gcaccagtag    300
gtcattaggt gcacggctac ggtaggtagc tagctatagt ttacaagagg aggctacaat    360
aatccacacc cagctgacgt ggtttgcgtg attcgtttcg tactttcgtg tgctttgcct    420
actgcactgc catactgtcn gaat                                            444
```

<210> SEQ ID NO 109
<211> LENGTH: 476
<212> TYPE: DNA
<213> ORGANISM: Zea mays
<220> FEATURE:
<221> NAME/KEY: misc_feature
<222> LOCATION: (436)..(436)
<223> OTHER INFORMATION: n is a, c, g, or t

<400> SEQUENCE: 109

```
agcccgaatt tgcatatttg actacgaact agcaaggcaa atcctttcga gcaagtctgg      60
gcatttcgtg aagaacgatg cgcaccctac tttgttggct ctggtcggca agggactcgg    120
gttcatggaa ggctctgact gggtgcgcca tcgcagggtg atcaaccctg ctttcaccat    180
tgacaagctt aaggtacacg caatgcctag ctctctctct ctctctcgct ttaaaaaga     240
agttcgtttg cagtatgcac gcgagcagca agaacaatgg ccgtgctcat tgcataaaca    300
```

```
gattgtgacc gagacgatgc tggacttcgc cgatagcatg gcaggtgagt tggaagctga    360
agcatcccag aacgagaacg gagaaacaca agtggatata tacaaacatt tcagcgatct    420
gacagttgac aatatngcct acgccatctt tggaagcagc tacaagttag aaatgg        476
```

<210> SEQ ID NO 110
<211> LENGTH: 720
<212> TYPE: DNA
<213> ORGANISM: Zea mays
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t

<400> SEQUENCE: 110

```
cntgagtttt tctcagagtg ttcgtgatgt tgtgttgggc agcggtgaaa tcgtatgctt    60
ctcacactcg agttgcttca tcctgacata ttcaatccat cctaactatt gactcgtttg   120
tttatgttgc aacttttcag atggttgatg atgttaaata tacagtttca catgtcgtgg   180
agcctatgga gcggagtttt acaaagataa ataagacaat tcatcaaatc tcagaaaacg   240
tcaagcagct tgagaagcaa aagaggaagg caaaggacga cagtcatctt attcccctag   300
aaccatggtc agaggaattt tcagaagctc atgaccatgt tgcgggcggt agtgccagtg   360
acagcggatt agctaagaca aggtacaaca ggatcttaaa taggccccgg aggtcattcg   420
agtccagatt gcgcagatgg ttctagcagc cagccggtgc tagtgggtta attgattttg   480
atcaaaagag gcggttaacc ttttcgctcc ggttgtttga caaaatgata gcaattctga   540
caaactagtt ctccctccgt tcttttcttc tttatttgct ggtgacaaat attcgagaan   600
ggagtttgga gtttggcacg gggtggaggc agtagccagc agctcttcat tattttgngg   660
gtgacaaata ttcatgaacg gagtttggag tttggcacgg ggtggaggca gtagccagca   720
```

<210> SEQ ID NO 111
<211> LENGTH: 639
<212> TYPE: DNA
<213> ORGANISM: Zea mays
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t

<400> SEQUENCE: 111

```
tttgttacct aaacatggag cagctaacaa atgcctgct ttctctgtat gatatgtatc     60
atgtacttca taagtgtgat tcacacagca aaaaggaggc tgagtattat tccttctatg   120
tgcttctaca tttgggatgc aagatacaca aaatggtaat ttgttttccc tttctcactt   180
cttccatgtt caaatttgtt cttaatccct ttcaagagct ttatgcttta ccttactcca   240
```

```
acttgtatcc aaaattaact ttctatttat cttcagatag attcactctc tttgtggtat    300
ggtcaattgg ctactccagt cagacggtca aaggaaatga tatttgctag atctttatta    360
aggtaacatc tagacgaatt gattgccaac atgaaccttc attctttgca tgctcctntt    420
tctgttcaca tagttaagcc cagagtctnt atgtgttttc attttctcta tgcctgacca    480
cttgtatgat ttggtcataa gtacttattg ttgattcata gttggctact tcagtgctga    540
gccatgttgt tttaaatctt agataattgt atatatctta tgtagatgct atcgcctagg    600
aaacttcaag cgtttctttt gcatggtagc aggngtacc                          639
```

<210> SEQ ID NO 112
<211> LENGTH: 711
<212> TYPE: DNA
<213> ORGANISM: Zea mays
<220> FEATURE:
<221> NAME/KEY: misc_feature
<222> LOCATION: (539)..(539)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (613)..(614)
<223> OTHER INFORMATION: n is a, c, g, or t
<220> FEATURE:
<221> NAME/KEY: misc_feature
<222> LOCATION: (628)..(630)
<223> OTHER INFORMATION: n is a, c, g, or t
<220> FEATURE:
<221> NAME/KEY: misc_feature
<222> LOCATION: (639)..(643)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (657)..(660)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (686)..(690)
<223> OTHER INFORMATION: n is a, c, g, or t
<220> FEATURE:
<221> NAME/KEY: misc_feature
<222> LOCATION: (693)..(699)
<223> OTHER INFORMATION: n is a, c, g, or t
<220> FEATURE:
<221> NAME/KEY: misc_feature
<222> LOCATION: (706)..(708)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t

<400> SEQUENCE: 112

```
aatgatgggc aaatcagtat taagttcttg tatcaaagga tgaggagcaa ttggttgtct     60
aggaccattg aactcagaag tacgagcaaa tcccaggaac agtttcttgg cccaaggatc    120
atacatctca tcggtgaact tataggcaaa atttcgatca gcacaccaaa catttatctg    180
gtgaagggga aagggctgtt aatgaacact gacaatatat gtgataaaaa cagatagatg    240
taaaagaaca actcttacaa tacttggagg ttccaaactc ttttaacatt tagagcaaaa    300
```

```
aatgtactca gatgactata gacactgatg gcctcatgca atgcaatata caaaagaaac    360
ccacatggac aagacaaatg gactcacagg tggtgctcta gctggcggaa taaaagcata    420
tgctgaacga agaagcctaa tgtttgaagc gagcctgtcg cgatgagaaa gcaccagtgc    480
ttcatatggg ccatcaattg gcccagtccc aatctttgtc ctaagcaaac tgggcttgnc    540
ctttgtagaa gaaagcaaca aacgggcaac tgcacgaact tttgtggaat cattntgact    600
ggactggatg ccnntatctt ctgaatcnnn gaattcatnn nnnatttcag cagtntnnnn    660
catatnccat tgcattactg aaaagnnnnn tcnnnnnnnc aatgannnan t             711

<210> SEQ ID NO 113
<211> LENGTH: 1441
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (556)..(560)
<223> OTHER INFORMATION: n is a, c, g, or t
<220> FEATURE:
<221> NAME/KEY: misc_feature
<222> LOCATION: (604)..(611)
<223> OTHER INFORMATION: n is a, c, g, or t
<220> FEATURE:
<221> NAME/KEY: misc_feature
<222> LOCATION: (619)..(626)
<223> OTHER INFORMATION: n is a, c, g, or t
<220> FEATURE:
<221> NAME/KEY: misc_feature
<222> LOCATION: (629)..(631)
<223> OTHER INFORMATION: n is a, c, g, or t
<220> FEATURE:
<221> NAME/KEY: misc_feature
<222> LOCATION: (634)..(758)
<223> OTHER INFORMATION: n is a, c, g, or t
<220> FEATURE:
<221> NAME/KEY: misc_feature
<222> LOCATION: (763)..(769)
<223> OTHER INFORMATION: n is a, c, g, or t
<220> FEATURE:
<221> NAME/KEY: misc_feature
<222> LOCATION: (775)..(784)
<223> OTHER INFORMATION: n is a, c, g, or t
<220> FEATURE:
<221> NAME/KEY: misc_feature
<222> LOCATION: (786)..(792)
<223> OTHER INFORMATION: n is a, c, g, or t
<220> FEATURE:
<221> NAME/KEY: misc_feature
<222> LOCATION: (799)..(808)
```

```
<223> OTHER INFORMATION: n is a, c, g, or t
<220> FEATURE:
<221> NAME/KEY: misc_feature
<222> LOCATION: (811)..(813)
<223> OTHER INFORMATION: n is a, c, g, or t
<220> FEATURE:
<221> NAME/KEY: misc_feature
<222> LOCATION: (816)..(829)
<223> OTHER INFORMATION: n is a, c, g, or t
<220> FEATURE:
<221> NAME/KEY: misc_feature
<222> LOCATION: (836)..(839)
<223> OTHER INFORMATION: n is a, c, g, or t
<220> FEATURE:
<221> NAME/KEY: misc_feature
<222> LOCATION: (841)..(845)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (869)..(872)
<223> OTHER INFORMATION: n is a, c, g, or t
<220> FEATURE:
<221> NAME/KEY: misc_feature
<222> LOCATION: (874)..(878)
<223> OTHER INFORMATION: n is a, c, g, or t
<220> FEATURE:
<221> NAME/KEY: misc_feature
<222> LOCATION: (890)..(898)
<223> OTHER INFORMATION: n is a, c, g, or t
<220> FEATURE:
<221> NAME/KEY: misc_feature
<222> LOCATION: (934)..(934)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1391)..(1391)
<223> OTHER INFORMATION: n is a, c, g, or t

<400> SEQUENCE: 113
tagtgctccn aaacggccaa gcntcaagcc agattagtag aaaacatact aatgancaat      60
agtgcaaaaa aatantacaa atacacccag cactaaaatg agatgagtgt atgtacctgt     120
gcagcttgaa ggtattaggc ccataccggt gagtggtatc cttttccaag tcttttggaa     180
ggttgatgat ttcaatggca tcaaatgggc atttctgcaa cagagattac agaagcaaga     240
agtgcattac atcaaatagg cacatcatac acagttacct ggagtaagtt agaaatctac     300
ctttacacag ataccacaac cgatgcacag ttcctcagaa atgaaagcga gtttcgacgc     360
cgaagtcact tcaatgcaaa gnttccctaa acagtaaaac agaatattgt cataaaagtg     420
atccatgcca agccagaaac tagatgatgt gcagaacaac aaagggaaga gaacaatata     480
ctgtatctat ttcagcgaaa tggatgatat tgtatttgga cactggacct tcacaagtta     540
cagtacgnac tatacnnnnn gcagcatgtg agaattctat tcaattcact aaacaagaga     600
tatnnnnnnn ntttctacnn nnnnnnaann nacnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
```

```
nnnnnnnnnn nnnnnnnnnn nnnnnnnnnn nnnnnnnncc tcnnnnnnna aaatnnnnnn       780
nnnntnnnnn nntgacgtnn nnnnnnnntg nnncannnnn nnnnnnnnnt catgannnna       840
nnnnncntac tgnangtagc atttggttnn nnannnnnta tatttttgan nnnnnnnntt       900
ggttgtatga aggaatgatc acggagcacg gtancttctc tagtgctcga cataactgat       960
gagttgcact atggttgtct gacttccctc gtccttgatg tcaaagaagg atttggggat      1020
gcactttgat tgttgggcaa gaactgtggt gaagatgcag tagctatacg gattatgcat      1080
ctgtggccac cacctaaaat tgttgaggtg aagcagtgtg atggagctat cgtcagtaaa      1140
ttggccaacc tttagagatt gttagtgtca taacagacta tgattgtgtt aggacatttc      1200
ttatgcgaga agtcactcag cctcgcattc agtcaatact gtatgttgaa aagccctatg      1260
ttttttacag tgaacattga tgtgaagctt cttcctggga aatggctnga accatatttt      1320
aatgtgagat gttgctgatc ttctactcaa aggctattgc aattttctga tatgaattta      1380
caagggaatg ntgtcctcgc actaaacaaa agtcaactgt gcaatatata tgaagaatgt      1440
a                                                                     1441

<210> SEQ ID NO 114
<211> LENGTH: 570
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (251)..(252)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t

<400> SEQUENCE: 114
cgtaagcact ccccatgtca cagccnctca gtttgttgac ccaaaccttc tttcccttat        60
agacacccct gaatgaattc gcnccaaacc aatcaacgaa ctcgatctcc tcngaacgca       120
gcatccagcg accaagctcc tcgccaccgg agcgaatggt ttgccattca tctactgaga       180
cgaagactga tgcctgtggt aggggagtgg gaagctgtgg tctgtgcgcc ggctcattgt       240
cgagtacccg nncatcatct ggatcaaaca tcgactcctc atcgaagttt ctngatcctt       300
cttcttgaca accgcagagc ccaaatggta gcttcacacc accactgttc tttctttgct       360
tctttactac cgatttcagc gcggactcaa cctggttctt gaagagcgcc tcgttcccag       420
tctgcacaag tatcatgacg acgccaagtg tcagccctct cttctcaaag atctggatct       480
tcttgcaaca gaacgaaggg ctgtctagtg atcctgacat tgactgccat gagagcgggg       540
ctgtgcaagc aaatgttagc tggaaaacag                                       570

<210> SEQ ID NO 115
<211> LENGTH: 22
<212> TYPE: DNA
```

<213> ORGANISM: Zea mays

<400> SEQUENCE: 115
cgtctccttt catctccggt at　　　　　　　　　　　　　　　　　　　22

<210> SEQ ID NO 116
<211> LENGTH: 18
<212> TYPE: DNA
<213> ORGANISM: Zea mays

<400> SEQUENCE: 116
gcaacaccct cgcagatg　　　　　　　　　　　　　　　　　　　　18

<210> SEQ ID NO 117
<211> LENGTH: 21
<212> TYPE: DNA
<213> ORGANISM: Zea mays

<400> SEQUENCE: 117
tgcaggttgc gtattttgtg a　　　　　　　　　　　　　　　　　　21

<210> SEQ ID NO 118
<211> LENGTH: 18
<212> TYPE: DNA
<213> ORGANISM: Zea mays

<400> SEQUENCE: 118
ctgggcacct tcgggatt　　　　　　　　　　　　　　　　　　　　18

<210> SEQ ID NO 119
<211> LENGTH: 22
<212> TYPE: DNA
<213> ORGANISM: Zea mays

<400> SEQUENCE: 119
actggcattt cttggcttca tc　　　　　　　　　　　　　　　　　　22

<210> SEQ ID NO 120
<211> LENGTH: 25
<212> TYPE: DNA
<213> ORGANISM: Zea mays

<400> SEQUENCE: 120
cttggcttgg ctaggtacag aacta　　　　　　　　　　　　　　　　25

<210> SEQ ID NO 121
<211> LENGTH: 20
<212> TYPE: DNA
<213> ORGANISM: Zea mays

<400> SEQUENCE: 121
ggcatgacag ttgggatcca　　　　　　　　　　　　　　　　　　　20

<210> SEQ ID NO 122
<211> LENGTH: 21
<212> TYPE: DNA
<213> ORGANISM: Zea mays

<400> SEQUENCE: 122
cacctgggag ctctgggtat c　　　　　　　　　　　　　　　　　　21

<210> SEQ ID NO 123
<211> LENGTH: 25

```
<212> TYPE: DNA
<213> ORGANISM: Zea mays

<400> SEQUENCE: 123
cctgagcact atgatcttcc agtac                                           25

<210> SEQ ID NO 124
<211> LENGTH: 18
<212> TYPE: DNA
<213> ORGANISM: Zea mays

<400> SEQUENCE: 124
ggtcagtgcg aggtgtcc                                                   18

<210> SEQ ID NO 125
<211> LENGTH: 17
<212> TYPE: DNA
<213> ORGANISM: Zea mays

<400> SEQUENCE: 125
gccgccaagg tccactt                                                    17

<210> SEQ ID NO 126
<211> LENGTH: 16
<212> TYPE: DNA
<213> ORGANISM: Zea mays

<400> SEQUENCE: 126
cgcaagcacc caacca                                                     16

<210> SEQ ID NO 127
<211> LENGTH: 25
<212> TYPE: DNA
<213> ORGANISM: Zea mays

<400> SEQUENCE: 127
ggttgccaat cagtacctat ttcag                                           25

<210> SEQ ID NO 128
<211> LENGTH: 25
<212> TYPE: DNA
<213> ORGANISM: Zea mays

<400> SEQUENCE: 128
ctccaaaaac tttgtggcct caaat                                           25

<210> SEQ ID NO 129
<211> LENGTH: 24
<212> TYPE: DNA
<213> ORGANISM: Zea mays

<400> SEQUENCE: 129
cctcttgatc ctctgaacct gcta                                            24

<210> SEQ ID NO 130
<211> LENGTH: 28
<212> TYPE: DNA
<213> ORGANISM: Zea mays

<400> SEQUENCE: 130
tgaagaagga ttgagatatg aaaagaca                                        28

<210> SEQ ID NO 131
```

```
<211> LENGTH: 23
<212> TYPE: DNA
<213> ORGANISM: Zea mays

<400> SEQUENCE: 131
ctgaggattc cgatccctaa cat                                              23

<210> SEQ ID NO 132
<211> LENGTH: 21
<212> TYPE: DNA
<213> ORGANISM: Zea mays

<400> SEQUENCE: 132
cgacggtctc ctcacctagc t                                                21

<210> SEQ ID NO 133
<211> LENGTH: 21
<212> TYPE: DNA
<213> ORGANISM: Zea mays

<400> SEQUENCE: 133
catttgcttt gctccgttct g                                                21

<210> SEQ ID NO 134
<211> LENGTH: 29
<212> TYPE: DNA
<213> ORGANISM: Zea mays

<400> SEQUENCE: 134
gcttgatttg tttttaacat acactatgg                                        29

<210> SEQ ID NO 135
<211> LENGTH: 21
<212> TYPE: DNA
<213> ORGANISM: Zea mays

<400> SEQUENCE: 135
ctcaccccac tatcggattc c                                                21

<210> SEQ ID NO 136
<211> LENGTH: 26
<212> TYPE: DNA
<213> ORGANISM: Zea mays

<400> SEQUENCE: 136
acaagtagct agcagaacat ggagaa                                           26

<210> SEQ ID NO 137
<211> LENGTH: 25
<212> TYPE: DNA
<213> ORGANISM: Zea mays

<400> SEQUENCE: 137
gttctccttc ggtttgctca tctat                                            25

<210> SEQ ID NO 138
<211> LENGTH: 27
<212> TYPE: DNA
<213> ORGANISM: Zea mays

<400> SEQUENCE: 138
ctgggttgtg aaaaacttca tttagtt                                          27
```

-continued

<210> SEQ ID NO 139
<211> LENGTH: 25
<212> TYPE: DNA
<213> ORGANISM: Zea mays

<400> SEQUENCE: 139
ggaagataga gaacagcgac aatgt                                         25

<210> SEQ ID NO 140
<211> LENGTH: 20
<212> TYPE: DNA
<213> ORGANISM: Zea mays

<400> SEQUENCE: 140
ccagcaggga aagagaagca                                               20

<210> SEQ ID NO 141
<211> LENGTH: 27
<212> TYPE: DNA
<213> ORGANISM: Zea mays

<400> SEQUENCE: 141
attaacatct ctggactttg gcattct                                       27

<210> SEQ ID NO 142
<211> LENGTH: 25
<212> TYPE: DNA
<213> ORGANISM: Zea mays

<400> SEQUENCE: 142
gctctaaatg gtttgctgct gtaag                                         25

<210> SEQ ID NO 143
<211> LENGTH: 18
<212> TYPE: DNA
<213> ORGANISM: Zea mays

<400> SEQUENCE: 143
tgtaggcagc ggcatctc                                                 18

<210> SEQ ID NO 144
<211> LENGTH: 20
<212> TYPE: DNA
<213> ORGANISM: Zea mays

<400> SEQUENCE: 144
agcaaggatg tccgcttcag                                               20

<210> SEQ ID NO 145
<211> LENGTH: 25
<212> TYPE: DNA
<213> ORGANISM: Zea mays

<400> SEQUENCE: 145
ggtgcaacct cagctcttat aaact                                         25

<210> SEQ ID NO 146
<211> LENGTH: 29
<212> TYPE: DNA
<213> ORGANISM: Zea mays

<400> SEQUENCE: 146
ggtagtatat gtgcattcat cgttttca                                      29

<210> SEQ ID NO 147
<211> LENGTH: 23
<212> TYPE: DNA
<213> ORGANISM: Zea mays

<400> SEQUENCE: 147
ttggagaggt ctctttcgtt cag                                              23

<210> SEQ ID NO 148
<211> LENGTH: 21
<212> TYPE: DNA
<213> ORGANISM: Zea mays

<400> SEQUENCE: 148
tgccatccac tgtactttgc a                                                21

<210> SEQ ID NO 149
<211> LENGTH: 21
<212> TYPE: DNA
<213> ORGANISM: Zea mays

<400> SEQUENCE: 149
caggcgtatg aattgcacga t                                                21

<210> SEQ ID NO 150
<211> LENGTH: 25
<212> TYPE: DNA
<213> ORGANISM: Zea mays

<400> SEQUENCE: 150
gcaatcagac gtatgttctt gaatg                                            25

<210> SEQ ID NO 151
<211> LENGTH: 21
<212> TYPE: DNA
<213> ORGANISM: Zea mays

<400> SEQUENCE: 151
cctcagcatt tttggcaagt g                                                21

<210> SEQ ID NO 152
<211> LENGTH: 25
<212> TYPE: DNA
<213> ORGANISM: Zea mays

<400> SEQUENCE: 152
aagaacaaac gcagaaaaca gattt                                            25

<210> SEQ ID NO 153
<211> LENGTH: 23
<212> TYPE: DNA
<213> ORGANISM: Zea mays

<400> SEQUENCE: 153
tgattcaatc actgtgccaa gac                                              23

<210> SEQ ID NO 154
<211> LENGTH: 25
<212> TYPE: DNA
<213> ORGANISM: Zea mays

<400> SEQUENCE: 154
gaagctttgt ttgattcggt tcaga                                            25

```
<210> SEQ ID NO 155
<211> LENGTH: 31
<212> TYPE: DNA
<213> ORGANISM: Zea mays

<400> SEQUENCE: 155
ctgaaattgt actggaagac tagagttatg t                                    31

<210> SEQ ID NO 156
<211> LENGTH: 22
<212> TYPE: DNA
<213> ORGANISM: Zea mays

<400> SEQUENCE: 156
ggaaggcctc caagacttgt tt                                              22

<210> SEQ ID NO 157
<211> LENGTH: 25
<212> TYPE: DNA
<213> ORGANISM: Zea mays

<400> SEQUENCE: 157
ggcaaggatc tgttttcacc aaata                                           25

<210> SEQ ID NO 158
<211> LENGTH: 24
<212> TYPE: DNA
<213> ORGANISM: Zea mays

<400> SEQUENCE: 158
gggaggacaa caactacatc ttca                                            24

<210> SEQ ID NO 159
<211> LENGTH: 19
<212> TYPE: DNA
<213> ORGANISM: Zea mays

<400> SEQUENCE: 159
gggtggcgga gaagttgac                                                  19

<210> SEQ ID NO 160
<211> LENGTH: 23
<212> TYPE: DNA
<213> ORGANISM: Zea mays

<400> SEQUENCE: 160
cttcggtgca agatagtcct gaa                                             23

<210> SEQ ID NO 161
<211> LENGTH: 25
<212> TYPE: DNA
<213> ORGANISM: Zea mays

<400> SEQUENCE: 161
agttgaccaa atagcagagc taacc                                           25

<210> SEQ ID NO 162
<211> LENGTH: 25
<212> TYPE: DNA
<213> ORGANISM: Zea mays

<400> SEQUENCE: 162
```
gcctaacaga tctcctactg aggtt                                        25

<210> SEQ ID NO 163
<211> LENGTH: 25
<212> TYPE: DNA
<213> ORGANISM: Zea mays

<400> SEQUENCE: 163
ttcgtggaat tcaccagatc tatct                                        25

<210> SEQ ID NO 164
<211> LENGTH: 20
<212> TYPE: DNA
<213> ORGANISM: Zea mays

<400> SEQUENCE: 164
cgaggtagca caggcagttg                                              20

<210> SEQ ID NO 165
<211> LENGTH: 25
<212> TYPE: DNA
<213> ORGANISM: Zea mays

<400> SEQUENCE: 165
tgtacattgt cgttcacatc ttgct                                        25

<210> SEQ ID NO 166
<211> LENGTH: 21
<212> TYPE: DNA
<213> ORGANISM: Zea mays

<400> SEQUENCE: 166
gccaaggtcc tgagcaaaat c                                            21

<210> SEQ ID NO 167
<211> LENGTH: 24
<212> TYPE: DNA
<213> ORGANISM: Zea mays

<400> SEQUENCE: 167
cgtgataatc tcaacctcct caga                                         24

<210> SEQ ID NO 168
<211> LENGTH: 25
<212> TYPE: DNA
<213> ORGANISM: Zea mays

<400> SEQUENCE: 168
ggtttcagaa gcacatagtg acctt                                        25

<210> SEQ ID NO 169
<211> LENGTH: 26
<212> TYPE: DNA
<213> ORGANISM: Zea mays

<400> SEQUENCE: 169
attacaacaa atgagaacac ccatgt                                       26

<210> SEQ ID NO 170
<211> LENGTH: 23
<212> TYPE: DNA
<213> ORGANISM: Zea mays

<400> SEQUENCE: 170
cagcatgtcc ttctcgtatc tga                                               23

<210> SEQ ID NO 171
<211> LENGTH: 19
<212> TYPE: DNA
<213> ORGANISM: Zea mays

<400> SEQUENCE: 171
ccctgggaag caatttcga                                                    19

<210> SEQ ID NO 172
<211> LENGTH: 26
<212> TYPE: DNA
<213> ORGANISM: Zea mays

<400> SEQUENCE: 172
caatcagcat taacacaaca acatgt                                            26

<210> SEQ ID NO 173
<211> LENGTH: 26
<212> TYPE: DNA
<213> ORGANISM: Zea mays

<400> SEQUENCE: 173
tcttctggtt cttgttgaca cttgag                                            26

<210> SEQ ID NO 174
<211> LENGTH: 20
<212> TYPE: DNA
<213> ORGANISM: Zea mays

<400> SEQUENCE: 174
cagttcgtgt tcggcagcta                                                   20

<210> SEQ ID NO 175
<211> LENGTH: 28
<212> TYPE: DNA
<213> ORGANISM: Zea mays

<400> SEQUENCE: 175
gtgaagagca attggttcaa gtagtaaa                                          28

<210> SEQ ID NO 176
<211> LENGTH: 20
<212> TYPE: DNA
<213> ORGANISM: Zea mays

<400> SEQUENCE: 176
agttggctgg ccatctgatg                                                   20

<210> SEQ ID NO 177
<211> LENGTH: 23
<212> TYPE: DNA
<213> ORGANISM: Zea mays

<400> SEQUENCE: 177
tgctcttgga cagttcaatg aca                                               23

<210> SEQ ID NO 178
<211> LENGTH: 25
<212> TYPE: DNA
<213> ORGANISM: Zea mays

```
<400> SEQUENCE: 178
gcaaattttg cccacataca ctgta                                          25

<210> SEQ ID NO 179
<211> LENGTH: 17
<212> TYPE: DNA
<213> ORGANISM: Zea mays

<400> SEQUENCE: 179
cagtacggcg gcaacga                                                   17

<210> SEQ ID NO 180
<211> LENGTH: 25
<212> TYPE: DNA
<213> ORGANISM: Zea mays

<400> SEQUENCE: 180
tcaaccaatt tcttgatttc gatgt                                          25

<210> SEQ ID NO 181
<211> LENGTH: 20
<212> TYPE: DNA
<213> ORGANISM: Zea mays

<400> SEQUENCE: 181
tgttgaccga gcagcaagag                                                20

<210> SEQ ID NO 182
<211> LENGTH: 20
<212> TYPE: DNA
<213> ORGANISM: Zea mays

<400> SEQUENCE: 182
ggctggacat agtggactgc                                                20

<210> SEQ ID NO 183
<211> LENGTH: 26
<212> TYPE: DNA
<213> ORGANISM: Zea mays

<400> SEQUENCE: 183
gaacaagcat gcatatatca ctcgta                                         26

<210> SEQ ID NO 184
<211> LENGTH: 23
<212> TYPE: DNA
<213> ORGANISM: Zea mays

<400> SEQUENCE: 184
ggcttgcgta ttcttgaact tgt                                            23

<210> SEQ ID NO 185
<211> LENGTH: 25
<212> TYPE: DNA
<213> ORGANISM: Zea mays

<400> SEQUENCE: 185
ccagagctgg aaacatccta tcaag                                          25

<210> SEQ ID NO 186
<211> LENGTH: 23
<212> TYPE: DNA
<213> ORGANISM: Zea mays
```

```
<400> SEQUENCE: 186
ctacgatgac gttgaggaga tca                                          23

<210> SEQ ID NO 187
<211> LENGTH: 25
<212> TYPE: DNA
<213> ORGANISM: Zea mays

<400> SEQUENCE: 187
gtccgcttac cagtttacta tcctt                                        25

<210> SEQ ID NO 188
<211> LENGTH: 17
<212> TYPE: DNA
<213> ORGANISM: Zea mays

<400> SEQUENCE: 188
agcaaccggc acatgga                                                 17

<210> SEQ ID NO 189
<211> LENGTH: 20
<212> TYPE: DNA
<213> ORGANISM: Zea mays

<400> SEQUENCE: 189
cggacaggat gcaacaacct                                              20

<210> SEQ ID NO 190
<211> LENGTH: 22
<212> TYPE: DNA
<213> ORGANISM: Zea mays

<400> SEQUENCE: 190
gcatttttgg gtcagtgaag ca                                           22

<210> SEQ ID NO 191
<211> LENGTH: 22
<212> TYPE: DNA
<213> ORGANISM: Zea mays

<400> SEQUENCE: 191
agttatgagg tttgccccaa ca                                           22

<210> SEQ ID NO 192
<211> LENGTH: 24
<212> TYPE: DNA
<213> ORGANISM: Zea mays

<400> SEQUENCE: 192
ggataatggc cgacatgttt gaca                                         24

<210> SEQ ID NO 193
<211> LENGTH: 20
<212> TYPE: DNA
<213> ORGANISM: Zea mays

<400> SEQUENCE: 193
gaagtcggag ctgctttggt                                              20

<210> SEQ ID NO 194
<211> LENGTH: 26
<212> TYPE: DNA
```

<213> ORGANISM: Zea mays

<400> SEQUENCE: 194
gggcctctat ttgtaatggt tgtatt    26

<210> SEQ ID NO 195
<211> LENGTH: 25
<212> TYPE: DNA
<213> ORGANISM: Zea mays

<400> SEQUENCE: 195
gagggaaggt gataatcatc gacat    25

<210> SEQ ID NO 196
<211> LENGTH: 19
<212> TYPE: DNA
<213> ORGANISM: Zea mays

<400> SEQUENCE: 196
cgtgctcagt gtgcagtct    19

<210> SEQ ID NO 197
<211> LENGTH: 25
<212> TYPE: DNA
<213> ORGANISM: Zea mays

<400> SEQUENCE: 197
cggagagatt gttcgaagaa tttta    25

<210> SEQ ID NO 198
<211> LENGTH: 22
<212> TYPE: DNA
<213> ORGANISM: Zea mays

<400> SEQUENCE: 198
agcatgagca gaacacgaat ca    22

<210> SEQ ID NO 199
<211> LENGTH: 25
<212> TYPE: DNA
<213> ORGANISM: Zea mays

<400> SEQUENCE: 199
cggagagatt gttcgaagaa tttta    25

<210> SEQ ID NO 200
<211> LENGTH: 18
<212> TYPE: DNA
<213> ORGANISM: Zea mays

<400> SEQUENCE: 200
gcgtggagcc cagaaaga    18

<210> SEQ ID NO 201
<211> LENGTH: 26
<212> TYPE: DNA
<213> ORGANISM: Zea mays

<400> SEQUENCE: 201
ggctttaagc agattagagc tttgag    26

<210> SEQ ID NO 202
<211> LENGTH: 25

<212> TYPE: DNA
<213> ORGANISM: Zea mays

<400> SEQUENCE: 202
ccttcgtcaa cttagttggg ttact                                    25

<210> SEQ ID NO 203
<211> LENGTH: 26
<212> TYPE: DNA
<213> ORGANISM: Zea mays

<400> SEQUENCE: 203
cacaaatcac agaagatgtc accaaa                                   26

<210> SEQ ID NO 204
<211> LENGTH: 24
<212> TYPE: DNA
<213> ORGANISM: Zea mays

<400> SEQUENCE: 204
actgtgctat acctaggcga ggaa                                     24

<210> SEQ ID NO 205
<211> LENGTH: 20
<212> TYPE: DNA
<213> ORGANISM: Zea mays

<400> SEQUENCE: 205
gatgtgggca aggcttctct                                          20

<210> SEQ ID NO 206
<211> LENGTH: 19
<212> TYPE: DNA
<213> ORGANISM: Zea mays

<400> SEQUENCE: 206
aactccttgg gacgcgttt                                           19

<210> SEQ ID NO 207
<211> LENGTH: 16
<212> TYPE: DNA
<213> ORGANISM: Zea mays

<400> SEQUENCE: 207
ggttcgcgcc ggagtt                                              16

<210> SEQ ID NO 208
<211> LENGTH: 18
<212> TYPE: DNA
<213> ORGANISM: Zea mays

<400> SEQUENCE: 208
tgcaacacac gcgcatgt                                            18

<210> SEQ ID NO 209
<211> LENGTH: 16
<212> TYPE: DNA
<213> ORGANISM: Zea mays

<400> SEQUENCE: 209
gcggaggctg cgatca                                              16

<210> SEQ ID NO 210

```
<211> LENGTH: 19
<212> TYPE: DNA
<213> ORGANISM: Zea mays

<400> SEQUENCE: 210
attgcggaga ggctgcttt                                                    19

<210> SEQ ID NO 211
<211> LENGTH: 23
<212> TYPE: DNA
<213> ORGANISM: Zea mays

<400> SEQUENCE: 211
ccgatgaggc ttctgtggaa tta                                               23

<210> SEQ ID NO 212
<211> LENGTH: 32
<212> TYPE: DNA
<213> ORGANISM: Zea mays

<400> SEQUENCE: 212
gctaagtatc tactatgaag ctcaaggtaa gg                                     32

<210> SEQ ID NO 213
<211> LENGTH: 18
<212> TYPE: DNA
<213> ORGANISM: Zea mays

<400> SEQUENCE: 213
tcccgtcaag ccaaagca                                                     18

<210> SEQ ID NO 214
<211> LENGTH: 20
<212> TYPE: DNA
<213> ORGANISM: Zea mays

<400> SEQUENCE: 214
acagacaccg tgtgcacgtt                                                   20

<210> SEQ ID NO 215
<211> LENGTH: 15
<212> TYPE: DNA
<213> ORGANISM: Zea mays

<400> SEQUENCE: 215
ggtccgcgcc aacga                                                        15

<210> SEQ ID NO 216
<211> LENGTH: 22
<212> TYPE: DNA
<213> ORGANISM: Zea mays

<400> SEQUENCE: 216
ccagacgaac tgtggagctc tt                                                22

<210> SEQ ID NO 217
<211> LENGTH: 23
<212> TYPE: DNA
<213> ORGANISM: Zea mays

<400> SEQUENCE: 217
gttccttctc gaagacgaga tca                                               23
```

```
<210> SEQ ID NO 218
<211> LENGTH: 25
<212> TYPE: DNA
<213> ORGANISM: Zea mays

<400> SEQUENCE: 218
cttccatgtc tcttcccaat agttg                                  25

<210> SEQ ID NO 219
<211> LENGTH: 25
<212> TYPE: DNA
<213> ORGANISM: Zea mays

<400> SEQUENCE: 219
gctctgtggg atatttgaag tccat                                  25

<210> SEQ ID NO 220
<211> LENGTH: 28
<212> TYPE: DNA
<213> ORGANISM: Zea mays

<400> SEQUENCE: 220
tgatatgata cccaatttct cttggtaa                               28

<210> SEQ ID NO 221
<211> LENGTH: 19
<212> TYPE: DNA
<213> ORGANISM: Zea mays

<400> SEQUENCE: 221
caaacccgtc cgaaatcgt                                         19

<210> SEQ ID NO 222
<211> LENGTH: 25
<212> TYPE: DNA
<213> ORGANISM: Zea mays

<400> SEQUENCE: 222
gaagagagct ctgggtgaca taaaa                                  25

<210> SEQ ID NO 223
<211> LENGTH: 29
<212> TYPE: DNA
<213> ORGANISM: Zea mays

<400> SEQUENCE: 223
gaacggagaa acacaagtgg atatataca                              29

<210> SEQ ID NO 224
<211> LENGTH: 26
<212> TYPE: DNA
<213> ORGANISM: Zea mays

<400> SEQUENCE: 224
ttttcttctt tatttgctgg tgacaa                                 26

<210> SEQ ID NO 225
<211> LENGTH: 22
<212> TYPE: DNA
<213> ORGANISM: Zea mays

<400> SEQUENCE: 225
tgattgccaa catgaacctt ca                                     22
```

```
<210> SEQ ID NO 226
<211> LENGTH: 24
<212> TYPE: DNA
<213> ORGANISM: Zea mays

<400> SEQUENCE: 226
agtcccaatc tttgtcctaa gcaa                                          24

<210> SEQ ID NO 227
<211> LENGTH: 19
<212> TYPE: DNA
<213> ORGANISM: Zea mays

<400> SEQUENCE: 227
cgacgccgaa gtcacttca                                                19

<210> SEQ ID NO 228
<211> LENGTH: 24
<212> TYPE: DNA
<213> ORGANISM: Zea mays

<400> SEQUENCE: 228
cccttataga cacccctgaa tgaa                                          24

<210> SEQ ID NO 229
<211> LENGTH: 27
<212> TYPE: DNA
<213> ORGANISM: Zea mays

<400> SEQUENCE: 229
agtgatgcga tctgtataga tgtgtgt                                       27

<210> SEQ ID NO 230
<211> LENGTH: 22
<212> TYPE: DNA
<213> ORGANISM: Zea mays

<400> SEQUENCE: 230
cgacggtccg gtaaattgtt ct                                            22

<210> SEQ ID NO 231
<211> LENGTH: 20
<212> TYPE: DNA
<213> ORGANISM: Zea mays

<400> SEQUENCE: 231
ggccatcaac attgccaact                                               20

<210> SEQ ID NO 232
<211> LENGTH: 24
<212> TYPE: DNA
<213> ORGANISM: Zea mays

<400> SEQUENCE: 232
tctcatcatc accagaacaa agct                                          24

<210> SEQ ID NO 233
<211> LENGTH: 17
<212> TYPE: DNA
<213> ORGANISM: Zea mays

<400> SEQUENCE: 233
cgccaccacc cgacagt                                                  17
```

<210> SEQ ID NO 234
<211> LENGTH: 23
<212> TYPE: DNA
<213> ORGANISM: Zea mays

<400> SEQUENCE: 234
tggtggcggt actgaaaact act                                            23

<210> SEQ ID NO 235
<211> LENGTH: 19
<212> TYPE: DNA
<213> ORGANISM: Zea mays

<400> SEQUENCE: 235
gtcgttgtcc gtggtgttc                                                 19

<210> SEQ ID NO 236
<211> LENGTH: 20
<212> TYPE: DNA
<213> ORGANISM: Zea mays

<400> SEQUENCE: 236
cagagcctcg agtggctgat                                                20

<210> SEQ ID NO 237
<211> LENGTH: 19
<212> TYPE: DNA
<213> ORGANISM: Zea mays

<400> SEQUENCE: 237
cgcaggcatt cgacttgag                                                 19

<210> SEQ ID NO 238
<211> LENGTH: 25
<212> TYPE: DNA
<213> ORGANISM: Zea mays

<400> SEQUENCE: 238
caagagttgc atgctttgta cgaat                                          25

<210> SEQ ID NO 239
<211> LENGTH: 18
<212> TYPE: DNA
<213> ORGANISM: Zea mays

<400> SEQUENCE: 239
gcccctgacg acctcgta                                                  18

<210> SEQ ID NO 240
<211> LENGTH: 22
<212> TYPE: DNA
<213> ORGANISM: Zea mays

<400> SEQUENCE: 240
ctcgaccgaa tcaacgtcta ca                                             22

<210> SEQ ID NO 241
<211> LENGTH: 23
<212> TYPE: DNA
<213> ORGANISM: Zea mays

<400> SEQUENCE: 241

-continued atccttgaca gcatccacat ttt    23

<210> SEQ ID NO 242
<211> LENGTH: 22
<212> TYPE: DNA
<213> ORGANISM: Zea mays

<400> SEQUENCE: 242
accaaaccct ggcaagaaag aa    22

<210> SEQ ID NO 243
<211> LENGTH: 24
<212> TYPE: DNA
<213> ORGANISM: Zea mays

<400> SEQUENCE: 243
gaatgggcag tcttatgtga aaaa    24

<210> SEQ ID NO 244
<211> LENGTH: 20
<212> TYPE: DNA
<213> ORGANISM: Zea mays

<400> SEQUENCE: 244
gcataaagcg ggaagtggaa    20

<210> SEQ ID NO 245
<211> LENGTH: 24
<212> TYPE: DNA
<213> ORGANISM: Zea mays

<400> SEQUENCE: 245
accacagatt gtcccgagta tttg    24

<210> SEQ ID NO 246
<211> LENGTH: 17
<212> TYPE: DNA
<213> ORGANISM: Zea mays

<400> SEQUENCE: 246
gcacggacac cgagctg    17

<210> SEQ ID NO 247
<211> LENGTH: 25
<212> TYPE: DNA
<213> ORGANISM: Zea mays

<400> SEQUENCE: 247
gccactgtta atgttgcttc ttgta    25

<210> SEQ ID NO 248
<211> LENGTH: 26
<212> TYPE: DNA
<213> ORGANISM: Zea mays

<400> SEQUENCE: 248
tgctgtcatg tttattgggt tatagg    26

<210> SEQ ID NO 249
<211> LENGTH: 20
<212> TYPE: DNA
<213> ORGANISM: Zea mays

<400> SEQUENCE: 249
ggctagtgcc aattgccaaa                                              20

<210> SEQ ID NO 250
<211> LENGTH: 21
<212> TYPE: DNA
<213> ORGANISM: Zea mays

<400> SEQUENCE: 250
cgtacggact gccaattgtt t                                            21

<210> SEQ ID NO 251
<211> LENGTH: 17
<212> TYPE: DNA
<213> ORGANISM: Zea mays

<400> SEQUENCE: 251
cctccccggc ctatgtg                                                 17

<210> SEQ ID NO 252
<211> LENGTH: 24
<212> TYPE: DNA
<213> ORGANISM: Zea mays

<400> SEQUENCE: 252
gccaaaccac agataaggaa acac                                         24

<210> SEQ ID NO 253
<211> LENGTH: 24
<212> TYPE: DNA
<213> ORGANISM: Zea mays

<400> SEQUENCE: 253
tctttccttg atgggaacaa tgct                                         24

<210> SEQ ID NO 254
<211> LENGTH: 20
<212> TYPE: DNA
<213> ORGANISM: Zea mays

<400> SEQUENCE: 254
ccggtgggta cctcagttga                                              20

<210> SEQ ID NO 255
<211> LENGTH: 22
<212> TYPE: DNA
<213> ORGANISM: Zea mays

<400> SEQUENCE: 255
agtttccgct gtacagtttg gt                                           22

<210> SEQ ID NO 256
<211> LENGTH: 20
<212> TYPE: DNA
<213> ORGANISM: Zea mays

<400> SEQUENCE: 256
tggctctgca catccaaaaa                                              20

<210> SEQ ID NO 257
<211> LENGTH: 24
<212> TYPE: DNA
<213> ORGANISM: Zea mays

<400> SEQUENCE: 257
tcgttatgcc cttctctctt agct                                          24

<210> SEQ ID NO 258
<211> LENGTH: 26
<212> TYPE: DNA
<213> ORGANISM: Zea mays

<400> SEQUENCE: 258
ctgttcgttg tttttaattc gtatcg                                        26

<210> SEQ ID NO 259
<211> LENGTH: 27
<212> TYPE: DNA
<213> ORGANISM: Zea mays

<400> SEQUENCE: 259
agcagcattg tttcttgtgt tcaatac                                       27

<210> SEQ ID NO 260
<211> LENGTH: 25
<212> TYPE: DNA
<213> ORGANISM: Zea mays

<400> SEQUENCE: 260
ccaaactctc gatgaccaag cataa                                         25

<210> SEQ ID NO 261
<211> LENGTH: 20
<212> TYPE: DNA
<213> ORGANISM: Zea mays

<400> SEQUENCE: 261
gccactgctt tctgcttcgt                                               20

<210> SEQ ID NO 262
<211> LENGTH: 20
<212> TYPE: DNA
<213> ORGANISM: Zea mays

<400> SEQUENCE: 262
tgctgccaaa cttcgatcgt                                               20

<210> SEQ ID NO 263
<211> LENGTH: 17
<212> TYPE: DNA
<213> ORGANISM: Zea mays

<400> SEQUENCE: 263
ccaggctcag gcaccat                                                  17

<210> SEQ ID NO 264
<211> LENGTH: 26
<212> TYPE: DNA
<213> ORGANISM: Zea mays

<400> SEQUENCE: 264
ccgctatttc aataatcact ctcaga                                        26

<210> SEQ ID NO 265
<211> LENGTH: 30
<212> TYPE: DNA
<213> ORGANISM: Zea mays

```
<400> SEQUENCE: 265 gtatttttt tcttttttag acgttgcttt                              30

<210> SEQ ID NO 266
<211> LENGTH: 24
<212> TYPE: DNA
<213> ORGANISM: Zea mays

<400> SEQUENCE: 266
gctggcttca ggcctactac taaa                                   24

<210> SEQ ID NO 267
<211> LENGTH: 21
<212> TYPE: DNA
<213> ORGANISM: Zea mays

<400> SEQUENCE: 267
ttcactgact gcgatgacga a                                      21

<210> SEQ ID NO 268
<211> LENGTH: 20
<212> TYPE: DNA
<213> ORGANISM: Zea mays

<400> SEQUENCE: 268
ggaggagacg catgcagaaa                                        20

<210> SEQ ID NO 269
<211> LENGTH: 24
<212> TYPE: DNA
<213> ORGANISM: Zea mays

<400> SEQUENCE: 269
aaaacgttga aaaggatgc caca                                    24

<210> SEQ ID NO 270
<211> LENGTH: 24
<212> TYPE: DNA
<213> ORGANISM: Zea mays

<400> SEQUENCE: 270
gcagtagcga atttacctga gact                                   24

<210> SEQ ID NO 271
<211> LENGTH: 28
<212> TYPE: DNA
<213> ORGANISM: Zea mays

<400> SEQUENCE: 271
gctgattcct taatcttgtg tttcaaca                               28

<210> SEQ ID NO 272
<211> LENGTH: 24
<212> TYPE: DNA
<213> ORGANISM: Zea mays

<400> SEQUENCE: 272
atatgatcaa ccctgcagaa ttca                                   24

<210> SEQ ID NO 273
<211> LENGTH: 27
<212> TYPE: DNA
```

<213> ORGANISM: Zea mays

<400> SEQUENCE: 273
cacgaatgga ctaaagacac ttaagaa    27

<210> SEQ ID NO 274
<211> LENGTH: 21
<212> TYPE: DNA
<213> ORGANISM: Zea mays

<400> SEQUENCE: 274
ctgccacaag acacagcctt t    21

<210> SEQ ID NO 275
<211> LENGTH: 22
<212> TYPE: DNA
<213> ORGANISM: Zea mays

<400> SEQUENCE: 275
gcttcatcaa ttggcagctc tt    22

<210> SEQ ID NO 276
<211> LENGTH: 21
<212> TYPE: DNA
<213> ORGANISM: Zea mays

<400> SEQUENCE: 276
ctggtcctct ttgctgtgtc a    21

<210> SEQ ID NO 277
<211> LENGTH: 20
<212> TYPE: DNA
<213> ORGANISM: Zea mays

<400> SEQUENCE: 277
ggcgggaagg tactggtttc    20

<210> SEQ ID NO 278
<211> LENGTH: 20
<212> TYPE: DNA
<213> ORGANISM: Zea mays

<400> SEQUENCE: 278
ccctgcttgg aatggacatt    20

<210> SEQ ID NO 279
<211> LENGTH: 23
<212> TYPE: DNA
<213> ORGANISM: Zea mays

<400> SEQUENCE: 279
ccactgttct ccagtcctct tca    23

<210> SEQ ID NO 280
<211> LENGTH: 25
<212> TYPE: DNA
<213> ORGANISM: Zea mays

<400> SEQUENCE: 280
acaatctgcg gcttatccta actag    25

<210> SEQ ID NO 281
<211> LENGTH: 20

<212> TYPE: DNA
<213> ORGANISM: Zea mays

<400> SEQUENCE: 281
gccaatgcga tgaagttgaa                                           20

<210> SEQ ID NO 282
<211> LENGTH: 24
<212> TYPE: DNA
<213> ORGANISM: Zea mays

<400> SEQUENCE: 282
tttgcgtgga ctctaactgc ttat                                      24

<210> SEQ ID NO 283
<211> LENGTH: 23
<212> TYPE: DNA
<213> ORGANISM: Zea mays

<400> SEQUENCE: 283
gaaggtgaca ttttcaggga tga                                       23

<210> SEQ ID NO 284
<211> LENGTH: 19
<212> TYPE: DNA
<213> ORGANISM: Zea mays

<400> SEQUENCE: 284
cgcttcacct gaggtagct                                            19

<210> SEQ ID NO 285
<211> LENGTH: 25
<212> TYPE: DNA
<213> ORGANISM: Zea mays

<400> SEQUENCE: 285
ttggagtctg tgacattcaa tttca                                     25

<210> SEQ ID NO 286
<211> LENGTH: 25
<212> TYPE: DNA
<213> ORGANISM: Zea mays

<400> SEQUENCE: 286
gctgtcgaac gacttctcaa gttat                                     25

<210> SEQ ID NO 287
<211> LENGTH: 18
<212> TYPE: DNA
<213> ORGANISM: Zea mays

<400> SEQUENCE: 287
tcgggcaaca accatcca                                             18

<210> SEQ ID NO 288
<211> LENGTH: 20
<212> TYPE: DNA
<213> ORGANISM: Zea mays

<400> SEQUENCE: 288
cccccagaat gatcaccaaa                                           20

<210> SEQ ID NO 289

```
<211> LENGTH: 26
<212> TYPE: DNA
<213> ORGANISM: Zea mays

<400> SEQUENCE: 289
ggtggtggaa atatttgaga tggtaa                                          26

<210> SEQ ID NO 290
<211> LENGTH: 22
<212> TYPE: DNA
<213> ORGANISM: Zea mays

<400> SEQUENCE: 290
acttccatac gaccaggtct ca                                              22

<210> SEQ ID NO 291
<211> LENGTH: 19
<212> TYPE: DNA
<213> ORGANISM: Zea mays

<400> SEQUENCE: 291
ctaccaaccc agcgacgaa                                                  19

<210> SEQ ID NO 292
<211> LENGTH: 24
<212> TYPE: DNA
<213> ORGANISM: Zea mays

<400> SEQUENCE: 292
gagacatcac ctgatcagtt agca                                            24

<210> SEQ ID NO 293
<211> LENGTH: 21
<212> TYPE: DNA
<213> ORGANISM: Zea mays

<400> SEQUENCE: 293
ggttcacctg catcgagaag a                                               21

<210> SEQ ID NO 294
<211> LENGTH: 25
<212> TYPE: DNA
<213> ORGANISM: Zea mays

<400> SEQUENCE: 294
gatccaacag atcactgagg taagg                                           25

<210> SEQ ID NO 295
<211> LENGTH: 21
<212> TYPE: DNA
<213> ORGANISM: Zea mays

<400> SEQUENCE: 295
ctgagcgtcc atcacagatc a                                               21

<210> SEQ ID NO 296
<211> LENGTH: 16
<212> TYPE: DNA
<213> ORGANISM: Zea mays

<400> SEQUENCE: 296
agcctcgccg gtgaag                                                     16
```

```
<210> SEQ ID NO 297
<211> LENGTH: 26
<212> TYPE: DNA
<213> ORGANISM: Zea mays

<400> SEQUENCE: 297
ccacctgaag taaagagggc tataga                                          26

<210> SEQ ID NO 298
<211> LENGTH: 20
<212> TYPE: DNA
<213> ORGANISM: Zea mays

<400> SEQUENCE: 298
ccatgcaaag catgaatcga                                                 20

<210> SEQ ID NO 299
<211> LENGTH: 23
<212> TYPE: DNA
<213> ORGANISM: Zea mays

<400> SEQUENCE: 299
ctgcagggat gaacatacac caa                                             23

<210> SEQ ID NO 300
<211> LENGTH: 22
<212> TYPE: DNA
<213> ORGANISM: Zea mays

<400> SEQUENCE: 300
cagaaaggtc aaccgctgtt tg                                              22

<210> SEQ ID NO 301
<211> LENGTH: 25
<212> TYPE: DNA
<213> ORGANISM: Zea mays

<400> SEQUENCE: 301
catcagtttc cgtacattgt ttgca                                           25

<210> SEQ ID NO 302
<211> LENGTH: 25
<212> TYPE: DNA
<213> ORGANISM: Zea mays

<400> SEQUENCE: 302
atgatgatcg tagaaggctt gatgt                                           25

<210> SEQ ID NO 303
<211> LENGTH: 20
<212> TYPE: DNA
<213> ORGANISM: Zea mays

<400> SEQUENCE: 303
cgtgccagtc tgaagagctt                                                 20

<210> SEQ ID NO 304
<211> LENGTH: 28
<212> TYPE: DNA
<213> ORGANISM: Zea mays

<400> SEQUENCE: 304
cgttaccaac ggaatatata agcaacac                                        28
```

<210> SEQ ID NO 305
<211> LENGTH: 20
<212> TYPE: DNA
<213> ORGANISM: Zea mays

<400> SEQUENCE: 305
tgcatccttt ttcccgtgaa                                          20

<210> SEQ ID NO 306
<211> LENGTH: 22
<212> TYPE: DNA
<213> ORGANISM: Zea mays

<400> SEQUENCE: 306
cggaatactt ggcaacgtcg at                                       22

<210> SEQ ID NO 307
<211> LENGTH: 23
<212> TYPE: DNA
<213> ORGANISM: Zea mays

<400> SEQUENCE: 307
ccacgacctc ttgagaaaaa gaa                                      23

<210> SEQ ID NO 308
<211> LENGTH: 22
<212> TYPE: DNA
<213> ORGANISM: Zea mays

<400> SEQUENCE: 308
gcttgggctt gaggtacaga ag                                       22

<210> SEQ ID NO 309
<211> LENGTH: 23
<212> TYPE: DNA
<213> ORGANISM: Zea mays

<400> SEQUENCE: 309
ccgttgacga ccatgatgta gag                                      23

<210> SEQ ID NO 310
<211> LENGTH: 20
<212> TYPE: DNA
<213> ORGANISM: Zea mays

<400> SEQUENCE: 310
gcacagtcga ggtggctata                                          20

<210> SEQ ID NO 311
<211> LENGTH: 24
<212> TYPE: DNA
<213> ORGANISM: Zea mays

<400> SEQUENCE: 311
ggaacaacat ccccaaatag agaa                                     24

<210> SEQ ID NO 312
<211> LENGTH: 29
<212> TYPE: DNA
<213> ORGANISM: Zea mays

<400> SEQUENCE: 312
ccttgatgta catattcatt tgggtctca                                29

<210> SEQ ID NO 313
<211> LENGTH: 24
<212> TYPE: DNA
<213> ORGANISM: Zea mays

<400> SEQUENCE: 313
ggaacaacat ccccaaatag agaa                                          24

<210> SEQ ID NO 314
<211> LENGTH: 18
<212> TYPE: DNA
<213> ORGANISM: Zea mays

<400> SEQUENCE: 314
gcggtcacag tggcgtaa                                                 18

<210> SEQ ID NO 315
<211> LENGTH: 25
<212> TYPE: DNA
<213> ORGANISM: Zea mays

<400> SEQUENCE: 315
ccagctccta cttaaacagg aactg                                         25

<210> SEQ ID NO 316
<211> LENGTH: 18
<212> TYPE: DNA
<213> ORGANISM: Zea mays

<400> SEQUENCE: 316
gcatccctcc gccactag                                                 18

<210> SEQ ID NO 317
<211> LENGTH: 28
<212> TYPE: DNA
<213> ORGANISM: Zea mays

<400> SEQUENCE: 317
accgctacat tgttaagtta tcaatggt                                      28

<210> SEQ ID NO 318
<211> LENGTH: 25
<212> TYPE: DNA
<213> ORGANISM: Zea mays

<400> SEQUENCE: 318
ccagaaggag gagtgttctc aaata                                         25

<210> SEQ ID NO 319
<211> LENGTH: 23
<212> TYPE: DNA
<213> ORGANISM: Zea mays

<400> SEQUENCE: 319
catctaaaag tcgcgttgct ctt                                           23

<210> SEQ ID NO 320
<211> LENGTH: 20
<212> TYPE: DNA
<213> ORGANISM: Zea mays

<400> SEQUENCE: 320

```
tgcctcaatc agcaaatcca                                              20

<210> SEQ ID NO 321
<211> LENGTH: 17
<212> TYPE: DNA
<213> ORGANISM: Zea mays

<400> SEQUENCE: 321
cagcgcgaca cgatggt                                                 17

<210> SEQ ID NO 322
<211> LENGTH: 22
<212> TYPE: DNA
<213> ORGANISM: Zea mays

<400> SEQUENCE: 322
tggtcttgca tctatggttg ga                                           22

<210> SEQ ID NO 323
<211> LENGTH: 18
<212> TYPE: DNA
<213> ORGANISM: Zea mays

<400> SEQUENCE: 323
acgacgctgt gggaaacg                                                18

<210> SEQ ID NO 324
<211> LENGTH: 20
<212> TYPE: DNA
<213> ORGANISM: Zea mays

<400> SEQUENCE: 324
cgtctcgtgc agtggtgaga                                              20

<210> SEQ ID NO 325
<211> LENGTH: 25
<212> TYPE: DNA
<213> ORGANISM: Zea mays

<400> SEQUENCE: 325
cattctgaaa ccagattcca atgct                                        25

<210> SEQ ID NO 326
<211> LENGTH: 22
<212> TYPE: DNA
<213> ORGANISM: Zea mays

<400> SEQUENCE: 326
gccgtgtagg aacaacagtg aa                                           22

<210> SEQ ID NO 327
<211> LENGTH: 23
<212> TYPE: DNA
<213> ORGANISM: Zea mays

<400> SEQUENCE: 327
ggttcatggg agagggaatt tga                                          23

<210> SEQ ID NO 328
<211> LENGTH: 20
<212> TYPE: DNA
<213> ORGANISM: Zea mays

<400> SEQUENCE: 328
```

```
gcgtttcagc tccgtgtgtt                                              20

<210> SEQ ID NO 329
<211> LENGTH: 17
<212> TYPE: DNA
<213> ORGANISM: Zea mays

<400> SEQUENCE: 329
gtcgccgcca tcatgtc                                                 17

<210> SEQ ID NO 330
<211> LENGTH: 17
<212> TYPE: DNA
<213> ORGANISM: Zea mays

<400> SEQUENCE: 330
tgtggcgctg caacgat                                                 17

<210> SEQ ID NO 331
<211> LENGTH: 24
<212> TYPE: DNA
<213> ORGANISM: Zea mays

<400> SEQUENCE: 331
ctgacaccag agtcatctga aggt                                         24

<210> SEQ ID NO 332
<211> LENGTH: 24
<212> TYPE: DNA
<213> ORGANISM: Zea mays

<400> SEQUENCE: 332
agcaaatctt ccttcatcct catc                                         24

<210> SEQ ID NO 333
<211> LENGTH: 25
<212> TYPE: DNA
<213> ORGANISM: Zea mays

<400> SEQUENCE: 333
ccagcaactt tactgtcttc actga                                        25

<210> SEQ ID NO 334
<211> LENGTH: 25
<212> TYPE: DNA
<213> ORGANISM: Zea mays

<400> SEQUENCE: 334
gagatccaga tttcatcaaa aacca                                        25

<210> SEQ ID NO 335
<211> LENGTH: 15
<212> TYPE: DNA
<213> ORGANISM: Zea mays

<400> SEQUENCE: 335
cggcgcgtgg acgta                                                   15

<210> SEQ ID NO 336
<211> LENGTH: 18
<212> TYPE: DNA
<213> ORGANISM: Zea mays
```

```
<400> SEQUENCE: 336
gccatttggg ccgtgatc                                              18

<210> SEQ ID NO 337
<211> LENGTH: 27
<212> TYPE: DNA
<213> ORGANISM: Zea mays

<400> SEQUENCE: 337
tctaacttgt agctgcttcc aaagatg                                    27

<210> SEQ ID NO 338
<211> LENGTH: 17
<212> TYPE: DNA
<213> ORGANISM: Zea mays

<400> SEQUENCE: 338
ccaccccgtg ccaaact                                               17

<210> SEQ ID NO 339
<211> LENGTH: 25
<212> TYPE: DNA
<213> ORGANISM: Zea mays

<400> SEQUENCE: 339
aagtggtcag gcatagagaa aatga                                      25

<210> SEQ ID NO 340
<211> LENGTH: 19
<212> TYPE: DNA
<213> ORGANISM: Zea mays

<400> SEQUENCE: 340
gtgcagttgc ccgtttgtt                                             19

<210> SEQ ID NO 341
<211> LENGTH: 25
<212> TYPE: DNA
<213> ORGANISM: Zea mays

<400> SEQUENCE: 341
ggcatggatc acttttatga caata                                      25

<210> SEQ ID NO 342
<211> LENGTH: 18
<212> TYPE: DNA
<213> ORGANISM: Zea mays

<400> SEQUENCE: 342
gcttggtcgc tggatgct                                              18

<210> SEQ ID NO 343
<211> LENGTH: 16
<212> TYPE: DNA
<213> ORGANISM: Zea mays

<400> SEQUENCE: 343
cttgtccagc tatacg                                                16

<210> SEQ ID NO 344
<211> LENGTH: 14
<212> TYPE: DNA
<213> ORGANISM: Zea mays
```

```
<400> SEQUENCE: 344
acggcagatt aaag                                                       14

<210> SEQ ID NO 345
<211> LENGTH: 14
<212> TYPE: DNA
<213> ORGANISM: Zea mays

<400> SEQUENCE: 345
tctgggaccg aagc                                                       14

<210> SEQ ID NO 346
<211> LENGTH: 14
<212> TYPE: DNA
<213> ORGANISM: Zea mays

<400> SEQUENCE: 346
cacacgcgag acag                                                       14

<210> SEQ ID NO 347
<211> LENGTH: 17
<212> TYPE: DNA
<213> ORGANISM: Zea mays

<400> SEQUENCE: 347
tggtagatag cagttct                                                    17

<210> SEQ ID NO 348
<211> LENGTH: 14
<212> TYPE: DNA
<213> ORGANISM: Zea mays

<400> SEQUENCE: 348
ctcgtgtatc tctg                                                       14

<210> SEQ ID NO 349
<211> LENGTH: 15
<212> TYPE: DNA
<213> ORGANISM: Zea mays

<400> SEQUENCE: 349
cacgacagac agaac                                                      15

<210> SEQ ID NO 350
<211> LENGTH: 13
<212> TYPE: DNA
<213> ORGANISM: Zea mays

<400> SEQUENCE: 350
acgggacgca ctc                                                        13

<210> SEQ ID NO 351
<211> LENGTH: 14
<212> TYPE: DNA
<213> ORGANISM: Zea mays

<400> SEQUENCE: 351
cggtcagccg tgcc                                                       14

<210> SEQ ID NO 352
<211> LENGTH: 17
<212> TYPE: DNA
```

<213> ORGANISM: Zea mays

<400> SEQUENCE: 352
acgagtcaat taaagtt                                                    17

<210> SEQ ID NO 353
<211> LENGTH: 16
<212> TYPE: DNA
<213> ORGANISM: Zea mays

<400> SEQUENCE: 353
cttgatcccg gcggtg                                                     16

<210> SEQ ID NO 354
<211> LENGTH: 14
<212> TYPE: DNA
<213> ORGANISM: Zea mays

<400> SEQUENCE: 354
tctgcagccg ctgc                                                       14

<210> SEQ ID NO 355
<211> LENGTH: 16
<212> TYPE: DNA
<213> ORGANISM: Zea mays

<400> SEQUENCE: 355
ccatcaacca taataa                                                     16

<210> SEQ ID NO 356
<211> LENGTH: 19
<212> TYPE: DNA
<213> ORGANISM: Zea mays

<400> SEQUENCE: 356
caattggagt aatgaattc                                                  19

<210> SEQ ID NO 357
<211> LENGTH: 14
<212> TYPE: DNA
<213> ORGANISM: Zea mays

<400> SEQUENCE: 357
cgaatccaca tctt                                                       14

<210> SEQ ID NO 358
<211> LENGTH: 15
<212> TYPE: DNA
<213> ORGANISM: Zea mays

<400> SEQUENCE: 358
cggttccaca gacgt                                                      15

<210> SEQ ID NO 359
<211> LENGTH: 17
<212> TYPE: DNA
<213> ORGANISM: Zea mays

<400> SEQUENCE: 359
atctcctgcc tgctgtg                                                    17

<210> SEQ ID NO 360
<211> LENGTH: 14

```
<212> TYPE: DNA
<213> ORGANISM: Zea mays

<400> SEQUENCE: 360
tggccttgtt ccgg                                                    14

<210> SEQ ID NO 361
<211> LENGTH: 15
<212> TYPE: DNA
<213> ORGANISM: Zea mays

<400> SEQUENCE: 361
caccaggtat agtcc                                                   15

<210> SEQ ID NO 362
<211> LENGTH: 16
<212> TYPE: DNA
<213> ORGANISM: Zea mays

<400> SEQUENCE: 362
catgcatgtt tttaag                                                  16

<210> SEQ ID NO 363
<211> LENGTH: 14
<212> TYPE: DNA
<213> ORGANISM: Zea mays

<400> SEQUENCE: 363
cgttcgagat cgag                                                    14

<210> SEQ ID NO 364
<211> LENGTH: 13
<212> TYPE: DNA
<213> ORGANISM: Zea mays

<400> SEQUENCE: 364
cgcatgaaat tga                                                     13

<210> SEQ ID NO 365
<211> LENGTH: 16
<212> TYPE: DNA
<213> ORGANISM: Zea mays

<400> SEQUENCE: 365
cctcacctgt aacaag                                                  16

<210> SEQ ID NO 366
<211> LENGTH: 16
<212> TYPE: DNA
<213> ORGANISM: Zea mays

<400> SEQUENCE: 366
cacgatagga attagt                                                  16

<210> SEQ ID NO 367
<211> LENGTH: 18
<212> TYPE: DNA
<213> ORGANISM: Zea mays

<400> SEQUENCE: 367
caaggtcgat ctctccct                                                18

<210> SEQ ID NO 368
```

-continued

```
<211> LENGTH: 15
<212> TYPE: DNA
<213> ORGANISM: Zea mays

<400> SEQUENCE: 368
aactgggatt actcc                                                      15

<210> SEQ ID NO 369
<211> LENGTH: 19
<212> TYPE: DNA
<213> ORGANISM: Zea mays

<400> SEQUENCE: 369
ttctaggacc cctcatcat                                                  19

<210> SEQ ID NO 370
<211> LENGTH: 17
<212> TYPE: DNA
<213> ORGANISM: Zea mays

<400> SEQUENCE: 370
tgggtactaa caacaag                                                    17

<210> SEQ ID NO 371
<211> LENGTH: 15
<212> TYPE: DNA
<213> ORGANISM: Zea mays

<400> SEQUENCE: 371
cttcttgaat cttcg                                                      15

<210> SEQ ID NO 372
<211> LENGTH: 15
<212> TYPE: DNA
<213> ORGANISM: Zea mays

<400> SEQUENCE: 372
acagtcggat ttaat                                                      15

<210> SEQ ID NO 373
<211> LENGTH: 21
<212> TYPE: DNA
<213> ORGANISM: Zea mays

<400> SEQUENCE: 373
cataaataaa gcacatattc a                                               21

<210> SEQ ID NO 374
<211> LENGTH: 18
<212> TYPE: DNA
<213> ORGANISM: Zea mays

<400> SEQUENCE: 374
cttgattaga ccaaagtg                                                   18

<210> SEQ ID NO 375
<211> LENGTH: 16
<212> TYPE: DNA
<213> ORGANISM: Zea mays

<400> SEQUENCE: 375
aggatgaata cttctc                                                     16
```

```
<210> SEQ ID NO 376
<211> LENGTH: 15
<212> TYPE: DNA
<213> ORGANISM: Zea mays

<400> SEQUENCE: 376
cctctacgat catcc                                                      15

<210> SEQ ID NO 377
<211> LENGTH: 15
<212> TYPE: DNA
<213> ORGANISM: Zea mays

<400> SEQUENCE: 377
cagcctcaac gctgg                                                      15

<210> SEQ ID NO 378
<211> LENGTH: 14
<212> TYPE: DNA
<213> ORGANISM: Zea mays

<400> SEQUENCE: 378
tgtcagctat ctcc                                                       14

<210> SEQ ID NO 379
<211> LENGTH: 14
<212> TYPE: DNA
<213> ORGANISM: Zea mays

<400> SEQUENCE: 379
tgtggagagg aacg                                                       14

<210> SEQ ID NO 380
<211> LENGTH: 15
<212> TYPE: DNA
<213> ORGANISM: Zea mays

<400> SEQUENCE: 380
cgaaggacta aagaa                                                      15

<210> SEQ ID NO 381
<211> LENGTH: 16
<212> TYPE: DNA
<213> ORGANISM: Zea mays

<400> SEQUENCE: 381
actttgggat aacgca                                                     16

<210> SEQ ID NO 382
<211> LENGTH: 16
<212> TYPE: DNA
<213> ORGANISM: Zea mays

<400> SEQUENCE: 382
ctcgacagaa gaacat                                                     16

<210> SEQ ID NO 383
<211> LENGTH: 17
<212> TYPE: DNA
<213> ORGANISM: Zea mays

<400> SEQUENCE: 383
cctcaacagt ggtagct                                                    17
```

```
<210> SEQ ID NO 384
<211> LENGTH: 13
<212> TYPE: DNA
<213> ORGANISM: Zea mays

<400> SEQUENCE: 384
cgcagggctc gtg                                                    13

<210> SEQ ID NO 385
<211> LENGTH: 20
<212> TYPE: DNA
<213> ORGANISM: Zea mays

<400> SEQUENCE: 385
catactcttc gatacatatt                                             20

<210> SEQ ID NO 386
<211> LENGTH: 14
<212> TYPE: DNA
<213> ORGANISM: Zea mays

<400> SEQUENCE: 386
atcagcggca gaaa                                                   14

<210> SEQ ID NO 387
<211> LENGTH: 13
<212> TYPE: DNA
<213> ORGANISM: Zea mays

<400> SEQUENCE: 387
agctcggaat gcg                                                    13

<210> SEQ ID NO 388
<211> LENGTH: 16
<212> TYPE: DNA
<213> ORGANISM: Zea mays

<400> SEQUENCE: 388
caacttgcgt tatttt                                                 16

<210> SEQ ID NO 389
<211> LENGTH: 15
<212> TYPE: DNA
<213> ORGANISM: Zea mays

<400> SEQUENCE: 389
caacacacac attaa                                                  15

<210> SEQ ID NO 390
<211> LENGTH: 20
<212> TYPE: DNA
<213> ORGANISM: Zea mays

<400> SEQUENCE: 390
ataaagcagc taatttgcta                                             20

<210> SEQ ID NO 391
<211> LENGTH: 16
<212> TYPE: DNA
<213> ORGANISM: Zea mays

<400> SEQUENCE: 391
ctgtttcctt gtttct                                                 16
```

```
<210> SEQ ID NO 392
<211> LENGTH: 16
<212> TYPE: DNA
<213> ORGANISM: Zea mays

<400> SEQUENCE: 392
agatggagta atttgg                                                       16

<210> SEQ ID NO 393
<211> LENGTH: 14
<212> TYPE: DNA
<213> ORGANISM: Zea mays

<400> SEQUENCE: 393
cttcgacaaa atgg                                                         14

<210> SEQ ID NO 394
<211> LENGTH: 17
<212> TYPE: DNA
<213> ORGANISM: Zea mays

<400> SEQUENCE: 394
tcaaatccaa aaagcag                                                      17

<210> SEQ ID NO 395
<211> LENGTH: 16
<212> TYPE: DNA
<213> ORGANISM: Zea mays

<400> SEQUENCE: 395
cggactaaag cacttt                                                       16

<210> SEQ ID NO 396
<211> LENGTH: 17
<212> TYPE: DNA
<213> ORGANISM: Zea mays

<400> SEQUENCE: 396
agaattgctg gatgcat                                                      17

<210> SEQ ID NO 397
<211> LENGTH: 15
<212> TYPE: DNA
<213> ORGANISM: Zea mays

<400> SEQUENCE: 397
ccagcttgtt tattc                                                        15

<210> SEQ ID NO 398
<211> LENGTH: 15
<212> TYPE: DNA
<213> ORGANISM: Zea mays

<400> SEQUENCE: 398
acgatcaagg caaac                                                        15

<210> SEQ ID NO 399
<211> LENGTH: 16
<212> TYPE: DNA
<213> ORGANISM: Zea mays

<400> SEQUENCE: 399
```

```
ctcattaaca gaaaat                                                      16

<210> SEQ ID NO 400
<211> LENGTH: 15
<212> TYPE: DNA
<213> ORGANISM: Zea mays

<400> SEQUENCE: 400
agtggttgaa aagat                                                       15

<210> SEQ ID NO 401
<211> LENGTH: 18
<212> TYPE: DNA
<213> ORGANISM: Zea mays

<400> SEQUENCE: 401
aagcgattca aagcacaa                                                    18

<210> SEQ ID NO 402
<211> LENGTH: 18
<212> TYPE: DNA
<213> ORGANISM: Zea mays

<400> SEQUENCE: 402
cgtaattgat taaacctc                                                    18

<210> SEQ ID NO 403
<211> LENGTH: 20
<212> TYPE: DNA
<213> ORGANISM: Zea mays

<400> SEQUENCE: 403
ttgctttaaa ttataaaatc                                                  20

<210> SEQ ID NO 404
<211> LENGTH: 20
<212> TYPE: DNA
<213> ORGANISM: Zea mays

<400> SEQUENCE: 404
ctgtgcatat ttggtgttag                                                  20

<210> SEQ ID NO 405
<211> LENGTH: 15
<212> TYPE: DNA
<213> ORGANISM: Zea mays

<400> SEQUENCE: 405
atggcacgtt gatca                                                       15

<210> SEQ ID NO 406
<211> LENGTH: 20
<212> TYPE: DNA
<213> ORGANISM: Zea mays

<400> SEQUENCE: 406
tagttacagt acaagaacaa                                                  20

<210> SEQ ID NO 407
<211> LENGTH: 14
<212> TYPE: DNA
<213> ORGANISM: Zea mays

<400> SEQUENCE: 407
```
aggagccctg ggag                                              14

<210> SEQ ID NO 408
<211> LENGTH: 15
<212> TYPE: DNA
<213> ORGANISM: Zea mays

<400> SEQUENCE: 408
ccttgacagc aaagt                                             15

<210> SEQ ID NO 409
<211> LENGTH: 19
<212> TYPE: DNA
<213> ORGANISM: Zea mays

<400> SEQUENCE: 409
ccaatataca gataatctg                                         19

<210> SEQ ID NO 410
<211> LENGTH: 18
<212> TYPE: DNA
<213> ORGANISM: Zea mays

<400> SEQUENCE: 410
cccgttcttg ttgaccag                                          18

<210> SEQ ID NO 411
<211> LENGTH: 13
<212> TYPE: DNA
<213> ORGANISM: Zea mays

<400> SEQUENCE: 411
tccccatgct ttc                                               13

<210> SEQ ID NO 412
<211> LENGTH: 17
<212> TYPE: DNA
<213> ORGANISM: Zea mays

<400> SEQUENCE: 412
aaaacaaggt atctttc                                           17

<210> SEQ ID NO 413
<211> LENGTH: 19
<212> TYPE: DNA
<213> ORGANISM: Zea mays

<400> SEQUENCE: 413
cttctactat caagattgc                                         19

<210> SEQ ID NO 414
<211> LENGTH: 18
<212> TYPE: DNA
<213> ORGANISM: Zea mays

<400> SEQUENCE: 414
cactgtacgc ttcaatgt                                          18

<210> SEQ ID NO 415
<211> LENGTH: 19
<212> TYPE: DNA
<213> ORGANISM: Zea mays

```
<400> SEQUENCE: 415
cttaggatca tcttttct                                              19

<210> SEQ ID NO 416
<211> LENGTH: 14
<212> TYPE: DNA
<213> ORGANISM: Zea mays

<400> SEQUENCE: 416
tctgaccaag aaac                                                  14

<210> SEQ ID NO 417
<211> LENGTH: 16
<212> TYPE: DNA
<213> ORGANISM: Zea mays

<400> SEQUENCE: 417
ctgctctagc atcgac                                                16

<210> SEQ ID NO 418
<211> LENGTH: 18
<212> TYPE: DNA
<213> ORGANISM: Zea mays

<400> SEQUENCE: 418
atttgcattt gctactcg                                              18

<210> SEQ ID NO 419
<211> LENGTH: 17
<212> TYPE: DNA
<213> ORGANISM: Zea mays

<400> SEQUENCE: 419
agaccaataa tcaatgc                                               17

<210> SEQ ID NO 420
<211> LENGTH: 16
<212> TYPE: DNA
<213> ORGANISM: Zea mays

<400> SEQUENCE: 420
caaatgcgga gtccag                                                16

<210> SEQ ID NO 421
<211> LENGTH: 14
<212> TYPE: DNA
<213> ORGANISM: Zea mays

<400> SEQUENCE: 421
agctccacaa cgat                                                  14

<210> SEQ ID NO 422
<211> LENGTH: 16
<212> TYPE: DNA
<213> ORGANISM: Zea mays

<400> SEQUENCE: 422
caccagatta aacctt                                                16

<210> SEQ ID NO 423
<211> LENGTH: 16
<212> TYPE: DNA
<213> ORGANISM: Zea mays
```

```
<400> SEQUENCE: 423
catctccctg tgcctc                                              16

<210> SEQ ID NO 424
<211> LENGTH: 15
<212> TYPE: DNA
<213> ORGANISM: Zea mays

<400> SEQUENCE: 424
ctgtgccttc ttggc                                               15

<210> SEQ ID NO 425
<211> LENGTH: 14
<212> TYPE: DNA
<213> ORGANISM: Zea mays

<400> SEQUENCE: 425
catgtgctaa cttc                                                14

<210> SEQ ID NO 426
<211> LENGTH: 16
<212> TYPE: DNA
<213> ORGANISM: Zea mays

<400> SEQUENCE: 426
cagacaaata atttca                                              16

<210> SEQ ID NO 427
<211> LENGTH: 14
<212> TYPE: DNA
<213> ORGANISM: Zea mays

<400> SEQUENCE: 427
catgtgctaa cttc                                                14

<210> SEQ ID NO 428
<211> LENGTH: 14
<212> TYPE: DNA
<213> ORGANISM: Zea mays

<400> SEQUENCE: 428
cggagtggca ttct                                                14

<210> SEQ ID NO 429
<211> LENGTH: 15
<212> TYPE: DNA
<213> ORGANISM: Zea mays

<400> SEQUENCE: 429
aggtttgcat actct                                               15

<210> SEQ ID NO 430
<211> LENGTH: 13
<212> TYPE: DNA
<213> ORGANISM: Zea mays

<400> SEQUENCE: 430
ccactcagaa aac                                                 13

<210> SEQ ID NO 431
<211> LENGTH: 19
<212> TYPE: DNA
```

```
<213> ORGANISM: Zea mays

<400> SEQUENCE: 431
catatttagc gtttcatca                                                  19

<210> SEQ ID NO 432
<211> LENGTH: 14
<212> TYPE: DNA
<213> ORGANISM: Zea mays

<400> SEQUENCE: 432
ccccatcaat gatt                                                       14

<210> SEQ ID NO 433
<211> LENGTH: 16
<212> TYPE: DNA
<213> ORGANISM: Zea mays

<400> SEQUENCE: 433
tttgttgcag aggaag                                                     16

<210> SEQ ID NO 434
<211> LENGTH: 15
<212> TYPE: DNA
<213> ORGANISM: Zea mays

<400> SEQUENCE: 434
tgagcaacta gcgcc                                                      15

<210> SEQ ID NO 435
<211> LENGTH: 13
<212> TYPE: DNA
<213> ORGANISM: Zea mays

<400> SEQUENCE: 435
tgacggcatc gac                                                        13

<210> SEQ ID NO 436
<211> LENGTH: 16
<212> TYPE: DNA
<213> ORGANISM: Zea mays

<400> SEQUENCE: 436
cagagcacac tagttt                                                     16

<210> SEQ ID NO 437
<211> LENGTH: 13
<212> TYPE: DNA
<213> ORGANISM: Zea mays

<400> SEQUENCE: 437
tcggtcgcca aac                                                        13

<210> SEQ ID NO 438
<211> LENGTH: 16
<212> TYPE: DNA
<213> ORGANISM: Zea mays

<400> SEQUENCE: 438
caacacacga cttagt                                                     16

<210> SEQ ID NO 439
<211> LENGTH: 17
```

```
<212> TYPE: DNA
<213> ORGANISM: Zea mays

<400> SEQUENCE: 439
tgagctgaga tgaacct                                                    17

<210> SEQ ID NO 440
<211> LENGTH: 20
<212> TYPE: DNA
<213> ORGANISM: Zea mays

<400> SEQUENCE: 440
aaatacatct aaaaacttca                                                 20

<210> SEQ ID NO 441
<211> LENGTH: 16
<212> TYPE: DNA
<213> ORGANISM: Zea mays

<400> SEQUENCE: 441
atgtgcatca acgatg                                                     16

<210> SEQ ID NO 442
<211> LENGTH: 14
<212> TYPE: DNA
<213> ORGANISM: Zea mays

<400> SEQUENCE: 442
atgcagcata cctg                                                       14

<210> SEQ ID NO 443
<211> LENGTH: 16
<212> TYPE: DNA
<213> ORGANISM: Zea mays

<400> SEQUENCE: 443
ttactctagc atcgcc                                                     16

<210> SEQ ID NO 444
<211> LENGTH: 14
<212> TYPE: DNA
<213> ORGANISM: Zea mays

<400> SEQUENCE: 444
cacgaacacg aagc                                                       14

<210> SEQ ID NO 445
<211> LENGTH: 16
<212> TYPE: DNA
<213> ORGANISM: Zea mays

<400> SEQUENCE: 445
cctttttaca tcctcc                                                     16

<210> SEQ ID NO 446
<211> LENGTH: 15
<212> TYPE: DNA
<213> ORGANISM: Zea mays

<400> SEQUENCE: 446
acaagagaga acttc                                                      15

<210> SEQ ID NO 447
```

```
<211> LENGTH: 15
<212> TYPE: DNA
<213> ORGANISM: Zea mays

<400> SEQUENCE: 447
acagagggat tggtg                                                    15

<210> SEQ ID NO 448
<211> LENGTH: 15
<212> TYPE: DNA
<213> ORGANISM: Zea mays

<400> SEQUENCE: 448
accatgcaac atatg                                                    15

<210> SEQ ID NO 449
<211> LENGTH: 15
<212> TYPE: DNA
<213> ORGANISM: Zea mays

<400> SEQUENCE: 449
cctctaggat cagcg                                                    15

<210> SEQ ID NO 450
<211> LENGTH: 18
<212> TYPE: DNA
<213> ORGANISM: Zea mays

<400> SEQUENCE: 450
atcggtaaag aagaagaa                                                 18

<210> SEQ ID NO 451
<211> LENGTH: 20
<212> TYPE: DNA
<213> ORGANISM: Zea mays

<400> SEQUENCE: 451
cagttgacaa tatagcctac                                               20

<210> SEQ ID NO 452
<211> LENGTH: 15
<212> TYPE: DNA
<213> ORGANISM: Zea mays

<400> SEQUENCE: 452
cgagaacgga gtttg                                                    15

<210> SEQ ID NO 453
<211> LENGTH: 15
<212> TYPE: DNA
<213> ORGANISM: Zea mays

<400> SEQUENCE: 453
atgctcctat ttctg                                                    15

<210> SEQ ID NO 454
<211> LENGTH: 14
<212> TYPE: DNA
<213> ORGANISM: Zea mays

<400> SEQUENCE: 454
tgggcttgac cttt                                                     14
```

```
<210> SEQ ID NO 455
<211> LENGTH: 13
<212> TYPE: DNA
<213> ORGANISM: Zea mays

<400> SEQUENCE: 455
atgcaaagct tcc                                                    13

<210> SEQ ID NO 456
<211> LENGTH: 13
<212> TYPE: DNA
<213> ORGANISM: Zea mays

<400> SEQUENCE: 456
ttcgcaccaa acc                                                    13

<210> SEQ ID NO 457
<211> LENGTH: 15
<212> TYPE: DNA
<213> ORGANISM: Zea mays

<400> SEQUENCE: 457
tgtccagcca tacgt                                                  15

<210> SEQ ID NO 458
<211> LENGTH: 13
<212> TYPE: DNA
<213> ORGANISM: Zea mays

<400> SEQUENCE: 458
cggcaaatta aag                                                    13

<210> SEQ ID NO 459
<211> LENGTH: 14
<212> TYPE: DNA
<213> ORGANISM: Zea mays

<400> SEQUENCE: 459
tgggactgaa gcga                                                   14

<210> SEQ ID NO 460
<211> LENGTH: 13
<212> TYPE: DNA
<213> ORGANISM: Zea mays

<400> SEQUENCE: 460
cgcgacacag cta                                                    13

<210> SEQ ID NO 461
<211> LENGTH: 19
<212> TYPE: DNA
<213> ORGANISM: Zea mays

<400> SEQUENCE: 461
agatagcaat tcttatcct                                              19

<210> SEQ ID NO 462
<211> LENGTH: 14
<212> TYPE: DNA
<213> ORGANISM: Zea mays

<400> SEQUENCE: 462
tcgtgtgtct ctgc                                                   14
```

```
<210> SEQ ID NO 463
<211> LENGTH: 15
<212> TYPE: DNA
<213> ORGANISM: Zea mays

<400> SEQUENCE: 463
cacgacaggc agaac                                                    15

<210> SEQ ID NO 464
<211> LENGTH: 13
<212> TYPE: DNA
<213> ORGANISM: Zea mays

<400> SEQUENCE: 464
cgggatgcac tcg                                                      13

<210> SEQ ID NO 465
<211> LENGTH: 14
<212> TYPE: DNA
<213> ORGANISM: Zea mays

<400> SEQUENCE: 465
cggtcagtcg tgcc                                                     14

<210> SEQ ID NO 466
<211> LENGTH: 17
<212> TYPE: DNA
<213> ORGANISM: Zea mays

<400> SEQUENCE: 466
acgagtcaat tgaagtt                                                  17

<210> SEQ ID NO 467
<211> LENGTH: 17
<212> TYPE: DNA
<213> ORGANISM: Zea mays

<400> SEQUENCE: 467
tcttgatccc agcggtg                                                  17

<210> SEQ ID NO 468
<211> LENGTH: 14
<212> TYPE: DNA
<213> ORGANISM: Zea mays

<400> SEQUENCE: 468
tctgctgccg ctgc                                                     14

<210> SEQ ID NO 469
<211> LENGTH: 15
<212> TYPE: DNA
<213> ORGANISM: Zea mays

<400> SEQUENCE: 469
aaccacaata atttc                                                    15

<210> SEQ ID NO 470
<211> LENGTH: 16
<212> TYPE: DNA
<213> ORGANISM: Zea mays

<400> SEQUENCE: 470
ttggagtagt gaattc                                                   16
```

```
<210> SEQ ID NO 471
<211> LENGTH: 15
<212> TYPE: DNA
<213> ORGANISM: Zea mays

<400> SEQUENCE: 471
cgaatccacg tcttg                                                15

<210> SEQ ID NO 472
<211> LENGTH: 15
<212> TYPE: DNA
<213> ORGANISM: Zea mays

<400> SEQUENCE: 472
ttccacggac gtcgt                                                15

<210> SEQ ID NO 473
<211> LENGTH: 14
<212> TYPE: DNA
<213> ORGANISM: Zea mays

<400> SEQUENCE: 473
tcctgccagc tgtg                                                 14

<210> SEQ ID NO 474
<211> LENGTH: 13
<212> TYPE: DNA
<213> ORGANISM: Zea mays

<400> SEQUENCE: 474
tggccctgtt ccg                                                  13

<210> SEQ ID NO 475
<211> LENGTH: 15
<212> TYPE: DNA
<213> ORGANISM: Zea mays

<400> SEQUENCE: 475
ccaggtagag tccaa                                                15

<210> SEQ ID NO 476
<211> LENGTH: 15
<212> TYPE: DNA
<213> ORGANISM: Zea mays

<400> SEQUENCE: 476
atgcatgctt ttaag                                                15

<210> SEQ ID NO 477
<211> LENGTH: 17
<212> TYPE: DNA
<213> ORGANISM: Zea mays

<400> SEQUENCE: 477
ttctcgttct agatcga                                              17

<210> SEQ ID NO 478
<211> LENGTH: 13
<212> TYPE: DNA
<213> ORGANISM: Zea mays

<400> SEQUENCE: 478
```
cgcatgaatt tga                                                          13

<210> SEQ ID NO 479
<211> LENGTH: 15
<212> TYPE: DNA
<213> ORGANISM: Zea mays

<400> SEQUENCE: 479
ctcacctgga acaag                                                        15

<210> SEQ ID NO 480
<211> LENGTH: 16
<212> TYPE: DNA
<213> ORGANISM: Zea mays

<400> SEQUENCE: 480
cacgatagga atgagt                                                       16

<210> SEQ ID NO 481
<211> LENGTH: 17
<212> TYPE: DNA
<213> ORGANISM: Zea mays

<400> SEQUENCE: 481
aaggtcgata tctccct                                                      17

<210> SEQ ID NO 482
<211> LENGTH: 18
<212> TYPE: DNA
<213> ORGANISM: Zea mays

<400> SEQUENCE: 482
ataactggga ttacttct                                                     18

<210> SEQ ID NO 483
<211> LENGTH: 16
<212> TYPE: DNA
<213> ORGANISM: Zea mays

<400> SEQUENCE: 483
taggaccccc catcat                                                       16

<210> SEQ ID NO 484
<211> LENGTH: 16
<212> TYPE: DNA
<213> ORGANISM: Zea mays

<400> SEQUENCE: 484
tgggtactga caacaa                                                       16

<210> SEQ ID NO 485
<211> LENGTH: 15
<212> TYPE: DNA
<213> ORGANISM: Zea mays

<400> SEQUENCE: 485
cttcttgaac cttcg                                                        15

<210> SEQ ID NO 486
<211> LENGTH: 15
<212> TYPE: DNA
<213> ORGANISM: Zea mays

<400> SEQUENCE: 486

```
acagtccgat ttaat                                                      15

<210> SEQ ID NO 487
<211> LENGTH: 20
<212> TYPE: DNA
<213> ORGANISM: Zea mays

<400> SEQUENCE: 487
ataaataaag cacgtattca                                                 20

<210> SEQ ID NO 488
<211> LENGTH: 16
<212> TYPE: DNA
<213> ORGANISM: Zea mays

<400> SEQUENCE: 488
tgattaggcc aaagtg                                                     16

<210> SEQ ID NO 489
<211> LENGTH: 16
<212> TYPE: DNA
<213> ORGANISM: Zea mays

<400> SEQUENCE: 489
aggatgacta cttctc                                                     16

<210> SEQ ID NO 490
<211> LENGTH: 15
<212> TYPE: DNA
<213> ORGANISM: Zea mays

<400> SEQUENCE: 490
cctctacaat catcc                                                      15

<210> SEQ ID NO 491
<211> LENGTH: 14
<212> TYPE: DNA
<213> ORGANISM: Zea mays

<400> SEQUENCE: 491
agcctcagcg ctgg                                                       14

<210> SEQ ID NO 492
<211> LENGTH: 16
<212> TYPE: DNA
<213> ORGANISM: Zea mays

<400> SEQUENCE: 492
atgtcatcta tctccg                                                     16

<210> SEQ ID NO 493
<211> LENGTH: 14
<212> TYPE: DNA
<213> ORGANISM: Zea mays

<400> SEQUENCE: 493
tggagtggaa cgct                                                       14

<210> SEQ ID NO 494
<211> LENGTH: 14
<212> TYPE: DNA
<213> ORGANISM: Zea mays
```

-continued

<400> SEQUENCE: 494
agcgaagggc taaa                                           14

<210> SEQ ID NO 495
<211> LENGTH: 16
<212> TYPE: DNA
<213> ORGANISM: Zea mays

<400> SEQUENCE: 495
tcactttgag ataacg                                         16

<210> SEQ ID NO 496
<211> LENGTH: 17
<212> TYPE: DNA
<213> ORGANISM: Zea mays

<400> SEQUENCE: 496
tctcgacaga tgaacat                                        17

<210> SEQ ID NO 497
<211> LENGTH: 17
<212> TYPE: DNA
<213> ORGANISM: Zea mays

<400> SEQUENCE: 497
cctcaacaga ggtagct                                        17

<210> SEQ ID NO 498
<211> LENGTH: 14
<212> TYPE: DNA
<213> ORGANISM: Zea mays

<400> SEQUENCE: 498
tcgcaggact cgtg                                           14

<210> SEQ ID NO 499
<211> LENGTH: 20
<212> TYPE: DNA
<213> ORGANISM: Zea mays

<400> SEQUENCE: 499
catactcttc aatacatatt                                     20

<210> SEQ ID NO 500
<211> LENGTH: 16
<212> TYPE: DNA
<213> ORGANISM: Zea mays

<400> SEQUENCE: 500
tcatcagtgg cagaaa                                         16

<210> SEQ ID NO 501
<211> LENGTH: 14
<212> TYPE: DNA
<213> ORGANISM: Zea mays

<400> SEQUENCE: 501
ctcgggatgc gaac                                           14

<210> SEQ ID NO 502
<211> LENGTH: 18
<212> TYPE: DNA
<213> ORGANISM: Zea mays

<400> SEQUENCE: 502
aacttgcatt attttatc                                                18

<210> SEQ ID NO 503
<211> LENGTH: 14
<212> TYPE: DNA
<213> ORGANISM: Zea mays

<400> SEQUENCE: 503
cacacgcatt aata                                                    14

<210> SEQ ID NO 504
<211> LENGTH: 20
<212> TYPE: DNA
<213> ORGANISM: Zea mays

<400> SEQUENCE: 504
ataaagcagc tagtttgcta                                              20

<210> SEQ ID NO 505
<211> LENGTH: 16
<212> TYPE: DNA
<213> ORGANISM: Zea mays

<400> SEQUENCE: 505
tgtttccctg tttctt                                                  16

<210> SEQ ID NO 506
<211> LENGTH: 17
<212> TYPE: DNA
<213> ORGANISM: Zea mays

<400> SEQUENCE: 506
atggagtagt ttggacc                                                 17

<210> SEQ ID NO 507
<211> LENGTH: 15
<212> TYPE: DNA
<213> ORGANISM: Zea mays

<400> SEQUENCE: 507
cttcgataaa atggc                                                   15

<210> SEQ ID NO 508
<211> LENGTH: 16
<212> TYPE: DNA
<213> ORGANISM: Zea mays

<400> SEQUENCE: 508
caaatccaag aagcag                                                  16

<210> SEQ ID NO 509
<211> LENGTH: 13
<212> TYPE: DNA
<213> ORGANISM: Zea mays

<400> SEQUENCE: 509
cggactcaag cac                                                     13

<210> SEQ ID NO 510
<211> LENGTH: 17
<212> TYPE: DNA

```
<213> ORGANISM: Zea mays

<400> SEQUENCE: 510
agaattgctg ggtgcat                                                    17

<210> SEQ ID NO 511
<211> LENGTH: 16
<212> TYPE: DNA
<213> ORGANISM: Zea mays

<400> SEQUENCE: 511
cagcttgtct attcac                                                     16

<210> SEQ ID NO 512
<211> LENGTH: 14
<212> TYPE: DNA
<213> ORGANISM: Zea mays

<400> SEQUENCE: 512
cgatcagggc aaac                                                       14

<210> SEQ ID NO 513
<211> LENGTH: 18
<212> TYPE: DNA
<213> ORGANISM: Zea mays

<400> SEQUENCE: 513
attaacagga aatgatgc                                                   18

<210> SEQ ID NO 514
<211> LENGTH: 15
<212> TYPE: DNA
<213> ORGANISM: Zea mays

<400> SEQUENCE: 514
tggttgcaaa gataa                                                      15

<210> SEQ ID NO 515
<211> LENGTH: 18
<212> TYPE: DNA
<213> ORGANISM: Zea mays

<400> SEQUENCE: 515
aagcgattca aaccacaa                                                   18

<210> SEQ ID NO 516
<211> LENGTH: 17
<212> TYPE: DNA
<213> ORGANISM: Zea mays

<400> SEQUENCE: 516
tgcgtaatta attaaac                                                    17

<210> SEQ ID NO 517
<211> LENGTH: 18
<212> TYPE: DNA
<213> ORGANISM: Zea mays

<400> SEQUENCE: 517
tgctttaaat taaaaaat                                                   18

<210> SEQ ID NO 518
<211> LENGTH: 19
```

```
<212> TYPE: DNA
<213> ORGANISM: Zea mays

<400> SEQUENCE: 518
tgtgcatatt tgatgttag                                                    19

<210> SEQ ID NO 519
<211> LENGTH: 15
<212> TYPE: DNA
<213> ORGANISM: Zea mays

<400> SEQUENCE: 519
atggcacatt gatca                                                        15

<210> SEQ ID NO 520
<211> LENGTH: 15
<212> TYPE: DNA
<213> ORGANISM: Zea mays

<400> SEQUENCE: 520
acagtgcaag aacaa                                                        15

<210> SEQ ID NO 521
<211> LENGTH: 14
<212> TYPE: DNA
<213> ORGANISM: Zea mays

<400> SEQUENCE: 521
aggagccccg ggag                                                         14

<210> SEQ ID NO 522
<211> LENGTH: 13
<212> TYPE: DNA
<213> ORGANISM: Zea mays

<400> SEQUENCE: 522
ccttgccagc aaa                                                          13

<210> SEQ ID NO 523
<211> LENGTH: 18
<212> TYPE: DNA
<213> ORGANISM: Zea mays

<400> SEQUENCE: 523
caatatacag gtaatctg                                                     18

<210> SEQ ID NO 524
<211> LENGTH: 17
<212> TYPE: DNA
<213> ORGANISM: Zea mays

<400> SEQUENCE: 524
ccgttcttgt taaccag                                                      17

<210> SEQ ID NO 525
<211> LENGTH: 13
<212> TYPE: DNA
<213> ORGANISM: Zea mays

<400> SEQUENCE: 525
catccccaag ctt                                                          13

<210> SEQ ID NO 526
```

-continued

```
<211> LENGTH: 17
<212> TYPE: DNA
<213> ORGANISM: Zea mays

<400> SEQUENCE: 526
aaacaaggta actttca                                                     17

<210> SEQ ID NO 527
<211> LENGTH: 16
<212> TYPE: DNA
<213> ORGANISM: Zea mays

<400> SEQUENCE: 527
ctactatcga gattgc                                                      16

<210> SEQ ID NO 528
<211> LENGTH: 18
<212> TYPE: DNA
<213> ORGANISM: Zea mays

<400> SEQUENCE: 528
cactgtacgc ttcgatgt                                                    18

<210> SEQ ID NO 529
<211> LENGTH: 19
<212> TYPE: DNA
<213> ORGANISM: Zea mays

<400> SEQUENCE: 529
cttaggatca tccttttct                                                   19

<210> SEQ ID NO 530
<211> LENGTH: 15
<212> TYPE: DNA
<213> ORGANISM: Zea mays

<400> SEQUENCE: 530
ctctgaccat gaaac                                                       15

<210> SEQ ID NO 531
<211> LENGTH: 16
<212> TYPE: DNA
<213> ORGANISM: Zea mays

<400> SEQUENCE: 531
ctgctctatc atcgac                                                      16

<210> SEQ ID NO 532
<211> LENGTH: 17
<212> TYPE: DNA
<213> ORGANISM: Zea mays

<400> SEQUENCE: 532
tttgcatttg gtactcg                                                     17

<210> SEQ ID NO 533
<211> LENGTH: 15
<212> TYPE: DNA
<213> ORGANISM: Zea mays

<400> SEQUENCE: 533
accaacaatc aatgc                                                       15
```

```
<210> SEQ ID NO 534
<211> LENGTH: 15
<212> TYPE: DNA
<213> ORGANISM: Zea mays

<400> SEQUENCE: 534
aaatgcggac tccag                                                    15

<210> SEQ ID NO 535
<211> LENGTH: 14
<212> TYPE: DNA
<213> ORGANISM: Zea mays

<400> SEQUENCE: 535
agctcgacaa cgat                                                     14

<210> SEQ ID NO 536
<211> LENGTH: 16
<212> TYPE: DNA
<213> ORGANISM: Zea mays

<400> SEQUENCE: 536
accagactaa accttt                                                   16

<210> SEQ ID NO 537
<211> LENGTH: 16
<212> TYPE: DNA
<213> ORGANISM: Zea mays

<400> SEQUENCE: 537
catctccatg tgcctc                                                   16

<210> SEQ ID NO 538
<211> LENGTH: 14
<212> TYPE: DNA
<213> ORGANISM: Zea mays

<400> SEQUENCE: 538
tgtgcctcct tggc                                                     14

<210> SEQ ID NO 539
<211> LENGTH: 16
<212> TYPE: DNA
<213> ORGANISM: Zea mays

<400> SEQUENCE: 539
cttcatgtgc caactt                                                   16

<210> SEQ ID NO 540
<211> LENGTH: 16
<212> TYPE: DNA
<213> ORGANISM: Zea mays

<400> SEQUENCE: 540
cagacaaatg atttca                                                   16

<210> SEQ ID NO 541
<211> LENGTH: 16
<212> TYPE: DNA
<213> ORGANISM: Zea mays

<400> SEQUENCE: 541
cttcatgtgc caactt                                                   16
```

```
<210> SEQ ID NO 542
<211> LENGTH: 15
<212> TYPE: DNA
<213> ORGANISM: Zea mays

<400> SEQUENCE: 542
acggagtgtc attct                                                    15

<210> SEQ ID NO 543
<211> LENGTH: 16
<212> TYPE: DNA
<213> ORGANISM: Zea mays

<400> SEQUENCE: 543
aaggtttgcg tactct                                                   16

<210> SEQ ID NO 544
<211> LENGTH: 14
<212> TYPE: DNA
<213> ORGANISM: Zea mays

<400> SEQUENCE: 544
cccactaaga aaac                                                     14

<210> SEQ ID NO 545
<211> LENGTH: 19
<212> TYPE: DNA
<213> ORGANISM: Zea mays

<400> SEQUENCE: 545
catatttagc gcttcatca                                                19

<210> SEQ ID NO 546
<211> LENGTH: 15
<212> TYPE: DNA
<213> ORGANISM: Zea mays

<400> SEQUENCE: 546
ttgttcccca ttaat                                                    15

<210> SEQ ID NO 547
<211> LENGTH: 15
<212> TYPE: DNA
<213> ORGANISM: Zea mays

<400> SEQUENCE: 547
ttgttgcaaa ggaag                                                    15

<210> SEQ ID NO 548
<211> LENGTH: 15
<212> TYPE: DNA
<213> ORGANISM: Zea mays

<400> SEQUENCE: 548
ctttgagcag ctagc                                                    15

<210> SEQ ID NO 549
<211> LENGTH: 14
<212> TYPE: DNA
<213> ORGANISM: Zea mays

<400> SEQUENCE: 549
tgacgggatc gact                                                     14
```

<210> SEQ ID NO 550
<211> LENGTH: 14
<212> TYPE: DNA
<213> ORGANISM: Zea mays

<400> SEQUENCE: 550
agcacactgg tttc                                                    14

<210> SEQ ID NO 551
<211> LENGTH: 13
<212> TYPE: DNA
<213> ORGANISM: Zea mays

<400> SEQUENCE: 551
tcggtcggca aac                                                     13

<210> SEQ ID NO 552
<211> LENGTH: 15
<212> TYPE: DNA
<213> ORGANISM: Zea mays

<400> SEQUENCE: 552
aacacgcgac ttagt                                                   15

<210> SEQ ID NO 553
<211> LENGTH: 15
<212> TYPE: DNA
<213> ORGANISM: Zea mays

<400> SEQUENCE: 553
agctgaggtg aacct                                                   15

<210> SEQ ID NO 554
<211> LENGTH: 18
<212> TYPE: DNA
<213> ORGANISM: Zea mays

<400> SEQUENCE: 554
atacatctaa caacttca                                                18

<210> SEQ ID NO 555
<211> LENGTH: 17
<212> TYPE: DNA
<213> ORGANISM: Zea mays

<400> SEQUENCE: 555
tatgtgcatc gacgatg                                                 17

<210> SEQ ID NO 556
<211> LENGTH: 13
<212> TYPE: DNA
<213> ORGANISM: Zea mays

<400> SEQUENCE: 556
tgcagcagac ctg                                                     13

<210> SEQ ID NO 557
<211> LENGTH: 15
<212> TYPE: DNA
<213> ORGANISM: Zea mays

<400> SEQUENCE: 557
ttactccagc atcgc                                            15

<210> SEQ ID NO 558
<211> LENGTH: 13
<212> TYPE: DNA
<213> ORGANISM: Zea mays

<400> SEQUENCE: 558
cgaacgcgaa gct                                              13

<210> SEQ ID NO 559
<211> LENGTH: 15
<212> TYPE: DNA
<213> ORGANISM: Zea mays

<400> SEQUENCE: 559
cttttcacat cctcc                                            15

<210> SEQ ID NO 560
<211> LENGTH: 14
<212> TYPE: DNA
<213> ORGANISM: Zea mays

<400> SEQUENCE: 560
caagagagaa tttc                                             14

<210> SEQ ID NO 561
<211> LENGTH: 15
<212> TYPE: DNA
<213> ORGANISM: Zea mays

<400> SEQUENCE: 561
acagagggtt tggtg                                            15

<210> SEQ ID NO 562
<211> LENGTH: 16
<212> TYPE: DNA
<213> ORGANISM: Zea mays

<400> SEQUENCE: 562
cgaccattca acatat                                           16

<210> SEQ ID NO 563
<211> LENGTH: 15
<212> TYPE: DNA
<213> ORGANISM: Zea mays

<400> SEQUENCE: 563
cctctaggat aagcg                                            15

<210> SEQ ID NO 564
<211> LENGTH: 18
<212> TYPE: DNA
<213> ORGANISM: Zea mays

<400> SEQUENCE: 564
atcggtaaag acgaagaa                                         18

<210> SEQ ID NO 565
<211> LENGTH: 19
<212> TYPE: DNA
<213> ORGANISM: Zea mays

```
<400> SEQUENCE: 565
agttgacaat atcgcctac                                            19

<210> SEQ ID NO 566
<211> LENGTH: 16
<212> TYPE: DNA
<213> ORGANISM: Zea mays

<400> SEQUENCE: 566
tcgagaatgg agtttg                                               16

<210> SEQ ID NO 567
<211> LENGTH: 14
<212> TYPE: DNA
<213> ORGANISM: Zea mays

<400> SEQUENCE: 567
tgctcctgtt tctg                                                 14

<210> SEQ ID NO 568
<211> LENGTH: 13
<212> TYPE: DNA
<213> ORGANISM: Zea mays

<400> SEQUENCE: 568
tgggcttggc ctt                                                  13

<210> SEQ ID NO 569
<211> LENGTH: 13
<212> TYPE: DNA
<213> ORGANISM: Zea mays

<400> SEQUENCE: 569
tgcaaagttt ccc                                                  13

<210> SEQ ID NO 570
<211> LENGTH: 13
<212> TYPE: DNA
<213> ORGANISM: Zea mays

<400> SEQUENCE: 570
ttcgcgccaa acc                                                  13
```